United States Patent
Galatsis et al.

(10) Patent No.: US 9,642,855 B2
(45) Date of Patent: *May 9, 2017

(54) SUBSTITUTED PYRROLO[2,3-D]PYRIMIDINES AS LRRK2 INHIBITORS

(71) Applicant: Pfizer Inc., New York, NY (US)

(72) Inventors: Paul Galatsis, Newton, MA (US); Matthew Merrill Hayward, Old Lyme, CT (US); Bethany Lyn Kormos, Somerville, MA (US); Travis T. Wager, Brookline, MA (US); Lei Zhang, Auburndale, MA (US); Antonia Friederike Stepan, Providence, RI (US); Jaclyn Louise Henderson, Cambridge, MA (US); Ravi G. Kurumbail, East Lyme, CT (US); Patrick Robert Verhoest, Newton, MA (US)

(73) Assignee: Pfizer Inc., New York, NY (US)

( * ) Notice: Subject to any disclaimer, the term of this patent is extended or adjusted under 35 U.S.C. 154(b) by 91 days.

This patent is subject to a terminal disclaimer.

(21) Appl. No.: 14/840,528

(22) Filed: Aug. 31, 2015

(65) Prior Publication Data

US 2015/0366874 A1    Dec. 24, 2015

Related U.S. Application Data

(63) Continuation of application No. 13/928,696, filed on Jun. 27, 2013, now Pat. No. 9,156,845.

(60) Provisional application No. 61/820,828, filed on May 8, 2013, provisional application No. 61/666,299, filed on Jun. 29, 2012.

(51) Int. Cl.
  *A61K 31/519*    (2006.01)
  *C07D 487/04*    (2006.01)
  *A61K 31/5377*   (2006.01)
  *C07D 519/00*    (2006.01)

(52) U.S. Cl.
  CPC ........ *A61K 31/5377* (2013.01); *C07D 487/04* (2013.01); *C07D 519/00* (2013.01)

(58) Field of Classification Search
  CPC ................... A61K 31/519; C07D 487/04
  USPC ............... 514/265.1; 544/143, 280; 546/286; 548/364.7
  See application file for complete search history.

(56) References Cited

U.S. PATENT DOCUMENTS

| 4,689,338 A | 8/1987 | Gerster |
| 5,389,640 A | 2/1995 | Gerster et al. |
| 5,502,187 A | 3/1996 | Ayer et al. |
| 5,506,347 A | 4/1996 | Erion et al. |
| 5,646,128 A | 7/1997 | Firestein et al. |
| 5,658,889 A | 8/1997 | Gruber et al. |
| 5,674,998 A | 10/1997 | Boyer et al. |
| 5,686,457 A | 11/1997 | Traxler et al. |
| 5,721,356 A | 2/1998 | Ugarkar et al. |
| 5,726,302 A | 3/1998 | Ugarkar et al. |
| 5,750,349 A | 5/1998 | Suzuki et al. |
| 5,763,596 A | 6/1998 | Boyer et al. |
| 5,763,597 A | 6/1998 | Ugarkar et al. |
| 5,795,977 A | 8/1998 | Ugarkar et al. |
| 5,864,033 A | 1/1999 | Browne et al. |
| 6,051,577 A | 4/2000 | Altmann |
| 6,096,749 A | 8/2000 | Traxler et al. |
| 6,610,847 B2 | 8/2003 | Blumenkopf et al. |
| 6,635,762 B1 | 10/2003 | Blumenkopf et al. |
| 6,890,929 B2 | 5/2005 | Blumenkopf et al. |
| 7,115,600 B2 | 10/2006 | Wager et al. |
| 7,285,293 B2 | 10/2007 | Castillo et al. |
| 7,569,569 B2 | 8/2009 | Blumenkopf et al. |
| 7,687,507 B2 | 3/2010 | Blumenkopf et al. |
| 7,964,607 B2 | 6/2011 | Verhoest et al. |

(Continued)

FOREIGN PATENT DOCUMENTS

| CN | 1102644 | 5/1995 |
| DE | 4304455 | 8/1994 |

(Continued)

OTHER PUBLICATIONS

Singapore Patent Application No. 1101408044Q, Search Report and Written Opinion, mailed Jan. 5, 2016, 10 pages.

(Continued)

*Primary Examiner* — Douglas M Willis
(74) *Attorney, Agent, or Firm* — John A. Wichtowski

(57) ABSTRACT

The present invention provides novel 4,5-disubstituted-7H-pyrrolo[2,3-d]pyrimidine derivatives of Formula I, and the pharmaceutically acceptable salts thereof

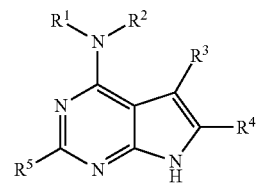

wherein $R^1$, $R^2$, $R^3$, $R^4$ and $R^5$ are as defined in the specification. The invention is also directed to pharmaceutical compositions comprising the compounds of formula I and to use of the compounds in the treatment of diseases associated with LRRK2, such as neurodegenerative diseases including Parkinson's disease or Alzheimer's disease, cancer, Crohn's disease or leprosy.

10 Claims, No Drawings

(56) References Cited

U.S. PATENT DOCUMENTS

| | | |
|---|---|---|
| 7,998,966 B2 | 8/2011 | Bearss et al. |
| 9,156,845 B2 | 10/2015 | Galatsis et al. |
| 2002/0019526 A1 | 2/2002 | Blumenkopf et al. |
| 2003/0073655 A1 | 4/2003 | Chain |
| 2003/0195205 A1 | 10/2003 | DeNinno et al. |
| 2003/0212273 A1 | 11/2003 | Blumenkopf et al. |
| 2004/0058922 A1 | 3/2004 | Blumenkopf et al. |
| 2004/0192898 A1 | 9/2004 | Jia et al. |
| 2004/0220186 A1 | 11/2004 | Bell et al. |
| 2005/0019328 A1 | 1/2005 | Schenk |
| 2005/0043354 A1 | 2/2005 | Wager et al. |
| 2005/0048049 A1 | 3/2005 | Schenk |
| 2005/0153989 A1 | 7/2005 | Grotzfeld et al. |
| 2005/0171128 A1 | 8/2005 | Blumenkopf et al. |
| 2005/0256135 A1 | 11/2005 | Lunn et al. |
| 2005/0261331 A1 | 11/2005 | Nielsen et al. |
| 2005/0267095 A1 | 12/2005 | Bernardelli et al. |
| 2005/0267100 A1 | 12/2005 | Elliott et al. |
| 2006/0106035 A1 | 5/2006 | Hendrix et al. |
| 2006/0111372 A1 | 5/2006 | Hendrix et al. |
| 2007/0031416 A1 | 2/2007 | Shiji et al. |
| 2007/0049615 A1 | 3/2007 | Ibrahim et al. |
| 2007/0149561 A1 | 6/2007 | Dhanak et al. |
| 2007/0179175 A1 | 8/2007 | Lunn |
| 2008/0096955 A1 | 4/2008 | Wager et al. |
| 2008/0176925 A1 | 7/2008 | Butler et al. |
| 2008/0293733 A1 | 11/2008 | Bearss et al. |
| 2009/0005356 A1 | 1/2009 | Blaney et al. |
| 2009/0118276 A1 | 5/2009 | Gopalsamy et al. |
| 2009/0275533 A1 | 11/2009 | Hsieh et al. |
| 2009/0298823 A1 | 12/2009 | Song et al. |
| 2009/0325953 A1 | 12/2009 | Sahoo et al. |
| 2010/0175140 A1 | 7/2010 | Smith |
| 2010/0184790 A1 | 7/2010 | Meijer et al. |
| 2011/0082140 A1 | 4/2011 | Dorsch et al. |
| 2011/0166175 A1 | 7/2011 | Klein |
| 2011/0190290 A1 | 8/2011 | Hood et al. |
| 2011/0201599 A1 | 8/2011 | Bahceci et al. |
| 2011/0218198 A1 | 9/2011 | Wucherer-Plietker et al. |
| 2011/0269772 A1 | 11/2011 | Bearss et al. |
| 2012/0245347 A1 | 9/2012 | Biehl et al. |
| 2014/0256704 A1 | 9/2014 | Vankyalapati et al. |

FOREIGN PATENT DOCUMENTS

| | | |
|---|---|---|
| DE | 102008025751 | 12/2009 |
| EP | 339358 | 11/1989 |
| EP | 535548 | 4/1993 |
| EP | 631179 | 12/1994 |
| EP | 676667 | 10/1995 |
| EP | 0682027 | 11/1995 |
| EP | 777150 | 6/1997 |
| EP | 795556 | 9/1997 |
| EP | 846981 | 6/1998 |
| EP | 0994728 | 4/2000 |
| EP | 1052264 | 11/2000 |
| EP | 1070987 | 1/2001 |
| EP | 1257584 | 10/2004 |
| EP | 2210887 | 7/2010 |
| EP | 2338486 | 6/2011 |
| EP | 0386722 | 9/2012 |
| JP | 3271289 | 12/1991 |
| JP | 5310700 | 11/1993 |
| JP | 6041114 | 2/1994 |
| JP | 6116239 | 4/1994 |
| JP | 6247966 | 9/1994 |
| JP | 10177243 | 6/1998 |
| JP | 10213887 | 8/1998 |
| JP | 2001302515 | 10/2001 |
| KR | 20100116765 | 11/2010 |
| KR | 20120019785 | 3/2012 |
| WO | 9320078 | 10/1993 |
| WO | 9408975 | 4/1994 |
| WO | 9511898 | 5/1995 |
| WO | 9640705 | 12/1996 |
| WO | 9640706 | 12/1996 |
| WO | 9640707 | 12/1996 |
| WO | 9823613 | 6/1998 |
| WO | 9844955 | 10/1998 |
| WO | 9965908 | 12/1999 |
| WO | 9965909 | 12/1999 |
| WO | 0198301 | 12/2001 |
| WO | 02051837 | 7/2002 |
| WO | 02089811 | 11/2002 |
| WO | 03076658 | 9/2003 |
| WO | 2004014368 | 2/2004 |
| WO | 2004016609 | 2/2004 |
| WO | 2004032868 | 4/2004 |
| WO | 2004055024 | 7/2004 |
| WO | 2005025616 | 3/2005 |
| WO | 2005044181 | 5/2005 |
| WO | 2005062795 | 7/2005 |
| WO | 2005097740 | 10/2005 |
| WO | 2005103050 | 11/2005 |
| WO | 2005121175 | 12/2005 |
| WO | 2006004703 | 1/2006 |
| WO | 2006036291 | 4/2006 |
| WO | 2006042102 | 4/2006 |
| WO | 2006045392 | 5/2006 |
| WO | 2006050976 | 5/2006 |
| WO | 2006052568 | 5/2006 |
| WO | 2006069081 | 6/2006 |
| WO | 2006091568 | 8/2006 |
| WO | 2006118959 | 11/2006 |
| WO | 2006136924 | 12/2006 |
| WO | 2007063385 | 6/2007 |
| WO | 2007069053 | 6/2007 |
| WO | 2007076423 | 7/2007 |
| WO | 2007088450 | 8/2007 |
| WO | 2007088462 | 8/2007 |
| WO | 2007099423 | 9/2007 |
| WO | 2007104763 | 9/2007 |
| WO | 2007105053 | 9/2007 |
| WO | 2007124096 | 11/2007 |
| WO | 2007135380 | 11/2007 |
| WO | 2007138431 | 12/2007 |
| WO | 2007149798 | 12/2007 |
| WO | 2008070908 | 6/2008 |
| WO | 2008075007 | 6/2008 |
| WO | 2008091799 | 7/2008 |
| WO | 2008122789 | 10/2008 |
| WO | 2008128072 | 10/2008 |
| WO | 2008129152 | 10/2008 |
| WO | 2008150914 | 12/2008 |
| WO | 2008155000 | 12/2008 |
| WO | 2009005730 | 1/2009 |
| WO | 2009030270 | 3/2009 |
| WO | 2009035159 | 3/2009 |
| WO | 2009071620 | 6/2009 |
| WO | 2009127642 | 10/2009 |
| WO | 2009131687 | 10/2009 |
| WO | 2009134658 | 11/2009 |
| WO | 2010000364 | 1/2010 |
| WO | 2010003133 | 1/2010 |
| WO | 2010020308 | 2/2010 |
| WO | 2010026335 | 3/2010 |
| WO | 2010031988 | 3/2010 |
| WO | 2010036380 | 4/2010 |
| WO | 2010080712 | 7/2010 |
| WO | 2010081835 | 7/2010 |
| WO | 2010085799 | 7/2010 |
| WO | 2010093191 | 8/2010 |
| WO | 2010106333 | 9/2010 |
| WO | 2010109005 | 9/2010 |
| WO | 2010127754 | 11/2010 |
| WO | 2010129053 | 11/2010 |
| WO | 2010141817 | 12/2010 |
| WO | 2011038572 | 4/2011 |
| WO | 2011045344 | 4/2011 |
| WO | 2011053861 | 5/2011 |
| WO | 2011055911 | 5/2011 |
| WO | 2011057204 | 5/2011 |
| WO | 2011060295 | 5/2011 |
| WO | 2011106168 | 9/2011 |

(56) References Cited

FOREIGN PATENT DOCUMENTS

| WO | 2011131980 | 10/2011 |
|----|------------|---------|
| WO | 2011137022 | 11/2011 |
| WO | 2011141756 | 11/2011 |
| WO | 2011147756 | 11/2011 |
| WO | 2011144622 | 12/2011 |
| WO | 2011149827 | 12/2011 |
| WO | 2011151360 | 12/2011 |
| WO | 2012028629 | 3/2012 |
| WO | 2012034526 | 3/2012 |
| WO | 2012038743 | 3/2012 |
| WO | 2012058193 | 5/2012 |
| WO | 2012062783 | 5/2012 |
| WO | 2012075046 | 6/2012 |
| WO | 2012118679 | 9/2012 |
| WO | 2012131365 | 10/2012 |
| WO | 2012135631 | 10/2012 |
| WO | 2012143143 | 10/2012 |
| WO | 2012143144 | 10/2012 |
| WO | 2012159079 | 11/2012 |
| WO | 2012162254 | 11/2012 |
| WO | 2012178015 | 12/2012 |
| WO | 2013007768 | 1/2013 |
| WO | 2013046029 | 4/2013 |
| WO | 2013139882 | 9/2013 |
| WO | 2013164321 | 11/2013 |
| WO | 2013166276 | 11/2013 |
| WO | 2014001973 | 1/2014 |
| WO | 2014060113 | 4/2014 |
| WO | 2014093383 | 6/2014 |
| WO | 2015022664 | 2/2015 |
| WO | 2015092592 | 6/2015 |

OTHER PUBLICATIONS

Korean Patent Application No. 2015-7002334 (PCT/IB2013/055039) Notice of Preliminary Rejection, dated Jul. 12, 2016, 12 pages.
International Patent Application No. PCT/IB2014/066563, filed Dec. 3, 2014,International Preliminary Report on Patentability, mailed Jun. 21, 2016, 6 pages.
International Patent Application PCT/IB2016/0553258, filed Sep. 7, 2016, Search Report and Written Opinion, mailed Oct. 24, 2016, 17 pages.
Lewis, Patrick, et al., "LRRK2 and Human Disease: A Complicated Question or a Question of Complexes?", Science Signaling, Jan. 17, 2012, pp. pe2, 5(207).
Gillardon, F., et al., "Parkinson's Disease-Linked Leucine-Rich Repeat Kinase 2(R1331G) Mutation Increases Proinflammatory Cytokine Release From Activated Primary Microglial Cells and Resultant Neurotoxicity", Neuroscience, Apr. 19, 2012, pp. 41-48, vol. 208.
Moehle, Mark S., et al., "LRRK2 Inhibition Attenuates Microglial Inflammatory Responses", The Journal of Neuroscience, Feb. 1, 2012, pp. 1602-1611, 32(5).
Haan, J., et al., "Amyloid in Central Nervous System Disease", Clinical Neurology and Neurosurgery, 1990, pp. 305-310, 92(4).
Glenner, George G., et al., "Amyloidosis of the Nervous System", The Journal of Neurological Sciences, 1989, pp. 1-28, 94(1-3).
Zimprich, Alexander, et al., "Mutations in LRRK2 Cause Autosomal-Dominant Parkinsonism with Pleomorphic Pathology", Neuron, Nov. 18, 2004, pp. 601-607, 44(4).
Zhao, Yi, et al., "LRRK2 Variant Associated with Alzheimer's Disease", Neurobiology of Aging, 2011, pp. 1990-1993, vol. 32.
Saunder-Pullman, Rachel, et al., "LRRK2 G2019S Mutations are Associated with an Increased Cancer Risk in Parkinson Disease", Movement Disorders, 2010, pp. 2536-2541, 25(15).
Liu, Zhihua, et al., "The Kinase LRRK2 is a Regulator of the Transcription Factor NFAT That Modulates the Severity of Inflammatory Bowel Disease", Nature Immunology, 2011, pp. 1063-1070, 12(11).

Haleblain, John, "Characterization of Habits and Crystalline Modification of Solids and Their Pharmaceutical Applications", The Journal of Pharmaceutical Sciences, Aug. 1975, pp. 1269-1288, 64(8).
Finnin, Barrie C., et al., "Transdermal Penetration Enhancers: Applications, Limitations, and Potential", The Journal of Pharmaceutical Sciences, Oct. 1999, pp. 955-958, 88(10).
Suzuki, Akira, "Recent Advances in the Cross-Coupling Reactions of Organoboron Derivatives with Organic Electrophiles, 1995-1998", Journal of Organometallic Chemistry, Mar. 15, 1999, pp. 147-168, 576(1-2).
Miyaura, Norio, et al., "Palladium-Catalyzed Cross-Coupling Reactions of Organoboron Compounds", Chemistry Review, 1995, pp. 2457-2483, 95(7).
Littke, Adam F., et al., "Versatile Catalysts for the Suzuki Cross-Coupling of Arylboronic Acids with Aryl and Vinyl Halides and Triflates under Mild Conditions", Journal of American Chemical Society, May 3, 2000, pp. 4020-4028, 122 (17).
Erdik, Ender, "Transition Metal Catalyzed Reactions of Organozinc Reagents", Tetrahedron, 1992, pp. 9577-9648, 48(44).
Banno, Tadashi, et al. "Some Applications of the Grignard Cross-Coupling Reaction in the Industrial Field", Journal of Organometallic Chemistry, Jul. 1, 2002, pp. 288-291, 653(1-2).
Gangloff, Anthony R., et al., "Synthesis of 3,5-disubstituted-1,2,4-oxadiazoles using tetrabutylammonium fluoride as mild and efficient catalyst", Tetrahedron Letters, Feb. 19, 2001, pp. 1441-1443, 42(8).
Boger, Dale, L., et al., "Thermal Cycloaddition of 1,3,5-Triazine with Enamines: Regiospecific Pyrimidine Annulation", Journal of Organic Chemistry, Jul. 1982, pp. 2673-2673, 47(13).
Sanz, Roberto, et al., "Regioselective Synthesis of 4- and 7-Alkoxyindoles from 2,3-Dihalophenols" Application to the Preparation of Indole Inhibitors of Phospholipase A2, Journal of Organic Chemistry, Mar. 28, 2007, pp. 5113-5118, 72(14).
Shie, Jiun-Jie, et al., "Microwave-Assisted One-Pot Tandem Reactions for Direct Conversion of Primary Alcohols and Aldehydes to Triazines and Tetrazoles in Aqueous Media", Journal of Organic Chemistry, Apr. 13, 2007, pp. 3141-3144, 72(8).
KR20120019785, Korean Patent, published Mar. 3, 2007, Machine Translation.
KR20100116765, Korean Patent, published Nov. 2, 2010, Machine Translation.
Boyer, S.H., et al., "Adenosine Kinase Inhibitors, 5. Synthesis, Enzyme Inhibition, and Analgesic Activity of Diaryl-erythrofuranosyltubercidin Analogues", Journal of Medicinal Chemistry, Oct. 6, 2005, pp. 6430-6441, 48(20).
Bookser, B.C., et al., Adenosine Kinase Inhibitors. 6. Water Solubility and Antinociceptive Activity of 5-Phenyl-7-(5-deoxay-beta-D-ribofuranosyl)pyrrolo[2,3-d]pyrimidines Substituted at C4 with Glycinamides and Related Compounds, Journal of Medicinal Chemistry, Dec. 1, 2005, pp. 7808-7820, 48(24).
Jorgensen, A., et al., "Synthesis of 7H-Pyrrolo[2,3-d]pyrimidin-4-amines", Liebigs Annalen Der Chemie, Jan. 1, 1985, pp. 142-148, vol. 1985.
Taylor, E.C., et al., "Synthesis of 4-Amino-5-cyanopyrrolo[2,3-d]pyrimidine, the Agycone of Toyocamycin", Journal of the American Chemical Society, May 14, 1964, pp. 951-952, 86(5).
Traxler, P.M., et al., "4-(Phenylamino)pyrrolopyrimidines: Potent and Selective ATP Site Directed Inhibitors of the EGF-Receptor Protein Tyrosine Kinase", Journal of Medicinal Chemistry, Jun. 1, 1996, pp. 2285-2292, 39(12).
Ugarkar, B.G., et al., "Adenosine Kinase Inhibtors, 2. Synthesis, Enzymen Inhibition and Antiseizure Acitivity of Diaryltubercidin Analogues", Journal of Medicinal Chemistry, Jul. 27, 2000, pp. 2894-2905, 43(15).
Wilder, L., et al., "7-Alkyl and 7-Cycloalkyl-5-aryl-pyrrolo[2,3-d]pyrimidines-Potent Inhibitors of the Tyrosine Kinase c-Src", Bioorganic and Medicinal Chemistry, Mar. 26, 2001, pp. 849-852, vol. 11.
Wu, T., et al., "One-Pot, Two-Step Microwave-Assisted Reaction in Constructing 4,5-Disubstituted Pyrazolopyrimidines", Organic Letters, Jun. 9, 2003, pp. 3587-3590, 5(20).

(56) References Cited

OTHER PUBLICATIONS

International Patent Application PCT/IB2013/055039, filed Jun. 19, 2013, Written Opinion of the International Searching Authority, mailed Oct. 14, 2013, 10 pages.
Chen, H., et al., "Discovery of Selective LRRK2 Inhibitors Guided by Computational Analysis and Molecular Modeling", Journal of Medicinal Chemistry, 2012, pp. 5536-5545, vol. 55.
U.S. Appl. No. 61/916,953, filed Dec. 17, 2013.
International Patent Application PCT/IB2013/055039, filed Jun. 19, 2013, International Search Report, mailed Oct. 14, 2013, 9 pages.
Reader, John C., et al., "Structure-Guided Evolution of Potent and Selective CHK1 Inhibitors through Scaffold Morphing", Journal of Medicinal Chemistry, 2011, pp. 8328-8242, 54(24).
Chen, Xiu-Mei, et al., "Structure-based and shape-complemented pharmacophore modeling for the discovery of novel checkpoint kinase 1 inhibitors", Journal of Molecular Modeling, 2010, pp. 1195-1204, 16(7).
Coumar, Mohane S., et al., "Identification, SAR Studies, and X-ray Co-crystallographic Analysis of a Novel Furanopyrimidine Aurora Kinase A Inhibitor", ChemMedChem, 2010, pp. 255-267, 5(2).
Foloppe, N., et al., "Structure-Based Design of Novel Chk1 Inhibitors: Insights into Hydrogen Bonding and Protein-Ligand Affinity", Journal of Medicinal Chemistry, 2005, pp. 4332-4345, 48(13).
Chen, Gang, et al., "Elucidating inhibitory models of the inhibitors of epidermal growth factor receptor by docking and 3D-QSAR", Bioorganic & Medicinal Chemistry, 2004, pp. 2409-2417, 12(9).
Peng, Tao, et al., 3D-QSAR and Receptor Modeling of Tyrosine Kinase Inhibitors with Flexible Atom Receptor Model (FLARM), Journal of Chemical Information and Computer Sciences, 2003, pp. 298-303, 43(1).
Peng, Tao, et al., "Pharmacophore Analysis of Epidermal Growth Factor Receptor Tyrosine Kinase Inhibitors", Institute of Process Engineering, Chinese Academy of Science, 2003, pp. 430-434, 61(3), Abstract.
Taylor, Edward C., et al., "Synthesis of Pyrrolo[2,3-d]pyrimidines. The Aglycone of Toycamycin", Journal of the American Chemical Society, 1965, pp. 1995-2003, 87(9).
Wempen, Iris, et al., "Pyrimidines. II. Synthesis of 6-Fluorouracil", Journal of Medicinal Chemistry, 1964, pp. 207-209, 7(2).

Caravatti, G., et al., "Pyrrolo[2,3-d]pyrimidine and Pyrazolo[3,4-d]pyrimidine Derivatives as Selective Inhibitors of the EFG Receptor Tyrosine Kinase", ACS Symposium Series, Aug. 24, 2001, pp. 231-244, Chapter 14, vol. 796.
Zahran, M. A., et al., "Synthesis and Reactions of 2-Deoxy-β-D-ribofuranosyl Derivatives of 3-Aryl-4H-pyrrolo[2,3-d]pyrimidin-4-imines", Monatshefte fur Chemie, 1995, pp. 1271-1277, 126(11).
Peng, Tao, et al., "Flexible Atom Receptor Model Study on Tyrosine Kinase Inhibitors", Acta Chim. Sinica, 2003, pp. 29-33, 61(1), Abstract.
Taiwan Patent Application No. 102122705 Office Action including Search Report dated Jul. 3, 1014, 12 pages.
Saleh, T., et al., "Ultrasound assisted one-pot, three-components synthesis of pyrimido[1,2-a]benzimidazoles and pyrazolol[3,4-b]pyridines: A new access via phenylsulfone synthon", Ultrasonics Sonochemistry, 2012, pp. 49-55,19(1).
Quiroga, J., et al., "A hydrogen-bonded dimer in 6-(4-bromophenyl)-3-methyl-1-phenyl-4,5-dihydro-1H-pyrazolo[3,4-b]pyridine and a chain of rings built from n-H . . . N and C-H . . . π(pyridine)hydrogen bonds in 3-(4-nitrophenyl)-4-phenyl-1H-pyrazolo[3,4-b]pyridine", Acta Crystallographica Sections C, Crystal Structure Communications, 2010, pp. o163-o167, 66(4).
Chebanov, V., et al., "Cyclocondensation reactions of 5-aminopyrazoles, pyruvic acids and aldehydes. Multicomponent approaches to pyrazolopyridines and related products", Tetrahedron, 2007, pp. 1229-1242, 63(5).
Singh, S.P., et al., "Synthesis of Some Novel Fluorinated Pyrazolo[3,4-b]Pyridines", Synthetic Communications, 2004, pp. 4359-4367, 34(23).
Quiroga, J., et al., "Synthesis and Structural Analysis of 5-Cyanoldihydropyrazolo[3,4-b]pyridines", Journal of Heterocyclic Chemistry, Jan.-Feb. 2001, pp. 53-60, 38(1).
Joshi, K., et al., "Synthesis of some new fluorine-containing 5-amino-1, 3-disubstituted pyrazoles and 1H-pyrazolo [3,4-b]pyridines", Journal of Heterocyclic Chemistry, Sep. 1979, pp. 1141-1145, 16(6).
Almansa, C., et al., "Versatile Three Component Coupling for the Synthesis of Pyrazolopyridines and Other Pyrido Fused Systems", Heterocycles, 2008, pp. 1695-1709, 75(7).
Quiroga, J., et al., "Three 3-aryl-5-cyanopyrazolo[3,4-b]pyridines", Acta Crystallographica, Section C: Crystal Structure Communications, 1999, iii, IUC9900168/1-3, C55(12).
International Patent Application PCT/IB2014/066563, Written Opinion and Search Report, mailed Feb. 24, 2015, 10 pages.

SUBSTITUTED PYRROLO[2,3-D]PYRIMIDINES AS LRRK2 INHIBITORS

This application is a continuation application of U.S. patent application Ser. No. 13/928,696, filed Jun. 27, 2013, which claims the benefit of U.S. Provisional Patent Application No. 61/820,828, filed on May 8, 2013 and U.S. Provisional Patent Application No. 61/666,299, filed on Jun. 29, 2012, the disclosures of which are hereby incorporated by reference in their entirety.

FIELD OF THE INVENTION

The present invention relates to small molecule inhibitors of leucine-rich repeat kinase 2 (LRRK2). This invention also relates to methods of inhibiting, in mammals, including humans, LRRK2 by administration of the small molecule LRRK2 inhibitors. The present invention also relates to the treatment of Parkinson's Disease (PD) and other neurodegenerative and/or neurological disorders in mammals, including humans with the LRRK2 inhibitors. More particularly, this invention relates to 4-(substituted-amino)-7H-pyrrolo[2,3-d]pyrimidine compounds useful for the treatment of neurodegenerative and/or neurological disorders, such as PD, Alzheimer's Disease (AD) and other LRRK2 associated disorders.

BACKGROUND OF THE INVENTION

LRRK2 is a 286 kDa active protein kinase in the ROCO protein family with a complex multidomain structure and which has structural homology to the MAP kinase kinase kinases (MAPKKK). LRRK2 has been shown to phosphorylate moeisin (at $Thr^{558}$), ezrin and radixin in vitro. LRRK2 has been found in various regions of the brain as well as in the heart, lung, spleen and kidney. Independent domains that have been established for the LRRK2 protein include an ankyrin-like (ANK) domain, a leucine-rich repeat (LRR) domain, a Ras (renin-angiotensin system) of complex (ROC) domain, a C-terminal of ROC (COR) domain, a kinase (Kinase) domain and a C-terminal WD40 domain. The ROC domain binds guanosine triphosphate (GTP) and the COR domain may be a regulator of the ROC domain's GTPase activity.

With multiple domains and both active kinase and guanosine triphosphatase (GTPase) activity, LRRK2 appears to play a complex role in multiple cellular processes. For example, LRRK2 has been associated with NFAT inhibition in the immune system and has been linked to vesicle trafficking, presynaptic homeostasis, mammalian target of rapamycin (mTOR) signaling, signaling through the receptor tyrosine kinase MET in papillary renal and thyroid carcinomas, cytoskeletal dynamics, the mitogen-activated protein kinase (MAPK) pathway, the tumor necrosis factor-α (TNF-α) pathway, the Wnt pathway and autophagy. Recent genome-wide association (GWA) genetic studies have implicated LRRK2 in the pathogenesis of various human diseases such as PD, inflammatory bowel disease (Crohn's disease), cancer and leprosy (Lewis, P. A. and Manzoni, C. Science Signaling 2012, 5(207), pe2).

Parkinson's Disease is a relatively common age-related neurodegenerative disorder resulting from the progressive loss of dopamine-producing neurons and which affects up to 4% of the population over 80. PD is characterized by both motoric and non-motoric symptoms such as tremor at rest, rigidity, akinesia and postural instability as well as non-motor symptoms such as impairment of cognition, sleep and sense of smell. Genome-wide association studies have linked LRRK2 to PD and many patients with point mutations in LRRK2 present symptoms that are indistinguishable from those with idiopathic PD. Over 20 LRRK2 mutations have been associated with autosomal-dominant parkinsonism, and the R1441C, R1441G, R1441H, Y1699C, G2019S, I2020T and N1437H missense mutations are considered to be pathogenic. The LRRK2 R1441G mutation has been shown to increase the release of proinflammatory cytokines (higher levels of TNF-α, IL-10, IL-12 and lower levels of IL-10) in microglial cells from transgenic mice and thus may result in direct toxicity to neurons (Gillardon, F. et al. Neuroscience 2012, 208, 41-48). In a murine model of neuroinflammation, induction of LRRK2 in microglia was observed and inhibition of LRRK2 kinase activity with small molecule LRRK2 inhibitors (LRRK2-IN-1 or sunitinib) or LRRK2 knockout resulted in attenuation of TNF-α secretion and nitric oxide synthase (iNOS) induction (Moehle, M. et al. J. Neurosci. 2012, 32(5), 1602-1611). The most common of the LRRK2 mutations, G2019S, is present in more than 85% of PD patients carrying LRRK2 mutations. This mutation, which is present in the LRRK2 kinase domain, leads to an enhancement of LRRK2 kinase activity. In the human brain LRRK2 expression is highest in the same regions of the brain that are impacted by PD, and LRRK2 is found in Lewy Bodies, a hallmark of PD. Recent studies indicate that a potent, selective, brain-penetrant kinase inhibitor for LRRK2 could be a therapeutic treatment for PD.

Dementia results from a wide variety of distinctive pathological processes. The most common pathological processes causing dementia are AD, cerebral amyloid angiopathy (CM) and prion-mediated diseases (see, e.g., Haan et al., Clin. Neurol. Neurosurg. 1990, 92(4):305-310; Glenner et al., J. Neurol. Sci. 1989, 94:1-28). AD is a progressive, neurodegenerative disorder characterized by memory impairment and cognitive dysfunction. AD affects nearly half of all people past the age of 85, the most rapidly growing portion of the United States population. As such, the number of AD patients in the United States is expected to increase from about 4 million to about 14 million by 2050. LRRK2 mutations have been associated with AD-like pathology, which suggests that there may be a partial overlap between the neurodegenerative pathways in both AD and PD (Zimprach, A. et al. Neuron 2004, 44, 601-607). In addition, the LRRK2 R1628P variant (COR domain) has been associated with an increased incidence of AD in a certain population, perhaps resulting from increased apoptosis and cell death (Zhao, Y. et al.; Neurobiology of Aging 2011, 32, 1990-1993.

An increased incidence of certain non-skin cancers such as renal, breast, lung and prostate cancers, as well as acute myelogenous leukemia (AML), has been reported in Parkinson's disease patients with the LRRK2 G2019S mutation (Saunders-Pullman, R. et al.; Movement Disorders, 2010, 25(15), 2536-2541). Since the G2019S mutation is associated with increased LRRK2 kinase activity, inhibition of this activity may be useful in the treatment of cancer, such as kidney, breast, lung, prostate and blood cancers.

Inflammatory bowel disease (IBD) or Crohn's disease (CD) is a complex disease and is believed to result from an inappropriate immune response to microbiota in the intestinal tract. Genome-wide association studies have recently identified LRRK2 as a major susceptibility gene for Crohn's disease, particularly the M2397T polymorphism in the WD40 domain (Liu, Z. et al. Nat. Immunol. 2011, 12, 1063-1070). In a recent study LRRK2 deficient mice were found to be more susceptible to dextran sodium sulfate induced colitis than their wild-type counterparts, indicating that LRRK2 may play a role in the pathogenesis of IBD (Liu, Z. and Lenardo, M.; Cell Research 2012, 1-3).

Both non-selective and selective small molecule compounds with LRRK2 inhibitory activity such as staurosporine, sunitinib, LRRK2-IN-1, CZC-25146, TAE684 and those in WO 2011/141756, WO 2012/028629 and WO 2012/058193 have been described. It is desirable to provide compounds which are potent and selective inhibitors of LRRK2 with a favorable pharmacokinetic profile and the ability to traverse the blood brain barrier. Accordingly, the present invention is directed to novel 4-(substituted-amino)-7H-pyrrolo[2,3-d]pyrimidine compounds with LRRK2 inhibitory activity and the use of these compounds in the treatment of diseases associated with LRRK2, such as neurodegenerative diseases, including PD.

SUMMARY OF THE INVENTION

A first embodiment of a first aspect of the present invention is a compound of Formula I

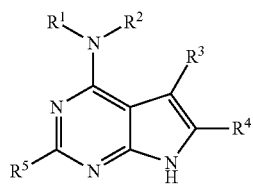

I or a pharmaceutically acceptable salt thereof wherein $R^1$ and $R^2$ are each independently hydrogen, $C_1$-$C_6$alkyl, $C_3$-$C_7$cycloalkyl, a four to seven membered heterocycloalkyl which contains one to three heteroatoms selected from N, O and S; or a five to six membered heteroaryl which contains one to four heteroatoms selected from N, O and S, wherein the $C_1$-$C_6$alkyl, $C_3$-$C_7$cycloalkyl, four to seven membered heterocycloalkyl, or five to six membered heteroaryl are optionally substituted with one to three $R^6$; or $R^1$ and $R^2$ taken together with the nitrogen to which they are attached are a four to seven membered heterocycloalkyl which optionally contains one to two additional heteroatoms selected from N, O and S, and optionally contains one double bond; a six to eleven membered heterobicycloalkyl which optionally contains one to two additional heteroatoms selected from N, O and S; or a six to twelve membered heterospirocycloalkyl which optionally contains one to two additional heteroatoms selected from N, O and S; and wherein the four to seven membered heterocycloalkyl, six to eleven membered heterobicycloalkyl or six to twelve membered heterospirocycloalkyl is optionally substituted with one to three $R^7$; $R^3$ is phenyl or a five to ten membered heteroaryl which contains one to four heteroatoms selected from N, O and S; wherein the phenyl and five to ten membered heteroaryl are optionally substituted with one to three $R^9$ and wherein the phenyl is optionally fused with a $C_5$-$C_6$cycloalkyl or a five to six membered heterocycloalkyl which contains one to three heteroatoms selected from N, O and S and which is optionally substituted with oxo; $R^4$ and $R^5$ are each independently hydrogen or $C_1$-$C_3$alkyl; $R^6$ at each occurrence is independently selected from $C_1$-$C_3$alkyl, $C_1$-$C_3$alkoxy, hydroxy, halo, —$NR^aR^b$, —$C(O)NR^aR^b$, or a four to seven membered heterocycloalkyl which contains one to three heteroatoms selected from N, O and S; $R^7$ at each occurrence is independently selected from halo, hydroxy, cyano, —$NR^aR^b$, —$C(O)NR^aR^b$, $C_1$-$C_6$alkyl, $C_1$-$C_6$alkoxy, phenyl, a five to six membered heteroaryl containing one to four heteroatoms selected from N, O and S, or two $R^7$ when attached to the same carbon and taken together can be oxo; wherein the $C_1$-$C_6$alkyl, phenyl and five to six membered heteroaryl are optionally substituted with one to three $R^8$; $R^8$ at each occurrence is independently hydroxy, halo, cyano, $C_1$-$C_3$alkoxy, $NR^aR^b$, $C_1$-$C_3$alkyl optionally substituted with one to three halo, $C_3$-$C_7$cycloalkyl, phenoxy optionally substituted with cyano, or a five to six membered heteroaryloxy containing one to four heteroatoms selected from N, O and S and which is optionally substituted with one or two halo or $C_1$-$C_3$alkyl; $R^9$ at each occurrence is independently cyano, halo, hydroxy, $C_1$-$C_3$alkyl-S—, —$CO_2H$, —$C(O)NH_2$, —$S(O)_2NH_2$, $C_1$-$C_3$alkyl optionally substituted with one to three halo or hydroxy, or $C_1$-$C_3$alkoxy optionally substituted with one to three halo or hydroxy; and $R^a$ and $R^b$ at each occurrence are each independently hydrogen, $C_1$-$C_6$alkyl, $C_3$-$C_7$cycloalkyl or —$C(O)C_1$-$C_6$alkyl.

A second embodiment of a first aspect of the present invention is the compound of the first embodiment of the first aspect wherein $R^4$ and $R^5$ are each hydrogen; or a pharmaceutically acceptable salt thereof.

A third embodiment of a first aspect of the present invention is the compound of the second embodiment of the first aspect wherein $R^1$ and $R^2$ taken together with the nitrogen to which they are attached are azetidin-1-yl, pyrrolidin-1-yl, piperidin-1-yl, morpholin-4-yl, thiomorpholin-4-yl, 6-oxa-3-aza-bicyclo[3.1.1]heptan-3-yl,

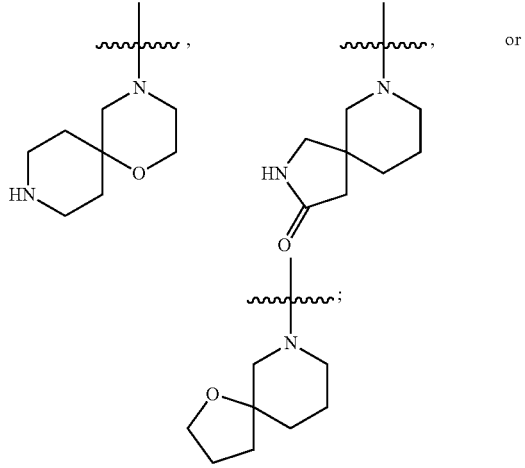

each of which is optionally substituted with one to three $R^7$; or a pharmaceutically acceptable salt thereof.

A fourth embodiment of a first aspect of the present invention is the compound of the third embodiment of the first aspect wherein $R^1$ and $R^2$ taken together with the nitrogen to which they are attached are piperidin-1-yl or morpholin-4-yl; each optionally substituted with a hydroxy, methyl or 5-methyl-1,2,4-oxadiazol-3-yl; or a pharmaceutically acceptable salt thereof.

A fifth embodiment of a first aspect of the present invention is the compound of the fourth embodiment of the first aspect wherein $R^1$ and $R^2$ taken together with the nitrogen to which they are attached are morpholin-4-yl optionally substituted with a methyl or 5-methyl-1,2,4-oxadiazol-3-yl; or a pharmaceutically acceptable salt thereof.

A sixth embodiment of a first aspect of the present invention is the compound of the second embodiment of the first aspect wherein $R^1$ and $R^2$ taken together with the nitrogen to which they are attached are methylamino, dimethylamino, diethylamino, N-methylcyclopropylamino or pyrazolylamino; each of which is optionally substituted with one to three $R^6$; or a pharmaceutically acceptable salt thereof.

An seventh embodiment of a first aspect of the present invention is the compound of the third embodiment of the first aspect wherein $R^3$ is phenyl substituted with one or two $R^9$; and each $R^9$ is independently selected from cyano, fluoro, chloro or methoxy; or a pharmaceutically acceptable salt thereof.

An eighth embodiment of a first aspect the present invention is the compound of the third embodiment of the first aspect wherein $R^3$ is pyrazolyl, isothiazolyl, or pyridinyl, each optionally substituted with one $R^9$; and $R^9$ is cyano or methyl; or a pharmaceutically acceptable salt thereof.

A ninth embodiment of a first aspect of the present invention is the compound of the first embodiment of the first aspect wherein $R^1$ and $R^2$ taken together with the nitrogen to which they are attached is selected from the group consisting of:

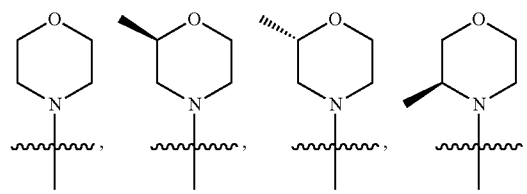

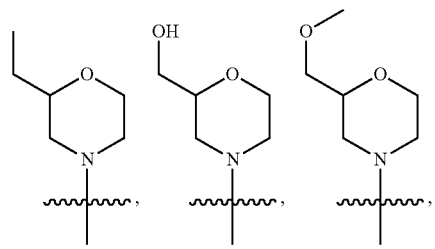

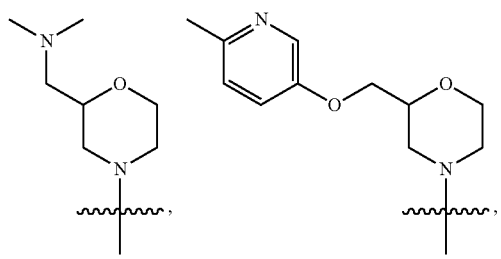

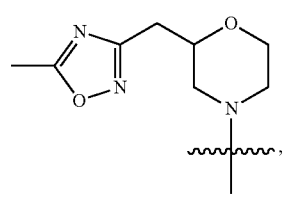

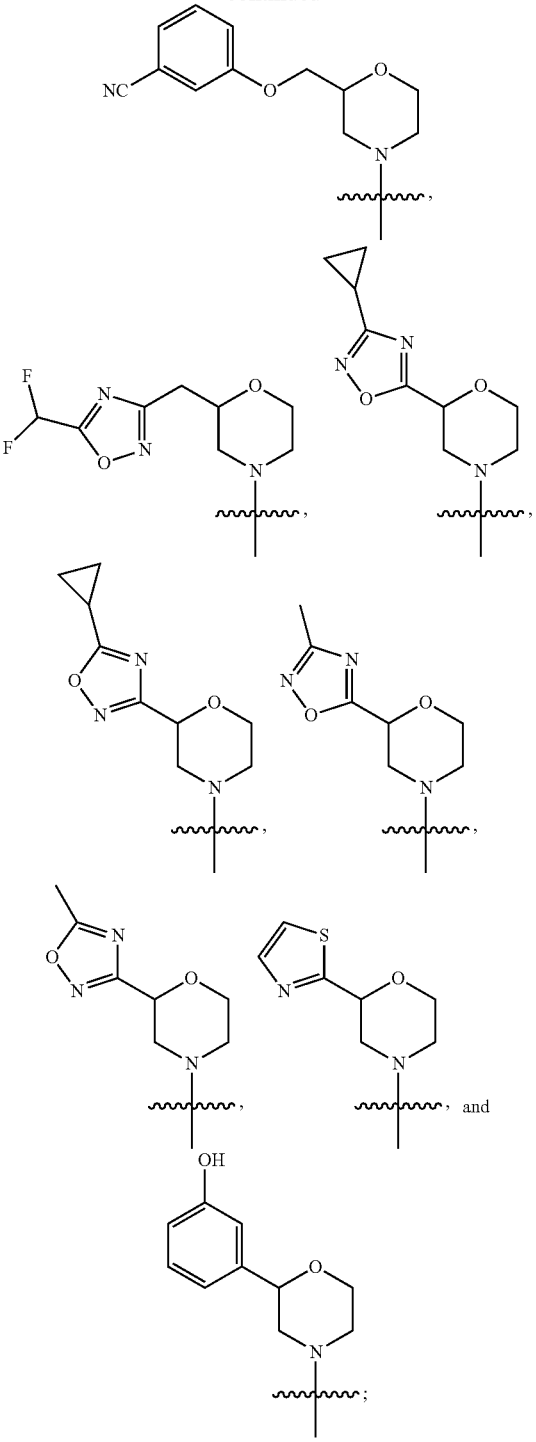

$R^3$ is 1-methylpyrazol-4-yl, 1H-pyrazol-4-yl, 2-cyanopyridin-6-yl, 3-methyl-1,2-thiazol-5-yl, 5-cyano-1-methylpyrrol-3-yl, 3-methylpyridin-5-yl, 3-cyanophenyl, 2-fluorophenyl, 3-fluorophenyl, 2,3-difluorophenyl, 2-fluoro-5-chlorophenyl, 2-fluoro-3-cyanophenyl or 2-methoxy-5-fluorophenyl; and $R^4$ and $R^5$ are each independently hydrogen or methyl; or a pharmaceutically acceptable salt thereof.

A tenth embodiment of a first aspect of the present invention is the compound of the ninth embodiment wherein $R^1$ and $R^2$ taken together with the nitrogen to which they are attached are a group selected from:

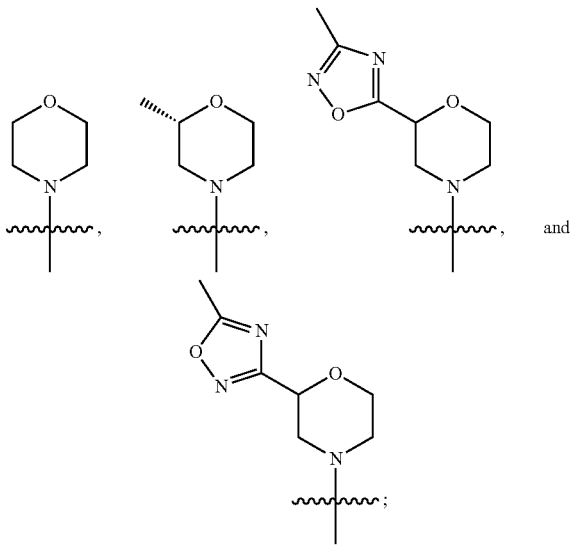

and $R^4$ and $R^5$ are each hydrogen; or a pharmaceutically acceptable salt thereof.

An eleventh embodiment of a first aspect of the present invention is the compound of the tenth embodiment of the first aspect wherein $R^1$ and $R^2$ taken together with the nitrogen to which they are attached is

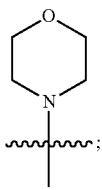 [SMILES: *N1CCOCC1]

or a pharmaceutically acceptable salt thereof.

A twelfth embodiment of a aspect of the present invention is the compound of the eleventh embodiment of the first aspect wherein $R^3$ is 3-cyanophenyl, 1-methylpyrazol-4-yl or 5-cyano-1-methylpyrrol-3-yl; or a pharmaceutically acceptable salt thereof.

A thirteenth embodiment of a first aspect of the present invention is the compound of the first embodiment of a first aspect wherein $R^1$ and $R^2$ taken together with the nitrogen to which they are attached are piperidinyl or 3-hydroxypiperidinyl; $R^3$ is 1-methylpyrazol-4-yl, 1H-pyrazol-4-yl, 2-cyanopyridin-6-yl, 3-methyl-1,2-thiazol-5-yl, 3-methylpyridin-5-yl, 3-cyanophenyl, 2-fluorophenyl, 3-fluorophenyl, 2,3-difluorophenyl, 2-fluoro-5-chlorophenyl, 2-fluoro-3-cyanophenyl or 2-methoxy-5-fluorophenyl; and $R^4$ and $R^5$ are each independently hydrogen or methyl; or a pharmaceutically acceptable salt thereof.

A fourteenth embodiment of a first aspect of the invention is a compound of the first embodiment of the first aspect selected from the group consisting of:
5-(1-methyl-1H-pyrazol-4-yl)-4-(morpholin-4-yl)-7H-pyrrolo[2,3-d]pyrimidine;
3-[6-methyl-4-(morpholin-4-yl)-7H-pyrrolo[2,3-d]pyrimidin-5-yl]benzonitrile;
6-[4-(morpholin-4-yl)-7H-pyrrolo[2,3-d]pyrimidin-5-yl]pyridine-2-carbonitrile;
3-[4-(morpholin-4-yl)-7H-pyrrolo[2,3-d]pyrimidin-5-yl]benzonitrile;
3-[4-(dimethylamino)-7H-pyrrolo[2,3-d]pyrimidin-5-yl]benzonitrile;
3-{4-[(2S)-2-methylmorpholin-4-yl]-7H-pyrrolo[2,3-d]pyrimidin-5-yl}benzonitrile;
(3-{4-[(3S)-3-methylpiperidin-1-yl]-7H-pyrrolo[2,3-d]pyrimidin-5-yl}phenyl)methanol;
4-(morpholin-4-yl)-5-(1H-pyrazol-4-yl)-7H-pyrrolo[2,3-d]pyrimidine;
3-[2-methyl-4-(morpholin-4-yl)-7H-pyrrolo[2,3-d]pyrimidin-5-yl]benzonitrile;
{3-[4-(dimethylamino)-7H-pyrrolo[2,3-d]pyrimidin-5-yl]phenyl}methanol;
3-[4-(3,3-dimethylpiperidin-1-yl)-7H-pyrrolo[2,3-d]pyrimidin-5-yl]benzonitrile;
3-[4-(piperidin-1-yl)-7H-pyrrolo[2,3-d]pyrimidin-5-yl]benzonitrile;
1-(5-phenyl-7H-pyrrolo[2,3-d]pyrimidin-4-yl)piperidine-3-carboxamide;
3-{4-[(3S)-3-hydroxypiperidin-1-yl]-7H-pyrrolo[2,3-d]pyrimidin-5-yl}benzonitrile;
4-[(3S)-3-methylpiperidin-1-yl]-5-phenyl-7H-pyrrolo[2,3-d]pyrimidine;
3-{4-[(3S)-3-methylpiperidin-1-yl]-7H-pyrrolo[2,3-d]pyrimidin-5-yl}benzonitrile;
4-[(3S)-3-methylpiperidin-1-yl]-5-(1-methyl-1H-pyrazol-4-yl)-7H-pyrrolo[2,3-d]pyrimidine;
5-phenyl-4-(pyrrolidin-1-yl)-7H-pyrrolo[2,3-d]pyrimidine;
[1-(5-phenyl-7H-pyrrolo[2,3-d]pyrimidin-4-yl)piperidin-4-yl]methanol;
1-{5-[3-(hydroxymethyl)phenyl]-7H-pyrrolo[2,3-d]pyrimidin-4-yl}piperidine-3-carbonitrile;
1-[5-(3-cyanophenyl)-7H-pyrrolo[2,3-d]pyrimidin-4-yl]piperidine-3-carbonitrile;
4-(3,5-cis-dimethylpiperidin-1-yl)-5-(1-methyl-1H-pyrazol-4-yl)-7H-pyrrolo[2,3-d]pyrimidine;
4-methoxy-3-[4-(3-methylpiperidin-1-yl)-7H-pyrrolo[2,3-d]pyrimidin-5-yl]benzonitrile;
3-[4-(dimethylamino)-7H-pyrrolo[2,3-d]pyrimidin-5-yl]-4-methoxybenzonitrile;
5-(5-chloro-2-methoxyphenyl)-N,N-dimethyl-7H-pyrrolo[2,3-d]pyrimidin-4-amine;
3-{4-[4-(1H-imidazol-2-yl)piperidin-1-yl]-7H-pyrrolo[2,3-d]pyrimidin-5-yl}benzonitrile;
3-{4-[3-(methoxymethyl)piperidin-1-yl]-7H-pyrrolo[2,3-d]pyrimidin-5-yl}benzonitrile;
3-[4-(9-methyl-1-oxa-4,9-diazaspiro[5.5]undec-4-yl)-7H-pyrrolo[2,3-d]pyrimidin-5-yl]benzonitrile;
3-[4-(3-methoxypiperidin-1-yl)-7H-pyrrolo[2,3-d]pyrimidin-5-yl]benzonitrile;
3-{4-[2-(methoxymethyl)morpholin-4-yl]-7H-pyrrolo[2,3-d]pyrimidin-5-yl}benzonitrile;
$N^3$-[5-(3-cyanophenyl)-7H-pyrrolo[2,3-d]pyrimidin-4-yl]-N,N-dimethyl-beta-alaninamide;
3-[4-(4,4-difluoropiperidin-1-yl)-7H-pyrrolo[2,3-d]pyrimidin-5-yl]benzonitrile;
3-[4-(4-fluoropiperidin-1-yl)-7H-pyrrolo[2,3-d]pyrimidin-5-yl]benzonitrile;
3-{4-[4-(1H-pyrazol-3-yl)piperidin-1-yl]-7H-pyrrolo[2,3-d]pyrimidin-5-yl}benzonitrile;
3-{4-[(3S)-3-fluoropyrrolidin-1-yl]-7H-pyrrolo[2,3-d]pyrimidin-5-yl}benzonitrile;
3-{4-[2-(1H-pyrazol-3-yl)morpholin-4-yl]-7H-pyrrolo[2,3-d]pyrimidin-5-yl}benzonitrile;

3-{4-[3-(1H-pyrazol-3-yl)piperidin-1-yl]-7H-pyrrolo[2,3-d]pyrimidin-5-yl}benzonitrile;
3-{4-[3-(1H-imidazol-2-yl)piperidin-1-yl]-7H-pyrrolo[2,3-d]pyrimidin-5-yl}benzonitrile;
3-{4-[(1-methylpiperidin-3-yl)amino]-7H-pyrrolo[2,3-d]pyrimidin-5-yl}benzonitrile;
3-[4-(3-oxo-2,7-diazaspiro[4.5]dec-7-yl)-7H-pyrrolo[2,3-d]pyrimidin-5-yl]benzonitrile;
3-[4-((3R)-3-methylpiperidin-1-yl)-7H-pyrrolo[2,3-d]pyrimidin-5-yl]benzonitrile;
3-(4-{[2-(morpholin-4-yl)ethyl]amino}-7H-pyrrolo[2,3-d]pyrimidin-5-yl)benzonitrile;
3-[4-(2-oxa-7-azaspiro[4.5]dec-7-yl)-7H-pyrrolo[2,3-d]pyrimidin-5-yl]benzonitrile;
N-{1-[5-(3-cyanophenyl)-7H-pyrrolo[2,3-d]pyrimidin-4-yl]piperidin-4-yl}acetamide;
5-(1H-indazol-5-yl)-4-[(3S)-3-methylpiperidin-1-yl]-7H-pyrrolo[2,3-d]pyrimidine;
3-{4-[(3S)-3-methylpiperidin-1-yl]-7H-pyrrolo[2,3-d]pyrimidin-5-yl}benzenesulfonamide;
5-(2-fluorophenyl)-4-[(3S)-3-methylpiperidin-1-yl]-7H-pyrrolo[2,3-d]pyrimidine;
5-(1H-indazol-4-yl)-4-[(3S)-3-methylpiperidin-1-yl]-7H-pyrrolo[2,3-d]pyrimidine;
5-(6-fluoro-5-methylpyridin-3-yl)-4-[(3S)-3-methyl piperidin-1-yl]-7H-pyrrolo[2,3-d]pyrimidine;
5-{4-[(3S)-3-methylpiperidin-1-yl]-7H-pyrrolo[2,3-d]pyrimidin-5-yl}-2,3-dihydro-1H-isoindol-1-one;
4-[(3S)-3-methylpiperidin-1-yl]-5-(pyridin-3-yl)-7H-pyrrolo[2,3-d]pyrimidine;
4-[(3S)-3-methylpiperidin-1-yl]-5-(5-methylpyridin-3-yl)-7H-pyrrolo[2,3-d]pyrimidine;
4-[(3S)-3-methylpiperidin-1-yl]-5-(7H-pyrrolo[2,3-b]pyridin-5-yl)-7H-pyrrolo[2,3-d]pyrimidine;
6-{4-[(3S)-3-methylpiperidin-1-yl]-7H-pyrrolo[2,3-d]pyrimidin-5-yl}-2,3-dihydro-1H-isoindol-1-one;
4-[(3S)-3-methylpiperidin-1-yl]-5-(1H-pyrrolo[3,2-b]pyridin-6-yl)-7H-pyrrolo[2,3-d]pyrimidine;
4-{4-[(3S)-3-methylpiperidin-1-yl]-7H-pyrrolo[2,3-d]pyrimidin-5-yl}phenol;
4-{4-[(3S)-3-methylpiperidin-1-yl]-7H-pyrrolo[2,3-d]pyrimidin-5-yl}benzamide;
3-{4-[(3S)-3-methylpiperidin-1-yl]-7H-pyrrolo[2,3-d]pyrimidin-5-yl}phenol;
5-(2-chloro-5-methylpyridin-3-yl)-4-[(3S)-3-methylpiperidin-1-yl]-7H-pyrrolo[2,3-d]pyrimidine;
3-{4-[(3S)-3-methylpiperidin-1-yl]-7H-pyrrolo[2,3-d]pyrimidin-5-yl}benzamide;
3-[4-(3-fluoropiperidin-1-yl)-7H-pyrrolo[2,3-d]pyrimidin-5-yl]benzonitrile;
3-[4-(4-methylpiperidin-1-yl)-7H-pyrrolo[2,3-d]pyrimidin-5-yl]benzonitrile;
3-{4-[(3S)-3-methylpiperidin-1-yl]-7H-pyrrolo[2,3-d]pyrimidin-5-yl}benzoic acid;
3-[4-(methylamino)-7H-pyrrolo[2,3-d]pyrimidin-5-yl]benzonitrile;
3-[4-(3,5-cis-dimethylpiperidin-1-yl)-7H-pyrrolo[2,3-d]pyrimidin-5-yl]-4-methoxybenzonitrile;
4-methoxy-3-{4-[(3S)-3-methyl piperidin-1-yl]-7H-pyrrolo[2,3-d]pyrimidin-5-yl}benzonitrile;
2-fluoro-3-{4-[(3S)-3-methyl piperidin-1-yl]-7H-pyrrolo[2,3-d]pyrimidin-5-yl}benzonitrile;
N,N-dimethyl-5-phenyl-7H-pyrrolo[2,3-d]pyrimidin-4-amine;
3-[4-(dimethylamino)-7H-pyrrolo[2,3-d]pyrimidin-5-yl]-2-fluorobenzonitrile;
3-[4-(pyrrolidin-1-yl)-7H-pyrrolo[2,3-d]pyrimidin-5-yl]benzonitrile;
3-[4-((3R)-3-methyl pyrrolidin-1-yl)-7H-pyrrolo[2,3-d]pyrimidin-5-yl]benzonitrile;
3-[4-(dimethylamino)-7H-pyrrolo[2,3-d]pyrimidin-5-yl]-4-fluorobenzonitrile;
3-[4-(diethylamino)-7H-pyrrolo[2,3-d]pyrimidin-5-yl]benzonitrile;
3-{4-[(2R)-2-(methoxymethyl) morpholin-4-yl]-7H-pyrrolo[2,3-d]pyrimidin-5-yl}benzonitrile;
3-[4-(dimethylamino)-7H-pyrrolo[2,3-d]pyrimidin-5-yl]-5-fluorobenzonitrile;
3-{4-[2-(1H-pyrazol-3-yl)morpholin-4-yl]-7H-pyrrolo[2,3-d]pyrimidin-5-yl}benzonitrile;
3-[4-((3S)-3-methyl pyrrolidin-1-yl)-7H-pyrrolo[2,3-d]pyrimidin-5-yl]benzonitrile;
2-fluoro-3-[4-(morpholin-4-yl)-7H-pyrrolo[2,3-d]pyrimidin-5-yl]benzonitrile;
3-{4-[(2R)-2-methylmorpholin-4-yl]-7H-pyrrolo[2,3-d]pyrimidin-5-yl}benzonitrile;
4-fluoro-3-[4-(morpholin-4-yl)-7H-pyrrolo[2,3-d]pyrimidin-5-yl]benzonitrile;
4-(4-fluoropiperidin-1-yl)-5-(1-methyl-1H-pyrazol-4-yl)-7H-pyrrolo[2,3-d]pyrimidine;
2-[4-(morpholin-4-yl)-7H-pyrrolo[2,3-d]pyrimidin-5-yl]benzonitrile;
5-(3-chlorophenyl)-4-(morpholin-4-yl)-7H-pyrrolo[2,3-d]pyrimidine;
5-(2-fluorophenyl)-4-(morpholin-4-yl)-7H-pyrrolo[2,3-d]pyrimidine;
5-(3-fluoro-5-methoxyphenyl)-4-(morpholin-4-yl)-7H-pyrrolo[2,3-d]pyrimidine;
5-(2,5-difluorophenyl)-4-(morpholin-4-yl)-7H-pyrrolo[2,3-d]pyrimidine;
5-(2,3-difluorophenyl)-4-(morpholin-4-yl)-7H-pyrrolo[2,3-d]pyrimidine;
5-(5-chloro-2-fluorophenyl)-4-(morpholin-4-yl)-7H-pyrrolo[2,3-d]pyrimidine;
{2-fluoro-3-[4-(morpholin-4-yl)-7H-pyrrolo[2,3-d]pyrimidin-5-yl]phenyl}methanol;
5-(2,4-difluorophenyl)-4-(morpholin-4-yl)-7H-pyrrolo[2,3-d]pyrimidine;
5-(3-fluorophenyl)-4-(morpholin-4-yl)-7H-pyrrolo[2,3-d]pyrimidine;
5-(3,5-difluorophenyl)-4-(morpholin-4-yl)-7H-pyrrolo[2,3-d]pyrimidine;
4-(morpholin-4-yl)-5-phenyl-7H-pyrrolo[2,3-d]pyrimidine;
5-(5-fluoro-2-methoxyphenyl)-4-(morpholin-4-yl)-7H-pyrrolo[2,3-d]pyrimidine;
5-(2-chlorophenyl)-4-(morpholin-4-yl)-7H-pyrrolo[2,3-d]pyrimidine;
5-(5-fluoro-2-methylphenyl)-4-(morpholin-4-yl)-7H-pyrrolo[2,3-d]pyrimidine;
5-(3-methoxyphenyl)-4-(morpholin-4-yl)-7H-pyrrolo[2,3-d]pyrimidine;
{2-fluoro-5-[4-(morpholin-4-yl)-7H-pyrrolo[2,3-d]pyrimidin-5-yl]phenyl}methanol;
5-(4-fluorophenyl)-4-(morpholin-4-yl)-7H-pyrrolo[2,3-d]pyrimidine;
{3-[4-(morpholin-4-yl)-7H-pyrrolo[2,3-d]pyrimidin-5-yl]phenyl}methanol;
5-(2-methoxyphenyl)-4-(morpholin-4-yl)-7H-pyrrolo[2,3-d]pyrimidine;
5-[3-(methylsulfanyl)phenyl]-4-(morpholin-4-yl)-7H-pyrrolo[2,3-d]pyrimidine;
4-(morpholin-4-yl)-5-(pyridin-3-yl)-7H-pyrrolo[2,3-d]pyrimidine;

4-[4-(morpholin-4-yl)-7H-pyrrolo[2,3-d]pyrimidin-5-yl]isoquinoline;
5-(5-bromopyridin-3-yl)-4-(morpholin-4-yl)-7H-pyrrolo[2,3-d]pyrimidine;
5-(2-chloro-5-methylphenyl)-4-(morpholin-4-yl)-7H-pyrrolo[2,3-d]pyrimidine;
5-(3-methylphenyl)-4-(morpholin-4-yl)-7H-pyrrolo[2,3-d]pyrimidine;
5-(1-methyl-1H-pyrazol-3-yl)-4-(morpholin-4-yl)-7H-pyrrolo[2,3-d]pyrimidine;
3-[4-(4-hydroxypiperidin-1-yl)-7H-pyrrolo[2,3-d]pyrimidin-5-yl]benzonitrile;
3-{4-[2-(3-methyl-1,2,4-oxadiazol-5-yl)morpholin-4-yl]-7H-pyrrolo[2,3-d]pyrimidin-5-yl}benzonitrile;
3-methyl-5-[4-(morpholin-4-yl)-7H-pyrrolo[2,3-d]pyrimidin-5-yl]benzonitrile;
3-{4-[2-(5-methyl-1,2,4-oxadiazol-3-yl)morpholin-4-yl]-7H-pyrrolo[2,3-d]pyrimidin-5-yl}benzonitrile;
3-[4-(6-oxa-3-azabicyclo[3.1.1]hept-3-yl)-7H-pyrrolo[2,3-d]pyrimidin-5-yl]benzonitrile;
3-chloro-5-[4-(morpholin-4-yl)-7H-pyrrolo[2,3-d]pyrimidin-5-yl]benzonitrile;
4-methoxy-3-[4-(morpholin-4-yl)-7H-pyrrolo[2,3-d]pyrimidin-5-yl]benzonitrile;
5-(5-chloro-2-methoxyphenyl)-4-(morpholin-4-yl)-7H-pyrrolo[2,3-d]pyrimidine;
6-methyl-5-(1-methyl-1H-pyrazol-4-yl)-4-(morpholin-4-yl)-7H-pyrrolo[2,3-d]pyrimidine;
3-methoxy-5-[4-(morpholin-4-yl)-7H-pyrrolo[2,3-d]pyrimidin-5-yl]benzonitrile;
5-(1-methyl-1H-pyrazol-4-yl)-4-(thiomorpholin-4-yl)-7H-pyrrolo[2,3-d]pyrimidine;
1-[5-(1-methyl-1H-pyrazol-4-yl)-7H-pyrrolo[2,3-d]pyrimidin-4-yl]piperidin-3-ol;
4-[(2S)-2-methylmorpholin-4-yl]-5-(1-methyl-1H-pyrazol-4-yl)-7H-pyrrolo[2,3-d]pyrimidine;
4-[(2R)-2-methylmorpholin-4-yl]-5-(1-methyl-1H-pyrazol-4-yl)-7H-pyrrolo[2,3-d]pyrimidine;
4-(3-fluoropiperidin-1-yl)-5-(1-methyl-1H-pyrazol-4-yl)-7H-pyrrolo[2,3-d]pyrimidine;
{4-[5-(1-methyl-1H-pyrazol-4-yl)-7H-pyrrolo[2,3-d]pyrimidin-4-yl]morpholin-2-yl}methanol;
5-(1-methyl-1H-pyrazol-4-yl)-4-(2-{[(6-methylpyridin-3-yl)oxy]methyl}morpholin-4-yl)-7H-pyrrolo[2,3-d]pyrimidine;
N,N-dimethyl-5-(1-methyl-1H-pyrazol-4-yl)-7H-pyrrolo[2,3-d]pyrimidin-4-amine;
N-cyclopropyl-N-methyl-5-(1-methyl-1H-pyrazol-4-yl)-7H-pyrrolo[2,3-d]pyrimidin-4-amine;
3-[4-(3,3-difluoropiperidin-1-yl)-7H-pyrrolo[2,3-d]pyrimidin-5-yl]benzonitrile;
3-[4-(3-aminopiperidin-1-yl)-7H-pyrrolo[2,3-d]pyrimidin-5-yl]benzonitrile;
3-[4-(2-{[5-(difluoromethyl)-1,2,4-oxadiazol-3-yl]methyl}morpholin-4-yl)-7H-pyrrolo[2,3-d]pyrimidin-5-yl]benzonitrile;
3-{4-[2-(1,3-thiazol-2-yl)morpholin-4-yl]-7H-pyrrolo[2,3-d]pyrimidin-5-yl}benzonitrile;
3-[4-(4-oxopiperidin-1-yl)-7H-pyrrolo[2,3-d]pyrimidin-5-yl]benzonitrile;
3-{4-[4-fluoro-4-(hydroxymethyl)piperidin-1-yl]-7H-pyrrolo[2,3-d]pyrimidin-5-yl}benzonitrile;
3-{4-[2-(3-hydroxyphenyl)morpholin-4-yl]-7H-pyrrolo[2,3-d]pyrimidin-5-yl}benzonitrile;
3-{4-[2-(5-cyclopropyl-1,2,4-oxadiazol-3-yl)morpholin-4-yl]-7H-pyrrolo[2,3-d]pyrimidin-5-yl}benzonitrile;
3-[4-(3,3-difluoropyrrolidin-1-yl)-7H-pyrrolo[2,3-d]pyrimidin-5-yl]benzonitrile;
3-(4-{2-[(3-cyanophenoxy)methyl]morpholin-4-yl}-7H-pyrrolo[2,3-d]pyrimidin-5-yl)benzonitrile;
3-[4-(3-hydroxypiperidin-1-yl)-7H-pyrrolo[2,3-d]pyrimidin-5-yl]benzonitrile;
1-[5-(3-cyanophenyl)-7H-pyrrolo[2,3-d]pyrimidin-4-yl]piperidine-3-carboxamide;
3-[4-(2-ethylmorpholin-4-yl)-7H-pyrrolo[2,3-d]pyrimidin-5-yl]benzonitrile;
3-{4-[2-(pyrimidin-4-yl)morpholin-4-yl]-7H-pyrrolo[2,3-d]pyrimidin-5-yl}benzonitrile;
3-{4-[2-(3-cyclopropyl-1,2,4-oxadiazol-5-yl)morpholin-4-yl]-7H-pyrrolo[2,3-d]pyrimidin-5-yl}benzonitrile;
3-(4-{2-[(dimethylamino)methyl]morpholin-4-yl}-7H-pyrrolo[2,3-d]pyrimidin-5-yl)benzonitrile;
3-[4-(1H-pyrazol-4-ylamino)-7H-pyrrolo[2,3-d]pyrimidin-5-yl]benzonitrile;
3-(4-{2-[(5-methyl-1,2,4-oxadiazol-3-yl)methyl]morpholin-4-yl}-7H-pyrrolo[2,3-d]pyrimidin-5-yl)benzonitrile;
3-{4-[3-(5-methyl-1,3,4-oxadiazol-2-yl)piperidin-1-yl]-7H-pyrrolo[2,3-d]pyrimidin-5-yl}benzonitrile;
3-[4-(dimethylamino)-7H-pyrrolo[2,3-d]pyrimidin-5-yl]-5-methoxybenzonitrile;
5-(1-ethyl-1H-pyrazol-4-yl)-4-(morpholin-4-yl)-7H-pyrrolo[2,3-d]pyrimidine;
5-(5-methylpyridin-3-yl)-4-(morpholin-4-yl)-7H-pyrrolo[2,3-d]pyrimidine;
5-(5-chloropyridin-3-yl)-4-(morpholin-4-yl)-7H-pyrrolo[2,3-d]pyrimidine;
5-(6-methoxypyrazin-2-yl)-4-(morpholin-4-yl)-7H-pyrrolo[2,3-d]pyrimidine;
5-(1,3-dimethyl-1H-pyrazol-4-yl)-4-(morpholin-4-yl)-7H-pyrrolo[2,3-d]pyrimidine;
3-{4-[(3S)-3-methylmorpholin-4-yl]-7H-pyrrolo[2,3-d]pyrimidin-5-yl}benzonitrile;
2-fluoro-3-[2-methyl-4-(morpholin-4-yl)-7H-pyrrolo[2,3-d]pyrimidin-5-yl]benzonitrile;
3-{4-[(3R)-3-hydroxypiperidin-1-yl]-7H-pyrrolo[2,3-d]pyrimidin-5-yl}benzonitrile;
1-[5-(3-fluorophenyl)-7H-pyrrolo[2,3-d]pyrimidin-4-yl]piperidin-3-ol;
5-(5-fluoro-2-methoxyphenyl)-4-[2-(5-methyl-1,2,4-oxadiazol-3-yl)morpholin-4-yl]-7H-pyrrolo[2,3-d]pyrimidine;
2-fluoro-3-[4-(4-fluoropiperidin-1-yl)-7H-pyrrolo[2,3-d]pyrimidin-5-yl]benzonitrile;
4-(4-fluoropiperidin-1-yl)-5-(2-methoxyphenyl)-7H-pyrrolo[2,3-d]pyrimidine;
5-(3-fluoro-5-methoxyphenyl)-4-(4-fluoropiperidin-1-yl)-7H-pyrrolo[2,3-d]pyrimidine;
3-[4-(4,4-difluoropiperidin-1-yl)-7H-pyrrolo[2,3-d]pyrimidin-5-yl]-2-fluorobenzonitrile;
1-[5-(5-methylpyridin-3-yl)-7H-pyrrolo[2,3-d]pyrimidin-4-yl]piperidin-3-ol;
5-(5-fluoro-2-methoxyphenyl)-4-(4-fluoropiperidin-1-yl)-7H-pyrrolo[2,3-d]pyrimidine;
1-[5-(3-fluoro-5-methoxyphenyl)-7H-pyrrolo[2,3-d]pyrimidin-4-yl]piperidin-3-ol;
1-[5-(2-methoxyphenyl)-7H-pyrrolo[2,3-d]pyrimidin-4-yl]piperidin-3-ol;
2-fluoro-3-{4-[2-(3-methyl-1,2,4-oxadiazol-5-yl)morpholin-4-yl]-7H-pyrrolo[2,3-d]pyrimidin-5-yl}benzonitrile;
2-fluoro-3-{4-[2-(methoxymethyl)morpholin-4-yl]-7H-pyrrolo[2,3-d]pyrimidin-5-yl}benzonitrile;
4-(azetidin-1-yl)-5-(5-fluoro-2-methoxyphenyl)-7H-pyrrolo[2,3-d]pyrimidine;

4-[(2S)-2-methylmorpholin-4-yl]-5-(5-methylpyridin-3-yl)-7H-pyrrolo[2,3-d]pyrimidine;

5-(3-fluorophenyl)-4-(pyrrolidin-1-yl)-7H-pyrrolo[2,3-d]pyrimidine;

5-(3-fluorophenyl)-4-[2-(5-methyl-1,2,4-oxadiazol-3-yl)morpholin-4-yl]-7H-pyrrolo[2,3-d]pyrimidine;

5-(2-methoxyphenyl)-4-[(2S)-2-methylmorpholin-4-yl]-7H-pyrrolo[2,3-d]pyrimidine;

5-(2-methoxyphenyl)-N,N-dimethyl-7H-pyrrolo[2,3-d]pyrimidin-4-amine;

2-fluoro-3-{4-[(3S)-3-fluoropyrrolidin-1-yl]-7H-pyrrolo[2,3-d]pyrimidin-5-yl}benzonitrile;

4-[(3S)-3-fluoropyrrolidin-1-yl]-5-(2-methoxyphenyl)-7H-pyrrolo[2,3-d]pyrimidine;

5-(2-methoxyphenyl)-4-(pyrrolidin-1-yl)-7H-pyrrolo[2,3-d]pyrimidine;

5-(3-fluoro-5-methoxyphenyl)-N,N-dimethyl-7H-pyrrolo[2,3-d]pyrimidin-4-amine;

2-fluoro-3-[4-(3-hydroxypiperidin-1-yl)-7H-pyrrolo[2,3-d]pyrimidin-5-yl]benzonitrile;

5-(5-fluoro-2-methoxyphenyl)-4-[(2S)-2-methylmorpholin-4-yl]-7H-pyrrolo[2,3-d]pyrimidine;

2-fluoro-3-{4-[(2S)-2-methylmorpholin-4-yl]-7H-pyrrolo[2,3-d]pyrimidin-5-yl}benzonitrile;

5-(5-fluoro-2-methoxyphenyl)-4-(3-fluoropiperidin-1-yl)-7H-pyrrolo[2,3-d]pyrimidine;

5-(3-fluorophenyl)-4-[(2S)-2-methylmorpholin-4-yl]-7H-pyrrolo[2,3-d]pyrimidine;

5-(5-fluoro-2-methoxyphenyl)-N,N-dimethyl-7H-pyrrolo[2,3-d]pyrimidin-4-amine;

2-fluoro-3-[4-(pyrrolidin-1-yl)-7H-pyrrolo[2,3-d]pyrimidin-5-yl]benzonitrile;

5-(5-fluoro-2-methoxyphenyl)-4-[(3S)-3-fluoropyrrolidin-1-yl]-7H-pyrrolo[2,3-d]pyrimidine;

2-fluoro-3-{4-[2-(5-methyl-1,2,4-oxadiazol-3-yl)morpholin-4-yl]-7H-pyrrolo[2,3-d]pyrimidin-5-yl}benzonitrile;

5-(4-methyl-1,3-thiazol-2-yl)-4-(morpholin-4-yl)-7H-pyrrolo[2,3-d]pyrimidine;

5-(4-methylpyridin-2-yl)-4-(morpholin-4-yl)-7H-pyrrolo[2,3-d]pyrimidine;

5-(2-fluoro-6-methoxyphenyl)-N,N-dimethyl-7H-pyrrolo[2,3-d]pyrimidin-4-amine;

5-(2-fluoro-6-methoxyphenyl)-4-(morpholin-4-yl)-7H-pyrrolo[2,3-d]pyrimidine;

5-(2,6-difluorophenyl)-4-(morpholin-4-yl)-7H-pyrrolo[2,3-d]pyrimidine;

5-(3-methyl-1,2-thiazol-5-yl)-4-(morpholin-4-yl)-7H-pyrrolo[2,3-d]pyrimidine;

5-(2-chloro-3-fluoro-6-methoxyphenyl)-4-(morpholin-4-yl)-7H-pyrrolo[2,3-d]pyrimidine;

5-(4-methoxypyridin-3-yl)-4-(morpholin-4-yl)-7H-pyrrolo[2,3-d]pyrimidine;

3-{4-[2-((5R)-5-methyl-1,2,4-oxadiazol-3-yl)morpholin-4-yl]-7H-pyrrolo[2,3-d]pyrimidin-5-yl}benzonitrile;

3-{4-[2-((5S)-5-methyl-1,2,4-oxadiazol-3-yl)morpholin-4-yl]-7H-pyrrolo[2,3-d]pyrimidin-5-yl}benzonitrile;

3-{4-[(2S)-2-(methoxymethyl)morpholin-4-yl]-7H-pyrrolo[2,3-d]pyrimidin-5-yl}benzonitrile;

or a pharmaceutically acceptable salt thereof.

A fifteenth embodiment of a first aspect of the present invention is a compound of the first embodiment of a first aspect selected from the group consisting of:

5-(1-methyl-1H-pyrazol-4-yl)-4-(morpholin-4-yl)-7H-pyrrolo[2,3-d]pyrimidine;

3-[6-methyl-4-(morpholin-4-yl)-7H-pyrrolo[2,3-d]pyrimidin-5-yl]benzonitrile;

6-[4-(morpholin-4-yl)-7H-pyrrolo[2,3-d]pyrimidin-5-yl]pyridine-2-carbonitrile;

3-[4-(morpholin-4-yl)-7H-pyrrolo[2,3-d]pyrimidin-5-yl]benzonitrile;

3-{4-[(2S)-2-methylmorpholin-4-yl]-7H-pyrrolo[2,3-d]pyrimidin-5-yl}benzonitrile;

4-(morpholin-4-yl)-5-(1H-pyrazol-4-yl)-7H-pyrrolo[2,3-d]pyrimidine;

3-[4-(piperidin-1-yl)-7H-pyrrolo[2,3-d]pyrimidin-5-yl]benzonitrile;

2-fluoro-3-[4-(morpholin-4-yl)-7H-pyrrolo[2,3-d]pyrimidin-5-yl]benzonitrile;

5-(2-fluorophenyl)-4-(morpholin-4-yl)-7H-pyrrolo[2,3-d]pyrimidine;

5-(2,3-difluorophenyl)-4-(morpholin-4-yl)-7H-pyrrolo[2,3-d]pyrimidine;

5-(5-chloro-2-fluorophenyl)-4-(morpholin-4-yl)-7H-pyrrolo[2,3-d]pyrimidine;

5-(3-fluorophenyl)-4-(morpholin-4-yl)-7H-pyrrolo[2,3-d]pyrimidine;

5-(5-fluoro-2-methoxyphenyl)-4-(morpholin-4-yl)-7H-pyrrolo[2,3-d]pyrimidine;

1-[5-(1-methyl-1H-pyrazol-4-yl)-7H-pyrrolo[2,3-d]pyrimidin-4-yl]piperidin-3-ol;

5-(5-methylpyridin-3-yl)-4-(morpholin-4-yl)-7H-pyrrolo[2,3-d]pyrimidine;

2-fluoro-3-[4-(3-hydroxypiperidin-1-yl)-7H-pyrrolo[2,3-d]pyrimidin-5-yl]benzonitrile;

2-fluoro-3-{4-[(2S)-2-methylmorpholin-4-yl]-7H-pyrrolo[2,3-d]pyrimidin-5-yl}benzonitrile;

2-fluoro-3-{4-[2-(5-methyl-1,2,4-oxadiazol-3-yl)morpholin-4-yl]-7H-pyrrolo[2,3-d]pyrimidin-5-yl}benzonitrile;

5-(3-methyl-1,2-thiazol-5-yl)-4-(morpholin-4-yl)-7H-pyrrolo[2,3-d]pyrimidine; and 3-{4-[2-(5-methyl-1,2,4-oxadiazol-3-yl)morpholin-4-yl]-7H-pyrrolo[2,3-d]pyrimidin-5-yl}benzonitrile;

or a pharmaceutically acceptable salt thereof.

A sixteenth embodiment of a first aspect of the present invention is the compound of the first embodiment of the first aspect selected from the group consisting of:

3-[6-(difluoromethyl)-4-(morpholin-4-yl)-7H-pyrrolo[2,3-d]pyrimidin-5-yl]benzonitrile;

5-(5,6-dihydro-2H-pyran-3-yl)-4-(morpholin-4-yl)-7H-pyrrolo[2,3-d]pyrimidine;

5-(3,4-dihydro-2H-pyran-5-yl)-4-(morpholin-4-yl)-7H-pyrrolo[2,3-d]pyrimidine;

4-(morpholin-4-yl)-5-[3-(1,2,4-oxadiazol-3-yl)phenyl]-7H-pyrrolo[2,3-d]pyrimidine;

3-{4-[2-(3-methyl-1,2-oxazol-5-yl)morpholin-4-yl]-7H-pyrrolo[2,3-d]pyrimidin-5-yl}benzonitrile;

2-methyl-3-[4-(morpholin-4-yl)-7H-pyrrolo[2,3-d]pyrimidin-5-yl]benzonitrile;

4-[4-(morpholin-4-yl)-7H-pyrrolo[2,3-d]pyrimidin-5-yl]pyridin-2(1H)-one;

5-(imidazo[2,1-b][1,3]thiazol-5-yl)-4-(morpholin-4-yl)-7H-pyrrolo[2,3-d]pyrimidine;

rel-3-{4-[(3aS,6aS)-hexahydro-5H-furo[2,3-c]pyrrol-5-yl]-7H-pyrrolo[2,3-d]pyrimidin-5-yl}benzonitrile;

rel-3-{4-[(3aR,6aS)-tetrahydro-1H-furo[3,4-c]pyrrol-5(3H)-yl]-7H-pyrrolo[2,3-d]pyrimidin-5-yl}benzonitrile;

rel-3-{4-[(4aR,7aS)-hexahydrocyclopenta[b][1,4]oxazin-4(4aH)-yl]-7H-pyrrolo[2,3-d]pyrimidin-5-yl}benzonitrile;

4-[5-(3-cyanophenyl)-7H-pyrrolo[2,3-d]pyrimidin-4-yl]morpholine-2-carbonitrile;

3-[4-(2,2-dimethylmorpholin-4-yl)-7H-pyrrolo[2,3-d]pyrimidin-5-yl]benzonitrile;

5-[4-(morpholin-4-yl)-7H-pyrrolo[2,3-d]pyrimidin-5-yl]
thiophene-2-carbonitrile;
5-(imidazo[1,2-b]pyridazin-3-yl)-4-(morpholin-4-yl)-7H-
pyrrolo[2,3-d]pyrimidine;
2-fluoro-3-{4-[2(R)-(3-methyl-1,2,4-oxadiazol-5-yl)mor-
pholin-4-yl]-7H-pyrrolo[2,3-d]pyrimidin-5-
yl}benzonitrile;
2-fluoro-3-{4-[2(S)-(3-methyl-1,2,4-oxadiazol-5-yl)mor-
pholin-4-yl]-7H-pyrrolo[2,3-d]pyrimidin-5-
yl}benzonitrile;
6-[4-(morpholin-4-yl)-7H-pyrrolo[2,3-d]pyrimidin-5-yl]
pyridine-2-carboxamide;
4-(morpholin-4-yl)-5-(pyrazolo[1,5-a]pyrimidin-3-yl)-7H-
pyrrolo[2,3-d]pyrimidine;
1-methyl-4-[4-(morpholin-4-yl)-7H-pyrrolo[2,3-d]pyrimi-
din-5-yl]-1H-pyrrole-2-carbonitrile;
5-(6-methylimidazo[2,1-b][1,3]thiazol-5-yl)-4-(morpholin-
4-yl)-7H-pyrrolo[2,3-d]pyrimidine;
3-{4-[2-(1,2-oxazol-5-yl)morpholin-4-yl]-7H-pyrrolo[2,3-
d]pyrimidin-5-yl}benzonitrile;
1-methyl-4-[4-(morpholin-4-yl)-7H-pyrrolo[2,3-d]pyrimi-
din-5-yl]-1H-imidazole-2-carbonitrile;
4-[4-(morpholin-4-yl)-7H-pyrrolo[2,3-d]pyrimidin-5-yl]
thiophene-2-carbonitrile;
4-(morpholin-4-yl)-5-(pyrazolo[1,5-a]pyridin-3-yl)-7H-pyr-
rolo[2,3-d]pyrimidine;
1,5-dimethyl-4-[4-(morpholin-4-yl)-7H-pyrrolo[2,3-d]py-
rimidin-5-yl]-1H-pyrrole-2-carbonitrile;
1-methyl-3-[4-(morpholin-4-yl)-7H-pyrrolo[2,3-d]pyrimi-
din-5-yl]-1H-pyrazole-5-carbonitrile; and
3-{4-[2-(cyanomethyl)morpholin-4-yl]-7H-pyrrolo[2,3-d]
pyrimidin-5-yl}benzonitrile;
or a pharmaceutically acceptable salt thereof.

A first embodiment of a second aspect of the present invention is a pharmaceutical composition comprising a therapeutically effective amount of a compound according to any one of the first through sixteenth embodiments of the first aspect of the invention, or a pharmaceutically acceptable salt thereof together with a pharmaceutically acceptable carrier.

A first embodiment of a third aspect of the present invention is a method of treating Parkinson's disease in a patient, the method comprising administering to a patient in need thereof a therapeutically effective amount of a compound or pharmaceutically acceptable salt thereof according to any one of the first through sixteenth embodiments of the first aspect of the invention.

Another aspect of the present invention is the compound or pharmaceutically acceptable salt thereof according to any one of the first through sixteenth embodiments of the first aspect of the invention for use in the treatment of Parkinson's disease.

Another aspect of the present invention is the use of any of the preceding compounds of formula I and their compositions for inhibiting LRRK2 kinase. In a further embodiment, the compounds of formula I or compositions thereof are useful for treating a neurodegenerative disease. In yet another embodiment, the neurodegenerative disease is Parkinson's Disease.

Accordingly, the invention is also directed to methods of treating a patient (preferably a human) for diseases in which the LRRK2 kinase is involved, such as Parkinson's Disease, by administering a therapeutically effective amount of a compound of any of the embodiments of formula I, or a pharmaceutically acceptable salt thereof, and a pharmaceutically acceptable carrier.

The invention is also directed to methods of inhibiting LRRK2 kinase activity, by administering a therapeutically effective amount of a compound of formula I or a pharmaceutically acceptable salt thereof, and a pharmaceutically acceptable carrier, to a mammal or a patient in need thereof. The invention is also directed to methods of treating disorders responsive to the inhibition of LRRK2 kinase activity, such as neurological disorders (particularly Parkinson's disease), certain cancers, and certain immunological disorders (such as Crohn's disease and leprosy) by administering a therapeutically effective amount of a compound of formula I or a pharmaceutically acceptable salt thereof, and a pharmaceutically acceptable carrier, to a mammal or a patient in need thereof.

The invention is also directed to methods for treating conditions or diseases of the central nervous system and neurological disorders in which the LRRK2 kinase is involved, particularly Parkinson's disease (but also including other neurological diseases which may include migraine; epilepsy; Alzheimer's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS) premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye, tinnitus, hearing impairment and loss, and brain edema) and pediatric psychiatric disorders (including attention deficit disorder, attention deficit/hyperactive disorder, conduct disorder, and autism) in a mammal, preferably a human, comprising administering to said mammal a therapeutically effective amount of a compound of formula I or a pharmaceutically acceptable salt thereof.

The text revision of the fourth edition of the Diagnostic and Statistical Manual of Mental Disorders (DSM-IV-TR) (2000, American Psychiatric Association, Washington D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress.

Preferred methods are for treating a neurological disorder, most preferably Parkinson's disease, (but also other neurological disorders such as migraine; epilepsy; Alzheimer's disease; Niemann-Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula I or pharmaceutically acceptable salt thereof. In addition, the compounds of Formula I and pharmaceutically acceptable salts thereof may also be employed in methods of treating other disorders associated with LRRK2 such as Crohn's disease, leprosy and certain cancers, such as kidney, breast, lung, prostate, lung and blood cancer.

Also provided herein are compositions comprising a pharmaceutically effective amount of one or more of the compounds described herein and a pharmaceutically acceptable vehicle, carrier or excipient.

The present invention is also directed to the use of a combination of a LRRK2 inhibitor compound of formula I, and one or more additional pharmaceutically active agent(s).

Other features and advantages of this invention will be apparent from this specification and the appendent claims which describe the invention.

DEFINITIONS

The term "alkyl" refers to a linear or branched-chain saturated hydrocarbyl substituent (i.e., a substituent obtained from a hydrocarbon by removal of a hydrogen); in one embodiment from one to six carbon atoms (i.e., $C_1$-$C_6$alkyl); in another embodiment, from one to three carbon atoms (i.e., $C_1$-$C_3$alkyl). Examples of such substituents include methyl, ethyl, propyl (including n-propyl and isopropyl), butyl (including n-butyl, isobutyl, sec-butyl and tert-butyl), pentyl, isoamyl, hexyl and the like.

The term "alkoxy" refers to a linear or branched-chain saturated hydrocarbyl substituent (i.e., a substituent obtained from a hydrocarbon by removal of a hydrogen) which is in turn attached to an oxygen atom; in one embodiment from one to six carbon atoms (i.e., $C_1$-$C_6$alkoxy); in another embodiment, from one to three carbon atoms (i.e., $C_1$-$C_3$alkoxy). Examples of such substituents include methoxy, ethoxy, propoxy (including n-propoxy and isopropoxy), butoxy (including n-butoxy, isobutoxy, sec-butoxy and tert-butoxy), pentoxy and the like.

The term "cycloalkyl" refers to a carbocyclic substituent obtained by removing a hydrogen from a saturated carbocyclic molecule and having the specified number of carbon atoms. In one embodiment, a cycloalkyl substituent has three to seven carbon atoms (i.e., $C_3$-$C_7$cycloalkyl). Examples of cycloalkyl include cyclopropyl, cyclobutyl, cyclopentyl, cyclohexyl and cycloheptyl. The term "cycloalkyl" includes mono-, bi- and tricyclic saturated carbocycles, as well as bridged and fused ring carbocycles, as well as spiro-fused ring systems.

In some instances, the number of atoms in a cyclic substituent containing one or more heteroatoms (i.e., heteroaryl or heterocycloalkyl) is indicated by the prefix "x to y membered", wherein x is the minimum and y is the maximum number of atoms forming the cyclic moiety of the substituent. The term "heterocycloalkyl" refers to a substituent obtained by removing a hydrogen from a saturated or partially saturated ring structure containing the specified number of ring atoms, wherein at least one of the ring atoms is a heteroatom (i.e., oxygen, nitrogen, or sulfur), with the remaining ring atoms being independently selected from the group consisting of carbon, oxygen, nitrogen, and sulfur. If the heterocycloalkyl substituent is in turn substituted with a group or substituent, the group or substituent may be bound to a nitrogen heteroatom, or it may be bound to a ring carbon atom, as appropriate. As used herein, the term "heterocycloalkyl" as used herein refers to a monocyclic ring system containing the heteroatoms N, O or S as specified. Thus, for example, "four to seven membered heterocycloalkyl" refers to a heterocycloalkyl containing from 4 to 7 atoms, including one or more heteroatoms, in the cyclic moiety of the heterocycloalkyl. The term "heterobicycloalkyl" as used herein refers to a non-spiro bicyclic ring system containing the heteroatoms N, O or S as specified. Thus, for example, "six to twelve membered heterobicycloalkyl" refers to a heterobicycloalkyl containing from 6 to 12 atoms, including one or more heteroatoms, in the cyclic moieties of the heterobicycloalkyl. The term "heterospirocycloalkyl" as used herein refers to a spirocyclic ring system containing the heteroatoms N, O or S as specified. For example, "six to twelve membered heterospirocycloalkyl" means a six to twelve membered spirocyclic ring system which contains at least one heteroatom as specified.

The term "hydrogen" refers to a hydrogen substituent, and may be depicted as —H.

The term "hydroxy" or "hydroxyl" refers to —OH. Compounds bearing a carbon to which one or more hydroxy substituents are attached include, for example, alcohols, enols and phenol.

The term "halo" or "halogen" refers to fluoro (which may be depicted as —F), chloro (which may be depicted as —Cl), bromo (which may be depicted as —Br), or iodo (which may be depicted as —I).

The term "heteroaryl" refers to an aromatic ring structure containing the specified number of ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A five to six membered heteroaryl is an aromatic ring system which has five or six ring atoms with at least one of the ring atoms being N, O or S. Similarly, a five to ten membered heteroaryl is an aromatic ring system which has five to ten ring atoms with at least one of the ring atoms being N, O or S. A heteroaryl may be a single ring or 2 fused rings. Examples of heteroaryl substituents include 6-membered ring substituents such as pyridyl, pyrazyl, pyrimidinyl, and pyridazinyl; 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused rings such as quinolinyl, isoquinolinyl, cinnolinyl, quinazolinyl, and 1,4-benzoxazinyl. In a group that has a heteroaryl substituent, the ring atom of the heteroaryl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom. The term "heteroaryl" also includes pyridyl N-oxides and groups containing a pyridine N-oxide ring.

Examples of single-ring heterocycloalkyls include azetidinyl, oxetanyl, thietanyl, dihydrofuranyl, tetrahydrofuranyl, dihydrothiophenyl, tetrahydrothiophenyl, pyrrolinyl, pyrrolidinyl, imidazolinyl, imidazolidinyl, pyrazolinyl, pyrazolidinyl, thiazolinyl, isothiazolinyl, thiazolidinyl, isothiazolidinyl, dihydropyranyl, piperidinyl, morpholinyl, piperazinyl, azepinyl, oxepinyl, thiepinyl, and diazepinyl.

Examples of 2-fused-ring heteroaryls include, indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, pyrrolopyridinyl, pyrazolopyridinyl and imidazothiazolyl.

Other examples of fused-ring heteroaryls include benzo-fused heteroaryls such as indolyl, isoindolyl, indoleninyl, isoindazolyl, benzazinyl (including quinolinyl or isoquinolinyl), phthalazinyl, quinoxalinyl, quinazolinyl, benzodiazinyl (including cinnolinyl or quinazolinyl).

The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-2-yl (C-attached).

If substituents are described as being "independently selected" from a group, each instance of a substituent is selected independent of the other. Each substituent therefore may be identical to or different from the other substituent(s).

As used herein the term "formula I" or "Formula I" may be referred to as a "compound(s) of the invention." Such terms are also defined to include all forms of the compound of formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention may have asymmetric carbon atoms. The carbon-carbon bonds of the compounds of the invention may be depicted herein using a solid line (-), a solid wedge ( ━ ), or a dotted wedge ( ⋅⋅⋅⋅⋅⋅ ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The present invention comprises the tautomeric forms of compounds of the invention. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism. The various ratios of the tautomers in solid and liquid form is dependent on the various substituents on the molecule as well as the particular crystallization technique used to isolate a compound.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, β-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of formula I with certain moieties known to those skilled in the art as "pro-moieties" as described, for example, in "Design of Prodrugs" by H. Bundgaard (Elsevier, 1985).

The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorus, sulfur, fluorine and chlorine, such as $^2H$, $^3H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

DETAILED DESCRIPTION OF THE INVENTION

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating"

is defined immediately above. The term "treating" also includes adjuvant and neo-adjuvant treatment of a subject.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, (hydroxypropyl)methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3$^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a LRRK2 inhibitor compound as provided in formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of formula I or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of Formula I, depending on the disease, disorder, or condition to be treated. For example, a pharmaceutical composition for use in treating Parkinson's disease may comprise a compound of formula I or a pharmaceutically acceptable salt thereof together with another agent such as a dopamine (levodopa, either alone or with a DOPA decarboxylase inhibitor), a monoamine oxidase (MAO) inhibitor, a catechol O-methyltransferase (COMT) inhibitor or an anticholinergic agent, or any combination thereof. Particularly preferred agents to combine with the compounds of formula I for use in treating Parkinson's disease include levodopa, carbidopa, tolcapone, entacapone, selegiline, benztropine and trihexyphenidyl, or any combination thereof. Pharmaceutically active agents that may be used in combination with the compounds of formula I and compositions thereof include, without limitation:

(i) levodopa (or its methyl or ethyl ester), alone or in combination with a DOPA decarboxylase inhibitor (e.g., carbidopa (SINEMET, CARBILEV, PARCOPA), benserazide (MADOPAR), α-methyldopa, monofluoromethyldopa, difluoromethyldopa, brocresine, or m-hydroxybenzylhydrazine);

(ii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(iii) catechol O-methyltransferase (COMT) inhibitors, such as nitecapone, tolcapone (TASMAR), entacapone (COMTAN), and tropolone;

(iv) monoamine oxidase (MAO) inhibitors, such as selegiline (EMSAM), selegiline hydrochloride (I-deprenyl, ELDEPRYL, ZELAPAR), dimethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(v) acetylcholinesterase inhibitors, such as donepezil hydrochloride (ARICEPT®, MEMAC), physostigmine salicylate (ANTILIRIUM®), physostigmine sulfate (ESERINE), ganstigmine, rivastigmine (EXELON®), ladostigil, NP-0361, galantamine hydrobromide (RAZADYNE®, REMINYL®, NIVALIN®), tacrine (COGNEX®), tolserine, memoquin, huperzine A (HUP-A; Neuro-Hitech), phenserine, bisnorcymserine (also known as BNC), and INM-176;

(vi) amyloid-β (or fragments thereof), such as $A\beta_{1-15}$ conjugated to pan HLA DR-binding epitope (PADRE®), ACC-001 (Elan/Wyeth), and Affitope;

(vii) antibodies to amyloid-β (or fragments thereof), such as ponezumab, solanezumab, bapineuzumab (also known as AAB-001), AAB-002 (Wyeth/Elan), Gantenerumab, intravenous Ig (GAMMAGARD®), LY2062430 (humanized m266; Lilly), and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(viii) amyloid-lowering or -inhibiting agents (including those that reduce amyloid production, accumulation and fibrillization) such as eprodisate, celecoxib, lovastatin, anapsos, colostrinin, pioglitazone, clioquinol (also known as PBT1), PBT2 (Prana Biotechnology), flurbiprofen (ANSAID®, FROBEN®) and its R-enantiomer tarenflurbil (FLURIZAN®), nitroflurbiprofen, fenoprofen (FENOPRON, NALFON®), ibuprofen (ADVIL®, MOTRIN®, NUROFEN®), ibuprofen lysinate, meclofenamic acid, meclofenamate sodium (MECLOMEN®), indomethacin (INDOCIN®), diclofenac sodium (VOLTAREN®), diclofenac potassium, sulindac (CLINORIL®), sulindac sulfide, diflunisal (DOLOBID®), naproxen (NAPROSYN®), naproxen sodium (ANAPROX®, ALEVE®), insulin-degrading enzyme (also known as insulysin), the gingko biloba extract EGb-761 (ROKAN®, TEBONIN®), tramiprosate (CEREBRIL®, ALZHEMED®), KIACTA®), neprilysin (also known as neutral endopeptidase (NEP)), scyllo-inositol (also known as scyllitol), atorvastatin (LIPITOR®), simvastatin (ZOCOR®), ibutamoren mesylate, BACE inhibitors such as LY450139 (Lilly), BMS-782450, GSK-188909; gamma secretase modulators and inhibitors such as ELND-007, BMS-708163 (Avagacestat), and DSP8658 (Dainippon); and RAGE (receptor for advanced glycation end-products) inhibitors, such as TTP488 (Transtech) and TTP4000 (Transtech), and those disclosed in U.S. Pat. No. 7,285,293, including PTI-777;

(ix) alpha-adrenergic receptor agonists, and beta-adrenergic receptor blocking agents (beta blockers); anticholinergics; anticonvulsants; antipsychotics; calcium channel blockers; catechol O-methyltransferase (COMT) inhibitors; central nervous system stimulants; corticosteroids; dopamine receptor agonists and antagonists; dopamine reuptake inhibitors; gamma-aminobutyric acid (GABA) receptor agonists; immunosuppressants; interferons; muscarinic receptor agonists; neuroprotective drugs; nicotinic receptor agonists; norepinephrine (noradrenaline) reuptake inhibitors; quinolines; and trophic factors;

(x) histamine 3 (H3) antagonists, such as PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600;

(xi) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), methadone, (DOLOPHINE), neramexane, perzinfotel, phencyclidine, tianeptine (STABLON), dizocilpine (also known as MK-801), ibogaine, voacangine, tiletamine, riluzole (RILUTEK), aptiganel (CERESTAT), gavestinel, and remacimide;

(xii) phosphodiesterase (PDE) inhibitors, including (a) PDE1 inhibitors; (b) PDE2 inhibitors; (c) PDE3 inhibitors; (d) PDE4 inhibitors; (e) PDE5 inhibitors; (f) PDE9 inhibitors (e.g., PF-04447943, BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)); and (g) PDE10 inhibitors such as 2-({4-[1-methyl-4-(pyridin-4-yl)-1H-pyrazol-3-yl]phenoxy}methyl)quinoline (PF-2545920);

(xiii) serotonin (5-hydroxytryptamine) 1A ($5-HT_{1A}$) receptor antagonists, such as spiperone, levo-pindolol, lecozotan;

(xiv) serotonin (5-hydroxytryptamine) 2C ($5-HT_{2C}$) receptor agonists, such as vabicaserin, and zicronapine; serotonin (5-hydroxytryptamine) 4 ($5-HT_4$) receptor agonists/antagonists, such as PRX-03140 (Epix) and PF-04995274;

(xv) serotonin (5-hydroxytryptamine) 3C ($5-HT_{3C}$) receptor antagonists, such as Ondansetron (Zofran);

(xvi) serotonin (5-hydroxytryptamine) 6 ($5-HT_6$) receptor antagonists, such as mianserin (TOLVON, BOLVIDON, NORVAL), methiothepin (also known as metitepine), ritanserin, SB-271046, SB-742457 (GlaxoSmithKline), Lu AE58054 (Lundbeck A/S), SAM-760, and PRX-07034 (Epix);

(xvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, caripazine and tesofensine;

(xviii) Glycine transporter-1 inhibitors such as paliflutine, ORG-25935, and ORG-26041; and mGluR modulators such as AFQ-059 and amantidine;

(xix) AMPA-type glutamate receptor modulators such as perampanel, mibampator, selurampanel, GSK-729327, and N-{(3S,4S)-4-[4-(5-cyanothiophen-2-yl)phenoxy]tetrahydrofuran-3-yl}propane-2-sulfonamide;
(xx) P450 inhibitors, such as ritonavir;
(xxi) tau therapy targets, such as davunetide;
and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

GENERAL SYNTHETIC SCHEMES

The compounds of Formula I may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in many cases, the compounds in Schemes 1 through 4 will be generated as a mixture of diastereomers and/or enantiomers; these may be separated at various stages of the synthetic schemes using conventional techniques or a combination of such techniques, such as, but not limited to, crystallization, normal-phase chromatography, reversed phase chromatography and chiral chromatography, to afford the single enantiomers of the invention.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Compounds of Formula I and intermediates thereof may be prepared according to the following reaction schemes and accompanying discussion. Unless otherwise indicated, $R^1$, $R^2$, $R^3$, $R^4$ and $R^5$ in the reaction schemes and discussions that follow are as defined hereinabove. In general, the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes may be described in the experimental section. The schemes and examples provided herein (including the corresponding description) are for illustration only, and not intended to limit the scope of the present invention.

Scheme 1 refers to preparation of compounds of Formula I. Referring to Scheme 1, compounds of Formula 1-1 and 1-2 [wherein X is a leaving group such as Br or I, and Pg is a suitable protecting group, such as 2-(trimethylsilyl)ethoxymethyl (SEM), p-toluenesulfonyl (tosyl) or tert-butoxycarbonyl (BOC)] are commercially available or can be made by methods described herein or other methods well known to those skilled in the art.

A compound of Formula 1-3 can be prepared by coupling a compound of Formula 1-1 with a compound of Formula 1-2, for example, by heating a mixture of a compound of Formula 1-1 with a compound of Formula 1-2 in the presence of a base, such as N,N-diisopropylethylamine, in an appropriate solvent, such as n-butanol, at temperatures ranging between 50° C. and 200° C. Suitable reaction times are typically from 20 minutes to 48 hours. Alternatively, a metal-catalyzed (such as using a palladium or copper catalyst) coupling may be employed to accomplish the aforesaid coupling. In this variant of the coupling, a mixture of a compound of Formula 1-1 and a compound of Formula 1-2 can be heated at temperatures ranging between 50° C. and 120° C. in the presence of a base [such as cesium carbonate], a metal catalyst [such as a palladium catalyst, e.g., palladium (II) acetate], and a ligand [such as 1,1'-binaphthalene-2,2'-diylbis(diphenylphosphane) (BINAP)] in an appropriate solvent, such as 1,4-dioxane. Suitable reaction times are typically from 30 minutes to 48 hours.

A compound of Formula 1-3 can subsequently be reacted with a compound of Formula $R^3$-M [wherein M can be $B(OH)_2$; $B(OR)_2$ wherein each R is independently H or $C_{1-6}$ alkyl, or wherein two (OR) groups, together with the B atom to which they are attached, form a 5- to 10-membered heterocyclic ring optionally substituted with one or more $C_{1-6}$ alkyl; a trialkyltin moiety; or the like] by a metal-catalyzed (such as using a palladium catalyst) coupling reaction to obtain a compound of Formula 1-4. Compounds of Formula $R^3$-M are commercially available or can be prepared by methods analogous to those described in the chemical art. Alternatively, a compound of Formula 1-3 can be converted to a compound of Formula 1-5 [wherein M is defined as above]. A compound of Formula 1-5 can then be reacted with a compound of Formula $R^3$—X [wherein X is defined as above] by a metal-catalyzed (such as using a palladium catalyst) coupling reaction to obtain a compound of Formula I. Compounds of Formula $R^3$—X are commercially available or can be prepared by methods analogous to those described in the chemical art. The type of reaction employed depends on the selection of X and M. For example, when X is halogen or triflate and the $R^3$-M reagent is a boronic acid or boronic ester, a Suzuki reaction may be used [A. Suzuki, J. Organomet. Chem. 1999, 576, 147-168; N. Miyaura and A. Suzuki, Chem. Rev. 1995, 95, 2457-2483; A. F. Littke et al., J. Am. Chem. Soc. 2000, 122, 4020-4028]. Alternatively, when X is halogen or triflate and M is trialkyltin, a Stille coupling may be employed [V. Farina et al., Organic Reactions 1997, 50, 1-652]. Where X is Br, I or triflate and M is Zn or Mg, a Negishi coupling or Kumada coupling may be used [E. Erdik, Tetrahedron 1992, 48, 9577-9648; T. Banno et al., J. Organomet. Chem. 2002, 653, 288-291]. Removal of the protecting group from compounds of Formula 1-4 under conditions well known to those skilled in the art affords compounds of Formula I.

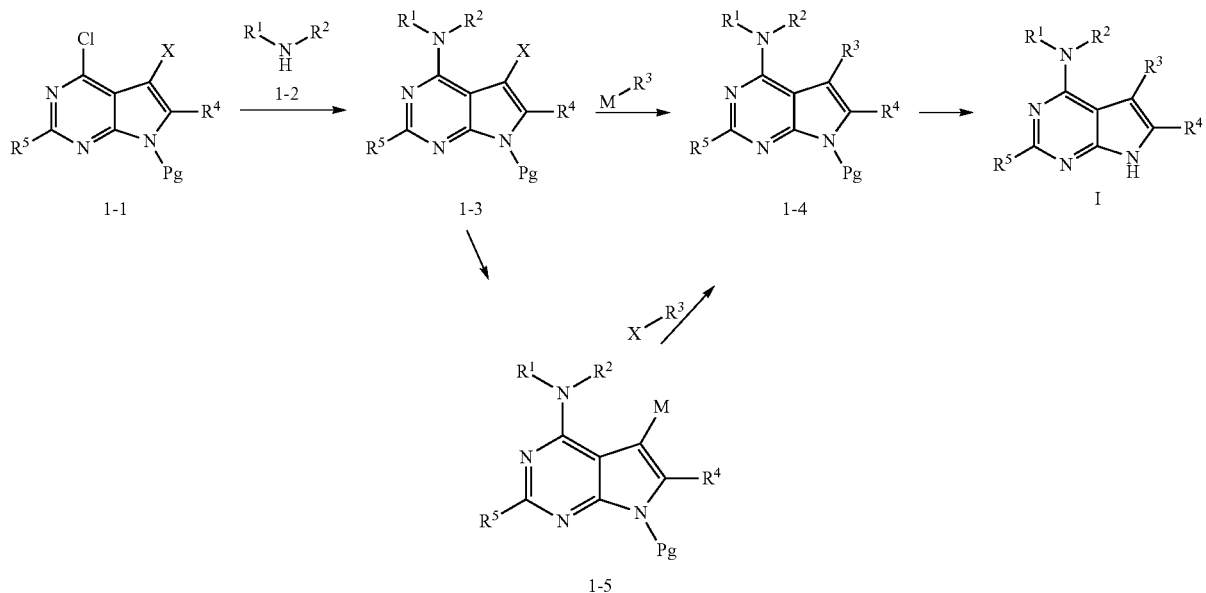

Scheme 1

Scheme 2 also refers to preparation of compounds of Formula I. Referring to Scheme 2, compounds of Formula I may be prepared utilizing analogous chemical transformations to those described in Scheme 1, but with a different ordering of steps. A compound of Formula 1-1 (as in Scheme 1) can be converted to a compound of Formula 2-1 either directly or after conversion to a compound of Formula 2-2 using methods analogous to those described in Scheme 1. A compound of Formula 2-1 may then be coupled to a compound of Formula 1-2 as in Scheme 1, to produce a compound of Formula 1-4. The coupling conditions employed may be analogous to those described for the preparation of a compound of Formula 1-3 in Scheme 1.

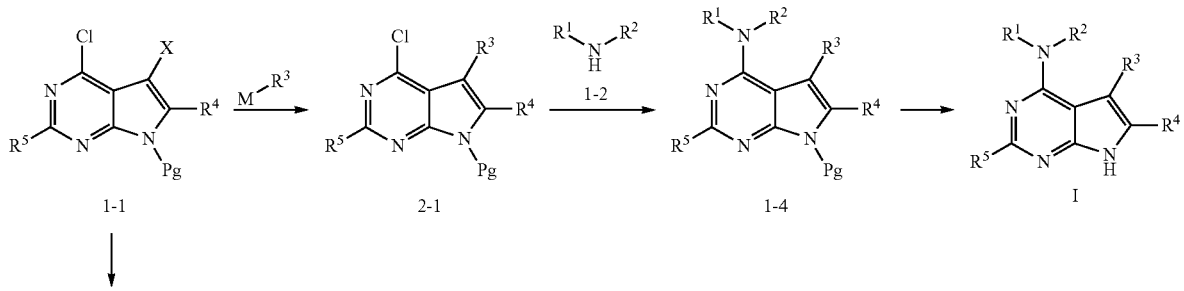

Scheme 2

-continued

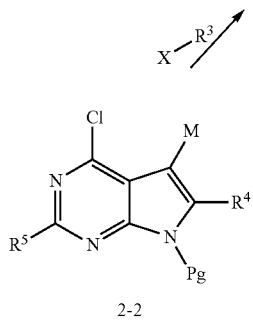

2-2

Scheme 3 refers to a preparation of a compound of Formula 1-1. Referring to Scheme 3, compounds of Formula 3-1 are commercially available or can be made by methods described herein or other methods well known to those skilled in the art. A compound of Formula 3-1 can be treated with a strong base and the intermediate can be subsequently reacted with an electrophile to obtain a compound of Formula 1-1 Examples of suitable reaction conditions for the reaction include mixing a compound of Formula 3-1 with a suitable base, such as lithium diisopropylamide, in a suitable reaction solvent such as tetrahydrofuran. This is followed by addition of an electrophile such as an alkyl iodide or bromide. Suitable temperatures for the aforesaid reaction are typically between −78° C. and 30° C. Suitable reaction times typically are from 20 minutes to 48 hours. A compound of Formula 1-1 can be converted to a compound of Formula I using chemistry described in Schemes 1 and 2.

Scheme 3

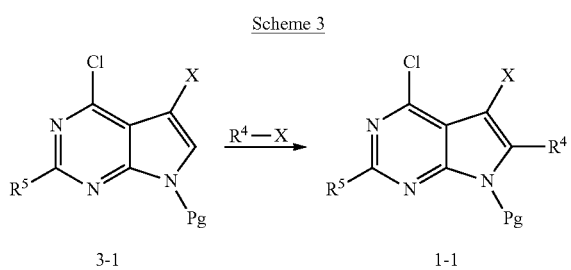

Scheme 4 refers to a preparation of a compound of Formula 4-5, wherein X is a leaving group such as Br or I. Referring to Scheme 4, compounds of Formula 4-1 (wherein each R is independently H or $C_{1-6}$ alkyl) and Formula 4-2 are commercially available or can be made by methods described herein or other methods well known to those skilled in the art.

A compound of Formula 4-3 can be prepared by condensation of a compound of Formula 4-1 with a compound of Formula 4-2, for example, through heating a compound of Formula 4-1 and a compound of Formula 4-2 in the presence of a base, such as sodium methoxide, in an appropriate solvent, such as ethanol, at temperatures ranging between 50° C. and 100° C. Suitable reaction times are typically between 1 and 24 hours. A compound of Formula 4-3 can be converted to a compound of Formula 4-4 by treatment with a chlorinating agent, such as phosphorus oxychloride, either in the presence of a suitable solvent or neat, at a temperature ranging between 70° C. and 120° C. and a reaction time of between 1 and 24 hours. A compound of Formula 4-4 may then be treated with an appropriate halogenating agent, such as N-iodosuccinimide, in a suitable solvent, such as dichloromethane, to produce a compound of Formula 4-5. Suitable reaction temperatures range from 0° C. to 50° C., and suitable reaction times are typically from 30 minutes to 24 hours. A compound of Formula 4-5 can be protected (i.e. the pyrrole ring nitrogen is protected) by methods well known in the art and then the corresponding protected compound can be converted to a compound of Formula I using chemistry described in Schemes 1, 2 and 3.

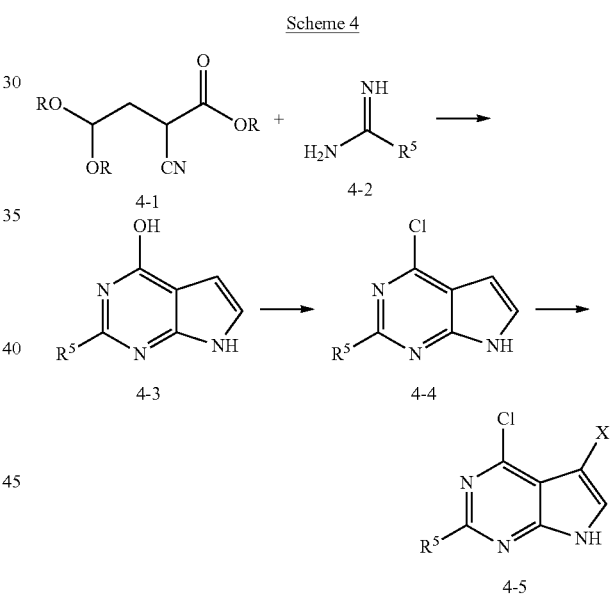

EXPERIMENTAL PROCEDURES AND WORKING EXAMPLES

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate. In some cases, Sure-Seal™ products from the Aldrich Chemical Company, Milwaukee, Wis. were used. In other cases, commercial solvents were passed through columns packed with 4A molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use.

Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluents/gradients were chosen to provide appropriate $R_f$s or retention times.

Preparation P1

5-Iodo-4-(morpholin-4-yl)-7-{[2-(trimethylsilyl)ethoxy]methyl}-7H-pyrrolo[2,3-d]pyrimidine (P1)

Step 1. Synthesis of 4-chloro-5-iodo-7-{[2-(trimethylsilyl)ethoxy]methyl}-7H-pyrrolo[2,3-d]pyrimidine (C1)

A solution of 4-chloro-5-iodo-7H-pyrrolo[2,3-d]pyrimidine (9.8 g, 35 mmol) in tetrahydrofuran (250 mL) was cooled to 0° C. and treated with sodium hydride (60% in oil, 1.54 g, 38.5 mmol) in three portions. After the reaction mixture had stirred at 0° C. for 1 hour, 2-(trimethylsilyl)ethoxymethyl chloride (6.4 g, 38 mmol) was added dropwise, and the reaction mixture was warmed to room temperature and allowed to stir for 3 hours. The reaction was quenched with saturated aqueous sodium chloride solution (250 mL), and the organic layer was dried over sodium sulfate, filtered, and concentrated in vacuo. Silica gel chromatography (Eluent: 10:1 petroleum ether/ethyl acetate) afforded the product as a white solid. Yield: 8 g, 20 mmol, 57%. $^1$H NMR (400 MHz, DMSO-$d_6$) δ 8.69 (s, 1H), 8.14 (s, 1H), 5.60 (s, 2H), 3.51 (t, J=8 Hz, 2H), 0.82 (t, J=8 Hz, 2H), −0.10 (s, 9H).

Step 2. Synthesis of 5-iodo-4-(morpholin-4-yl)-7-{[2-(trimethylsilyl)ethoxy]methyl}-7H-pyrrolo[2,3-d]pyrimidine (P1)

Morpholine (2.45 g, 28.1 mmol) and N,N-diisopropylethylamine (6.63 g, 51.3 mmol) were added to a solution of 4-chloro-5-iodo-7-{[2-(trimethylsilyl)ethoxy]methyl}-7H-pyrrolo[2,3-d]pyrimidine (C1) (10.5 g, 25.6 mmol) in n-butanol (300 mL), and the reaction mixture was heated at reflux for 18 hours, then concentrated under reduced pressure. Aqueous hydrochloric acid (0.1 M, 100 mL) was added and the resulting solid was collected by filtration, washed with water (20 mL) and dried under vacuum to provide the product as a yellow solid. Yield: 8.0 g, 17 mmol, 66%. LCMS m/z 461.2 [M+H$^+$]. $^1$H NMR (400 MHz, DMSO-$d_6$) δ 8.39 (s, 1H), 7.81 (s, 1H), 5.52 (s, 2H), 3.80-3.86 (m, 4H), 3.46-3.53 (m, 6H), 0.77-0.84 (m, 2H), −0.10 (s, 9H).

Preparation P2

4-(Morpholin-4-yl)-5-(4,4,5,5-tetramethyl-1,3,2-dioxaborolan-2-yl)-7-{[2-(trimethylsilyl)ethoxy]methyl}-7H-pyrrolo[2,3-d]pyrimidine (P2)

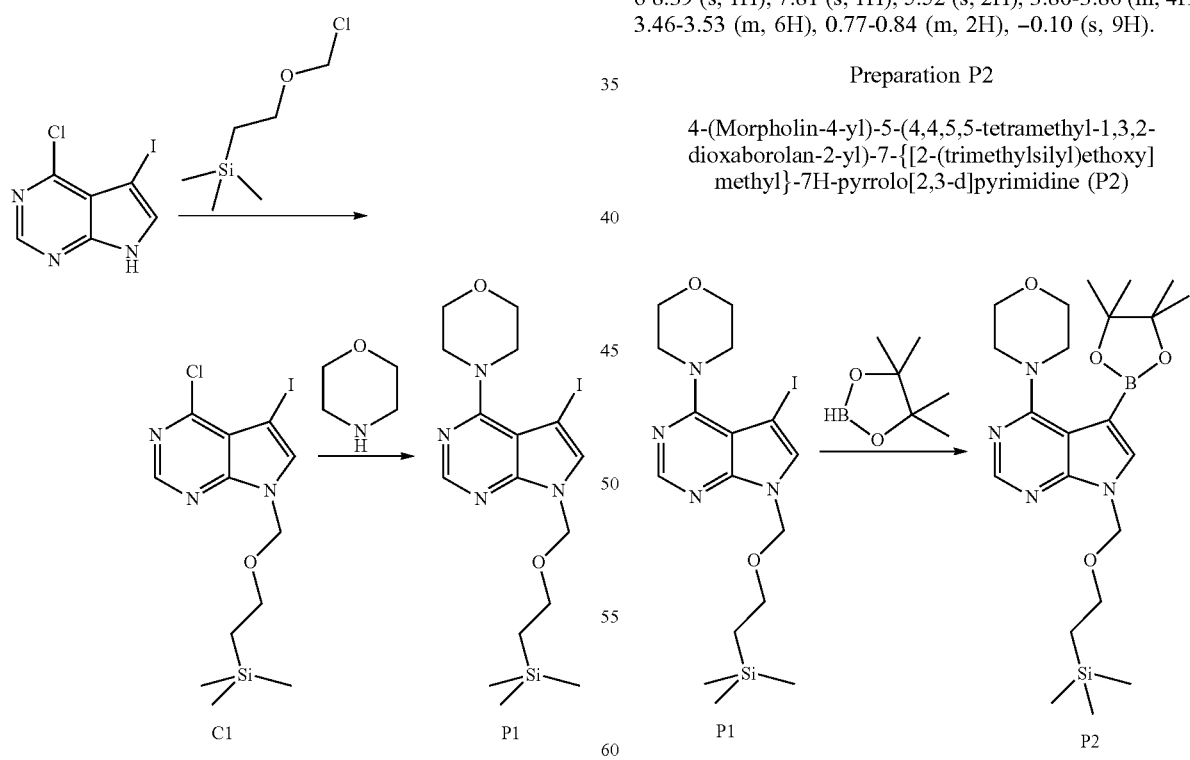

To a solution of 5-iodo-4-(morpholin-4-yl)-7-{[2-(trimethylsilyl)ethoxy]methyl}-7H-pyrrolo[2,3-d]pyrimidine (P1) (500 mg, 1.09 mmol) and 4,4,5,5-tetramethyl-1,3,2-dioxaborolane (543 mg, 4.24 mmol) in 1,4-dioxane (20 mL) was added tris(dibenzylideneacetone)dipalladium(0) (99.7 mg, 0.109 mmol), triethylamine (439 mg, 4.34 mmol) and 2-dicyclohexylphosphino-2',4',6'-triisopropylbiphenyl (XPhos, 51.8 mg, 0.109 mmol), and the reaction mixture was heated at 95° C. for 18 hours. After cooling to room temperature, the reaction mixture was diluted with water (100 mL) and extracted with ethyl acetate (3×50 mL). The combined organic layers were washed with saturated aqueous sodium chloride solution (100 mL), dried over sodium sulfate, filtered, and concentrated in vacuo. Purification via silica gel chromatography (Gradient: 0% to 30% ethyl acetate in petroleum ether) afforded the product as a yellow oil. Yield: 415 mg, 0.901 mmol, 83%. LCMS m/z 461.3 [M+H⁺]. ¹H NMR (400 MHz, CDCl₃) δ 8.45 (s, 1H), 7.73 (s, 1H), 5.59 (s, 2H), 3.87-3.93 (m, 4H), 3.68-3.74 (m, 4H), 3.49-3.56 (m, 2H), 1.35 (s, 12H), 0.87-0.93 (m, 2H), −0.06 (s, 9H).

Preparation P3

5-Bromo-4-chloro-7-[(4-methylphenyl)sulfonyl]-7H-pyrrolo[2,3-d]pyrimidine (P3)

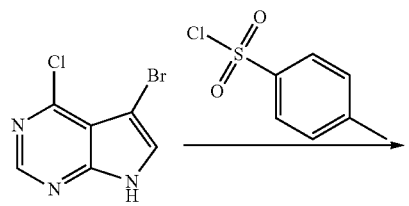

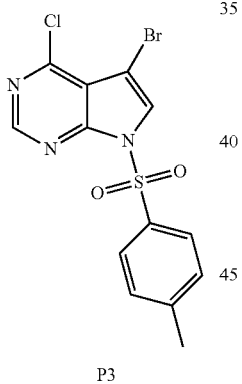

P3

4-Methylbenzenesulfonyl chloride (5.21 g, 27.3 mmol) was added to a suspension of 5-bromo-4-chloro-7H-pyrrolo[2,3-d]pyrimidine (6.34 g, 27.3 mmol) in acetone (70 mL). After addition of an aqueous solution of sodium hydroxide (1.11 g, 27.8 mmol in 15 mL water), the reaction mixture was stirred at room temperature for 16 hours. The mixture was then diluted with water (125 mL), stirred for 10 minutes, and filtered. The collected solids were washed with water to afford the product as a solid. Yield: 8.88 g, 23.0 mmol, 84%. LCMS m/z 385.9, 387.9, 389.8 [M+H⁺]. ¹H NMR (400 MHz, DMSO-d₆) δ 8.84 (s, 1H), 8.42 (s, 1H), 8.06 (br d, J=8.4 Hz, 2H), 7.46-7.51 (m, 2H), 2.37 (br s, 3H).

Preparation P4

7-[(4-Methylphenyl)sulfonyl]-4-(3-methylpiperidin-1-yl)-5-(4,4,5,5-tetramethyl-1,3,2-dioxaborolan-2-yl)-7H-pyrrolo[2,3-d]pyrimidine (P4)

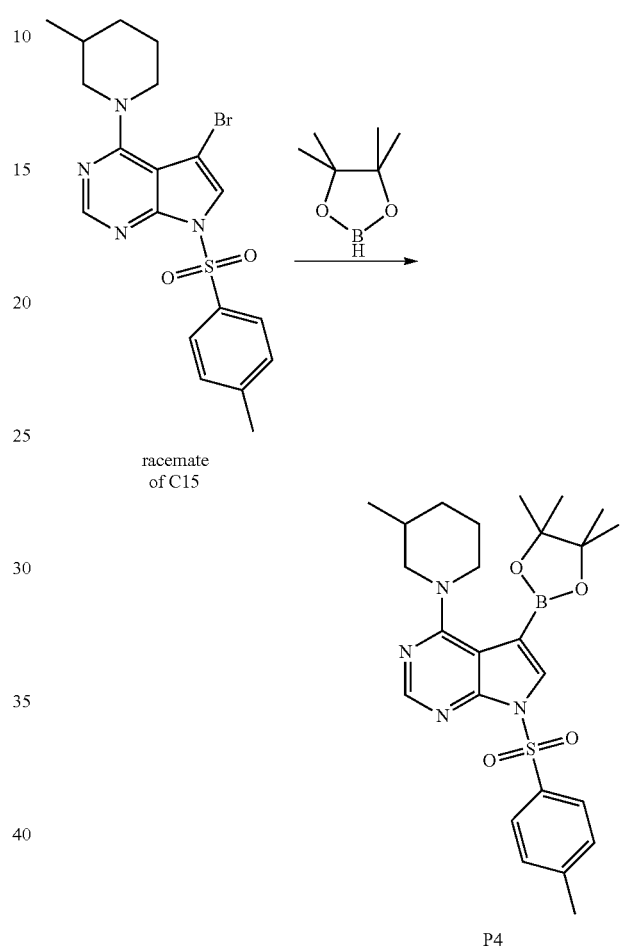

P4

5-Bromo-7-[(4-methylphenyl)sulfonyl]-4-(3-methylpiperidin-1-yl)-7H-pyrrolo[2,3-d]pyrimidine (racemic version of C15, see Example 7) (1.44 g, 3.20 mmol) was added to a solution of triethylamine (1.3 g, 13 mmol) in 1,4-dioxane (15 mL). 4,4,5,5-Tetramethyl-1,3,2-dioxaborolane (1.64 g, 12.8 mmol) was then slowly added, and the mixture was degassed by bubbling nitrogen through it for 5 minutes. 2-Dicyclohexylphosphino-2',4',6'-triisopropylbiphenyl (XPhos, 137 mg, 0.287 mmol) and tris(dibenzylideneacetone)dipalladium(0) (146 mg, 0.160 mmol) were then introduced, and the reaction mixture was heated at 95° C. for 18 hours. After cooling, the mixture was filtered through cotton and the filtrate was concentrated in vacuo. Chromatography on silica gel (Gradient: 0% to 75% ethyl acetate in heptane) afforded the product as a solid. Yield: 1.25 g, 2.52 mmol, 79%. ¹H NMR (400 MHz, CDCl₃) δ 8.41 (s, 1H), 8.10 (br d, J=8.4 Hz, 2H), 7.95 (s, 1H), 7.30 (br d, J=8.6 Hz, 2H), 4.28 (br d, J=13 Hz, 1H), 4.18-4.24 (m, 1H), 2.99 (ddd, J=13, 11, 4 Hz, 1H), 2.70 (dd, J=12.9, 10.9 Hz, 1H), 2.40 (s, 3H), 1.77-1.85 (m, 1H), 1.56-1.70 (m, 4H), 1.35 (s, 12H), 0.88 (d, J=6.6 Hz, 3H).

Preparation P5

5-Iodo-4-[(3S)-3-methylpiperidin-1-yl]-7-{[2-(trimethylsilyl)ethoxy]methyl}-7H-pyrrolo[2,3-d]pyrimidine (P5)

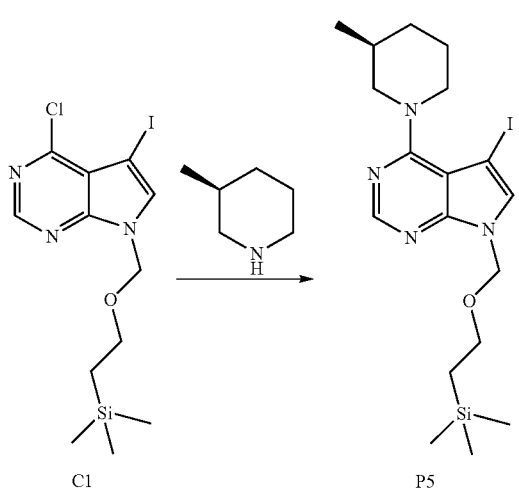

4-Chloro-5-iodo-7-{[2-(trimethylsilyl)ethoxy]methyl}-7H-pyrrolo[2,3-d]pyrimidine (C1) was converted to the product using the method described for synthesis of 5-bromo-7-[(4-methylphenyl)sulfonyl]-4-[(3S)-3-methylpiperidin-1-yl]-7H-pyrrolo[2,3-d]pyrimidine (C15) in Example 7. Yield: 7.38 g, 15.6 mmol, 80%. LCMS m/z 473.1 [M+H$^+$]. $^1$H NMR (400 MHz, CDCl$_3$) δ 8.42 (s, 1H), 7.34 (s, 1H), 5.55 (s, 2H), 4.06-4.17 (m, 2H), 3.50-3.57 (m, 2H), 2.91 (ddd, J=12.6, 11.5, 3.5 Hz, 1H), 2.58 (dd, J=12.6, 10.8 Hz, 1H), 1.95-2.07 (m, 1H), 1.76-1.95 (m, 3H), 1.11-1.23 (m, 1H), 0.96 (d, J=6.8 Hz, 3H), 0.88-0.94 (m, 2H), −0.04 (s, 9H).

Preparation P6

4-Chloro-5-(1-methyl-1H-pyrazol-4-yl)-7H-pyrrolo[2,3-d]pyrimidine (P6)

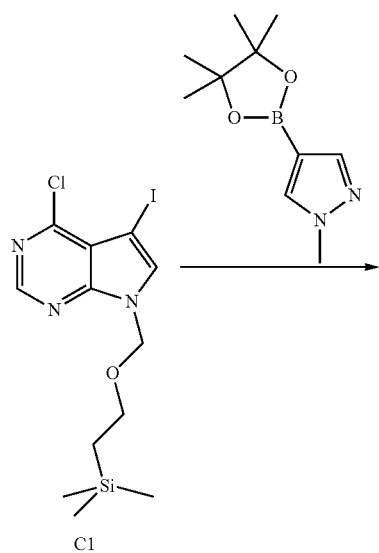

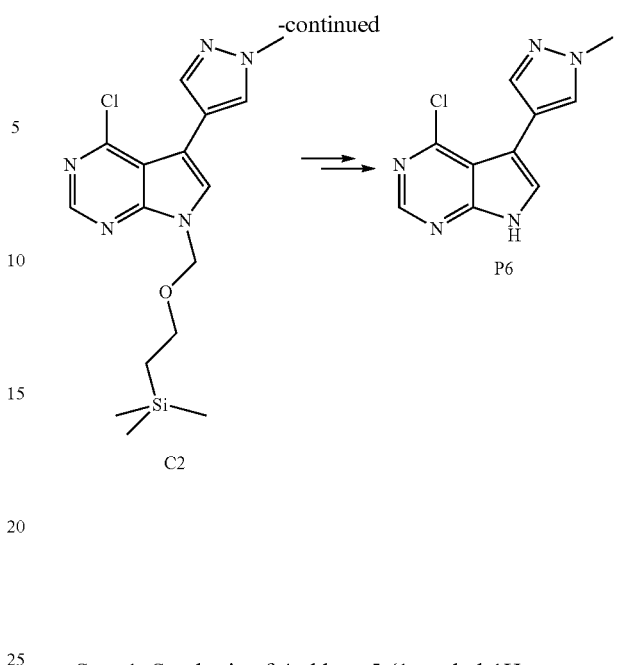

Step 1. Synthesis of 4-chloro-5-(1-methyl-1H-pyrazol-4-yl)-7-{[2-(trimethylsilyl)ethoxy]methyl}-7H-pyrrolo[2,3-d]pyrimidine (C2)

To a solution of 4-chloro-5-iodo-7-{[2-(trimethylsilyl)ethoxy]methyl}-7H-pyrrolo[2,3-d]pyrimidine (C1) (4.1 g, 10 mmol), 1-methyl-4-(4,4,5,5-tetramethyl-1,3,2-dioxaborolan-2-yl)-1H-pyrazole (2.1 g, 10 mmol) and potassium carbonate (2.8 g, 20 mmol) in aqueous 1,4-dioxane was added dichlorobis(triphenylphosphine)palladium(II) (350 mg, 0.50 mmol). The reaction mixture was degassed and purged with nitrogen; this procedure was carried out a total of three times. After heating at reflux for 18 hours, the reaction mixture was cooled to room temperature, diluted with water (200 mL) and extracted with ethyl acetate (3×200 mL). The combined organic layers were washed with saturated aqueous sodium chloride solution (500 mL), dried over sodium sulfate, filtered, and concentrated in vacuo. Purification by chromatography on silica gel (Gradient: 0% to 10% ethyl acetate in petroleum ether) afforded the product as a white solid. Yield: 2.0 g, 5.5 mmol, 55%. $^1$H NMR (400 MHz, CDCl$_3$) δ 8.66 (s, 1H), 7.68 (d, J=0.5 Hz, 1H), 7.62 (br s, 1H), 7.36 (s, 1H), 5.68 (s, 2H), 3.99 (s, 3H), 3.54-3.59 (m, 2H), 0.91-0.97 (m, 2H), −0.03 (s, 9H).

Step 2. Synthesis of 4-chloro-5-(1-methyl-1H-pyrazol-4-yl)-7H-pyrrolo[2,3-d]pyrimidine (P6)

4-Chloro-5-(1-methyl-1H-pyrazol-4-yl)-7-{[2-(trimethylsilyl)ethoxy]methyl}-7H-pyrrolo[2,3-d]pyrimidine (C2) was converted to the product using the method described for synthesis of 3-[6-methyl-4-(morpholin-4-yl)-7H-pyrrolo[2,3-d]pyrimidin-5-yl]benzonitrile (2) in Example 2. In this case the product, obtained as a yellow solid, was purified by recrystallization from ethyl acetate, rather than via preparative HPLC. Yield: 1.0 g, 4.3 mmol, 43% over two steps. LCMS m/z 234.0 [M+H$^+$]. $^1$H NMR (400 MHz, DMSO-d$_6$) δ 12.66 (br s, 1H), 8.58 (s, 1H), 7.91 (s, 1H), 7.69 (d, J=2.5 Hz, 1H), 7.63 (d, J=0.7 Hz, 1H), 3.89 (s, 3H).

Preparation P7

N,N-Dimethyl-5-(4,4,5,5-tetramethyl-1,3,2-dioxaborolan-2-yl)-7-{[2-(trimethylsilyl)ethoxy]methyl}-7H-pyrrolo[2,3-d]pyrimidin-4-amine (P7)

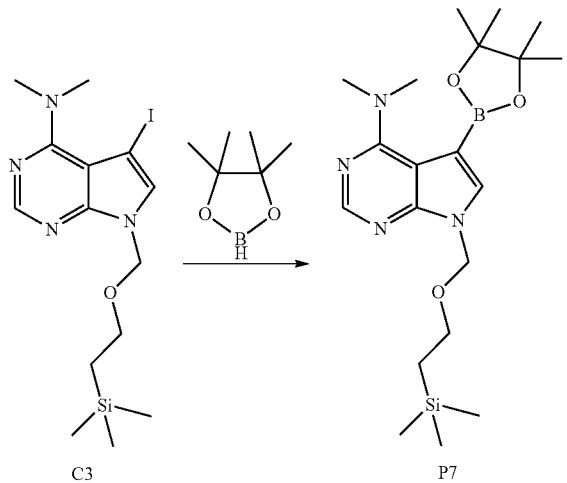

5-Iodo-N,N-dimethyl-7-{[2-(trimethylsilyl)ethoxy]methyl}-7H-pyrrolo[2,3-d]pyrimidin-4-amine [C3, prepared from 4-chloro-5-iodo-7-{[2-(trimethylsilyl)ethoxy]methyl}-7H-pyrrolo[2,3-d]pyrimidine (C1) according to the method described for synthesis of 3-[4-(dimethylamino)-7H-pyrrolo[2,3-d]pyrimidin-5-yl]benzonitrile (5) in Example 5] was converted to the product according to the method described for synthesis of 4-(morpholin-4-yl)-5-(4,4,5,5-tetramethyl-1,3,2-dioxaborolan-2-yl)-7-{[2-(trimethylsilyl)ethoxy]methyl}-7H-pyrrolo[2,3-d]pyrimidine (P2) in Preparation P2. The product was obtained as a yellow solid. Yield: 342 mg, 0.817 mmol, 69%. LCMS m/z 419.3 [M+H⁺]. ¹H NMR (400 MHz, CDCl₃) δ 8.37 (s, 1H), 7.57 (s, 1H), 5.56 (s, 2H), 3.49-3.57 (m, 2H), 3.25 (s, 6H), 1.36 (s, 12H), 0.86-0.94 (m, 2H), −0.06 (s, 9H).

EXAMPLE 1

5-(1-Methyl-1H-pyrazol-4-yl)-4-(morpholin-4-yl)-7H-pyrrolo[2,3-d]pyrimidine (1)

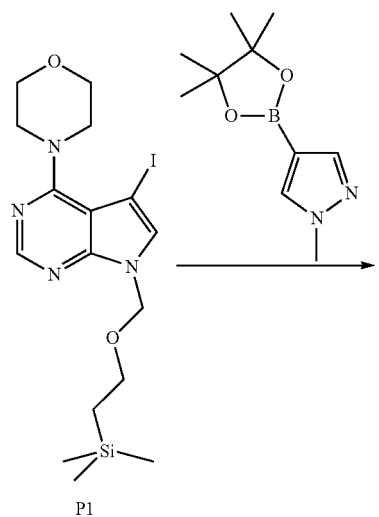

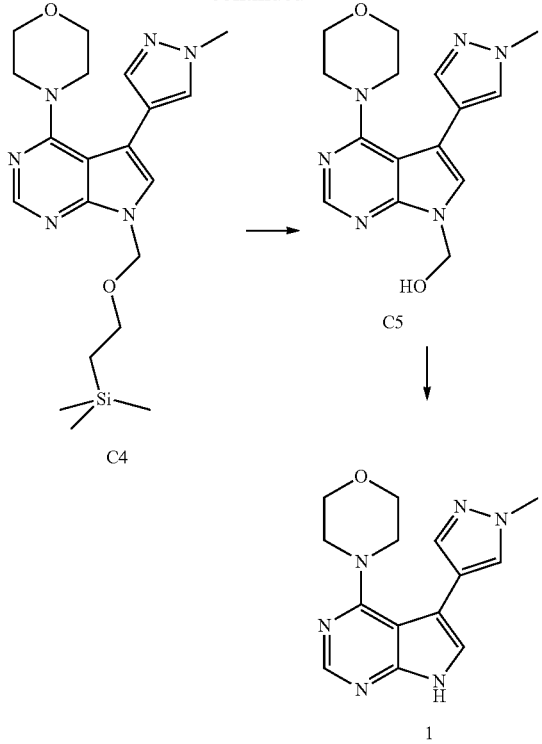

Step 1. Synthesis of 5-(1-methyl-1H-pyrazol-4-yl)-4-(morpholin-4-yl)-7-{[2-(trimethylsilyl)ethoxy]methyl}-7H-pyrrolo[2,3-d]pyrimidine (C4)

To a solution of 5-iodo-4-(morpholin-4-yl)-7-{[2-(trimethylsilyl)ethoxy]methyl}-7H-pyrrolo[2,3-d]pyrimidine (P1) (500 mg, 1.1 mmol) and 1-methyl-4-(4,4,5,5-tetramethyl-1,3,2-dioxaborolan-2-yl)-1H-pyrazole (272 mg, 1.31 mmol) in a mixture of ethanol and water (4:1, 10 mL) were added dichlorobis(triphenylphosphine)palladium(II) (41 mg, 58 μmol) and potassium carbonate (447 mg, 3.23 mmol). The reaction mixture was degassed and purged with nitrogen; this procedure was carried out a total of three times. It was then heated at 100° C. for 18 hours. After concentration in vacuo, the residue was purified via chromatography on silica gel (Eluent: 1:1 ethyl acetate/petroleum ether) to provide the product as a yellow solid. Yield: 200 mg, 0.48 mmol, 44%. ¹H NMR (400 MHz, DMSO-d₆) δ 8.39 (s, 1H), 7.86 (s, 1H), 7.59 (s, 1H), 7.52 (s, 1H), 5.57 (s, 2H), 3.90 (s, 3H), 3.50-3.58 (m, 6H), 3.20-3.27 (m, 4H), 0.83 (dd, J=8.0, 7.9 Hz, 2H), −0.09 (s, 9H).

Step 2. Synthesis of [5-(1-methyl-1H-pyrazol-4-yl)-4-(morpholin-4-yl)-7H-pyrrolo[2,3-d]pyrimidin-7-yl]methanol (C5)

A solution of 5-(1-methyl-1H-pyrazol-4-yl)-4-(morpholin-4-yl)-7-{[2-(trimethylsilyl)ethoxy]methyl}-7H-pyrrolo[2,3-d]pyrimidine (C4) (200 mg, 0.48 mmol) in trifluoroacetic acid (5 mL) was stirred at room temperature for 2 hours. The reaction mixture was concentrated under reduced pressure to afford the product as a yellow oil, which was used for the next step without additional purification.

Step 3. Synthesis of 5-(1-methyl-1H-pyrazol-4-yl)-4-(morpholin-4-yl)-7H-pyrrolo[2,3-d]pyrimidine (1)

A solution of [5-(1-methyl-1H-pyrazol-4-yl)-4-(morpholin-4-yl)-7H-pyrrolo[2,3-d]pyrimidin-7-yl]methanol (C5) (material from the previous step, ≤0.48 mmol) in methanol (5 mL) was brought to a pH of >12 via addition of solid potassium carbonate. The reaction mixture was stirred for 30 minutes, filtered, and concentrated in vacuo. Purification via preparative HPLC (Column: Agella Venusil ASB C18, 5 μm; Mobile phase A: 0.225% formic acid in water; Mobile phase B: acetonitrile; Eluent: 13% B) provided the product as a yellow solid. Yield over two steps: 90 mg, 0.32 mmol, 67%. LCMS m/z 285.1 [M+H⁺]. ¹H NMR (400 MHz, DMSO-d₆) δ 12.96 (br s, 1H), 8.47 (s, 1H), 7.85 (s, 1H), 7.57 (s, 1H), 7.52 (d, J=2.5 Hz, 1H), 3.90 (s, 3H), 3.53-3.59 (m, 4H), 3.45-3.51 (m, 4H).

EXAMPLE 2

3-[6-Methyl-4-(morpholin-4-yl)-7H-pyrrolo[2,3-d]pyrimidin-5-yl]benzonitrile (2)

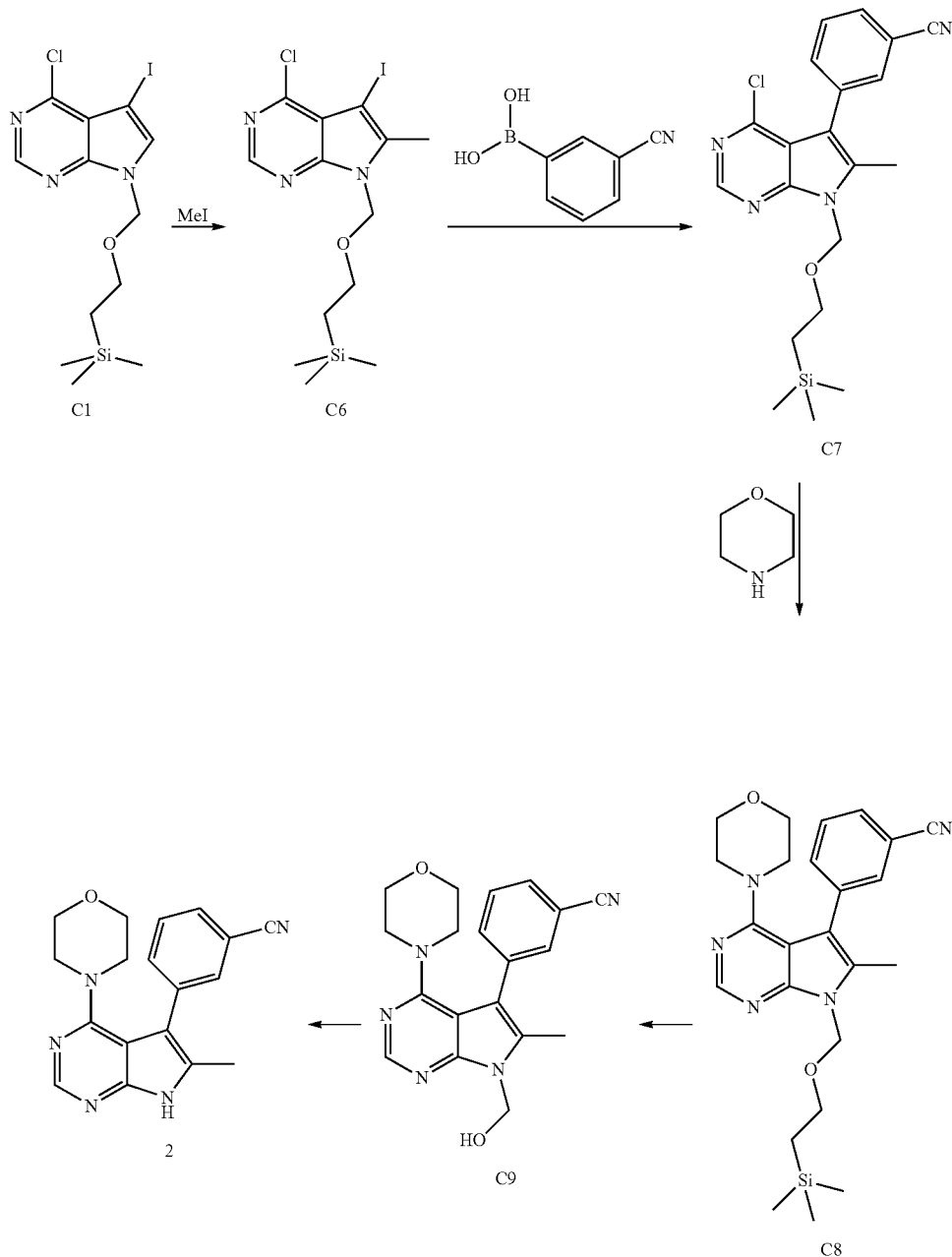

Step 1. Synthesis of 4-chloro-5-iodo-6-methyl-7-{[2-(trimethylsilyl)ethoxy]methyl}-7H-pyrrolo[2,3-d]pyrimidine (C6)

To a −78° C. solution of 4-chloro-5-iodo-7-{[2-(trimethylsilyl)ethoxy]methyl}-7H-pyrrolo[2,3-d]pyrimidine (C1) (15.0 g, 36.6 mmol) in tetrahydrofuran (500 mL) was added lithium diisopropylamide (2 M solution in heptane/tetrahydrofuran/ethylbenzene, 183 mL, 366 mmol), and the reaction mixture was stirred at −20° C. for 2 hours, then re-cooled to −78° C. Iodomethane (52.1 g, 367 mmol) was added at −78° C., and the reaction mixture was allowed to stir at −20° C. for 2 hours. Saturated aqueous ammonium chloride solution was added, and the mixture was extracted with ethyl acetate (3×500 mL). The combined organic layers were washed with water (100 mL) and with saturated aqueous sodium chloride solution (100 mL), dried over sodium sulfate, filtered, and concentrated in vacuo. Purification via chromatography on silica gel (Eluent: 10:1 petroleum ether/ethyl acetate) afforded the product as a yellow oil. Yield: 10 g, 24 mmol, 66%. LCMS m/z 424.1 [M+H$^+$]. $^1$H NMR (400 MHz, CDCl$_3$) δ 8.58 (s, 1H), 5.69 (s, 2H), 3.48-3.54 (m, 2H), 2.60 (s, 3H), 0.88-0.95 (m, 2H), −0.05 (s, 9H).

Step 2. Synthesis of 3-(4-chloro-6-methyl-7-{[2-(trimethylsilyl)ethoxy]methyl}-7H-pyrrolo[2,3-d]pyrimidin-5-yl)benzonitrile (C7)

To a solution of 4-chloro-5-iodo-6-methyl-7-{[2-(trimethylsilyl)ethoxy]methyl}-7H-pyrrolo[2,3-d]pyrimidine (C6) (300 mg, 0.71 mmol) and (3-cyanophenyl)boronic acid (104 mg, 0.708 mmol) in a mixture of 1,2-dimethoxyethane and water (5:1, 10 mL) was added potassium carbonate (193 mg, 1.40 mmol) and [1,1'-bis(diphenylphosphino)ferrocene]dichloropalladium(II) (17 mg, 23 μmol). The reaction mixture was degassed and purged with nitrogen; this procedure was carried out a total of three times. After heating at reflux for 18 hours, the reaction mixture was cooled to room temperature and extracted with ethyl acetate (3×50 mL). The combined organic layers were washed with saturated aqueous sodium chloride solution (50 mL), dried over sodium sulfate, filtered and concentrated in vacuo. Purification via silica gel chromatography (Gradient: 0% to 20% ethyl acetate in petroleum ether) afforded the product as a yellow oil. Yield: 140 mg, 0.351 mmol, 50%. LCMS m/z 399.2 [M+H$^+$].

Step 3. Synthesis of 3-[6-methyl-4-(morpholin-4-yl)-7-{[2-(trimethylsilyl)ethoxy]methyl}-7H-pyrrolo[2,3-d]pyrimidin-5-yl]benzonitrile (C8)

To a solution of 3-(4-chloro-6-methyl-7-{[2-(trimethylsilyl)ethoxy]methyl}-7H-pyrrolo[2,3-d]pyrimidin-5-yl)benzonitrile (C7) (140 mg, 0.351 mmol) in n-butanol (5 mL) was added morpholine (30.6 mg, 0.351 mmol) and N,N-diisopropylethylamine (90.9 mg, 0.703 mmol). The reaction mixture was heated at 100° C. for 18 hours, then concentrated in vacuo to provide the product as a yellow solid. Yield: 125 mg, 0.278 mmol, 79%. LCMS m/z 450.3 [M+H$^+$].

Step 4. Synthesis of 3-[7-(hydroxymethyl)-6-methyl-4-(morpholin-4-yl)-7H-pyrrolo[2,3-d]pyrimidin-5-yl]benzonitrile (C9)

A solution of 3-[6-methyl-4-(morpholin-4-yl)-7-{[2-(trimethylsilyl)ethoxy]methyl}- 7H-pyrrolo[2,3-d]pyrimidin-5-yl]benzonitrile (C8) (125 mg, 0.278 mmol) in trifluoroacetic acid (10 mL) was stirred at room temperature for 2 hours, then concentrated in vacuo to provide the product as a yellow solid (125 mg). This was used in the next step without additional purification. LCMS m/z 349.9 [M+H$^+$].

Step 5. Synthesis of 3-[6-methyl-4-(morpholin-4-yl)-7H-pyrrolo[2,3-d]pyrimidin-5-yl]benzonitrile (2)

A solution of 3-[7-(hydroxymethyl)-6-methyl-4-(morpholin-4-yl)-7H-pyrrolo[2,3-d]pyrimidin-5-yl]benzonitrile (C9) (from the previous step, 125 mg, ≤0.278 mmol) in acetonitrile (5 mL) was adjusted to a pH of >11 by addition of solid potassium carbonate. The mixture was filtered and concentrated in vacuo; purification via preparative HPLC (Column: Boston Symmetrix ODS-H, 5 μm; Mobile phase A: 0.225% formic acid in water; Mobile phase B: acetonitrile; Gradient: 19% to 39% B) afforded the product as a yellow solid. Yield: 54 mg, 0.17 mmol, 61% over two steps. LCMS m/z 319.9 [M+H$^+$]. $^1$H NMR (400 MHz, DMSO-d$_6$) δ 12.17 (br s, 1H), 8.34 (s, 1H), 7.77-7.83 (m, 2H), 7.65-7.74 (m, 2H), 3.27-3.33 (m, 4H), 2.98-3.06 (m, 4H), 2.36 (s, 3H).

EXAMPLE 3

6-[4-(Morpholin-4-yl)-7H-pyrrolo[2,3-d]pyrimidin-5-yl]pyridine-2-carbonitrile (3)

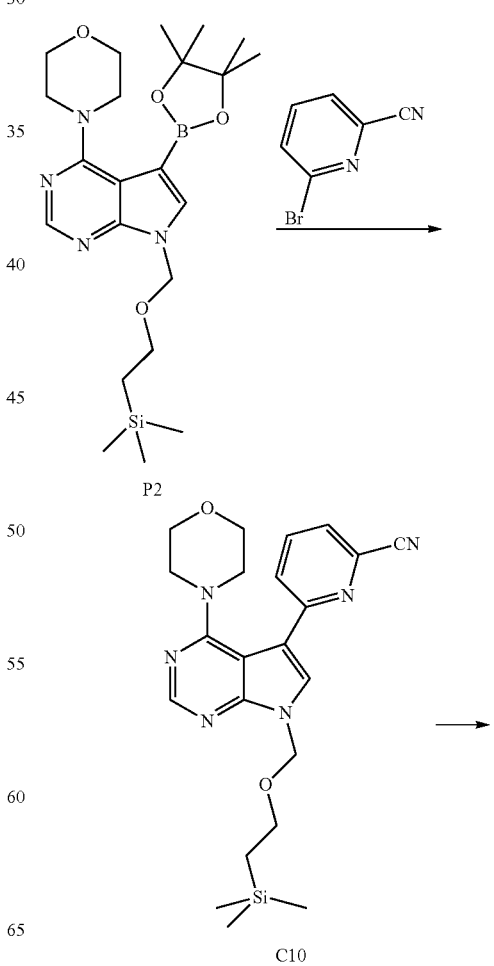

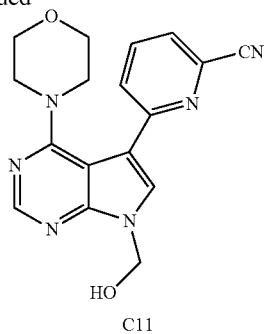

C11

↓

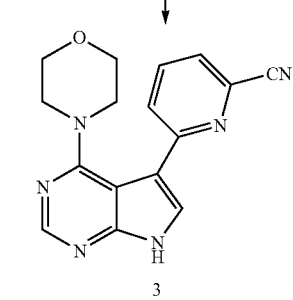

3

Step 1. Synthesis of 6-[4-(morpholin-4-yl)-7-{[2-(trimethylsilyl)ethoxy]methyl}-7H-pyrrolo[2,3-d]pyrimidin-5-yl]pyridine-2-carbonitrile (C10)

To a solution of 6-bromopyridine-2-carbonitrile (80 mg, 0.44 mmol) and 4-(morpholin-4-yl)-5-(4,4,5,5-tetramethyl-1,3,2-dioxaborolan-2-yl)-7-{[2-(trimethylsilyl)ethoxy]methyl}-7H-pyrrolo[2,3-d]pyrimidine (P2) (241 mg, 0.523 mmol) in 1,4-dioxane (2.5 mL) and water (0.5 mL) was added tetrakis(triphenylphosphine)palladium(0) (51 mg, 44 μmol) and sodium carbonate (140 mg, 1.32 mmol). The reaction mixture was heated at 120° C. under microwave irradiation for 15 minutes, then diluted with water (30 mL) and extracted with ethyl acetate (3×50 mL). The combined organic layers were washed with saturated aqueous sodium chloride solution (100 mL), dried over sodium sulfate, filtered, and concentrated in vacuo; purification via preparative thin layer chromatography (Eluent: 1:1 petroleum ether/ethyl acetate) afforded the product as a brown oil. Yield: 110 mg, 0.252 mmol, 57%. $^1$H NMR (400 MHz, CDCl$_3$) δ 8.52 (s, 1H), 7.84-7.93 (m, 2H), 7.74 (s, 1H), 7.59 (dd, J=7.0, 1.2 Hz, 1H), 5.66 (s, 2H), 3.56-3.65 (m, 6H), 3.34-3.40 (m, 4H), 0.93 (dd, J=8.3, 8.0 Hz, 2H), −0.05 (s, 9H).

Step 2. Synthesis of 6-[7-(hydroxymethyl)-4-(morpholin-4-yl)-7H-pyrrolo[2,3-d]pyrimidin-5-yl]pyridine-2-carbonitrile (C11)

A solution of 6-[4-(morpholin-4-yl)-7-{[2-(trimethylsilyl)ethoxy]methyl}-7H-pyrrolo[2,3-d]pyrimidin-5-yl]pyridine-2-carbonitrile (C10) (110 mg, 0.252 mmol) in trifluoroacetic acid (3 mL) was stirred at room temperature for 2 hours. The reaction mixture was concentrated in vacuo to provide the product as a yellow oil, which was used for the next step without additional purification.

Step 3. Synthesis of 6-[4-(morpholin-4-yl)-7H-pyrrolo[2,3-d]pyrimidin-5-yl]pyridine-2-carbonitrile (3)

A solution of 6-[7-(hydroxymethyl)-4-(morpholin-4-yl)-7H-pyrrolo[2,3-d]pyrimidin-5-yl]pyridine-2-carbonitrile (C11) (from the previous step, 85 mg, ≤0.25 mmol) in acetonitrile (3 mL) was brought to a pH of >12 via addition of solid potassium carbonate. After 30 minutes at room temperature, the reaction mixture was filtered and concentrated in vacuo. Purification via preparative HPLC (Column: Phenomenex Gemini C18, 8 μm; Mobile phase A: ammonia in water, pH 10; Mobile phase B: acetonitrile; Gradient: 10% to 50% B) afforded the product as a white solid. Yield: 15.2 mg, 49.6 μmol, 20% over two steps. LCMS m/z 307.2 [M+H$^+$]. $^1$H NMR (400 MHz, DMSO-d$_6$) δ 8.38 (s, 1H), 8.13 (dd, J=8.1, 7.7 Hz, 1H), 7.96 (br d, J=8 Hz, 1H), 7.89 (br d, J=8 Hz, 1H), 7.86 (s, 1H), 3.50-3.55 (m, 4H), 3.19-3.24 (m, 4H).

EXAMPLE 4

3-[4-(Morpholin-4-yl)-7H-pyrrolo[2,3-d]pyrimidin-5-yl]benzonitrile (4)

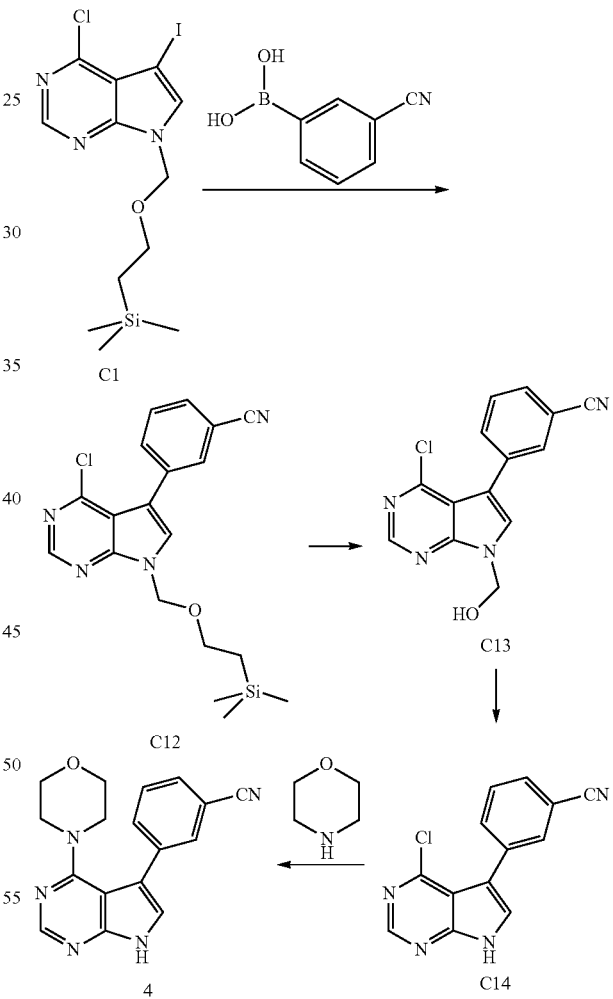

Step 1. Synthesis of 3-(4-chloro-7-{[2-(trimethylsilyl)ethoxy]methyl}-7H-pyrrolo[2,3-d]pyrimidin-5-yl)benzonitrile (C12)

To a stirred mixture of 4-chloro-5-iodo-7-{[2-(trimethylsilyl)ethoxy]methyl}-7H-pyrrolo[2,3-d]pyrimidine (C1)

(8.2 g, 20 mmol), (3-cyanophenyl)boronic acid (3.2 g, 22 mmol) and potassium carbonate (8.3 g, 60 mmol) in a mixture of 1,2-dimethoxyethane and water (4:1 ratio, 250 mL) was added [1,1'-bis(diphenylphosphino)ferrocene]dichloropalladium(II) (731 mg, 1.00 mmol). The reaction mixture was degassed and then charged with nitrogen; this procedure was carried out a total of three times. The reaction mixture was heated at reflux for 3 hours, then cooled to room temperature and diluted with saturated aqueous sodium chloride solution (100 mL). The organic layer was dried over sodium sulfate, filtered, and concentrated under reduced pressure. Purification via silica gel column chromatography (Eluent: 10:1 petroleum ether/ethyl acetate) provided the product as a yellow oil. Yield: 5.0 g, 12 mmol, 60%. $^1$H NMR (400 MHz, DMSO-$d_6$) δ 8.75 (s, 1H), 8.13 (s, 1H), 8.00-8.02 (m, 1H), 7.84-7.92 (m, 2H), 7.68 (dd, J=7.8, 7.8 Hz, 1H), 5.70 (s, 2H), 3.60 (dd, J=8.0, 8.0 Hz, 2H), 0.86 (dd, J=8.0, 8.0 Hz, 2H), −0.08 (s, 9H).

Step 2. Synthesis of 3-[4-chloro-7-(hydroxymethyl)-7H-pyrrolo[2,3-d]pyrimidin-5-yl]benzonitrile (C13)

A solution of 3-(4-chloro-7-{[2-(trimethylsilyl)ethoxy]methyl}-7H-pyrrolo[2,3-d]pyrimidin-5-yl)benzonitrile (C12) (3.8 g, 9.9 mmol) in trifluoroacetic acid (25 mL) was stirred at room temperature for 2 hours. The reaction mixture was concentrated in vacuo to afford the product (4 g, >100% mass recovery) as a yellow oil, which was used in the next step without further purification.

Step 3. Synthesis of 3-(4-chloro-7H-pyrrolo[2,3-d]pyrimidin-5-yl)benzonitrile (C14)

A solution of 3-[4-chloro-7-(hydroxymethyl)-7H-pyrrolo[2,3-d]pyrimidin-5-yl]benzonitrile (C13) (4 g from the previous step, ≤9.9 mmol) in methanol (100 mL) was adjusted to pH >12 by addition of solid potassium carbonate. Solvent was removed in vacuo and the residue was mixed with water (100 mL). The resulting solid was isolated via filtration and washed with water, providing the product as a white solid. Yield: 1.3 g, 5.1 mmol, 52% over two steps. LCMS m/z 255.0 [M+H$^+$].

Step 4. Synthesis of 3-[4-(morpholin-4-yl)-7H-pyrrolo[2,3-d]pyrimidin-5-yl]benzonitrile (4)

Morpholine (871 mg, 10 mmol) and N,N-diisopropylethylamine (2.6 g, 20 mmol) were added to a solution of 3-(4-chloro-7H-pyrrolo[2,3-d]pyrimidin-5-yl)benzonitrile (C14) (2.5 g, 9.8 mmol) in n-butanol (100 mL), and the reaction mixture was heated at reflux for 3 hours. Solvents were removed in vacuo and the residue was purified using chromatography on silica gel (Eluent: 1:1 ethyl acetate/petroleum ether). Subsequent recrystallization from ethyl acetate and tert-butyl methyl ether afforded the product as a white solid. Yield: 770 mg, 2.52 mmol, 26%. LCMS m/z 306.0 [M+H$^+$]. $^1$H NMR (400 MHz, DMSO-$d_6$) δ 12.34 (br s, 1H), 8.41 (s, 1H), 7.99-8.02 (m, 1H), 7.89 (br d, J=8 Hz, 1H), 7.76 (br d, J=7.5 Hz, 1H), 7.71 (s, 1H), 7.68 (dd, J=7.8, 7.8 Hz, 1H), 3.44-3.50 (m, 4H), 3.11-3.17 (m, 4H).

EXAMPLE 5

3-[4-(Dimethylamino)-7H-pyrrolo[2,3-d]pyrimidin-5-yl]benzonitrile (5)

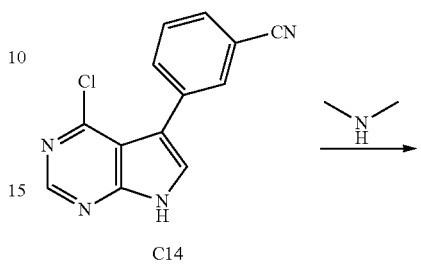

A mixture of 3-(4-chloro-7H-pyrrolo[2,3-d]pyrimidin-5-yl)benzonitrile (C14) (157 mg, 0.616 mmol), dimethylamine (189 mg, 4.19 mmol) and triethylamine (182 mg, 1.80 mmol) in n-butanol (12 mL) was heated under microwave irradiation at 150° C. for 25 minutes. After concentration in vacuo, the residue was purified by preparative HPLC (Column: Phenomenex Gemini C18, 8 μm; Mobile phase A: ammonia in water, pH 10; Mobile phase B: acetonitrile; Gradient: 25% to 65% B) to give the product as a white solid. Yield: 72.1 mg, 0.274 mmol, 44%. LCMS m/z 263.8 [M+H$^+$]. $^1$H NMR (400 MHz, DMSO-$d_6$) δ 12.15 (br s, 1H), 8.28 (s, 1H), 7.93 (br s, 1H), 7.78 (br d, J=7.8 Hz, 1H), 7.73 (br d, J=7.8 Hz, 1H), 7.62 (br dd, J=8.0, 7.8 Hz, 1H), 7.57 (br s, 1H), 2.73 (s, 6H).

EXAMPLE 6

3-{4-[(2S)-2-Methylmorpholin-4-yl]-7H-pyrrolo[2,3-d]pyrimidin-5-yl}benzonitrile (6)

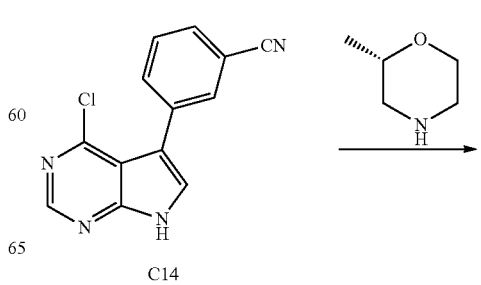

-continued

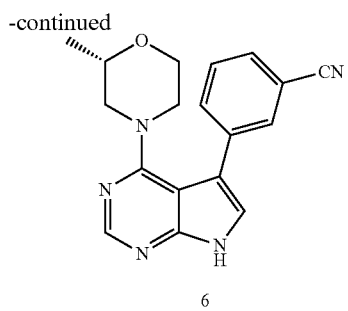

6

To a solution of 3-(4-chloro-7H-pyrrolo[2,3-d]pyrimidin-5-yl)benzonitrile (C14) (100 mg, 0.393 mmol) and (2S)-2-methylmorpholine (54 mg, 0.53 mmol) in n-butanol (20 mL) was added N,N-diisopropylethylamine (152 mg, 1.18 mol), and the reaction mixture was heated at 100° C. for 18 hours. The reaction mixture was then concentrated in vacuo; purification via preparative HPLC (Column: Phenomenex Gemini C18, 8 μm; Mobile phase A: ammonia in water, pH 10; Mobile phase B: acetonitrile; Gradient: 27% to 47% B) provided the product as a white solid. Yield: 17.5 mg, 54.8 μmol, 14%. LCMS m/z 320.2 [M+H$^+$]. $^1$H NMR (400 MHz, CDCl$_3$) δ 10.71 (br s, 1H), 8.53 (br s, 1H), 7.73-7.89 (m, 2H), 7.51-7.69 (m, 2H), 7.28 (s, 1H, assumed; partially obscured by solvent peak), 3.56-3.77 (m, 3H), 3.39-3.54 (m, 2H), 2.86-2.98 (m, 1H), 2.53-2.65 (m, 1H), 0.93-1.03 (m, 3H).

EXAMPLE 7

(3-{4-[(3S)-3-Methylpiperidin-1-yl]-7H-pyrrolo[2,3-d]pyrimidin-5-yl}phenyl)methanol (7

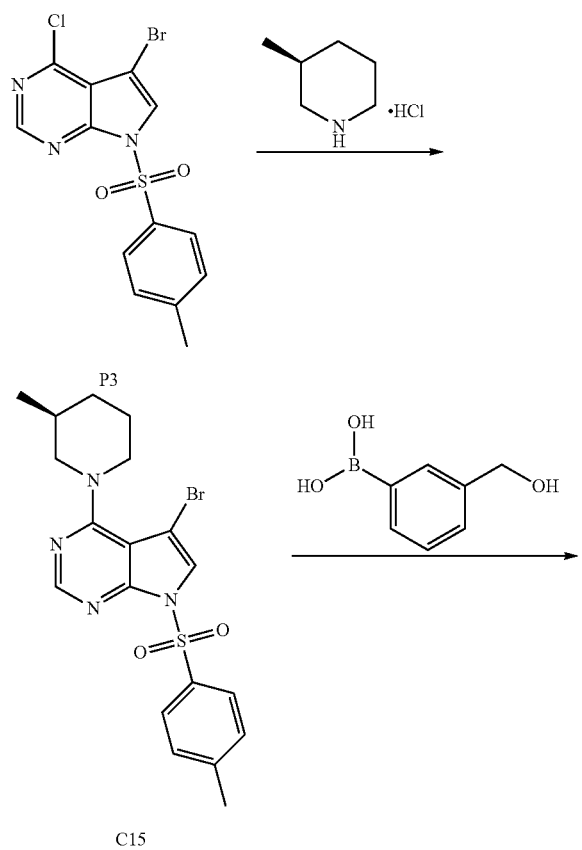

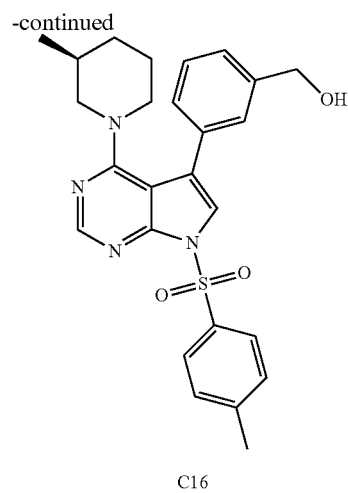

Step 1. Synthesis of 5-bromo-7-[(4-methylphenyl)sulfonyl]-4-[(3S)-3-methylpiperidin-1-yl]-7H-pyrrolo[2,3-d]pyrimidine (C15)

5-Bromo-4-chloro-7-[(4-methylphenyl)sulfonyl]-7H-pyrrolo[2,3-d]pyrimidine (P3) was reacted with the hydrochloride salt of (3S)-3-methylpiperidine according to the method described for preparation of 3-{4-[(2S)-2-methylmorpholin-4-yl]-7H-pyrrolo[2,3-d]pyrimidin-5-yl}benzonitrile (6) in Example 6. In this case, purification was effected via silica gel chromatography (Eluent: 5:1 petroleum ether/ethyl acetate), providing the product as a white solid. Yield: 4.3 g, 9.6 mmol, 92%.

Step 2. Synthesis of (3-{7-[(4-methylphenyl)sulfonyl]-4-[(3S)-3-methylpiperidin-1-yl]-7H-pyrrolo[2,3-d]pyrimidin-5-yl}phenyl)methanol (C16)

A mixture of 5-bromo-7-[(4-methylphenyl)sulfonyl]-4-[(3S)-3-methylpiperidin-1-yl]-7H-pyrrolo[2,3-d]pyrimidine (C15) (0.225 g, 0.501 mmol), [3-(hydroxymethyl)phenyl]boronic acid (0.104 g, 0.684 mmol), sodium carbonate (0.159 g, 1.50 mmol) and dichlorobis(triphenylphosphine)palladium(II) (36 mg, 51 μmol) in acetonitrile (2 mL) and water (2 mL) was heated to 150° C. under microwave irradiation for 15 minutes. The reaction was concentrated in vacuo to afford the product (0.35 g, >100%), which was used directly in the following step without additional purification.

Step 3. Synthesis of (3-{4-[(3S)-3-methylpiperidin-1-yl]-7H-pyrrolo[2,3-d]pyrimidin-5-yl}phenyl)methanol (7)

To a stirred solution of (3-{7-[(4-methylphenyl)sulfonyl]-4-[(3S)-3-methylpiperidin-1-yl]-7H-pyrrolo[2,3-d]pyrimidin-5-yl}phenyl)methanol (C16) from the previous step (<0.50 mmol) in 2-propanol (20 mL) was added lithium hydroxide monohydrate (0.42 g, 10 mmol) and water (3 mL)

and the reaction mixture was stirred at room temperature for 18 hours. After concentration in vacuo, the residue was purified by preparative HPLC (Column: Waters XBridge; Mobile phase A: 0.1% ammonia in water; Mobile phase B: acetonitrile; Gradient: 44% to 60% B) to provide the product as a white solid. Yield: 130 mg, 0.403 mmol, 80% over two steps. LCMS m/z 323.4 [M+H$^+$]. $^1$H NMR (400 MHz, CD$_3$OD) δ 8.24 (s, 1H), 7.46 (br s, 1H), 7.35-7.43 (m, 2H), 7.30 (br d, J=6 Hz, 1H), 7.23 (s, 1H), 4.67 (s, 2H), 3.89 (br d, J=13 Hz, 1H), 3.79 (br d, J=12 Hz, 1H), 2.58-2.69 (m, 1H), 2.27 (dd, J=12.0, 11.0 Hz, 1H), 1.62-1.71 (m, 1H), 1.30-1.52 (m, 3H), 0.87-1.01 (m, 1H), 0.60 (d, J=6.5 Hz, 3H).

EXAMPLE 8

4-(Morpholin-4-yl)-5-(1H-pyrazol-4-yl)-7H-pyrrolo[2,3-d]pyrimidine, formate salt (8)

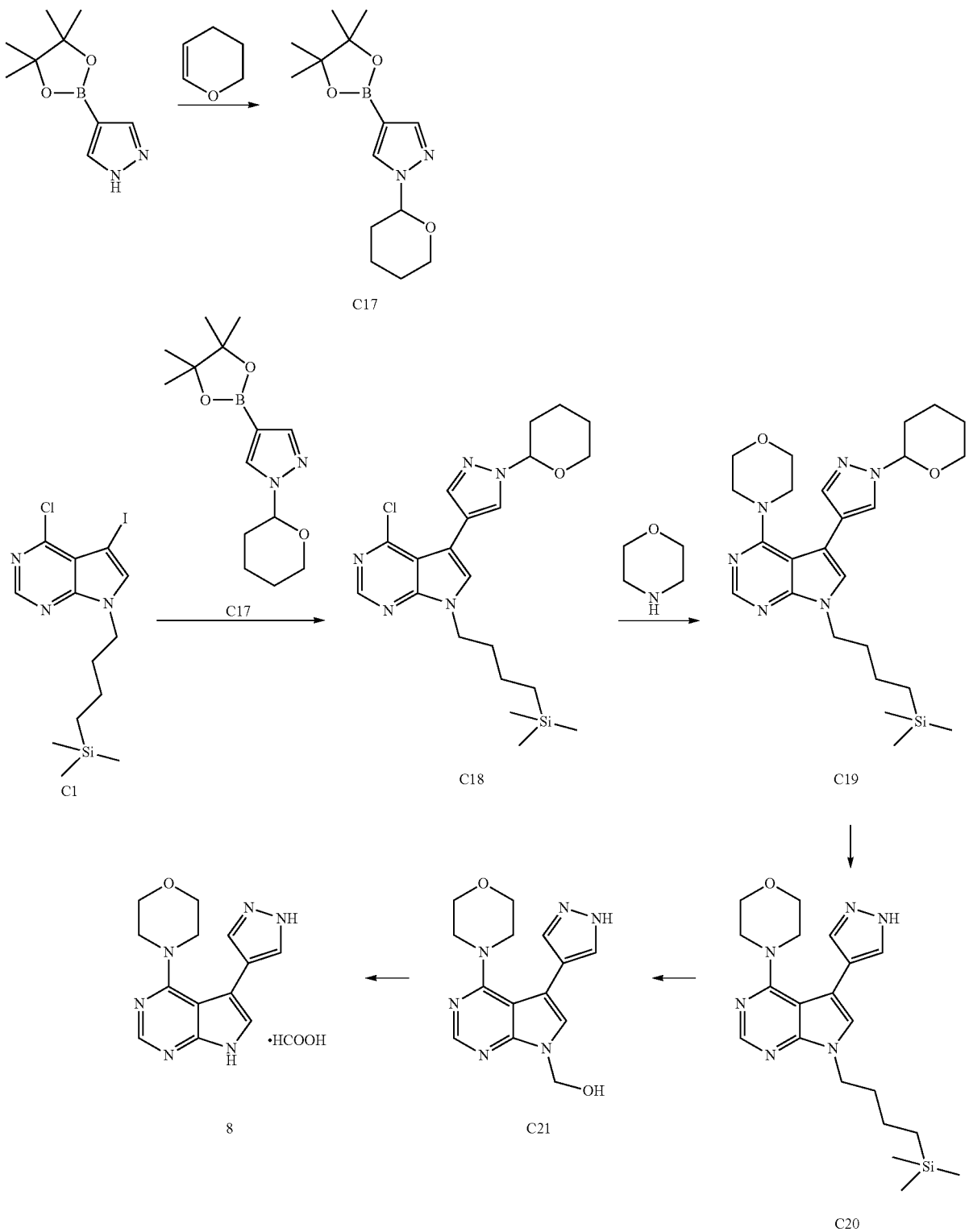

Step 1. Synthesis of 1-(tetrahydro-2H-pyran-2-yl)-4-(4,4,5,5-tetramethyl-1,3,2-dioxaborolan-2-yl)-1H-pyrazole (C17)

3,4-Dihydro-2H-pyran (5.6 g, 67 mmol) and trifluoroacetic acid (1.17 g, 10.3 mmol) were added to a solution of 4-(4,4,5,5-tetramethyl-1,3,2-dioxaborolan-2-yl)-1H-pyrazole (10.0 g, 51.5 mmol) in toluene (200 mL), and the reaction mixture was heated to 90° C. for 2 hours. After cooling to room temperature, the reaction mixture was partitioned between ethyl acetate (200 mL) and saturated aqueous sodium bicarbonate solution (100 mL), and the aqueous layer was extracted with ethyl acetate (100 mL). The combined organic layers were washed with saturated aqueous sodium chloride solution (100 mL), dried over sodium sulfate, filtered, and concentrated in vacuo. Silica gel chromatography (Gradient: 10% to 50% ethyl acetate in petroleum ether) provided the product as a white solid. Yield: 13.4 g, 48.2 mmol, 94%. $^1$H NMR (400 MHz, CDCl$_3$) δ 7.94 (s, 1H), 7.83 (s, 1H), 5.41 (dd, J=9.5, 2.5 Hz, 1H), 4.01-4.08 (m, 1H), 3.65-3.74 (m, 1H), 1.98-2.18 (m, 3H), 1.6-1.76 (m, 3H), 1.32 (s, 12H).

Step 2. Synthesis of 4-chloro-5-[1-(tetrahydro-2H-pyran-2-yl)-1H-pyrazol-4-yl]-7-{[2-(trimethylsilyl)ethoxy]methyl}-7H-pyrrolo[2,3-d]pyrimidine (C18)

A mixture of 4-chloro-5-iodo-7-{[2-(trimethylsilyl)ethoxy]methyl}-7H-pyrrolo[2,3-d]pyrimidine (C1) (2.0 g, 4.9 mmol), 1-(tetrahydro-2H-pyran-2-yl)-4-(4,4,5,5-tetramethyl-1,3,2-dioxaborolan-2-yl)-1H-pyrazole (C17) (1.91 g, 6.87 mmol), potassium phosphate (4.0 g, 19 mmol) and tetrakis(triphenylphosphine)palladium(0) (0.10 g, 87 μmol) was degassed several times with nitrogen and irradiated in a microwave synthesizer at 130° C. for 1.5 hours. The reaction mixture was partitioned between ethyl acetate (400 mL) and water (60 mL), and the aqueous layer was extracted with ethyl acetate (200 mL). The combined organic layers were washed with saturated aqueous sodium chloride solution (100 mL), dried over sodium sulfate, filtered, and concentrated under reduced pressure. Chromatography on silica gel (Gradient: 10% to 80% ethyl acetate in petroleum ether) afforded the product as a brown oil. Yield: 1.33 g, 3.06 mmol, 62%. $^1$H NMR (400 MHz, CDCl$_3$) δ 8.67 (s, 1H), 7.87 (s, 1H), 7.76 (s, 1H), 7.38 (s, 1H), 5.68 (s, 2H), 5.46 (dd, J=9.4, 2.9 Hz, 1H), 4.08-4.15 (m, 1H), 3.71-3.79 (m, 1H), 3.57 (dd, J=8.3, 8.0 Hz, 2H), 2.04-2.24 (m, 3H), 1.61-1.79 (m, 3H), 0.94 (dd, J=8.3, 8.3 Hz, 2H), −0.03 (s, 9H).

Step 3. Synthesis of 4-(morpholin-4-yl)-5-[1-(tetrahydro-2H-pyran-2-yl)-1H-pyrazol-4-yl]-7-{[2-(trimethylsilyl)ethoxy]methyl}-7H-pyrrolo[2,3-d]pyrimidine (C19)

A solution of 4-chloro-5-[1-(tetrahydro-2H-pyran-2-yl)-1H-pyrazol-4-yl]-7-{[2-(trimethylsilyl)ethoxy]methyl}-7H-pyrrolo[2,3-d]pyrimidine (C18) (3.3 g, 7.6 mmol), morpholine (0.99 g, 11 mmol) and N,N-diisopropylethylamine (6 mL, 34 mmol) in n-butanol (15 mL) was irradiated in a microwave synthesizer at 100° C. for 30 minutes. After removal of solvents in vacuo, the residue was purified by silica gel chromatography (Gradient: 10% to 50% ethyl acetate in petroleum ether) to provide the product as a brown oil. Yield: 2.6 g, 5.4 mmol, 71%. $^1$H NMR (400 MHz, CDCl$_3$) δ 8.50 (s, 1H), 7.79 (s, 1H), 7.71 (s, 1H), 7.17 (s, 1H), 5.62 (s, 2H), 5.44 (dd, J=6.5, 6.0 Hz, 1H), 4.08-4.15 (m, 1H), 3.71-3.79 (m, 1H), 3.62-3.67 (m, 4H), 3.58 (dd, J=8.5, 8.0 Hz, 2H), 3.33-3.39 (m, 4H), 2.06-2.19 (m, 3H), 1.62-1.79 (m, 3H), 0.93 (dd, J=8.5, 7.5 Hz, 2H), −0.04 (s, 9H).

Step 4. Synthesis of 4-(morpholin-4-yl)-5-(1H-pyrazol-4-yl)-7-{[2-(trimethylsilyl)ethoxy]methyl}-7H-pyrrolo[2,3-d]pyrimidine (C20)

To a solution of 4-(morpholin-4-yl)-5-[1-(tetrahydro-2H-pyran-2-yl)-1H-pyrazol-4-yl]-7-{[2-(trimethylsilyl)ethoxy]methyl}-7H-pyrrolo[2,3-d]pyrimidine (C19) (4.0 g, 8.2 mmol) in dichloromethane (20 mL) was added a solution of hydrogen chloride in 1,4-dioxane (4 M, 100 mL). The reaction mixture was stirred at room temperature for 2 hours, then poured into a mixture of ethyl acetate (300 mL) and saturated aqueous sodium bicarbonate solution (300 mL). The aqueous layer was extracted with ethyl acetate (2×300 mL), and the combined organic layers were washed with saturated aqueous sodium chloride solution (100 mL), dried over sodium sulfate, filtered, and concentrated under reduced pressure. Purification via silica gel chromatography (Gradient: 10% to 80% ethyl acetate in petroleum ether) afforded the product as a yellow oil. Yield: 2.18 g, 5.44 mmol, 66%. LCMS m/z 401.3 [M+H$^+$]. $^1$H NMR (400 MHz, CDCl$_3$) δ 8.51 (s, 1H), 7.78 (s, 2H), 7.19 (s, 1H), 5.64 (s, 2H), 3.56-3.66 (m, 6H), 3.34-3.40 (m, 4H), 0.91-0.98 (m, 2H), −0.03 (s, 9H).

Step 5. Synthesis of [4-(morpholin-4-yl)-5-(1H-pyrazol-4-yl)-7H-pyrrolo[2,3-d]pyrimidin-7-yl]methanol (C21)

4-(Morpholin-4-yl)-5-(1H-pyrazol-4-yl)-7-{[2-(trimethylsilyl)ethoxy]methyl}-7H-pyrrolo[2,3-d]pyrimidine (C20) (0.13 g, 0.32 mmol) was dissolved in trifluoroacetic acid (10 mL) and stirred at room temperature for 2 hours. Removal of solvent in vacuo provided the product (100 mg) as a brown solid; this was used in the next step without further purification. LCMS m/z 301.2 [M+H$^+$].

Step 6. Synthesis of 4-(morpholin-4-yl)-5-(1H-pyrazol-4-yl)-7H-pyrrolo[2,3-d]pyrimidine, Formate Salt (8)

To a solution of [4-(morpholin-4-yl)-5-(1H-pyrazol-4-yl)-7H-pyrrolo[2,3-d]pyrimidin-7-yl]methanol (C21) (from the previous step, 0.10 g, 50.32 mmol) in acetonitrile (10 mL) was added potassium carbonate (0.34 g, 2.5 mmol) and the reaction mixture was stirred at room temperature for 30 minutes. The mixture was filtered and the filter cake was washed with ethyl acetate (3×20 mL). The combined filtrates were concentrated in vacuo; purification via preparative HPLC (Column: DIKMA Diamonsil(2) C18, 5 μm; Mobile phase A: 0.225% formic acid in water; Mobile phase B: acetonitrile; Gradient: 0% to 17% B) afforded the product as a pale solid. Yield: 36 mg, 0.11 mmol, 34% over 2 steps. LCMS m/z 271.2 [M+H$^+$]. $^1$H NMR (400 MHz, CDCl$_3$) δ 10.72 (br s, 1H), 8.47 (s, 1H), 7.78 (s, 2H), 7.19 (s, 1H), 3.60-3.67 (m, 4H), 3.41-3.48 (m, 4H).

EXAMPLE 9
3-[2-Methyl-4-(morpholin-4-yl)-7H-pyrrolo[2,3-d]pyrimidin-5-yl]benzonitrile (9)
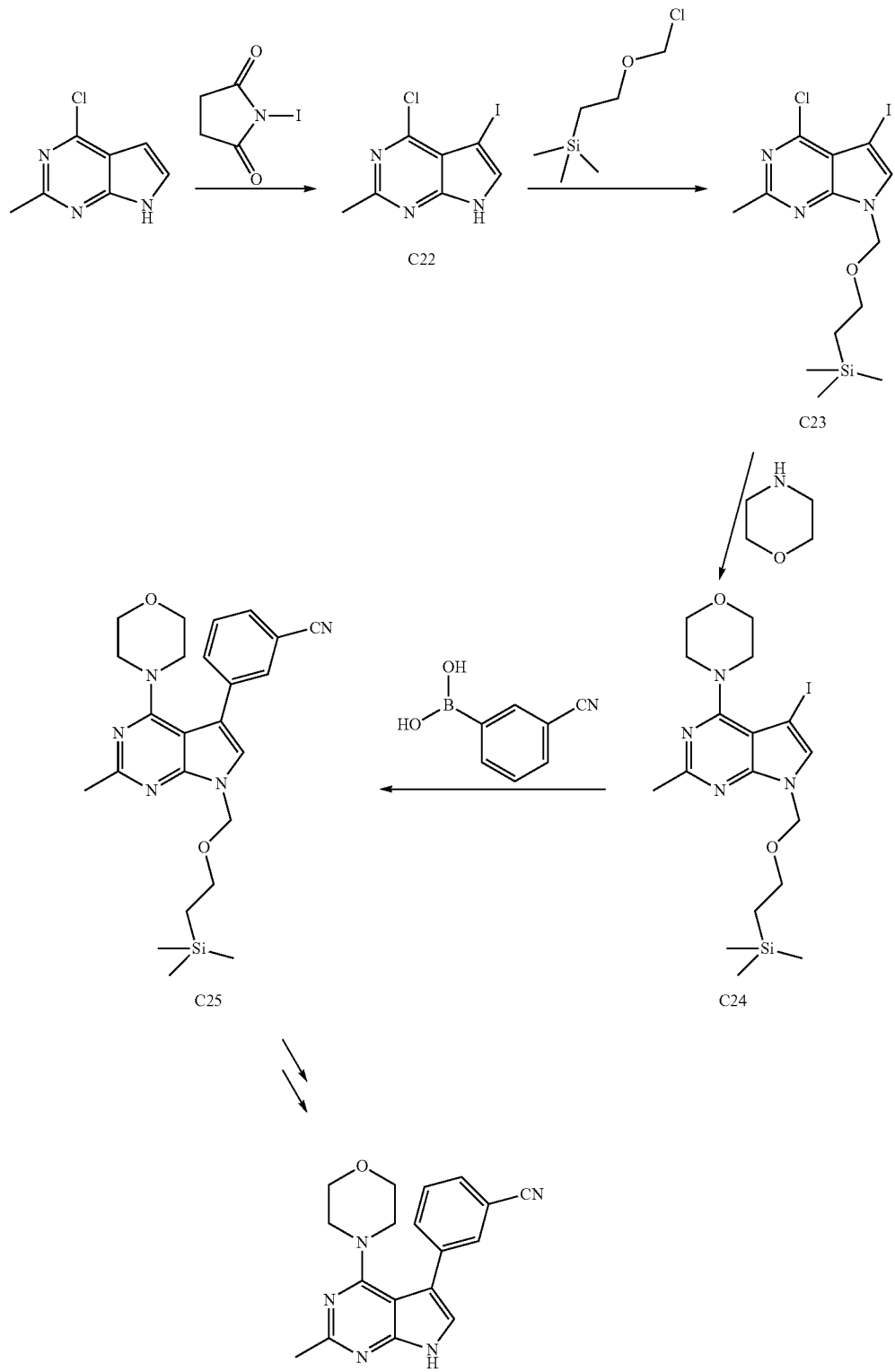

Step 1. Synthesis of 4-chloro-5-iodo-2-methyl-7H-pyrrolo[2,3-d]pyrimidine (C22)

To a solution of 4-chloro-2-methyl-7H-pyrrolo[2,3-d]pyrimidine (400 mg, 2.4 mmol) in dichloromethane (10 mL) was added N-iodosuccinimide (537 mg, 2.39 mmol). The mixture was stirred at room temperature for 2 hours, then washed with aqueous sodium sulfite solution, dried over sodium sulfate, filtered, and concentrated in vacuo to provide the product as a brown solid. Yield: 330 mg, 1.12 mmol, 47%. LCMS m/z 293.8 [M+H$^+$].

Step 2. Synthesis of 4-chloro-5-iodo-2-methyl-7-{[2-(trimethylsilyl)ethoxy]methyl}-7H-pyrrolo[2,3-d]pyrimidine (C23)

4-Chloro-5-iodo-2-methyl-7H-pyrrolo[2,3-d]pyrimidine (C22) was converted to the product according to the method used for synthesis of 4-chloro-5-iodo-7-{[2-(trimethylsilyl)ethoxy]methyl}-7H-pyrrolo[2,3-d]pyrimidine (C1) in Preparation P1. The product was obtained as a yellow oil. Yield: 400 mg, 0.94 mmol, 84%. LCMS m/z 424.0 [M+H$^+$].

Step 3. Synthesis of 5-iodo-2-methyl-4-(morpholin-4-yl)-7-{[2-(trimethylsilyl)ethoxy]methyl}-7H-pyrrolo[2,3-d]pyrimidine (C24)

The product was prepared from 4-chloro-5-iodo-2-methyl-7-{[2-(trimethylsilyl)ethoxy]methyl}-7H-pyrrolo[2,3-d]pyrimidine (C23) according to the method described for synthesis of 3-{4-[(2S)-2-methylmorpholin-4-yl]-7H-pyrrolo[2,3-d]pyrimidin-5-yl}benzonitrile (6) in Example 6. In this case, purification was carried out via silica gel chromatography (Gradient: 0% to 50% ethyl acetate in petroleum ether) to provide the product as a yellow oil. Yield: 300 mg, 0.63 mmol, 67%. LCMS m/z 475.2 [M+H$^+$].

Step 4. Synthesis of 3-[2-methyl-4-(morpholin-4-yl)-7-{[2-(trimethylsilyl)ethoxy]methyl}-7H-pyrrolo[2,3-d]pyrimidin-5-yl]benzonitrile (C25)

To a solution of 5-iodo-2-methyl-4-(morpholin-4-yl)-7-{[2-(trimethylsilyl)ethoxy]methyl}-7H-pyrrolo[2,3-d]pyrimidine (C24) (100 mg, 0.21 mmol), (3-cyanophenyl)boronic acid (62 mg, 0.42 mmol) and potassium carbonate (100 mg, 0.72 mmol) in a mixture of ethanol and water (4:1, 5 mL) was added dichlorobis(triphenylphosphine)palladium (15 mg, 21 µmol). The reaction mixture was degassed and purged with nitrogen; this procedure was carried out a total of three times. After the reaction mixture had heated at 90° C. for 3 hours, it was allowed to cool and concentrated in vacuo. Purification via preparative thin layer chromatography (Eluent: 1:1 petroleum ether/ethyl acetate) provided the product as a yellow oil. Yield: 52 mg, 0.12 mmol, 57%. LCMS m/z 451.3 [M+H$^+$].

Step 5. Synthesis of 3-[2-methyl-4-(morpholin-4-yl)-7H-pyrrolo[2,3-d]pyrimidin-5-yl]benzonitrile (9)

3-[2-Methyl-4-(morpholin-4-yl)-7-{[2-(trimethylsilyl)ethoxy]methyl}-7H-pyrrolo[2,3-d]pyrimidin-5-yl]benzonitrile (C25) was converted to the product using the method described for synthesis of 5-(1-methyl-1H-pyrazol-4-yl)-4-(morpholin-4-yl)-7H-pyrrolo[2,3-d]pyrimidine (1) in Example 1. In this case, preparative HPLC purification was carried out using a Phenomenex Gemini C18 column, 8 µm; Mobile phase A: ammonia in water, pH 10; Mobile phase B: acetonitrile; Gradient: 30% to 50% B. The product was obtained as a white solid. Yield: 17.3 mg, 54.2 µmol, 45% over 2 steps. LCMS m/z 320.1 [M+H$^+$]. $^1$H NMR (400 MHz, CD$_3$OD) δ 7.91-7.93 (m, 1H), 7.85-7.88 (m, 1H), 7.60-7.69 (m, 2H), 7.38 (s, 1H), 3.51-3.55 (m, 4H), 3.24-3.28 (m, 4H), 2.59 (s, 3H).

EXAMPLE 10

{3-[4-(Dimethylamino)-7H-pyrrolo[2,3-d]pyrimidin-5-yl]phenyl}methanol (10)

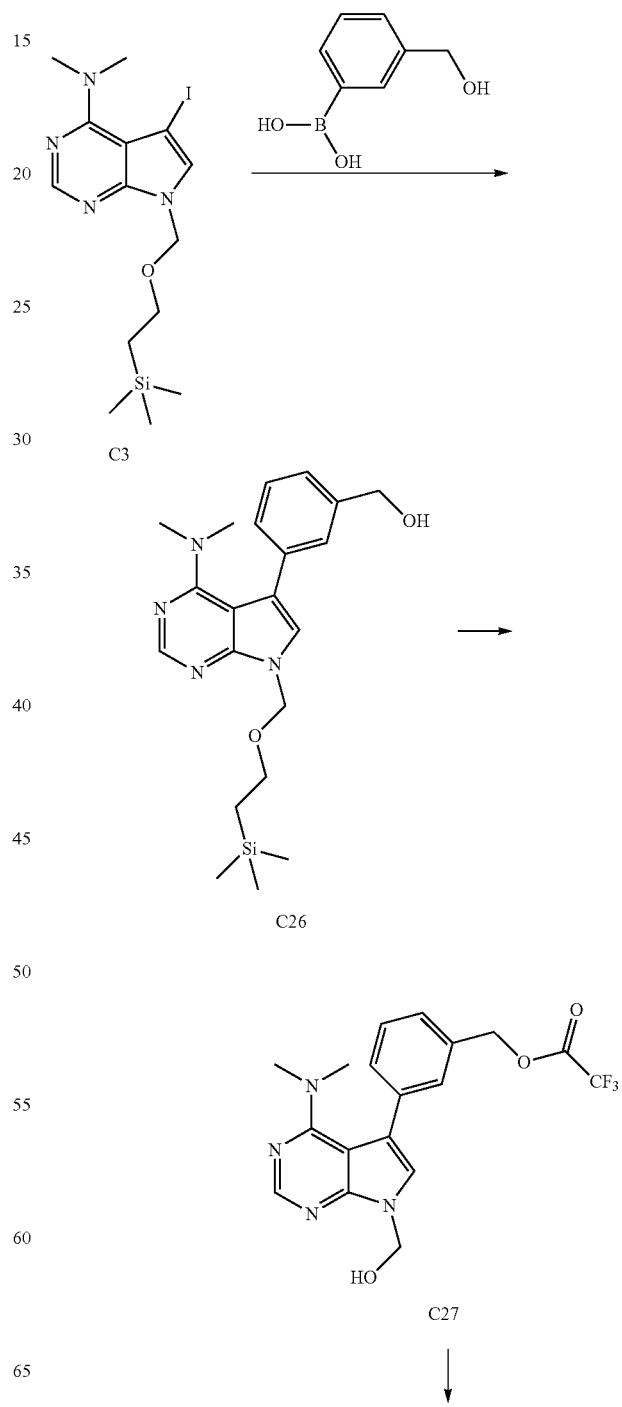

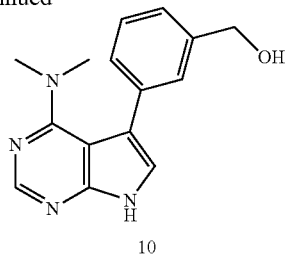

10

Step 1. Synthesis of {3-[4-(dimethylamino)-7-{[2-(trimethylsilyl)ethoxy]methyl}-7H-pyrrolo[2,3-d]pyrimidin-5-yl]phenyl}methanol (C26)

A solution of 5-iodo-N,N-dimethyl-7-{[2-(trimethylsilyl)ethoxy]methyl}-7H-pyrrolo[2,3-d]pyrimidin-4-amine (C3) (418 mg, 1.00 mmol), [3-(hydroxymethyl)phenyl]boronic acid (228 mg, 1.50 mmol), tetrakis(triphenylphosphine)palladium(0) (115 mg, 0.100 mmol), and cesium carbonate (625 mg, 1.92 mmol) in 1,4-dioxane (6 mL) and water (1.5 mL) was purged with nitrogen, then heated under microwave irradiation at 120° C. for 20 minutes. The reaction mixture was diluted with saturated aqueous sodium chloride solution (50 mL) and extracted with dichloromethane (3×60 mL). The combined organic layers were dried over sodium sulfate, filtered, and concentrated in vacuo. Chromatography on silica gel (Gradient: 2% to 17% ethyl acetate in petroleum ether) afforded the product as a brown oil. Yield: 369 mg, 0.926 mmol, 93%. LCMS m/z 399.0 [M+H+].

Step 2. Synthesis of 3-[4-(dimethylamino)-7-(hydroxymethyl)-7H-pyrrolo[2,3-d]pyrimidin-5-yl]benzyl trifluoroacetate (C27)

A solution of {3-[4-(dimethylamino)-7-{[2-(trimethylsilyl)ethoxy]methyl}-7H-pyrrolo[2,3-d]pyrimidin-5-yl]phenyl}methanol (C26) (397 mg, 0.996 mmol) in trifluoroacetic acid (10 mL) was stirred at room temperature for 2 hours. The reaction mixture was concentrated in vacuo to provide the product (400 mg) as a brown oil. This material was taken directly into the following step. LCMS m/z 395.1 [M+H+].

Step 3. Synthesis of {3-[4-(dimethylamino)-7H-pyrrolo[2,3-d]pyrimidin-5-yl]phenyl}methanol (10)

A mixture of 3-[4-(dimethylamino)-7-(hydroxymethyl)-7H-pyrrolo[2,3-d]pyrimidin-5-yl]benzyl trifluoroacetate (C27) (from the previous step, 400 mg, 50.996 mmol) and potassium carbonate (500 mg, 3.6 mmol) in methanol (10 mL) was stirred at 80° C. for 30 minutes. The reaction mixture was diluted with saturated aqueous sodium chloride solution (50 mL) and extracted with dichloromethane (3×60 mL); the combined organic layers were dried over sodium sulfate, filtered, and concentrated in vacuo. Purification via preparative HPLC (Column: Phenomenex Gemini C18, 8 μm; Mobile phase A: ammonia in water, pH 10; Mobile phase B: acetonitrile; Gradient: 21% to 33% B) afforded the product as a white solid. Yield: 77.7 mg, 0.290 mmol, 29% over two steps. LCMS m/z 268.9 [M+H+]. $^1$H NMR (400 MHz, CDCl$_3$) δ 10.83 (br s, 1H), 8.39 (s, 1H), 7.50 (br s, 1H), 7.38-7.42 (m, 2H), 7.29-7.34 (m, 1H), 7.11 (s, 1H), 4.78 (s, 2H), 2.84 (s, 6H).

EXAMPLE 198

3-[6-(Difluoromethyl)-4-(morpholin-4-yl)-7H-pyrrolo[2,3-d]pyrimidin-5-yl]benzonitrile (198)

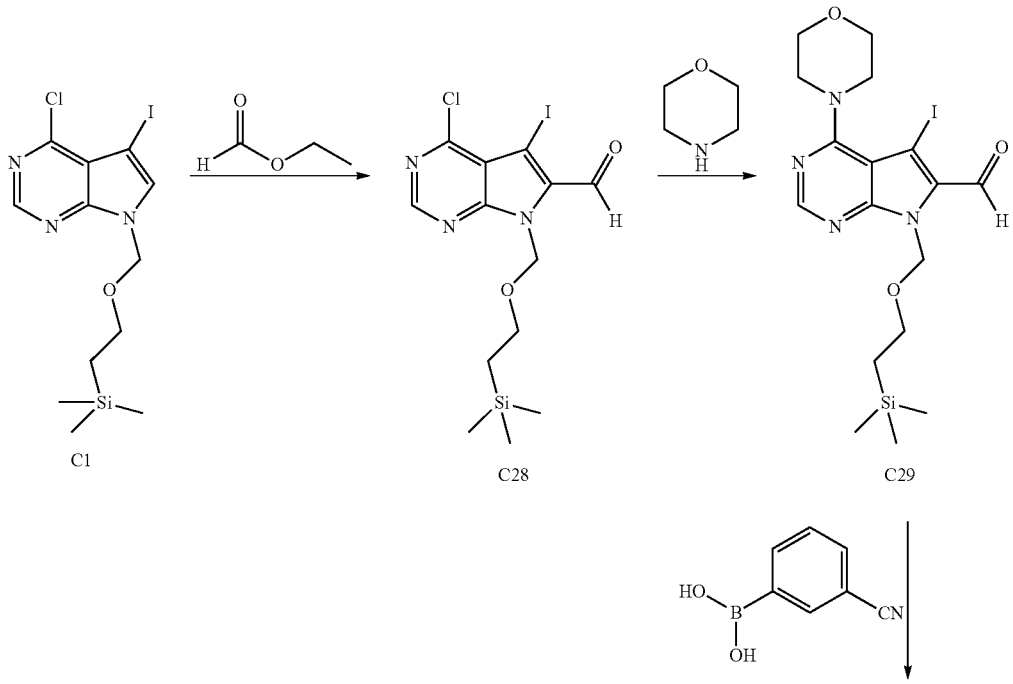

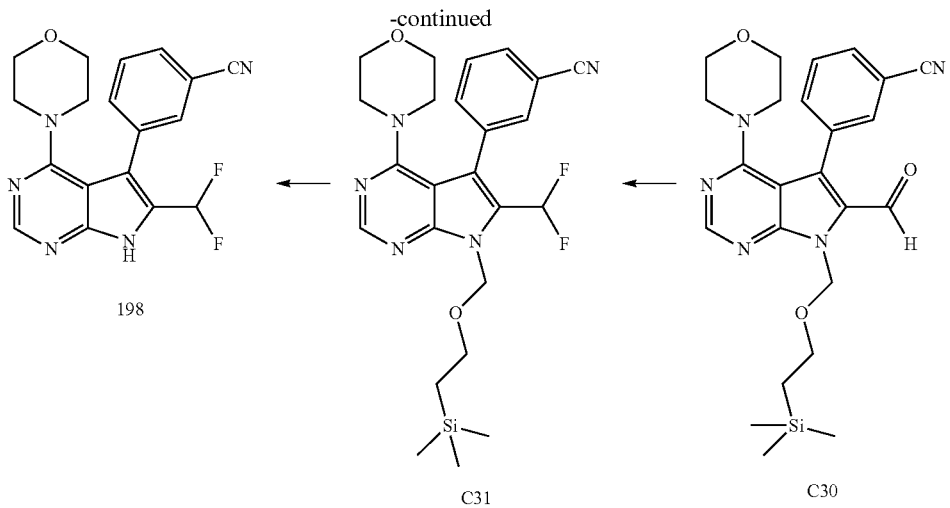

Step 1. Synthesis of 4-chloro-5-iodo-7-{[2-(trimethylsilyl)ethoxy]methyl}-7H-pyrrolo[2,3-d]pyrimidine-6-carbaldehyde (C28)

A solution of diisopropylamine (2.9 g, 29 mmol) in tetrahydrofuran (30 mL) was cooled to −78° C. and treated drop-wise with n-butyllithium (2.5 M, 11.6 mL, 29 mmol). The reaction mixture was stirred at 0° C. for 1 hour, and then cooled to −78° C. A solution of 4-chloro-5-iodo-7-{[2-(trimethylsilyl)ethoxy]methyl}-7H-pyrrolo[2,3-d]pyrimidine (C1) (8.0 g, 20 mmol) in tetrahydrofuran (10 mL) was added drop-wise, and stirred was continued at −78° C. for 1 hour. After drop-wise addition of a solution of ethyl formate (2.6 g, 35 mmol) in tetrahydrofuran (10 mL) to the −78° C. reaction mixture, it was allowed to warm to room temperature and stir for 18 hours. It was then cooled to 0° C., and the reaction was quenched by addition of saturated aqueous ammonium chloride solution (20 mL), then extracted with ethyl acetate (3×50 mL). The combined organic layers were washed with saturated aqueous sodium chloride solution (50 mL), dried over sodium sulfate, filtered, and concentrated. Purification via silica gel chromatography (Gradient: 0% to 25% ethyl acetate in petroleum ether) afforded the product as a yellow oil. Yield: 5.0 g, 11 mmol, 55%. $^1$H NMR (400 MHz, CDCl$_3$) δ 10.11 (s, 1H), 8.80 (s, 1H), 6.05 (s, 2H), 3.55-3.62 (m, 2H), 0.89-0.96 (m, 2H), −0.05 (s, 9H).

Step 2. Synthesis of 5-iodo-4-(morpholin-4-yl)-7-{[2-(trimethylsilyl)ethoxy]methyl}-7H-pyrrolo[2,3-d]pyrimidine-6-carbaldehyde (C29)

Morpholine (1.09 g, 12.5 mmol) and N,N-diisopropylethylamine (2.94 g, 22.7 mmol) were added to a solution of 4-chloro-5-iodo-7-{[2-(trimethylsilyl)ethoxy]methyl}-7H-pyrrolo[2,3-d]pyrimidine-6-carbaldehyde (C28) (5.0 g, 11 mmol) in acetonitrile (20 mL). The reaction mixture was stirred at reflux for 16 hours, whereupon it was cooled and concentrated in vacuo; the residue was purified by chromatography on silica gel (Gradient: 0% to 20% ethyl acetate in petroleum ether) to provide the product as a yellow oil. Yield: 4.0 g, 8.2 mmol, 74%. $^1$H NMR (400 MHz, CDCl$_3$) δ 9.99 (s, 1H), 8.54 (s, 1H), 6.01 (s, 2H), 3.92-3.98 (m, 4H), 3.70-3.75 (m, 4H), 3.58-3.65 (m, 2H), 0.91-0.96 (m, 2H), −0.05 (s, 9H).

Step 3. Synthesis of 3-[6-formyl-4-(morpholin-4-yl)-7-{[2-(trimethylsilyl)ethoxy]methyl}-7H-pyrrolo[2,3-d]pyrimidin-5-yl]benzonitrile (C30)

5-Iodo-4-(morpholin-4-yl)-7-{[2-(trimethylsilyl)ethoxy]methyl}-7H-pyrrolo[2,3-d]pyrimidine-6-carbaldehyde (C29) was converted to the product using the method described for synthesis of 3-(4-chloro-6-methyl-7-{[2-(trimethylsilyl)ethoxy]methyl}-7H-pyrrolo[2,3-d]pyrimidin-5-yl)benzonitrile (C7) in Example 2. The product was obtained as a yellow solid. Yield: 1.5 g, 3.2 mmol, 78%. $^1$H NMR (400 MHz, CDCl$_3$) δ 9.75 (s, 1H), 8.60 (s, 1H), 7.77-7.83 (m, 2H), 7.72-7.76 (m, 1H), 7.67 (br dd, J=8, 8 Hz, 1H), 6.09 (s, 2H), 3.66-3.71 (m, 2H), 3.38-3.44 (m, 4H), 3.23-3.28 (m, 4H), 0.94-1.01 (m, 2H), −0.03 (s, 9H).

Step 4. Synthesis of 3-[6-(difluoromethyl)-4-(morpholin-4-yl)-7-{[2-(trimethylsilyl)ethoxy]methyl}-7H-pyrrolo[2,3-d]pyrimidin-5-yl]benzonitrile (C31)

A solution of 3-[6-formyl-4-(morpholin-4-yl)-7-{[2-(trimethylsilyl)ethoxy]methyl}-7H-pyrrolo[2,3-d]pyrimidin-5-yl]benzonitrile (C30) (200 mg, 0.43 mmol) and (diethylamino)sulfur trifluoride (276 mg, 1.71 mmol) in dichloromethane (10 mL) was stirred at 40° C. for 16 hours. The reaction mixture was poured into saturated aqueous sodium bicarbonate solution (10 mL) and extracted with dichloromethane (3×20 mL). The combined organic layers were washed with saturated aqueous sodium chloride solution (50 mL), dried over sodium sulfate, filtered, and concentrated; purification by preparative thin-layer chromatography on silica gel (Eluent: 1:1 ethyl acetate/petroleum ether) afforded the product as a yellow solid. Yield: 150 mg, 0.31 mmol, 72%. $^1$H NMR (400 MHz, CDCl$_3$) δ 8.58 (s, 1H), 7.76 (ddd, J=7.3, 1.6, 1.5 Hz, 1H), 7.72-7.74 (m, 1H), 7.61-7.70 (m, 2H), 6.74 (t, $J_{HF}$=52.5 Hz, 1H), 5.86 (s, 2H), 3.65-3.72 (m, 2H), 3.34-3.42 (m, 4H), 3.15-3.21 (m, 4H), 0.95-1.02 (m, 2H), −0.02 (s, 9H).

Step 5. Synthesis of 3-[6-(difluoromethyl)-4-(morpholin-4-yl)-7H-pyrrolo[2,3-d]pyrimidin-5-yl]benzonitrile (198)

A solution of 3-[6-(difluoromethyl)-4-(morpholin-4-yl)-7-{[2-(trimethylsilyl)ethoxy]methyl}-7H-pyrrolo[2,3-d]pyrimidin-5-yl]benzonitrile (C31) (10 mg, 21 µmol) in trifluoroacetic acid (2 mL) was stirred at room temperature for 24 hours. The reaction mixture was concentrated and purified by preparative reversed phase high-performance liquid chromatography (Column: DIKMA Diamonsil(2) C18, 5 µm; Eluent: 22% acetonitrile in water containing 0.225% formic acid) to provide the product as a white solid. Yield: 2.0 mg, 5.6 µmol, 27%. LCMS m/z 355.9 [M+H$^+$]. $^1$H NMR (400 MHz, DMSO-d$_6$) δ 13.06 (br s, 1H), 8.47 (s, 1H), 7.92 (ddd, J=6.7, 2.1, 1.7 Hz, 1H), 7.83-7.85 (m, 1H), 7.69-7.76 (m, 2H), 7.02 (t, J$_{HF}$=52.5 Hz, 1H), 3.22-3.30 (m, 4H), 3.03-3.10 (m, 4H).

EXAMPLE 199 and EXAMPLE 200

5-(5,6-Dihydro-2H-pyran-3-yl)-4-(morpholin-4-yl)-7H-pyrrolo[2,3-d]pyrimidine (199) and 5-(3,4-Dihydro-2H-pyran-5-yl)-4-(morpholin-4-yl)-7H-pyrrolo[2,3-d]pyrimidine (200)

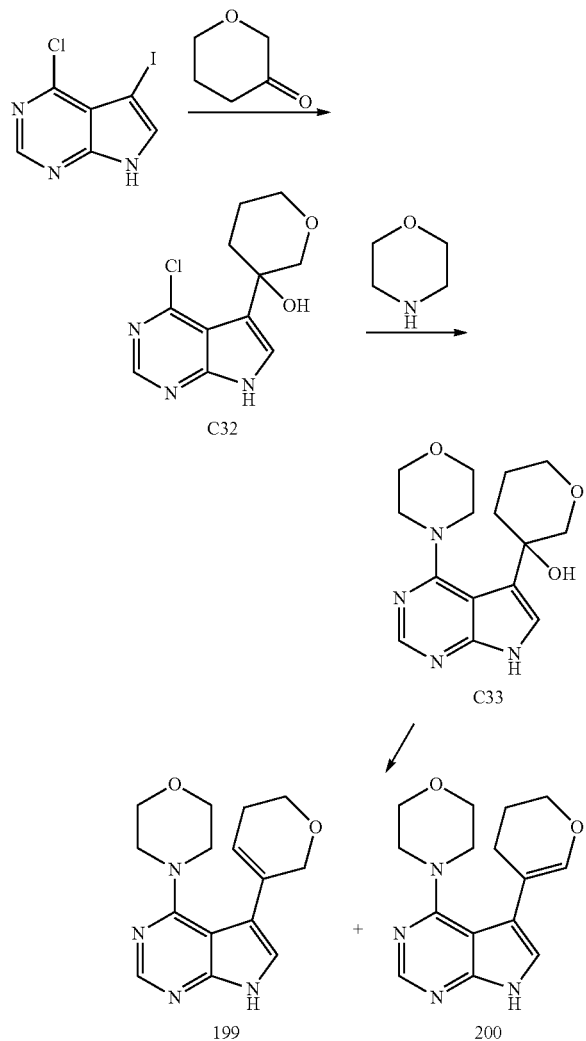

Step 1. Synthesis of 3-(4-chloro-7H-pyrrolo[2,3-d]pyrimidin-5-yl)tetrahydro-2H-pyran-3-ol (C32)

To a −78° C. solution of 4-chloro-5-iodo-7H-pyrrolo[2,3-d]pyrimidine (1.5 g, 5.4 mmol) in tetrahydrofuran (50 mL) was added n-butyllithium (2.5 M, 6.4 mL, 16.1 mmol) drop-wise. After the reaction mixture had been stirred at −78° C. for 2 hours, it was treated with dihydro-2H-pyran-3(4H)-one (1.61 g, 16.1 mmol), warmed to room temperature, and stirred for 18 hours. The reaction was quenched with water (50 mL), and the aqueous layer was extracted with ethyl acetate (3×30 mL); the combined organic layers were washed with saturated aqueous sodium chloride solution (100 mL), dried over sodium sulfate, filtered, and concentrated. Silica gel chromatography (Gradient: 0% to 50% ethyl acetate in petroleum ether) afforded the product as a yellow oil. Yield: 200 mg, 0.79 mmol, 15%. LCMS m/z 254.0 [M+H$^+$].

Step 2. Synthesis of 3-[4-(morpholin-4-yl)-7H-pyrrolo[2,3-d]pyrimidin-5-yl]tetrahydro-2H-pyran-3-ol (C33)

To a solution of 3-(4-chloro-7H-pyrrolo[2,3-d]pyrimidin-5-yl)tetrahydro-2H-pyran-3-ol (C32) (200 mg, 0.79 mmol) and morpholine (134 mg, 1.54 mol) in n-butanol (10 mL) was added N,N-diisopropylethylamine (305 mg, 2.36 mol), and the reaction mixture was heated at 70° C. for 2 hours. After concentration in vacuo, preparative reversed phase high-performance liquid chromatography (Column: Phenomenex Gemini C18, 8 µm; Mobile phase A: aqueous ammonia, pH 10; Mobile phase B: acetonitrile; Gradient: 9% to 29% B) provided the product as a white solid. Yield: 180 mg, 0.59 mmol, 75%. LCMS m/z 305.1 [M+H$^+$]. $^1$H NMR (400 MHz, CDCl$_3$+D$_2$O) δ 8.73 (s, 1H), 7.52 (s, 1H), 3.92-4.03 (m, 4H), 3.74-3.88 (m, 4H), 3.32-3.40 (m, 2H), 3.15-3.24 (m, 2H), 2.07-2.16 (m, 1H), 1.88-2.06 (m, 2H), 1.57-1.68 (m, 1H).

Step 3. Synthesis of 5-(5,6-dihydro-2H-pyran-3-yl)-4-(morpholin-4-yl)-7H-pyrrolo[2,3-d]pyrimidine (199) and 5-(3,4-dihydro-2H-pyran-5-yl)-4-(morpholin-4-yl)-7H-pyrrolo[2,3-d]pyrimidine (200)

Triethylsilane (10 mL) and trifluoroacetic acid (10 mL) were added over 10 minutes to a solution of 3-[4-(morpholin-4-yl)-7H-pyrrolo[2,3-d]pyrimidin-5-yl]tetrahydro-2H-pyran-3-ol (C33) (40 mg, 0.13 mmol) in dichloromethane (10 mL). The reaction mixture was stirred at room temperature for 2 hours, whereupon it was concentrated in vacuo. Preparative reversed phase high-performance liquid chromatography (Column: Boston Symmetrix ODS-H, 5 µm; Mobile phase A: water containing 0.225% formic acid; Mobile phase B: acetonitrile; Gradient: 11% to 31% B) afforded 199 as a white solid (Yield: 11.3 mg, 39.5 µmol, 30%) and 200, also as a white solid (Yield: 7.0 mg, 24 µmol, 18%).

199: LCMS m/z 287.0 [M+H$^+$]. $^1$H NMR (400 MHz, DMSO-d$_6$) δ 11.97 (br s, 1H), 8.29 (s, 1H), 7.31 (s, 1H), 5.87-5.93 (m, 1H), 4.30-4.36 (m, 2H), 3.68-3.78 (m, 6H), 3.36-3.43 (m, 4H), 2.21-2.29 (m, 2H).

200: LCMS m/z 287.0 [M+H$^+$]. $^1$H NMR (400 MHz, DMSO-d$_6$) δ 11.83 (br s, 1H), 8.26 (s, 1H), 7.18 (s, 1H), 6.65 (s, 1H), 3.92-3.97 (m, 2H), 3.69-3.76 (m, 4H), 3.40-3.46 (m, 4H), 2.29-2.36 (m, 2H), 1.88-1.96 (m, 2H).

EXAMPLE 201

4-(Morpholin-4-yl)-5-[3-(1,2,4-oxadiazol-3-yl)phenyl]-7H-pyrrolo[2,3-d]pyrimidine (201)

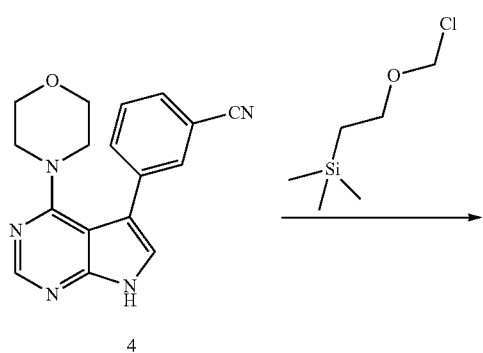

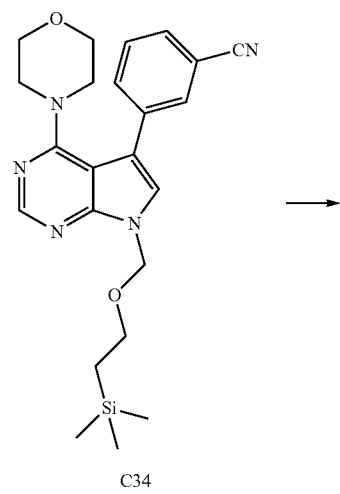

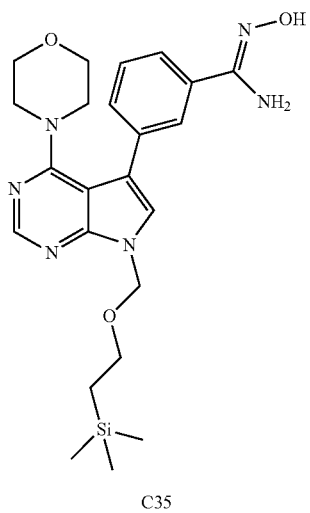

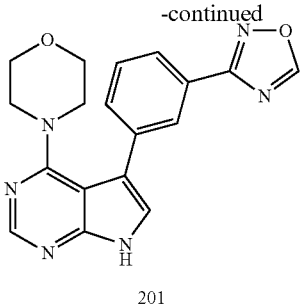

Step 1. Synthesis of 3-[4-(morpholin-4-yl)-7-{[2-(trimethylsilyl)ethoxy]methyl}-7H-pyrrolo[2,3-d]pyrimidin-5-yl]benzonitrile (C34)

3-[4-(Morpholin-4-yl)-7H-pyrrolo[2,3-d]pyrimidin-5-yl]benzonitrile (4) was converted to the product using the method described for synthesis of 4-chloro-5-iodo-7-{[2-(trimethylsilyl)methyl]-7H-pyrrolo[2,3-d]pyrimidine (C1) in Preparation P1. The product was obtained as a yellow solid. Yield: 0.90 g, 2.1 mmol, 70%. $^1$H NMR (400 MHz, CDCl$_3$) δ 8.55 (s, 1H), 7.86 (br s, 1H), 7.79 (br d, J=7.6 Hz, 1H), 7.63 (br d, J=7.6 Hz, 1H), 7.57 (dd, J=7.6, 7.6 Hz, 1H), 7.29 (s, 1H), 5.67 (s, 2H), 3.58-3.64 (m, 2H), 3.52-3.58 (m, 4H), 3.27-3.32 (m, 4H), 0.92-0.98 (m, 2H), −0.03 (s, 9H).

Step 2. Synthesis of N'-hydroxy-3-[4-(morpholin-4-yl)-7-{[2-(trimethylsilyl)ethoxy]methyl}-7H-pyrrolo[2,3-d]pyrimidin-5-yl]benzenecarboximidamide (C35)

Hydroxylamine hydrochloride (278 mg, 4.00 mmol) and sodium carbonate (318 mg, 3.00 mmol) were added to a stirred solution of 3-[4-(morpholin-4-yl)-7-{[2-(trimethylsilyl)ethoxy]methyl}-7H-pyrrolo[2,3-d]pyrimidin-5-yl]benzonitrile (C34) (436 mg, 1.00 mmol) in ethanol (10 mL) and water (5 mL). The reaction mixture was heated at reflux for 2 hours, then concentrated in vacuo, poured into water (25 mL), and extracted with ethyl acetate (3×10 mL). The combined organic layers were washed with saturated aqueous sodium chloride solution (25 mL), dried over sodium sulfate, filtered, and concentrated, affording the product as a white solid. Yield: 280 mg, 0.60 mmol, 60%. $^1$H NMR (400 MHz, DMSO-d$_6$) δ 9.67 (s, 1H), 8.43 (s, 1H), 7.89 (br s, 1H), 7.72 (s, 1H), 7.64 (br d, J=7.8 Hz, 1H), 7.53 (br d, J=7.8 Hz, 1H), 7.46 (dd, J=7.6, 7.6 Hz, 1H), 5.89 (br s, ~1.6H), 5.61 (s, 2H), 3.53-3.61 (m, 2H), 3.39-3.47 (m, 4H), 3.13-3.21 (m, 4H), 0.81-0.88 (m, 2H), −0.09 (s, 9H).

Step 3. Synthesis of 4-(morpholin-4-yl)-5-[3-(1,2,4-oxadiazol-3-yl)phenyl]-7H-pyrrolo[2,3-d]pyrimidine (201)

Triethyl orthoformate (760 mg, 5.1 mol) and boron trifluoride diethyl etherate (370 mg, 2.6 mol) were added to a 0° C. solution of N'-hydroxy-3-[4-(morpholin-4-yl)-7-{[2-(trimethylsilyl)ethoxy]methyl}-7H-pyrrolo[2,3-d]pyrimidin-5-yl]benzenecarboximidamide (C35) (600 mg, 1.3 mmol) in tetrahydrofuran (25 mL). The reaction mixture was heated at 40° C. for 18 hours, then poured into water (50 mL) and extracted with ethyl acetate (3×25 mL). The combined organic layers were washed with saturated aqueous sodium chloride solution (50 mL), dried over sodium sulfate, filtered, and concentrated. Purification via preparative reversed phase high-performance liquid chromatography (Column: Phenomenex Gemini C18, 8 μm; Mobile phase A: aqueous ammonia, pH 10; Mobile phase B: acetonitrile; Gradient: 30% to 50% B) provided the product as a yellow solid. Yield: 62 mg, 0.18 mmol, 14%. LCMS m/z 349.0 [M+H$^+$]. $^1$H NMR (400 MHz, DMSO-d$_6$) δ 9.77 (s, 1H), 8.40 (s, 1H), 8.24 (br s, 1H), 7.98 (br d, J=7.5 Hz, 1H), 7.82 (br d, J=7.3 Hz, 1H), 7.63-7.70 (m, 2H), 3.39-3.45 (m, 4H), 3.13-3.20 (m, 4H).

EXAMPLE 202

3-{4-[2-(3-Methyl-1,2-oxazol-5-yl)morpholin-4-yl]-7H-pyrrolo[2,3-d]pyrimidin-5-yl}benzonitrile (202)

NMR (400 MHz, CDCl$_3$) δ 7.27-7.38 (m, 5H), 6.22 (s, 1H), 4.11-4.19 (m, 1H), 3.76-3.84 (m, 1H), 3.60 (AB quartet, J$_{AB}$=13.0 Hz, Δν$_{AB}$=13.2 Hz, 2H), 2.99 (br d, J=11.0 Hz, 1H), 2.71-2.79 (m, 1H), 2.55 (d, J=11.0 Hz, 1H), 2.42 (ddd, J=11.7, 11.5, 3.6 Hz, 1H), 2.29 (s, 3H).

Step 2. Synthesis of 4-benzyl-2-(3-methyl-1,2-oxazol-5-yl)morpholine (C37)

Trimethylsilyl trifluoromethanesulfonate (2.9 g, 13 mmol) and triethylsilane (2.6 g, 22 mmol) were added to a solution of 4-benzyl-2-(3-methyl-1,2-oxazol-5-yl)morpholin-2-ol (C36) (1.2 g, 4.4 mmol) in dichloromethane (15 mL), and the reaction mixture was heated at 80° C. for 2 hours. The reaction mixture was then adjusted to a pH of ~5 to 6 via addition of saturated aqueous sodium bicarbonate solution. After extraction with dichloromethane (3×20 mL),

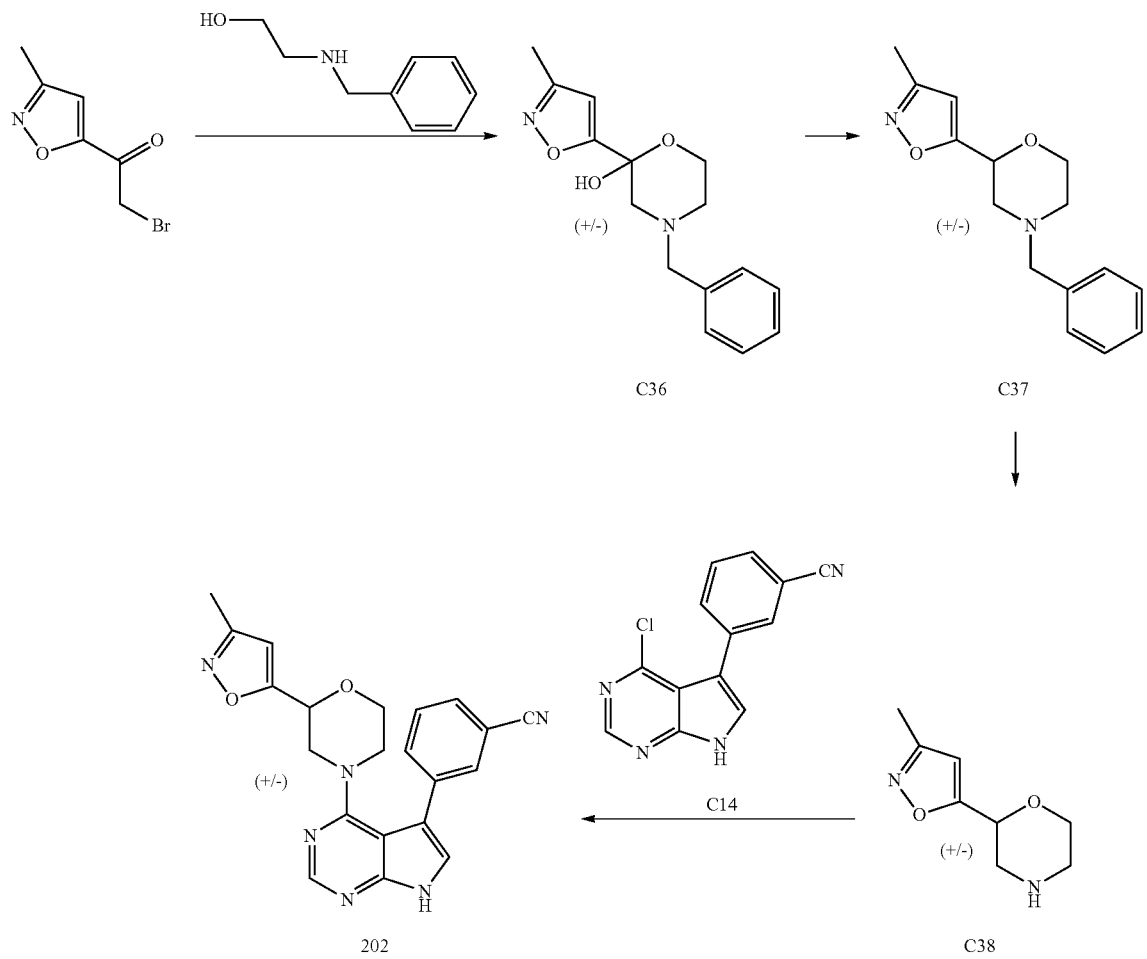

Step 1. Synthesis of 4-benzyl-2-(3-methyl-1,2-oxazol-5-yl)morpholin-2-ol (C36)

A solution of 2-bromo-1-(3-methyl-1,2-oxazol-5-yl)ethanone (2.50 g, 12.2 mmol) and 2-(benzylamino)ethanol (3.70 g, 24.5 mmol) in acetonitrile (25 mL) was stirred at 35° C. for 18 hours. The reaction mixture was concentrated in vacuo and purified using silica gel chromatography (Gradient: 0% to 50% ethyl acetate in petroleum ether) to provide the product as a yellow oil. Yield: 1.2 g, 4.4 mmol, 36%. $^1$H the combined organic layers were washed with saturated aqueous sodium chloride solution (25 mL), dried over sodium sulfate, filtered, and concentrated. Purification via silica gel chromatography (Gradient: 0% to 50% ethyl acetate in petroleum ether) afforded the product as a yellow oil. Yield: 500 mg, 1.9 mmol, 43%. LCMS m/z 258.9 [M+H$^+$]. $^1$H NMR (400 MHz, CDCl$_3$) δ 7.27-7.37 (m, 5H), 6.07 (s, 1H), 4.75 (dd, J=9.7, 2.3 Hz, 1H), 3.96 (ddd, J=11.3, 2.8, 2.4 Hz, 1H), 3.81 (ddd, J=11.3, 10.8, 2.5 Hz, 1H), 3.52-3.61 (m, 2H), 3.02 (br d, J=11.4 Hz, 1H), 2.68-2.75 (m, 1H), 2.29 (s, 3H), 2.27-2.37 (m, 2H).

Step 3. Synthesis of 2-(3-methyl-1,2-oxazol-5-yl)morpholine (C38)

Ammonium cerium(IV) nitrate (442 mg, 0.806 mmol) was added to a solution of 4-benzyl-2-(3-methyl-1,2-oxazol-5-yl)morpholine (C37) (100 mg, 0.39 mmol) in acetonitrile/water (5:1 mixture, 6 mL). The reaction mixture was stirred at 25° C. for 4 hours, then concentrated in vacuo; preparative thin-layer chromatography on silica gel (Eluent: 10:1 dichloromethane/methanol) provided the product as a yellow oil. Yield: 40 mg, 0.24 mmol, 62%. $^1$H NMR (400 MHz, CDCl$_3$) δ 6.11 (s, 1H), 4.79 (dd, J=10.0, 2.4 Hz, 1H), 4.01 (ddd, J=11.8, 2.5, 2.4 Hz, 1H), 3.81-3.89 (m, 1H), 3.35 (dd, J=12.7, 2.5 Hz, 1H), 2.99-3.07 (m, 3H), 2.30 (s, 3H).

Step 4. Synthesis of 3-{4-[2-(3-methyl-1,2-oxazol-5-yl)morpholin-4-yl]-7H-pyrrolo[2,3-d]pyrimidin-5-yl}benzonitrile (202)

To a solution of 2-(3-methyl-1,2-oxazol-5-yl)morpholine (C38) (20 mg, 0.12 mmol) in n-butanol (7 mL) was added 3-(4-chloro-7H-pyrrolo[2,3-d]pyrimidin-5-yl)benzonitrile (C14) (36.2 mg, 0.142 mol), and the reaction mixture was placed in a sealed tube and heated at 150° C. in a microwave reactor for 2 hours. After removal of solvent, the residue was purified by preparative reversed phase high-performance liquid chromatography (Column: YMC-Actus Triart C18, 5 μm; Mobile phase A: water containing 0.225% formic acid; Mobile phase B: acetonitrile; Gradient: 33% to 53% B) to afford the product as a white solid. Yield: 0.78 mg, 2.0 μmol, 2%. LCMS m/z 387.0 [M+H$^+$]. $^1$H NMR (400 MHz, DMSO-d$_6$), characteristic peaks: δ 12.45 (br s, 1H), 8.45 (s, 1H), 8.00-8.03 (m, 1H), 7.85 (br d, J=8 Hz, 1H), 7.76 (br d, J=8 Hz, 1H), 7.72 (d, J=2.8 Hz, 1H), 7.66 (dd, J=8, 8 Hz, 1H), 6.25 (s, 1H), 4.58-4.63 (m, 1H), 3.71-3.83 (m, 2H), 3.01-3.09 (m, 1H), 2.88-2.97 (m, 1H), 2.20 (s, 3H).

METHODS

METHOD A

Introduction of a 4-Amino Substituent onto 3-(4-chloro-7H-pyrrolo[2,3-d]pyrimidin-5-yl)benzonitrile Via Chloride Displacement

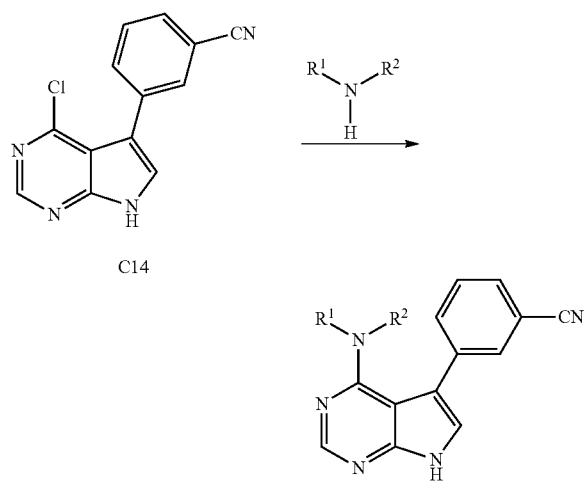

A solution of 3-(4-chloro-7H-pyrrolo[2,3-d]pyrimidin-5-yl)benzonitrile (C14) in dimethyl sulfoxide (0.1 M, 500 μL, 50 μmol) was added to a vial containing the appropriate amine (150 μmol). After addition of cesium fluoride (23 mg, 150 μmol), the reaction mixture was shaken at 100° C. for 16 hours, then purified via preparative HPLC using an appropriate gradient with one of the following systems: 1) Column: DIKMA Diamonsil(2) C18, 5 μm; Mobile phase A: 0.1% trifluoroacetic acid in water; Mobile phase B: acetonitrile; 2) Column: Boston Symmetrix ODS-H, 5 μm or Phenomenex Synergi C18, 4 μm or Agella Venusil ASB C18, 5 μm; Mobile phase A: 0.225% formic acid in water; Mobile phase B: acetonitrile.

METHOD B

Synthesis of 5-substituted-4-[(3S)-3-methylpiperidin-1-yl]-7H-pyrrolo[2,3-d]pyrimidines Via Suzuki Reaction

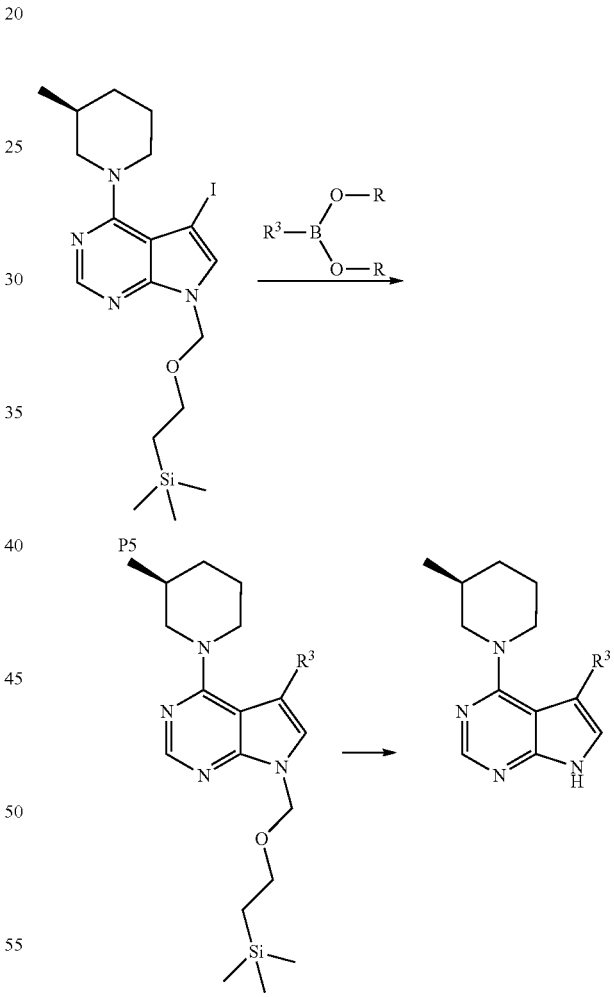

Step 1. Suzuki Reaction

A solution of the appropriate boronic ester in aqueous 1,4-dioxane (1:5 v/v water/1,4-dioxane) (0.3 M, 400 μL, 120 μmol) was combined with a solution of 5-iodo-4-[(3S)-3-methylpiperidin-1-yl]-7-{[2-(trimethylsilyl)ethoxy]methyl}-7H-pyrrolo[2,3-d]pyrimidine (P5) (0.25 M in 1:5 water/1,4-dioxane; 400 μL, 100 μmol). The solution was treated with cesium carbonate (65 mg, 200 μmol) and degassed by bubbling nitrogen through it. [1,1'-Bis(di-tertbutylphosphino)ferrocene]dichloropalladium(II) (3 mg, 5 µmol) was added to the reaction mixture, which was again degassed with nitrogen, then shaken at 150° C. for 4 hours. After removal of solvent using a Speedvac® concentrator, the products were purified via preparative thin layer chromatography in an appropriate solvent system and taken to the following step.

Step 2. Deprotection

The product from the previous step was treated with a solution of trifluoroacetic acid in dichloromethane (1:5 v/v; 2 mL), and the reaction mixture was shaken at 30° C. for 2 hours. After concentration using the Speedvac®, the residue was treated with a solution of ammonium hydroxide in methanol (1:4 v/v; 2 mL) and shaken at 30° C. for 16 hours. Solvents were removed on the Speedvac® and the product was purified via preparative HPLC using an appropriate gradient (Column: DIKMA Diamonsil(2) C18, 5 µm or Agella Venusil ASB C18, 5 µm; Mobile phase A: 0.225% formic acid in water; Mobile phase B: acetonitrile).

METHOD C

Synthesis of 5-substituted-4-(morpholin-4-yl)-7H-pyrrolo[2,3-d]pyrimidines Via Suzuki Reaction

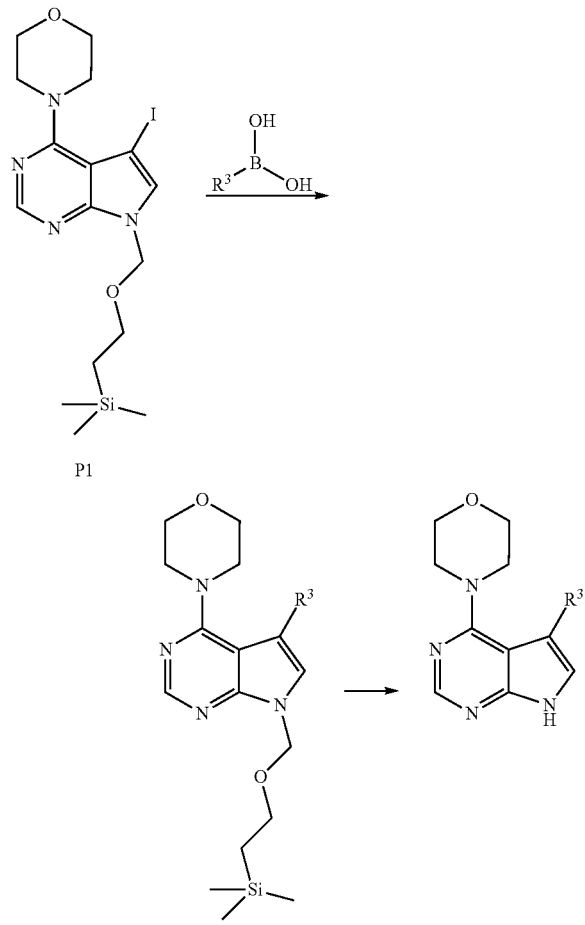

Step 1. Suzuki Reaction

A solution of 5-iodo-4-(morpholin-4-yl)-7-{[2-(trimethylsilyl)ethoxy]methyl}-7H-pyrrolo[2,3-d]pyrimidine (P1) in 1,4-dioxane (0.20 M, 400 µL, 80 µmol) was combined with a solution of the appropriate boronic acid in 1,4-dioxane (0.50 M, 200 µL, 100 µmol). An aqueous solution of potassium phosphate (0.80 M, 200 µL, 160 µmol) was added, followed by [1,1'-bis(di-tert-butylphosphino)ferrocene]dichloropalladium(II) (3 mg, 5 µmol), and the reaction mixture was shaken at 100° C. for 16 hours. The mixture was filtered and the filtrate was concentrated on a Speedvac®. The residue was partitioned between dichloromethane and saturated aqueous sodium carbonate solution, and the aqueous layer was extracted with dichloromethane (2×1 mL). The combined organic layers were dried over sodium sulfate, filtered, and concentrated using the Speedvac® to afford the crude product, which was used directly in the next step.

Step 2. Deprotection

The product of the preceding reaction was treated with a solution of concentrated hydrochloric acid in ethanol (1:6 v/v; 1 mL), and the reaction mixture was shaken at 80° C. for 16 hours. After removal of solvents on the Speedvac®, the residue was purified via preparative HPLC using an appropriate gradient with one of the following systems: 1) Column: Kromasil Eternity-5-C18, 5 µm or Boston Symmetrix ODS-H, 5 µm or Phenomenex Synergi C18, 4 µm; Mobile phase A: 0.225% formic acid in water; Mobile phase B: acetonitrile; 2) Column: Phenomenex Gemini C18, 8 µm; Mobile phase A: aqueous ammonium hydroxide, pH 10; Mobile phase B: acetonitrile.

METHOD D

Introduction of a 4-Amino Substituent onto 7H-pyrrolo[2,3-d]pyrimidines Via Chloride Displacement

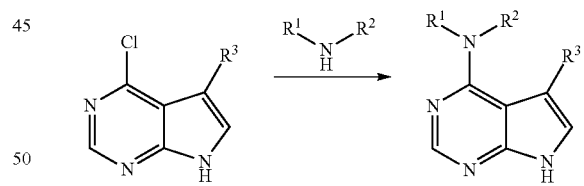

A solution of the 4-chloro-7H-pyrrolo[2,3-d]pyrimidine substrate in dimethyl sulfoxide (0.5 M, 200 µL, 100 µmol) was added to a solution of the appropriate amine in dimethyl sulfoxide (0.8 M, 200 µL, 160 µmol). N,N-Diisopropylethylamine (120 µL, 700 µmol) was added, and the reaction mixture was shaken at 80° C. for 16 hours. After removal of solvents using a Speedvac®, the product was purified via preparative HPLC using an appropriate gradient with one of the following systems: 1) Column: Phenomenex Gemini C18, 8 µm or Agela Durashell C18, 5 µm; Mobile phase A: aqueous ammonium hydroxide, pH 10; Mobile phase B: acetonitrile; or 2) Column: DIKMA Diamonsil(2) C18, 5 µm or Phenomenex Synergi C18, 4 µm; Mobile phase A: 0.225% formic acid in water; Mobile phase B: acetonitrile.

METHOD E

Synthesis of 4-amino-substituted, 5-substituted-7H-pyrrolo[2,3-d]pyrimidines from 4-chloro-5-iodo-7-{[2-(trimethylsilyl)ethoxy]methyl}-7H-pyrrolo[2,3-d]pyrimidine

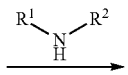
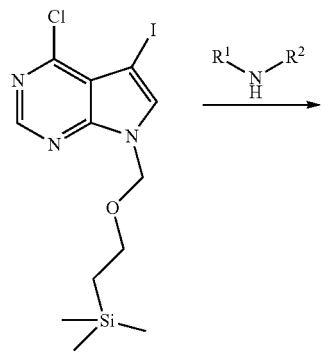

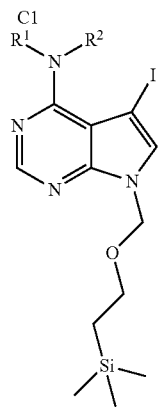
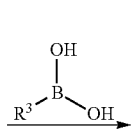
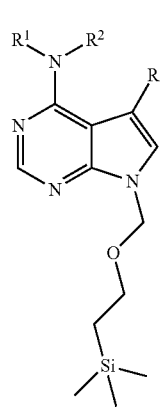

Step 1. Amine Displacement Reaction

A solution of 4-chloro-5-iodo-7-{[2-(trimethylsilyl)ethoxy]methyl}-7H-pyrrolo[2,3-d]pyrimidine (C1) in N,N-dimethylformamide (0.25 M, 500 μL, 125 μmol) was added to the appropriate amine (150 μmol). Triethylamine (35 μL, 250 μmol) was added, and the reaction mixture was shaken at 100° C. for 16 hours. This solution was used directly in the following step.

Step 2. Suzuki Reaction

The product solution from the preceding step (≤125 μmol) was mixed with a solution of the appropriate boronic acid in N,N-dimethylformamide (0.25 M, 500 μL, 125 μmol). An aqueous solution of cesium carbonate (1.25 M, 200 μL, 250 μmol) was added, followed by [1,1'-bis(di-tert-butylphosphino)ferrocene]dichloropalladium(II) (1.6 mg, 2.5 μmol), and the reaction mixture was shaken at 120° C. for 4 hours. Removal of solvent using a Speedvac® provided a residue, which was used directly in the following step.

Step 3. Deprotection

The product from the previous step (≤125 μmol) was treated with a solution of concentrated hydrochloric acid in ethanol (1:6 v/v; 2 mL), and the reaction mixture was shaken at 80° C. for 16 hours. After removal of solvent via the Speedvac®, the residue was taken up in a solution of ammonium hydroxide (30% aqueous) in methanol (1:4 v/v, 2 mL). The mixture was shaken at 30° C. for 16 hours, concentrated on the Speedvac® and purified via preparative HPLC using an appropriate gradient (Column: DIKMA Diamonsil(2) C18, 5 μm or Agella Venusil ASB C18, 5 μm; Mobile phase A: 0.225% formic acid in water; Mobile phase B: acetonitrile).

METHOD F

Introduction of a 5-substituent onto 5-(4,4,5,5-tetramethyl-1,3,2-dioxaborolan-2-yl)-7-{[2-(trimethylsilyl)ethoxy]methyl}-7H-pyrrolo[2,3-d]pyrimidin-4-amines Via Suzuki Reaction

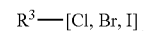
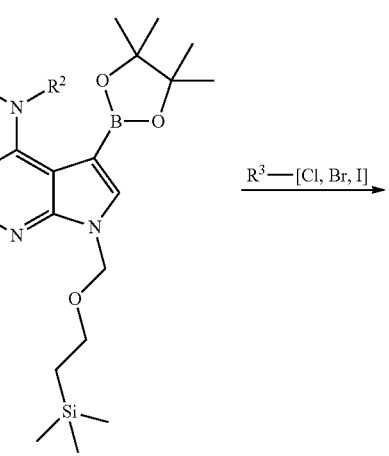

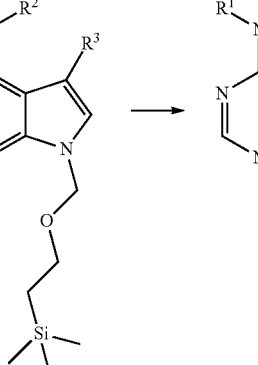
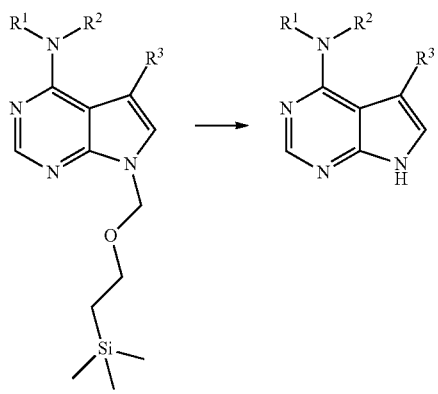

Step 1. Suzuki Reaction

A solution of the 5-(4,4,5,5-tetramethyl-1,3,2-dioxaborolan-2-yl)-7-{[2-(trimethylsilyl)ethoxy]methyl}-7H-pyrrolo[2,3-d]pyrimidine substrate in 1,4-dioxane (0.1 M, 1 mL, 100 μmol) was added to the appropriate aryl or heteroaryl halide (100 μmol). An aqueous solution of cesium carbonate (1.0 M, 200 μL, 200 μmol) was added, followed by [1,1'-bis(di-tert-butylphosphino)ferrocene]dichloropalladium(II) (1.3 mg, 2.0 μmol), and the reaction mixture was shaken at 120° C. for 4 hours. Removal of solvent using a Speedvac® provided a residue, which was used directly in the following step.

Step 2. Deprotection

Protecting group removal and purification were carried out as described in the final step of Method E.

The following table (Table 1) provides Examples 11-197 and Examples 203-225 of the present invention, the structure of the compound, reference to the method of preparation and characterizing data for the compound. Certain of the compounds depicted in the table are racemic and others are depicted as single enantiomers with the absolute stereochemistry as shown. In certain cases the racemic compound has been separated into the individual enantiomers, although the absolute stereochemistry of the single enantiomer(s) may not have been determined. In the table the individual separated enantiomers may be referred to as ENT-1 or ENT-2, which are abbreviations for the separated enantiomer-1 and enantiomer-2, respectively. It is to be understood that one of the compounds designated as ENT-1 or ENT-2 will have the (R) absolute stereochemistry at the chiral center while the other will have the (S) absolute stereochemistry.

TABLE 1

| Example # | Structure | Method of Preparation; Non-commercial starting materials | $^1$H NMR (400 MHz, DMSO-$d_6$) δ (ppm); Mass spectrum, observed ion m/z (M + H$^+$) or HPLC retention time; Mass spectrum m/z (M + H$^+$) (unless otherwise indicated) |
|---|---|---|---|
| 11 | 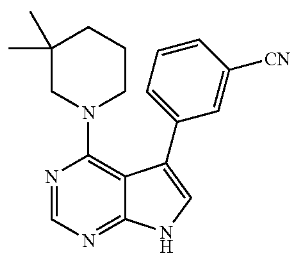 [SMILES: CC1(C)CCCN(c2ncnc3[nH]cc(-c4cccc(C#N)c4)c23)C1] | Ex 6 | 12.20 (br s, 1H), 8.32 (s, 1H), 7.90 (dd, J = 1.8, 1.5 Hz, 1H), 7.83 (ddd, J = 8.0, 1.5, 1.3 Hz, 1H), 7.76 (ddd, J = 8, 1.5, 1 Hz, 1H), 7.65 (dd, J = 7.8, 7.5 Hz, 1H), 7.59 (d, J = 2.3 Hz, 1H), 2.96-3.03 (m, 4H), 1.20-1.27 (m, 2H), 1.10-1.19 (m, 2H), 0.87 (s, 6H); 331.9 |
| 12 | 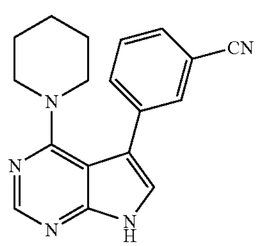 [SMILES: N#Cc1cccc(-c2c[nH]c3ncnc(N4CCCCC4)c23)c1] | Ex 6 | 12.21 (br s, 1H), 8.35 (s, 1H), 7.95 (br s, 1H), 7.85 (br d, J = 7.5 Hz, 1H), 7.74 (br d, J = 7.5 Hz, 1H), 7.61-7.67 (m, 2H), 3.13-3.19 (m, 4H), 1.40-1.48 (m, 2H), 1.29-1.38 (m, 4H); 303.9 |
| 13 | 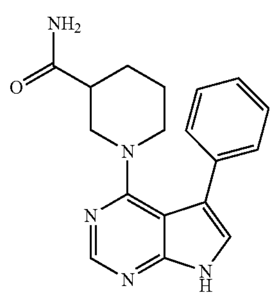 [SMILES: NC(=O)C1CCCN(c2ncnc3[nH]cc(-c4ccccc4)c23)C1] | Ex 6 | 12.05 (br s, 1H), 8.31 (s, 1H), 7.37-7.50 (m, 5H), 7.24-7.31 (m, 1H), 7.08 (br s, 1H), 6.73 (br s, 1H), 3.93 (br d, J = 12.4 Hz, 1H), 3.65 (br d, J = 12.4 Hz, 1H), 2.74 (dd, J = 12.4, 11.7 Hz, 1H), 2.5-2.58 (m, 1H, assumed; partially obscured by solvent peak), 2.21-2.31 (m, 1H), 1.68-1.78 (m, 1H), 1.26-1.44 (m, 2H), 1.15-1.26 (m, 1H); 322.2 |
| 14 | 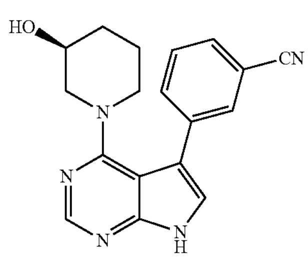 [SMILES: N#Cc1cccc(-c2c[nH]c3ncnc(N4CCC[C@H](O)C4)c23)c1] | Ex 5 | $^1$H NMR (400 MHz, CDCl$_3$), characteristic peaks: δ 10.44 (br s, 1H), 8.46 (s, 1H), 7.82 (dd, J = 1.5, 1.3 Hz, 1H), 7.75 (ddd, J = 7.7, 1.5, 1.5 Hz, 1H), 7.62 (ddd, J = 7.8, 1.5, 1.3 Hz, 1H), 7.54 (dd, J = 8.0, 7.5 Hz, 1H), 7.28 (d, J = 2.5 Hz, 1H), 4.83 (br s, 1H), 4.14 (br d, J = 14 Hz, 1H), 3.95-4.00 (m, 1H), 3.45 (dd, J = 13.9, 2.4 Hz, 1H), 3.13-3.21 (m, 1H), 2.82-2.91 (m, 1H), 1.13-1.22 (m, 1H); 320.2 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 15 | 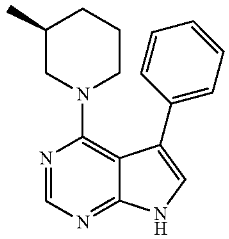 [SMILES: C[C@H]1CCCN(c2ncnc3[nH]cc(-c4ccccc4)c23)C1] | Ex 7[1] | $^1$H NMR (400 MHz, CD$_3$OD) δ 8.25 (s, 1H), 7.38-7.49 (m, 4H), 7.27-7.33 (m, 1H), 7.21 (s, 1H), 3.91 (br d, J = 13 Hz, 1H), 3.78 (br d, J = 13 Hz, 1H), 2.63 (ddd, J = 12.6, 12.6, 3.0 Hz, 1H), 2.25 (dd, J = 12.6, 11.0 Hz, 1H), 1.62-1.70 (m, 1H), 1.31-1.52 (m, 3H), 0.88-1.00 (m, 1H), 0.59 (d, J = 6.5 Hz, 3H); 293.3 |
| 16 | 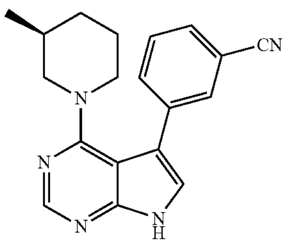 | Ex 6 | $^1$H NMR (400 MHz, CDCl$_3$) δ 10.55 (br s, 1H), 8.49 (s, 1H), 7.83 (br s, 1H), 7.75 (br d, J = 7.5 Hz, 1H), 7.61 (br d, J = 7.5 Hz, 1H), 7.54 (dd, J = 8.0, 7.5 Hz, 1H), 7.23 (s, 1H), 3.84 (br d, J = 13 Hz, 1H), 3.77 (br d, J = 13 Hz, 1H), 2.61-2.70 (m, 1H), 2.34 (dd, J = 12.0, 11.5 Hz, 1H), 1.65-1.77 (m, 1H), 1.29-1.55 (m, 3H), 0.91-1.03 (m, 1H), 0.68 (d, J = 6.5 Hz, 3H); 318.3 |
| 17 | 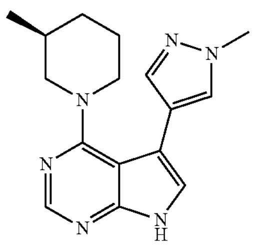 | Ex 7[2] | $^1$H NMR (400 MHz, CD$_3$OD) δ 8.23 (s, 1H), 7.71 (s, 1H), 7.57 (s, 1H), 7.19 (s, 1H), 3.95 (s, 3H), 3.88-3.95 (m, 1H), 3.83 (br d, J = −12 Hz, 1H), 2.66-2.74 (m, 1H), 2.33 (dd, J = 12, 11 Hz, 1H), 1.71-1.79 (m, 1H), 1.40-1.62 (m, 3H), 0.96-1.08 (m, 1H), 0.72 (d, J = 6.8 Hz, 3H), 297.6 |
| 18 | 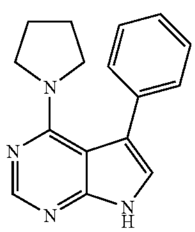 [SMILES: c1ccc(-c2c[nH]c3ncnc(N4CCCC4)c23)cc1] | Ex 6 | 3.10 minutes[3]; 265.1 |
| 19 | 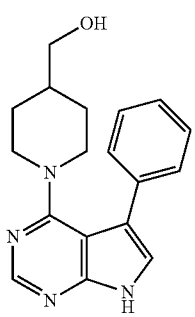 [SMILES: OCC1CCN(c2ncnc3[nH]cc(-c4ccccc4)c23)CC1] | Ex 6 | 12.02 (br s, 1H), 8.29 (s, 1H), 7.45-7.51 (m, 2H), 7.37-7.45 (m, 3H), 7.24-7.30 (m, 1H), 4.39 (t, J = 5.1 Hz, 1H), 3.82 (br d, J = 12.4 Hz, 2H), 3.11-3.18 (m, 2H), 2.61 (br dd, J = 12, 11 Hz, 2H), 1.35-1.46 (m, 3H), 0.88-1.03 (m, 2H); 309.1 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 20 | 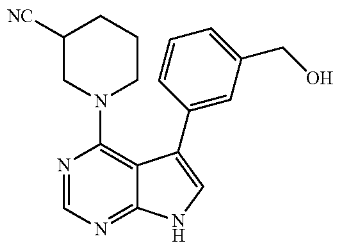 [SMILES: N#CC1CCCN(c2ncnc3[nH]cc(-c4cccc(CO)c4)c23)C1] | Ex 7 | $^1$H NMR (400 MHz, CD$_3$OD) δ 8.34 (s, 1H), 7.50 (br s, 1H), 7.43-7.46 (m, 2H), 7.32-7.35 (m, 1H), 7.30 (s, 1H), 4.70 (s, 2H), 3.64-3.71 (m, 1H), 3.46-3.54 (m, 1H), 3.21-3.27 (m, 1H), 3.09-3.18 (m, 1H), 2.85-2.92 (m, 1H), 1.82-1.91 (m, 1H), 1.67-1.77 (m, 1H), 1.41-1.51 (m, 1H), 1.19-1.31 (m, 1H); 334.3 |
| 21 | 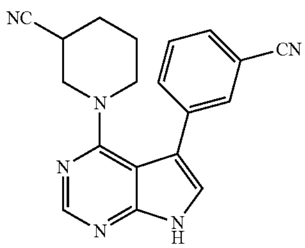 [SMILES: N#Cc1cccc(-c2c[nH]c3ncnc(N4CCCC(C#N)C4)c23)c1] | Ex 7 | $^1$H NMR (400 MHz, CD$_3$OD) δ 8.39 (s, 1H), 7.92 (br s, 1H), 7.87 (br d, J = 7 Hz, 1H), 7.63-7.72 (m, 2H), 7.47 (s, 1H), 3.58-3.70 (m, 2H), 3.06-3.19 (m, 2H), 2.96-3.04 (m, 1H), 1.74-1.92 (m, 2H), 1.38-1.50 (m, 1H), 1.17-1.30 (m, 1H); 329.4 |
| 22 | 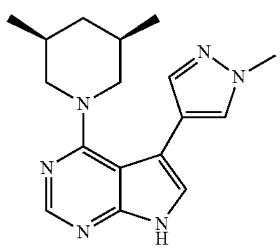 | Ex 7$^2$ | $^1$H NMR (400 MHz, CD$_3$OD) δ 8.23 (s, 1H), 7.69 (s, 1H), 7.55 (s, 1H), 7.18 (s, 1H), 3.94 (s, 3H), 3.89 (br d, J = 12 Hz, 2H), 2.20 (dd, J = 12.0, 11.5 Hz, 2H), 1.73 (br d, J = 12.6 Hz, 1H), 1.48-1.62 (m, 2H), 0.74 (d, J = 7.0 Hz, 6H), 0.65 (dt, J = 12, 12 Hz, 1H); 311.5 |
| 23 | 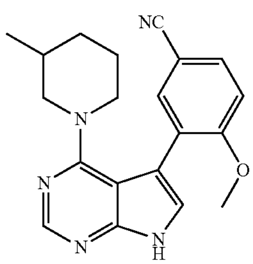 [SMILES: COc1ccc(C#N)cc1-c1c[nH]c2ncnc(N3CCCC(C)C3)c12] | Ex 3[4, 5, 6]; P4 | $^1$H NMR (300 MHz, DMSO-d$_6$), characteristic peaks: δ 12.01 (br s, 1H), 8.26 (s, 1H), 7.81 (dd, J = 8.4, 2.1 Hz, 1H), 7.68 (d, J = 2.1 Hz, 1H), 7.36 (d, J = 2.1 Hz, 1H), 7.26 (d, J = 9.1 Hz, 1H), 3.82 (s, 3H), 3.74-3.84 (m, 1H), 3.57-3.66 (m, 1H), 2.17 (dd, J = 12.5, 11.2 Hz, 1H), 1.56-1.66 (m, 1H), 1.38-1.50 (m, 1H), 1.05-1.24 (m, 2H), 0.80-0.96 (m, 1H), 0.55 (d, J = 6.3 Hz, 3H); 348.2 |
| 24 | 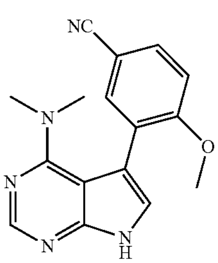 [SMILES: COc1ccc(C#N)cc1-c1c[nH]c2ncnc(N(C)C)c12] | Ex 1[1, 7] | 8.17 (s, 1H), 7.80 (dd, J = 8.5, 2.5 Hz, 1H), 7.70 (d, J = 2.0 Hz, 1H), 7.30 (s, 1H), 7.22 (d, J = 9.0 Hz, 1H), 3.80 (s, 3H), 2.73 (s, 6H); 293.8 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 25 | 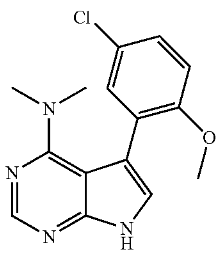 [SMILES: COc1ccc(Cl)cc1-c1c[nH]c2ncnc(N(C)C)c12] | Ex 7[1, 8] | 11.88 (br s, 1H), 8.16 (s, 1H), 7.30-7.35 (m, 2H), 7.25 (d, J = 2.6 Hz, 1H), 7.06 (d, J = 8.5 Hz, 1H), 3.71 (s, 3H), 2.75 (s, 6H); 303.2 |
| 26 | 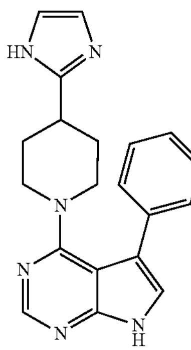 | Method A | 2.07 minutes[9]; 370 |
| 27 | 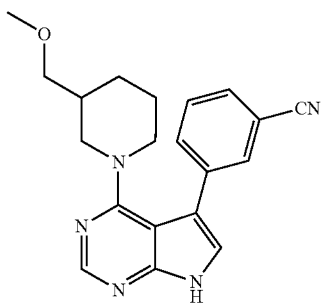 [SMILES: COCC1CCCN(c2ncnc3[nH]cc(-c4cccc(C#N)c4)c23)C1] | Method A | 2.58 minutes[9]; 348 |
| 28 | 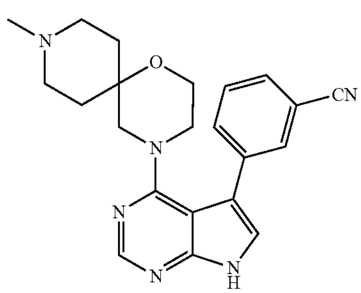 [SMILES: CN1CCC2(CC1)CN(c1ncnc3[nH]cc(-c4cccc(C#N)c4)c13)CCO2] | Ex 6 | 12.29 (br s, 1H), 8.37 (s, 1H), 7.92 (dd, J = 1.5, 1.5 Hz, 1H), 7.86 (ddd, J = 7.5, 1.5, 1.5 Hz, 1H), 7.77 (ddd, J = 7.5, 1.5, 1.5 Hz, 1H), 7.62-7.68 (m, 2H), 3.23-3.28 (m, 2H), 3.19 (s, 2H), 2.95-3.00 (m, 2H), 2.25-2.32 (m, 2H), 2.14-2.23 (m, 2H), 2.13 (s, 3H), 1.74-1.82 (m, 2H), 1.45-1.54 (m, 2H); 389.2 |
| 29 | 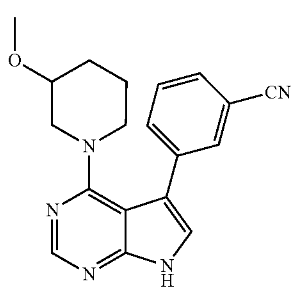 [SMILES: COC1CCCN(c2ncnc3[nH]cc(-c4cccc(C#N)c4)c23)C1] | Method A | 2.46 minutes[9]; 334 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 30 | 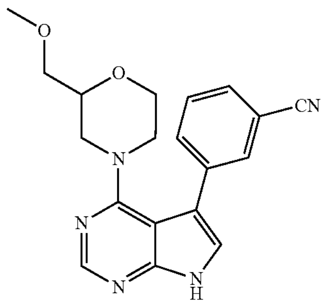 [SMILES: COCC1CN(c2ncnc3[nH]cc(-c4cccc(C#N)c4)c23)CCO1] | Method A | 2.42 minutes$^9$; 350 |
| 31 | 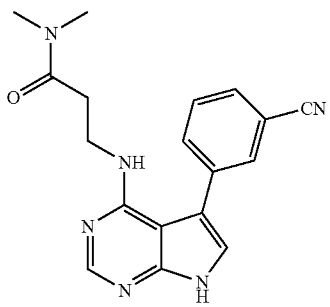 [SMILES: CN(C)C(=O)CCNc1ncnc2[nH]cc(-c3cccc(C#N)c3)c12] | Method A | 2.23 minutes$^9$; 335 |
| 32 | 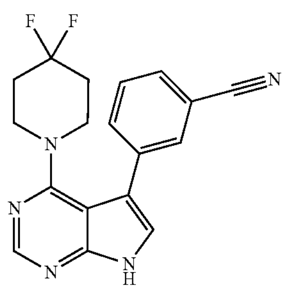 [SMILES: N#Cc1cccc(-c2c[nH]c3ncnc(N4CCC(F)(F)CC4)c23)c1] | Method A | 2.78 minutes$^9$; 340 |
| 33 | 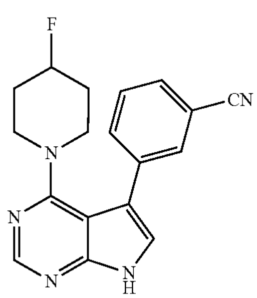 [SMILES: N#Cc1cccc(-c2c[nH]c3ncnc(N4CCC(F)CC4)c23)c1] | Method A | 2.27 minutes$^{10}$; 322 |
| 33A | 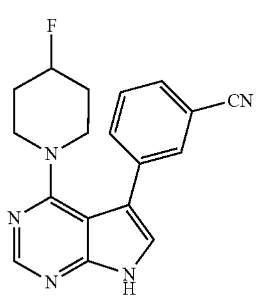 [SMILES: N#Cc1cccc(-c2c[nH]c3ncnc(N4CCC(F)CC4)c23)c1] | Ex 6 | $^1$H NMR (400 MHz, CDCl$_3$) δ 10.65 (br s, 1H), 8.51 (s, 1H), 7.84 (s, 1H), 7.76 (br d, J = 7.5 Hz, 1H), 7.62 (br d, J = 8 Hz, 1H), 7.55 (br dd, J = 8, 7.5 Hz, 1H), 7.24-7.30 (1H, assumed, obscured by solvent peak), 4.75 (br d, J$_{HF}$ = 48 Hz, 1H), 3.32-3.51 (m, 4H), 1.65-1.84 (m, 4H, assumed; partially obscured by water peak); 322.2 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 34 | 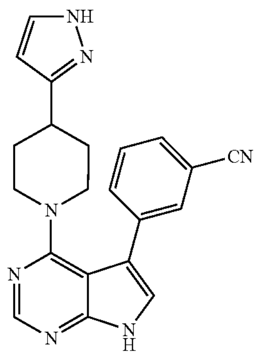 [SMILES: N#Cc1cccc(-c2c[nH]c3ncnc(N4CCC(c5cc[nH]n5)CC4)c23)c1] | Method A | 2.33 minutes[9]; 370 |
| 35 | 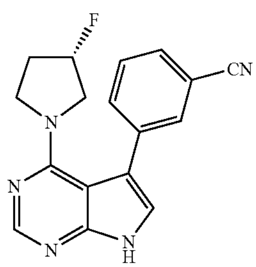 [SMILES: N#Cc1cccc(-c2c[nH]c3ncnc(N4CC[C@H](F)C4)c23)c1] | Method A | 2.33 minutes[9]; 308 |
| 36 | 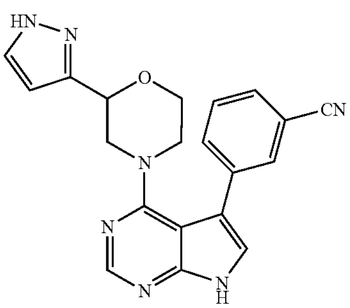 [SMILES: N#Cc1cccc(-c2c[nH]c3ncnc(N4CCOC(c5cc[nH]n5)C4)c23)c1] | Method A | 2.33 minutes[9]; 372 |
| 37 | 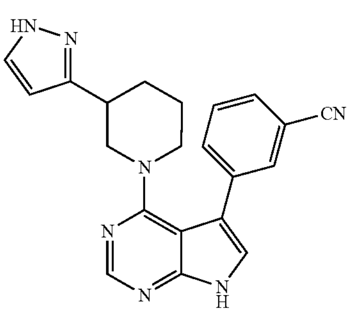 [SMILES: N#Cc1cccc(-c2c[nH]c3ncnc(N4CCCC(c5cc[nH]n5)C4)c23)c1] | Method A | 2.42 minutes[9]; 370 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 38 | 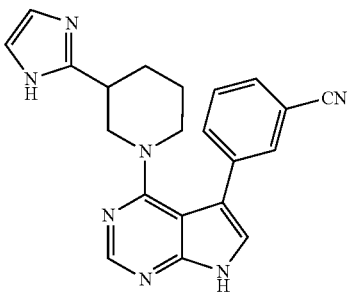 [SMILES: N#Cc1cccc(-c2c[nH]c3ncnc(N4CCCC(c5ncc[nH]5)C4)c23)c1] | Method A | 2.15 minutes$^9$; 370 |
| 39 | 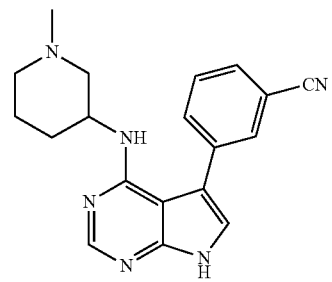 [SMILES: CN1CCCC(Nc2ncnc3[nH]cc(-c4cccc(C#N)c4)c23)C1] | Method A | 2.08 minutes$^9$; 333 |
| 40 | 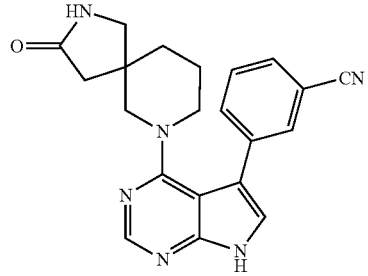 [SMILES: N#Cc1cccc(-c2c[nH]c3ncnc(N4CCCC5(CNC(=O)C5)C4)c23)c1] | Method A | 2.27 minutes$^9$; 373 |
| 41 | 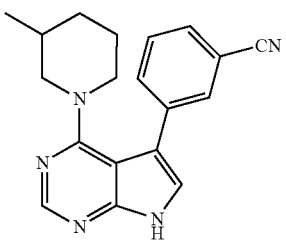  ENT-2 | Ex 6$^{11, 12}$ | $^1$H NMR (400 MHz, CD$_3$OD) δ 8.30 (s, 1H), 7.84 (br s, 1H), 7.81 (br d, J = 7.5 Hz, 1H), 7.66 (br d, J = 7.5 Hz, 1H), 7.61 (dd, J = 8.0, 7.5 Hz, 1H), 7.39 (s, 1H), 3.81 (br d, J = 13.0 Hz, 1H), 3.70 (br d, J = 12.6 Hz, 1H), 2.65 (ddd, J = 12.6, 12.3, 2.8 Hz, 1H), 2.29 (dd, J = 12.6, 11.0 Hz, 1H), 1.65-1.74 (m 1H), 1.47-1.56 (m, 1H), 1.31-1.46 (m, 2H), 0.91-1.04 (m, 1H), 0.64 (d, J = 6.5 Hz, 3H); 318.0 |
| 42 | 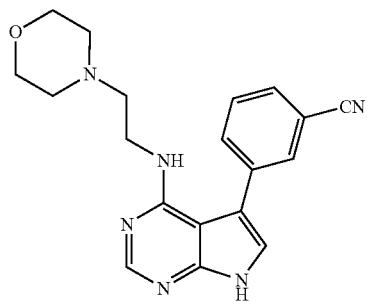 [SMILES: N#Cc1cccc(-c2c[nH]c3ncnc(NCCN4CCOCC4)c23)c1] | Method A | 1.99 minutes$^9$; 349 |

TABLE 1-continued

| Example # | Structure | Method of Preparation; Non-commercial starting materials | ¹H NMR (400 MHz, DMSO-d₆) δ (ppm); Mass spectrum, observed ion m/z (M + H⁺) or HPLC retention time; Mass spectrum m/z (M + H⁺) (unless otherwise indicated) |
|---|---|---|---|
| 43 | 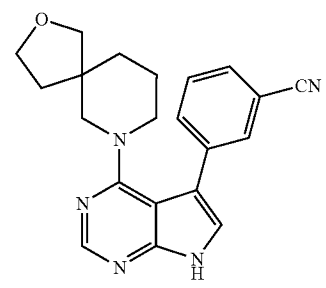 [SMILES: N#Cc1cccc(-c2c[nH]c3ncnc(N4CCCC5(CCOC5)C4)c23)c1] | Method A | 2.47 minutes[9]; 360 |
| 44 | 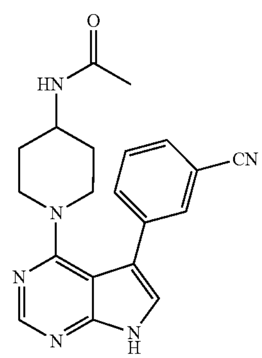 [SMILES: CC(=O)NC1CCN(c2ncnc3[nH]cc(-c4cccc(C#N)c4)c23)CC1] | Method A | 2.13 minutes[9]; 361 |
| 45 | 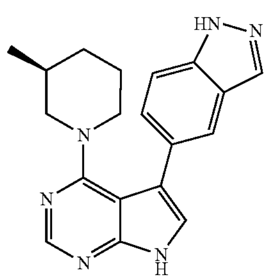 [SMILES: C[C@H]1CCCN(c2ncnc3[nH]cc(-c4ccc5[nH]ncc5c4)c23)C1] | Method B | 2.06 minutes[10]; 333 |
| 46 | 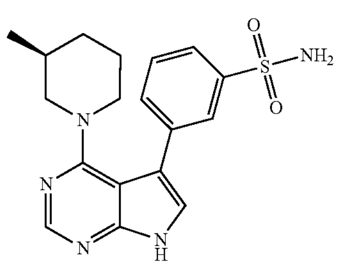 [SMILES: C[C@H]1CCCN(c2ncnc3[nH]cc(-c4cccc(S(N)(=O)=O)c4)c23)C1] | Method B | 2.32 minutes[9]; 372 |
| 47 | 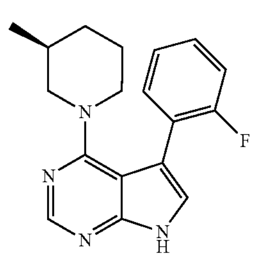 [SMILES: C[C@H]1CCCN(c2ncnc3[nH]cc(-c4ccccc4F)c23)C1] | Method B | 2.53 minutes[10]; 311 |

TABLE 1-continued
| Example # | Structure | Method of Preparation; Non-commercial starting materials | $^1$H NMR (400 MHz, DMSO-$d_6$) δ (ppm); Mass spectrum, observed ion m/z (M + H$^+$) or HPLC retention time; Mass spectrum m/z (M + H$^+$) (unless otherwise indicated) |
|---|---|---|---|
| 48 | 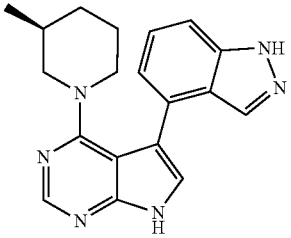 [SMILES: C[C@H]1CCCN(c2ncnc3[nH]cc(-c4cccc5[nH]ncc45)c23)C1] | Method B | 2.15 minutes[10]; 333 |
| 49 | 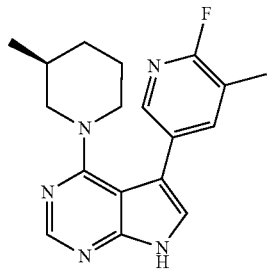 | Method B | 2.39 minutes[10]; 326 |
| 50 | 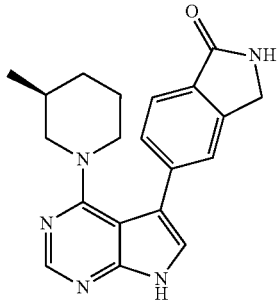 [SMILES: C[C@H]1CCCN(c2ncnc3[nH]cc(-c4ccc5c(c4)CNC5=O)c23)C1] | Method B | 1.86 minutes[10]; 348 |
| 51 | 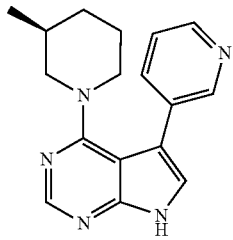 [SMILES: C[C@H]1CCCN(c2ncnc3[nH]cc(-c4cccnc4)c23)C1] | Method B | 2.04 minutes[9]; 294 |
| 52 | 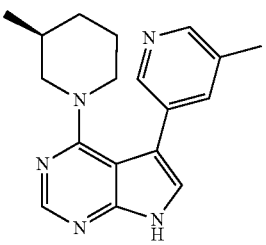 | Method B | 1.69 minutes[10]; 308 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 53 | 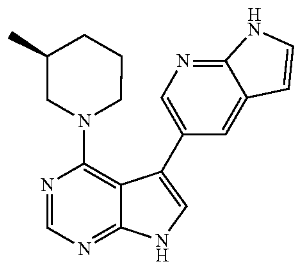 [SMILES: C[C@H]1CCCN(c2ncnc3[nH]cc(-c4cnc5[nH]ccc5c4)c23)C1] | Method B | 2.02 minutes[10]; 333 |
| 54 | 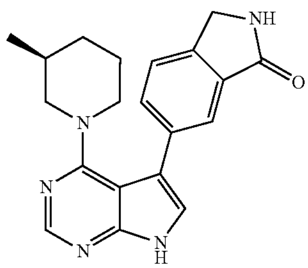 [SMILES: C[C@H]1CCCN(c2ncnc3[nH]cc(-c4ccc5c(c4)C(=O)NC5)c23)C1] | Method B | 1.96 minutes[10]; 348 |
| 55 | 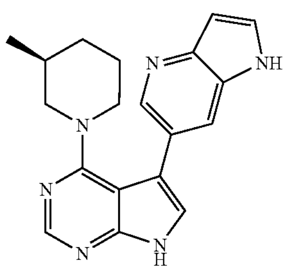 [SMILES: C[C@H]1CCCN(c2ncnc3[nH]cc(-c4cnc5cc[nH]c5c4)c23)C1] | Method B | 1.11 minutes[10]; 333 |
| 56 | 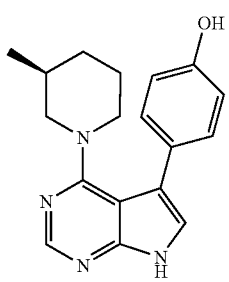 [SMILES: C[C@H]1CCCN(c2ncnc3[nH]cc(-c4ccc(O)cc4)c23)C1] | Method B | 2.11 minutes[10]; 309 |
| 57 | 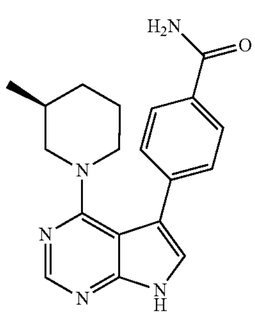 [SMILES: C[C@H]1CCCN(c2ncnc3[nH]cc(-c4ccc(C(N)=O)cc4)c23)C1] | Method B | 2.17 minutes[9]; 336 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 58 | 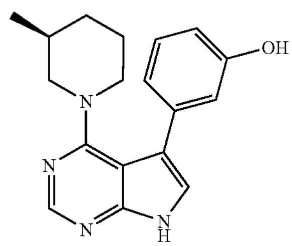 [SMILES: C[C@H]1CCCN(c2ncnc3[nH]cc(-c4cccc(O)c4)c23)C1] | Method B | 2.66 minutes[13]; 309 |
| 59 | 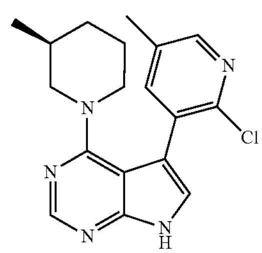 [SMILES: Cc1cnc(Cl)c(-c2c[nH]c3ncnc(N4CCC[C@H](C)C4)c23)c1] | Method B | 2.31 minutes[10]; 342 |
| 60 | 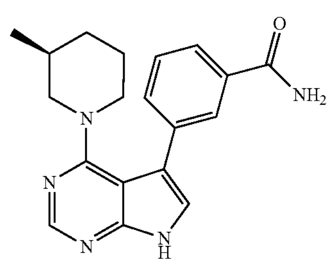 [SMILES: C[C@H]1CCCN(c2ncnc3[nH]cc(-c4cccc(C(N)=O)c4)c23)C1] | Ex 1[7, 14]; P5 | characteristic peaks, 12.09 (br s, 1H), 8.31 (s, 1H), 7.99-8.03 (m, 2H), 7.79 (br d, J = 7.5 Hz, 1H), 7.62 (br d, J = 7.5 Hz, 1H), 7.47-7.52 (m, 2H), 7.36 (br s, 1H), 3.75 (br d, J = 13 Hz, 1H), 3.68 (br d, J = 12 Hz, 1H), 2.21 (dd, J = 12, 11 Hz, 1H), 1.54-1.61 (m, 1H), 1.33-1.43 (m, 2H), 1.19-1.32 (m, 1H), 0.81-0.95 (m, 1H), 0.54 (d, J = 7.0 Hz, 3H); 336.2 |
| 61 | 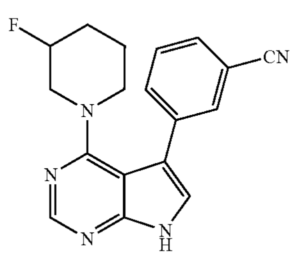 [SMILES: N#Cc1cccc(-c2c[nH]c3ncnc(N4CCCC(F)C4)c23)c1] | Ex 6 | 8.35 (s, 1H), 7.92 (br s, 1H), 7.82 (br d, J = 8 Hz, 1H), 7.74 (br d, J = 7.5 Hz, 1H), 7.60-7.66 (m, 2H), 4.60 (br d, J$_{HF}$ = 47 Hz, 1H), 3.26-3.4 (m, 2H, assumed; partially obscured by water peak), 3.16-3.25 (m, 1H), 3.01-3.10 (m, 1H), 1.71-1.87 (m, 1H), 1.59-1.70 (m, 1H), 1.48-1.58 (m, 1H), 1.11-1.21 (m, 1H); 322.2 |
| 62 | 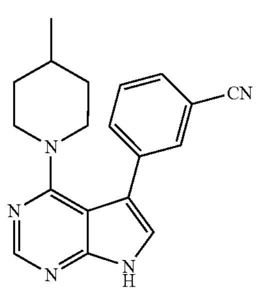 [SMILES: CC1CCN(c2ncnc3[nH]cc(-c4cccc(C#N)c4)c23)CC1] | Ex 6 | 12.83 (br s, 1H), 8.44 (s, 1H), 7.96 (br s, 1H), 7.83 (br d, J = 8 Hz, 1H), 7.80 (br d, J = 8 Hz, 1H), 7.75 (d, J = 2.5 Hz, 1H), 7.67 (dd, J = 8.0, 7.5 Hz, 1H), 3.75 (br d, J = 13 Hz, 2H), 2.84 (br dd, J = 13, 12 Hz, 2H), 1.42-1.55 (m, 3H), 0.91-1.03 (m, 2H), 0.83 (d, J = 6.0 Hz, 3H); 318.2 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 63 | 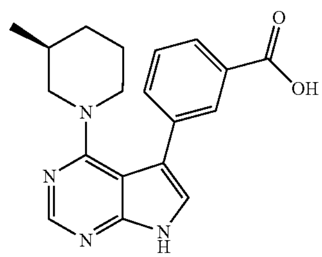 [SMILES: C[C@H]1CCCN(c2ncnc3[nH]cc(-c4cccc(C(=O)O)c4)c23)C1] | Ex 1$^{7, 14}$; P5 | $^1$H NMR (400 MHz, CDCl$_3$), characteristic peaks: δ 8.42 (s, 1H), 8.28-8.31 (m, 1H), 8.09 (br d, J = 7 Hz, 1H), 7.69 (br d, J = 7 Hz, 1H), 7.52-7.58 (m, 1H), 3.90-4.03 (m, 2H), 2.63-2.73 (m, 1H), 2.32-2.41 (m, 1H), 0.65 (d, J = 6 Hz, 3H); 337.0 |
| 64 | 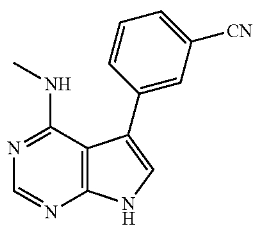 [SMILES: CNc1ncnc2[nH]cc(-c3cccc(C#N)c3)c12] | Ex 6 | 11.94 (br s, 1H), 8.22 (s, 1H), 7.86 (dd, J = 1.5, 1.5 Hz, 1H), 7.73-7.78 (m, 2H), 7.64 (dd, J = 7.8, 7.5 Hz, 1H), 7.35 (s, 1H), 5.76 (q, J = 4.6 Hz, 1H), 2.90 (d, J = 4.8 Hz, 3H); 250.1 |
| 65 | 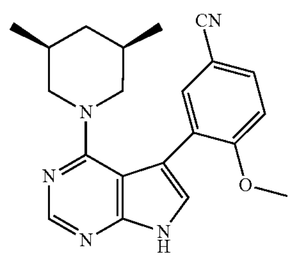 | Ex 4 | $^1$H NMR (400 MHz, CD$_3$OD) δ 8.24 (s, 1H), 7.72 (dd, J = 8.7, 2.1 Hz, 1H), 7.65 (d, J = 2.0 Hz, 1H), 7.28 (s, 1H), 7.23 (d, J = 8.8 Hz, 1H), 3.87 (s, 3H), 3.83 (br d, J = 12 Hz, 2H), 2.13 (dd, J = 12.0, 12.0 Hz, 2H), 1.68 (br d, J = 13 Hz, 1H), 1.25-1.37 (m, 2H), 0.68 (d, J = 6.5 Hz, 6H), 0.60 (dt, J = 12, 12 Hz, 1H); 362.1 |
| 66 | 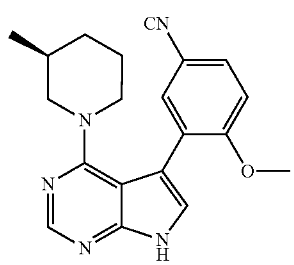 | Ex 1$^{7, 14}$; P5 | $^1$H NMR (400 MHz, CDCl$_3$) δ 10.70 (br s, 1H), 8.42 (s, 1H), 7.61-7.67 (m, 2H), 7.25-7.29 (m, 1H, assumed; partially obscured by solvent peak), 7.03 (d, J = 8.5 Hz, 1H), 3.89 (s, 3H), 3.87-3.96 (m, 1H), 3.81 (br d, J = 13 Hz, 1H), 2.61 (ddd, J = 13, 13, 3 Hz, 1H), 2.29 (dd, J = 12.6, 11.0 Hz, 1H), 1.66-1.75 (m, 1H), 1.45-1.54 (m 1H), 1.18-1.37 (m, 2H), 0.89-1.00 (m, 1H), 0.65 (d, J = 7.0 Hz, 3H); 348.2 |
| 67 | 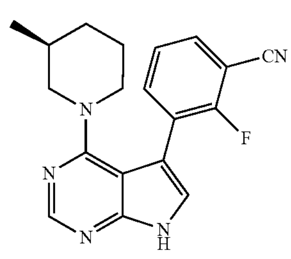 [SMILES: C[C@H]1CCCN(c2ncnc3[nH]cc(-c4cccc(C#N)c4F)c23)C1] | Ex 1$^{7, 14}$; P5 | $^1$H NMR (400 MHz, CDCl$_3$), characteristic peaks: δ 10.36 (br s, 1H), 8.45 (s, 1H), 7.70 (ddd, J = 7.5, 7.5, 1.8 Hz, 1H), 7.59 (ddd, J = 7.8, 5.5, 1.8 Hz, 1H), 7.31-7.37 (m, 2H), 3.76-3.88 (m, 2H), 2.66 (ddd, J = 13, 12, 2.5 Hz, 1H), 2.36 (dd, J = 12.7, 11.2 Hz, 1H), 1.46-1.54 (m, 1H), 1.35-1.45 (m, 1H), 1.22-1.34 (m, 1H), 0.92-1.03 (m, 1H), 0.69 (d, J = 6.5 Hz, 3H); 336.2 |
| 68 | 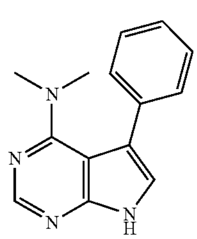 [SMILES: CN(C)c1ncnc2[nH]cc(-c3ccccc3)c12] | Ex 1$^{1, 7}$; C3 | $^1$H NMR (400 MHz, CDCl$_3$) δ 8.39 (s, 1H), 7.48 (br d, J = 8 Hz, 2H), 7.41 (br dd, J = 8, 8 Hz, 2H), 7.30-7.34 (m, 1H), 7.09 (s, 1H), 2.84 (s, 6H); 239.1 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 69 | 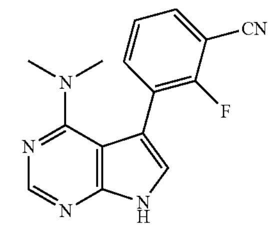 [SMILES: CN(C)c1ncnc2[nH]cc(-c3cccc(C#N)c3F)c12] | Ex 1[1, 7]; C3 | 12.24 (br s, 1H), 8.25 (s, 1H), 7.84-7.91 (m, 1H), 7.75-7.82 (m, 1H), 7.51 (br s, 1H), 7.47 (dd, J = 8.0, 7.5 Hz, 1H), 2.73 (s, 6H); 282.2 |
| 70 | 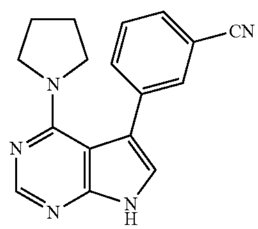 [SMILES: N#Cc1cccc(-c2c[nH]c3ncnc(N4CCCC4)c23)c1] | Ex 5 | 8.35 (s, 1H), 7.92 (s, 1H), 7.85 (d, J = 7.5 Hz, 1H), 7.76 (d, J = 7.5 Hz, 1H), 7.63 (dd, J = 8.0, 7.5 Hz, 1H), 7.57 (br s, 1H), 3.19-3.3 (br m, 4H), 1.70-1.79 (br m, 4H); 290.1 |
| 71 | ENT-2 | Ex 5[15, 12] | $^1$H NMR (400 MHz, CD$_3$OD) δ 8.15 (s, 1H), 7.78-7.80 (m, 1H), 7.73 (ddd, J = 7.8, 1.6, 1.3 Hz, 1H), 7.69 (ddd, J = 7.8, 1.5, 1.2 Hz, 1H), 7.58 (dd, J = 7.8, 7.8 Hz, 1H), 7.19 (s, 1H), 3.36-3.44 (m, 2H), 3.21-3.30 (m, 1H), 2.75 (dd, J = 10.4, 8.2 Hz, 1H), 2.05-2.15 (m, 1H), 1.82-1.91 (m, 1H), 1.30-1.41 (m, 1H), 0.90 (d, J = 6.5 Hz, 3H); 304.1 |
| 72 | 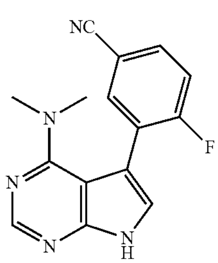 [SMILES: CN(C)c1ncnc2[nH]cc(-c3cc(C#N)ccc3F)c12] | Ex 1[1, 7]; C3 | $^1$H NMR (400 MHz, CD$_3$OD) δ 8.23 (s, 1H), 7.87 (dd, J = 6.9, 2.1 Hz, 1H), 7.76 (ddd, J = 8.5, 4.5, 2.3 Hz, 1H), 7.37-7.42 (m, 2H), 2.85 (s, 6H); 282.1 |
| 73 | 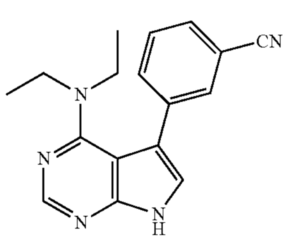 [SMILES: CCN(CC)c1ncnc2[nH]cc(-c3cccc(C#N)c3)c12] | Ex 6 | $^1$H NMR (400 MHz, DMSO-d$_6$ + D$_2$O) δ 8.29 (s, 1H) 7.88-7.90 (m, 1H), 7.84 (br d, J = 8.5 Hz, 1H), 7.71 (br d, J = 8.0 Hz, 1H), 7.61 (dd, J = 8.0, 7.5 Hz, 1H), 7.56 (s, 1H), 3.20 (q, J = 7.0 Hz, 4H), 0.88 (t, J = 7.0 Hz, 6H); 292.0 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 74 | ENT-1 | Ex 6[16, 17] | $^1$H NMR (400 MHz, CDCl$_3$) δ 11.17 (br s, 1H), 8.52 (s, 1H), 7.83 (br s, 1H), 7.76 (br d, J = 8.0 Hz, 1H), 7.64 (br d, J = 7.5 Hz, 1H), 7.57 (dd, J = 8.0, 7.5 Hz, 1H), 7.29 (s, 1H), 3.73-3.84 (m, 2H), 3.63 (br d, J = 13.6 Hz, 1H), 3.51-3.59 (m, 1H), 3.47 (ddd, J = 12.0, 11.5, 2.5 Hz, 1H), 3.30 (s, 3H), 3.20-3.30 (m, 2H), 2.96 (ddd, J = 13, 12, 3.5 Hz, 1H), 2.79 (dd, J = 12.8, 10.8 Hz, 1H); 350.2 |
| 75 | 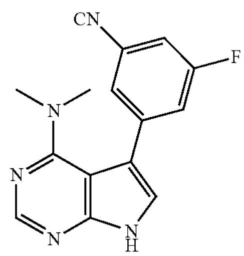 | Ex 1[1, 7]; C3 | 8.31 (s, 1H), 7.81-7.83 (m, 1H), 7.71-7.76 (m, 1H), 7.67 (s, 1H), 7.64-7.69 (m, 1H), 2.76 (s, 6H); 282.1 |
| 76 | ENT-2 | Ex 6[18, 12] | $^1$H NMR (400 MHz, CDCl$_3$), characteristic peaks: δ 8.51 (br s, 1H), 7.84 (s, 1H), 7.77 (br d, J = 7.5 Hz, 1H), 7.62 (br d, J = 8 Hz, 1H), 7.56 (dd, J = 8.0, 7.5 Hz, 1H), 7.51 (br s, 1H), 6.06 (br s, 1H), 4.55 (br d, J = 10 Hz, 1H), 3.99 (br d, J = 13 Hz, 1H), 3.84-3.91 (m, 1H), 3.60-3.75 (m, 2H), 3.02-3.13 (m, 2H); 372.1 |
| 77 | ENT-1 | Ex 5[15, 17] | $^1$H NMR (400 MHz, CD$_3$OD) δ 8.19 (s, 1H), 7.82 (br s, 1H), 7.71-7.77 (m, 2H), 7.61 (dd, J = 7.5, 7.5 Hz, 1H), 7.29 (s, 1H), 3.40-3.49 (m, 2H), 3.24-3.3 (m, 1H, assumed; partially obscured by solvent peak), 2.76 (dd, J = 9.5, 9.0 Hz, 1H), 2.10-2.22 (m, 1H), 1.88-1.98 (m, 1H), 1.36-1.48 (m, 1H), 0.91 (d, J = 6.5 Hz, 3H), 304.0 |
| 78 | 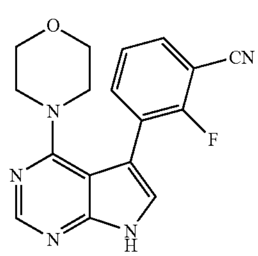 | Ex 1[7] | 8.38 (s, 1H), 7.80-7.90 (m, 2H), 7.64 (d, J = 1.0 Hz, 1H), 7.52 (dd, J = 8.0, 7.5 Hz, 1H), 3.35-3.41 (m, 4H), 3.09-3.15 (m, 4H); 323.9 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 79 | 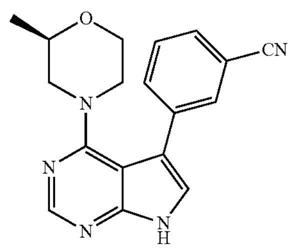 [SMILES: C[C@@H]1CN(c2ncnc3[nH]cc(-c4cccc(C#N)c4)c23)CCO1] | Ex 6 | $^1$H NMR (400 MHz, CDCl$_3$) δ 11.02 (br s, 1H), 8.53 (s, 1H), 7.85 (s, 1H), 7.78 (d, J = 7.0 Hz, 1H), 7.53-7.68 (m, 2H), 7.30 (s, 1H), 3.57-3.77 (m, 3H), 3.39-3.54 (m, 2H), 2.92 (br dd, J = 12, 12 Hz, 1H), 2.59 (dd, J = 11.5, 11.0 Hz, 1H), 0.98 (d, J = 6.0 Hz, 3H); 319.9 |
| 80 | 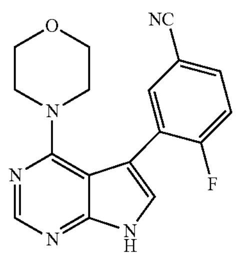 [SMILES: N#Cc1ccc(F)c(-c2c[nH]c3ncnc(N4CCOCC4)c23)c1] | Ex1$^7$ | $^1$H NMR (400 MHz, DMSO-d$_6$ + D$_2$O) δ 8.35 (s, 1H), 7.97 (dd, J = 7.0, 2.0 Hz, 1H), 7.81-7.87 (m, 1H), 7.61 (s, 1H), 7.53 (dd, J = 9.0, 9.0 Hz, 1H), 3.36-3.42 (m, 4H), 3.08-3.15 (m, 4H); 324.2 |
| 81 | 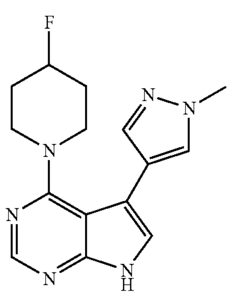 [SMILES: Cn1cc(-c2c[nH]c3ncnc(N4CCC(F)CC4)c23)cn1] | Ex 4$^{2, 4}$ | $^1$H NMR (400 MHz, DMSO-d$_6$ + D$_2$O) δ 8.36 (s, 1H), 7.81 (s, 1H), 7.54 (s, 1H), 7.46 (s, 1H), 4.84 (br d, J$_{HF}$ = 48 Hz, 1H), 3.85 (s, 3H), 3.43-3.58 (m, 4H), 1.58-1.88 (m, 4H); 301.1 |
| 82 | 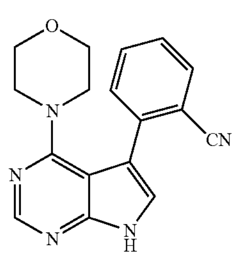 [SMILES: N#Cc1ccccc1-c1c[nH]c2ncnc(N3CCOCC3)c12] | Method C | 2.27 minutes$^9$; 306 |
| 83 | 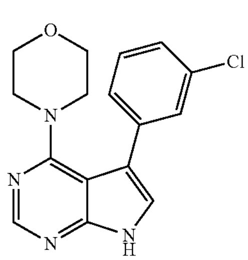 [SMILES: Clc1cccc(-c2c[nH]c3ncnc(N4CCOCC4)c23)c1] | Method C | 2.39 minutes$^{10}$; 315 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 84 | 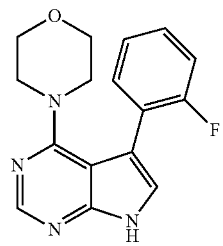 [SMILES: Fc1ccccc1-c1c[nH]c2ncnc(N3CCOCC3)c12] | Method C | 2.39 minutes[9]; 299 |
| 85 | 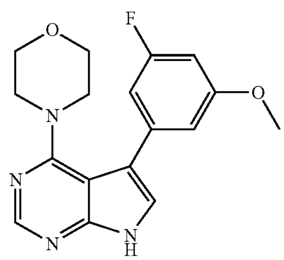 [SMILES: COc1cc(F)cc(-c2c[nH]c3ncnc(N4CCOCC4)c23)c1] | Method C | 2.54 minutes[9]; 329 |
| 86 | 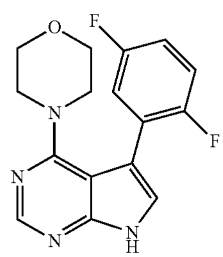 [SMILES: Fc1ccc(F)c(-c2c[nH]c3ncnc(N4CCOCC4)c23)c1] | Method C | 2.46 minutes[9]; 317 |
| 87 | 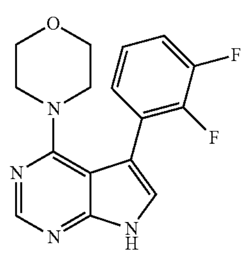 [SMILES: Fc1cccc(-c2c[nH]c3ncnc(N4CCOCC4)c23)c1F] | Method C | 2.47 minutes[9]; 317 |
| 88 | 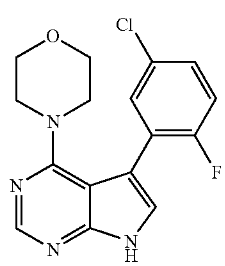 [SMILES: Fc1ccc(Cl)cc1-c1c[nH]c2ncnc(N3CCOCC3)c12] | Method C | 2.38 minutes[10]; 333 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 89 | 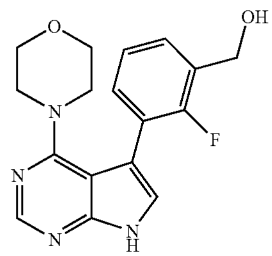 [SMILES: OCc1cccc(-c2c[nH]c3ncnc(N4CCOCC4)c23)c1F] | Method C | 2.07 minutes[9]; 329 |
| 90 | 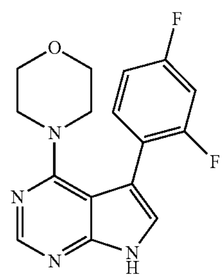 [SMILES: Fc1ccc(-c2c[nH]c3ncnc(N4CCOCC4)c23)c(F)c1] | Method C | 2.46 minutes[9]; 317 |
| 91 | 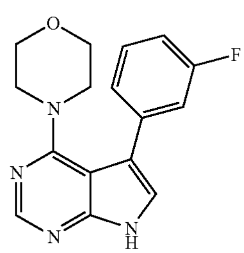 [SMILES: Fc1cccc(-c2c[nH]c3ncnc(N4CCOCC4)c23)c1] | Method C | 2.46 minutes[9]; 299 |
| 92 | 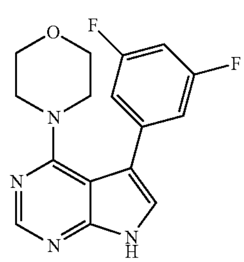 [SMILES: Fc1cc(F)cc(-c2c[nH]c3ncnc(N4CCOCC4)c23)c1] | Method C | 2.57 minutes[9]; 317 |
| 93 | 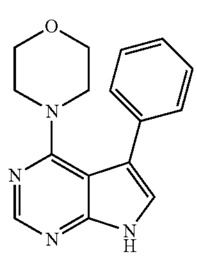 [SMILES: c1ccc(-c2c[nH]c3ncnc(N4CCOCC4)c23)cc1] | Method C | 2.40 minutes[9]; 281 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 94 | 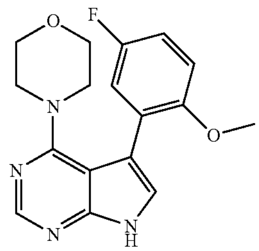 [SMILES: COc1ccc(F)cc1-c1c[nH]c2ncnc(N3CCOCC3)c12] | Method C | 2.41 minutes[9]; 329 |
| 95 | 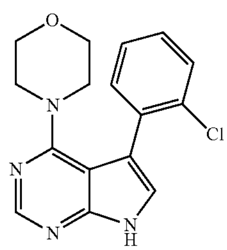 [SMILES: Clc1ccccc1-c1c[nH]c2ncnc(N3CCOCC3)c12] | Method C | 2.46 minutes[9]; 315 |
| 96 | 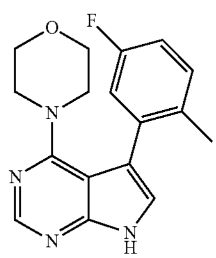 [SMILES: Cc1ccc(F)cc1-c1c[nH]c2ncnc(N3CCOCC3)c12] | Method C | 2.51 minutes[9]; 313 |
| 97 | 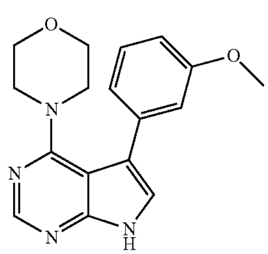 [SMILES: COc1cccc(-c2c[nH]c3ncnc(N4CCOCC4)c23)c1] | Method C | 2.42 minutes[9]; 311 |
| 98 | 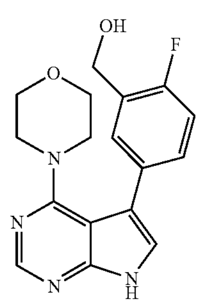 [SMILES: OCc1cc(-c2c[nH]c3ncnc(N4CCOCC4)c23)ccc1F] | Method C | 2.18 minutes[9]; 329 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 99 | 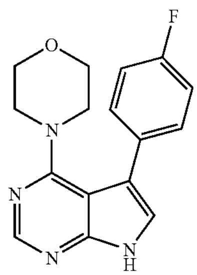 [SMILES: Fc1ccc(-c2c[nH]c3ncnc(N4CCOCC4)c23)cc1] | Method C | 2.44 minutes[9]; 299 |
| 100 | 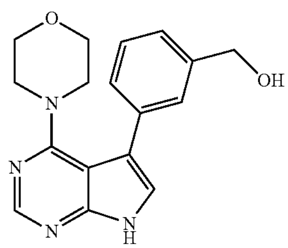 [SMILES: OCc1cccc(-c2c[nH]c3ncnc(N4CCOCC4)c23)c1] | Method C | 2.11 minutes[9]; 311 |
| 101 | 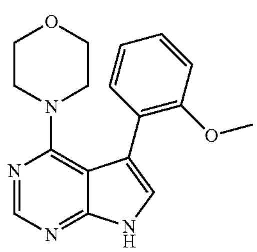 [SMILES: COc1ccccc1-c1c[nH]c2ncnc(N3CCOCC3)c12] | Method C | 2.36 minutes[9]; 311 |
| 102 | 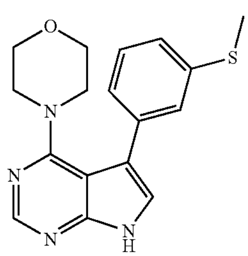 [SMILES: CSc1cccc(-c2c[nH]c3ncnc(N4CCOCC4)c23)c1] | Method C | 2.34 minutes[9]; 327 |
| 103 | 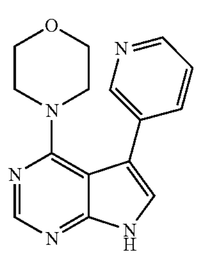 [SMILES: c1cncc(-c2c[nH]c3ncnc(N4CCOCC4)c23)c1] | Method C | 1.44 minutes[9]; 282 |

TABLE 1-continued

| Example # | Structure | Method of Preparation; Non-commercial starting materials | $^1$H NMR (400 MHz, DMSO-$d_6$) δ (ppm); Mass spectrum, observed ion m/z (M + H$^+$) or HPLC retention time; Mass spectrum m/z (M + H$^+$) (unless otherwise indicated) |
|---|---|---|---|
| 104 | 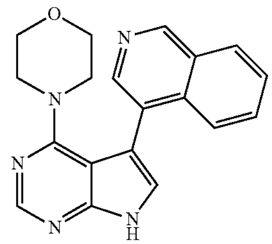 [SMILES: c1ccc2c(-c3c[nH]c4ncnc(N5CCOCC5)c34)cncc2c1] | Method C | 1.96 minutes[9]; 332 |
| 105 | 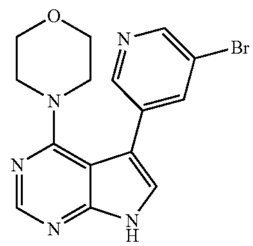 [SMILES: Brc1cncc(-c2c[nH]c3ncnc(N4CCOCC4)c23)c1] | Method C | 2.34 minutes[9]; 360 |
| 106 | 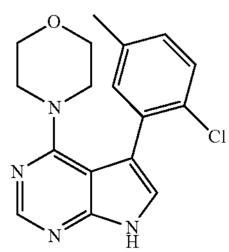 [SMILES: Cc1ccc(Cl)c(-c2c[nH]c3ncnc(N4CCOCC4)c23)c1] | Method C | 2.14 minutes[10]; 329 |
| 107 | 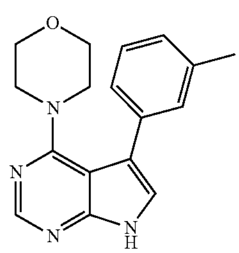 [SMILES: Cc1cccc(-c2c[nH]c3ncnc(N4CCOCC4)c23)c1] | Method C | 2.30 minutes[9]; 295 |
| 108 | 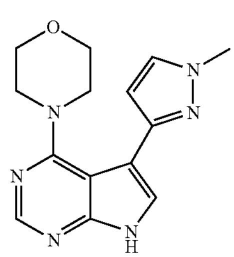 [SMILES: Cn1ccc(-c2c[nH]c3ncnc(N4CCOCC4)c23)n1] | Ex 3[19] | $^1$H NMR (400 MHz, CDCl3) δ 9.70 (br s, 1H), 8.45 (s, 1H), 7.43 (d, J = 2.0 Hz, 1H), 7.33 (d, J = 2.0 Hz, 1H), 6.43 (d, J = 2.0 Hz, 1H), 3.99 (s, 3H), 3.66 (dd, J = 4.8, 4.8 Hz, 4H), 3.42 (dd, J = 4.9, 4.4 Hz, 4H); 285.2 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 109 | 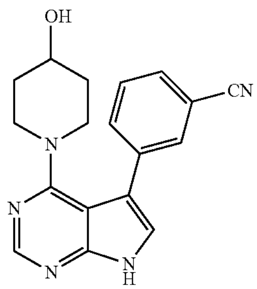 [SMILES: N#Cc1cccc(-c2c[nH]c3ncnc(N4CCC(O)CC4)c23)c1] | Ex 5 | $^1$H NMR (400 MHz, CDCl$_3$), characteristic peaks: δ 10.64 (br s, 1H), 8.50 (s, 1H), 7.84-7.86 (m, 1H), 7.77 (ddd, J = 7.7, 1.8, 1.4 Hz, 1H), 7.61 (ddd, half of ABXY pattern, J = 7.8, 1.5, 1.5 Hz, 1H), 7.55 (dd, half of ABX pattern, J = 7.8, 7.8 Hz, 1H), 3.77-3.85 (m, 1H), 3.67-3.76 (m, 2H), 3.03 (ddd, J = 13.2, 9.8, 3.0 Hz, 2H), 1.71-1.80 (m, 2H), 1.35-1.46 (m, 2H); 319.8 |
| 110 | 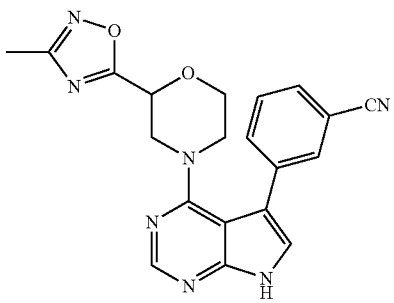 [SMILES: Cc1noc(C2CN(c3ncnc4[nH]cc(-c5cccc(C#N)c5)c34)CCO2)n1] | Ex 5 | characteristic peaks: 12.35 (br s, 1H), 8.43 (s, 1H), 8.01 (br s, 1H), 7.69-7.81 (m, 3H), 7.59 (dd, J = 7.5, 7.5 Hz, 1H), 4.94 (br d, J = 8 Hz, 1H), 3.91 (br d, J = 13.5 Hz, 1H), 3.62-3.70 (m, 1H), 3.43-3.51 (m, 1H), 2.88-2.97 (m, 1H), 2.35 (s, 3H); 388.2 |
| 111 | 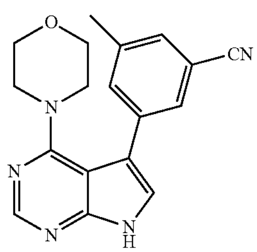 [SMILES: Cc1cc(C#N)cc(-c2c[nH]c3ncnc(N4CCOCC4)c23)c1] | Ex 3 | 8.39 (s, 1H), 7.81 (br s, 1H), 7.71 (br s, 1H), 7.68 (s, 1H), 7.57 (br s, 1H), 3.46 (dd, J = 4.5, 4.5 Hz, 4H), 3.10-3.16 (m, 4H), 2.43 (s, 3H); 320.2 |
| 112 | 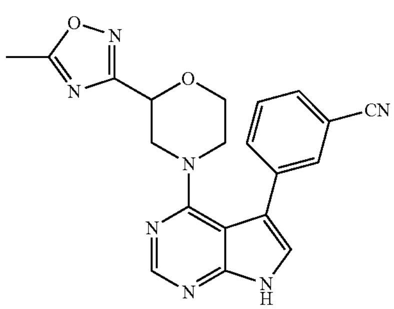 [SMILES: Cc1nc(C2CN(c3ncnc4[nH]cc(-c5cccc(C#N)c5)c34)CCO2)no1] | Ex 5[20] | characteristic peaks: 8.43 (s, 1H), 8.00 (br s, 1H), 7.85 (br d, J = 8.0 Hz, 1H), 7.75 (br d, J = 7.5 Hz, 1H), 7.71 (s, 1H), 7.65 (dd, J = 7.5, 7.5 Hz, 1H), 4.65-4.70 (m, 1H), 3.82-3.88 (m, 1H), 3.68-3.75 (m, 1H), 3.43-3.51 (m, 1H), 3.19 (dd, J = 13, 10 Hz, 1H), 2.85-2.94 (m, 1H), 2.57 (s, 3H); 388.2 |
| 113 | 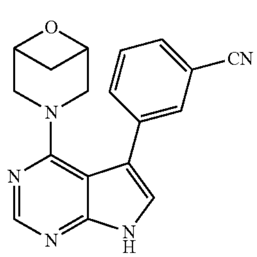 [SMILES: N#Cc1cccc(-c2c[nH]c3ncnc(N4CC5CC(C4)O5)c23)c1] | Ex 5 | 12.21 (br s, 1H), 8.32 (s, 1H), 7.92-7.94 (m, 1H), 7.81 (br d, J = 8 Hz, 1H), 7.75 (br d, J = 8 Hz, 1H), 7.60 (dd, J = 8.0, 7.5 Hz, 1H), 7.55 (d, J = 2.5 Hz, 1H), 4.36 (br d, J = 6.0 Hz, 2H), 3.72 (d, J = 12.6 Hz, 2H), 3.43 (d, J = 12.6 Hz, 2H), 2.91-2.98 (m, 1H), 1.89 (d, J = 8.5 Hz, 1H); 318.1 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 114 | 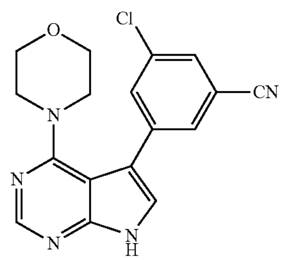 [SMILES: N#Cc1cc(Cl)cc(-c2c[nH]c3ncnc(N4CCOCC4)c23)c1] | Ex 3 | 8.41 (s, 1H), 8.04 (br s, 1H), 7.97 (br s, 1H), 7.90 (br s, 1H), 7.83 (s, 1H), 3.49-3.56 (m, 4H), 3.10-3.17 (m, 4H); 340.1 |
| 115 | 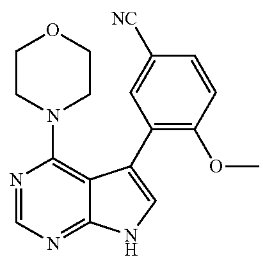 [SMILES: COc1ccc(C#N)cc1-c1c[nH]c2ncnc(N3CCOCC3)c12] | Ex 3 | 8.33 (s, 1H), 7.82 (dd, J = 8.5, 2.0 Hz, 1H), 7.73 (d, J = 2.0 Hz, 1H), 7.48 (s, 1H), 7.28 (d, J = 9.0 Hz, 1H), 3.85 (s, 3H), 3.3-3.38 (m, 4H, assumed; partially obscured by water peak), 3.08-3.15 (m, 4H); 336.2 |
| 116 | 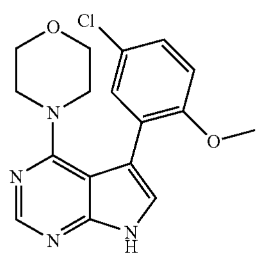 [SMILES: COc1ccc(Cl)cc1-c1c[nH]c2ncnc(N3CCOCC3)c12] | Ex 3 | $^1$H NMR (400 MHz, DMSO-d$_6$ + D$_2$O) δ 8.29 (s, 1H), 7.41 (s, 1H), 7.33 (dd, half of ABX pattern, J = 8.5, 2.8 Hz, 1H), 7.30 (d, half of AB quartet, J = 2.5 Hz, 1H), 7.10 (d, J = 8.5 Hz, 1H), 3.74 (s, 3H), 3.33-3.39 (m, 4H), 3.08-3.14 (m, 4H); 345.2 |
| 117 | 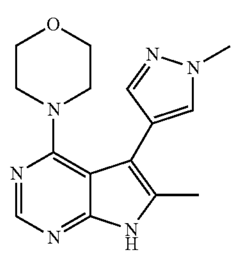 [SMILES: Cc1[nH]c2ncnc(N3CCOCC3)c2c1-c1cnn(C)c1] | Ex 2$^2$ | 11.89 (br s, 1H), 8.25 (s, 1H), 7.74 (s, 1H), 7.48 (s, 1H), 3.90 (s, 3H), 3.43-3.49 (m, 4H), 3.08-3.15 (m, 4H), 2.31 (s, 3H); 299.1 |
| 118 | 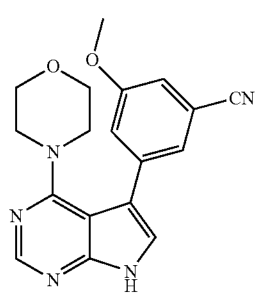 [SMILES: COc1cc(C#N)cc(-c2c[nH]c3ncnc(N4CCOCC4)c23)c1] | Ex 3 | $^1$H NMR (400 MHz, DMSO-d$_6$ + D$_2$O) δ 8.36 (s, 1H), 7.67 (s, 1H), 7.54-7.57 (m, 1H), 7.39-7.42 (m, 1H), 7.30-7.33 (m, 1H), 3.86 (s, 3H), 3.43-3.50 (m, 4H), 3.10-3.16 (m, 4H); 335.9 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 119 | 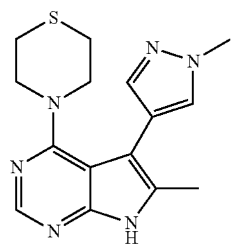 [SMILES: Cc1[nH]c2ncnc(N3CCSCC3)c2c1-c1cnn(C)c1] | Method D$^{21}$; P6 | 2.06 minutes$^9$; 301 |
| 120 | 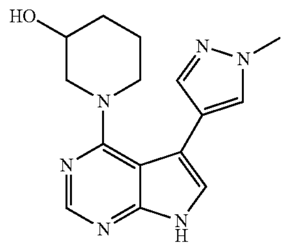 [SMILES: Cn1cc(-c2c[nH]c3ncnc(N4CCCC(O)C4)c23)cn1] | Method D$^{21}$; P6 | 1.90 minutes$^{13}$; 299 |
| 121 | 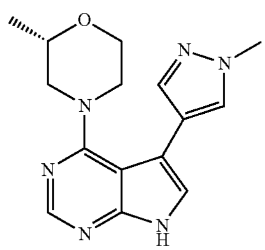 | Method D$^{21}$; P6 | 1.96 minutes$^9$; 299 |
| 122 | 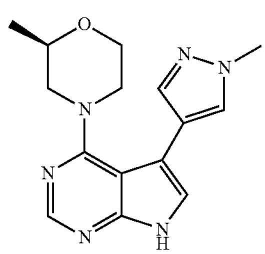 | Method D$^{21}$; P6 | 1.96 minutes$^9$; 299 |
| 123 | 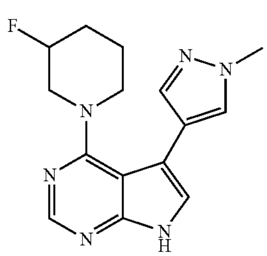 [SMILES: Cn1cc(-c2c[nH]c3ncnc(N4CCCC(F)C4)c23)cn1] | Method D$^{21}$; P6 | 2.02 minutes$^9$; 301 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 124 | 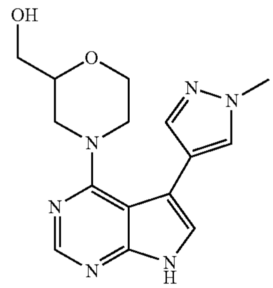 [SMILES: Cn1cc(-c2c[nH]c3ncnc(N4CCOC(CO)C4)c23)cn1] | Method D[21]; P6 | 1.80 minutes[13]; 315 |
| 125 | 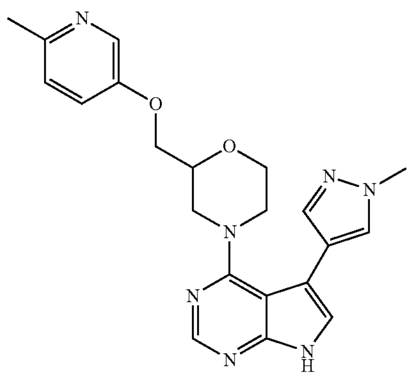 | Method D[21]; P6[22] | 1.89 minutes[9]; 406 |
| 126 | 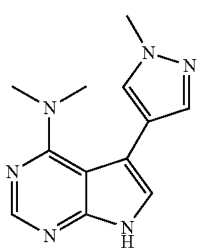 [SMILES: CN(C)c1ncnc2[nH]cc(-c3cnn(C)c3)c12] | Method D[21]; P6[22] | 1.76 minutes[9]; 243 |
| 127 | 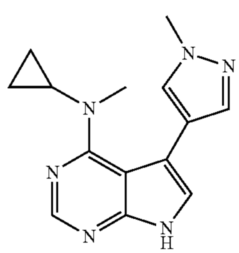 [SMILES: CN(c1ncnc2[nH]cc(-c3cnn(C)c3)c12)C1CC1] | Method D[21]; P6[22] | 1.92 minutes[9]; 269 |
| 128 | 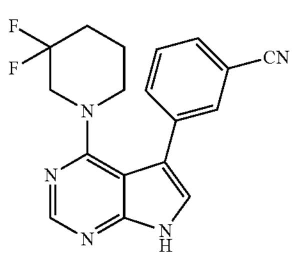 [SMILES: N#Cc1cccc(-c2c[nH]c3ncnc(N4CCCC(F)(F)C4)c23)c1] | Method D; C14 | 2.49 minutes[13]; 340 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 129 | 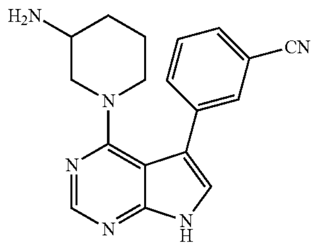 [SMILES: N#Cc1cccc(-c2c[nH]c3ncnc(N4CCCC(N)C4)c23)c1] | Method D; C14 | 2.05 minutes[13]; 319 |
| 130 | 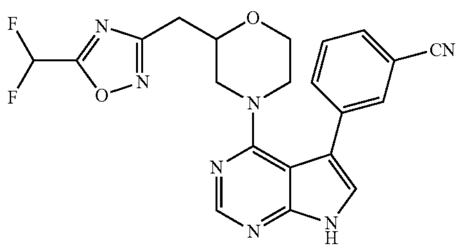 [SMILES: N#Cc1cccc(-c2c[nH]c3ncnc(N4CCOC(Cc5noc(C(F)F)n5)C4)c23)c1] | Method D; C14[23] | 2.43 minutes[13]; 438 |
| 131 | 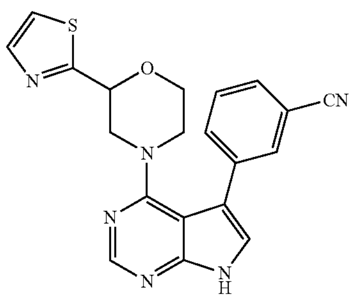 [SMILES: N#Cc1cccc(-c2c[nH]c3ncnc(N4CCOC(c5nccs5)C4)c23)c1] | Method D; C14 | 2.39 minutes[13]; 389 |
| 132 | 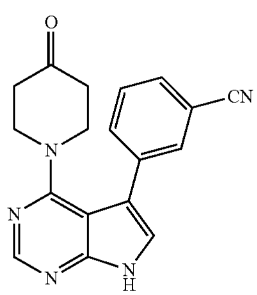 [SMILES: N#Cc1cccc(-c2c[nH]c3ncnc(N4CCC(=O)CC4)c23)c1] | Method D; C14 | 2.13 minutes[13]; 318 |
| 133 | 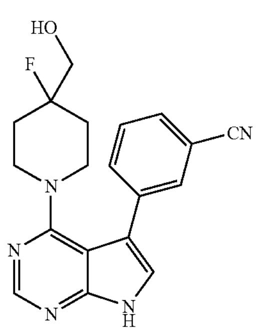 [SMILES: N#Cc1cccc(-c2c[nH]c3ncnc(N4CCC(F)(CO)CC4)c23)c1] | Method D; C14 | 2.03 minutes[9]; 352 |

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 134 | 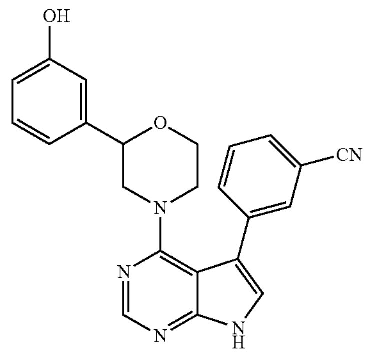 [SMILES: N#Cc1cccc(-c2c[nH]c3ncnc(N4CCOC(c5cccc(O)c5)C4)c23)c1] | Method D; C14 | 2.36 minutes[9]; 398 |
| 135 | 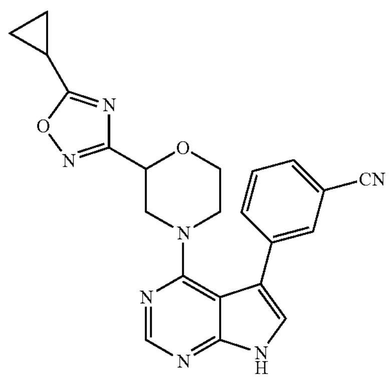 [SMILES: N#Cc1cccc(-c2c[nH]c3ncnc(N4CCOC(c5noc(C6CC6)n5)C4)c23)c1] | Method D; C14[24] | 2.49 minutes[9]; 414 |
| 136 | 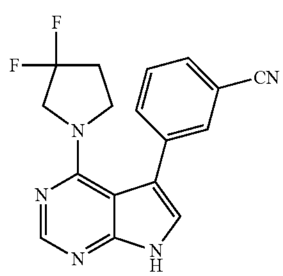 [SMILES: N#Cc1cccc(-c2c[nH]c3ncnc(N4CCC(F)(F)C4)c23)c1] | Method D; C14 | 2.08 minutes[10]; 326 |
| 137 | 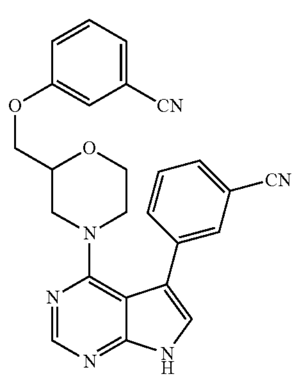 [SMILES: N#Cc1cccc(OCC2CN(c3ncnc4[nH]cc(-c5cccc(C#N)c5)c34)CCO2)c1] | Method D; C14[25] | 2.43 minutes[10]; 437 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 138 | 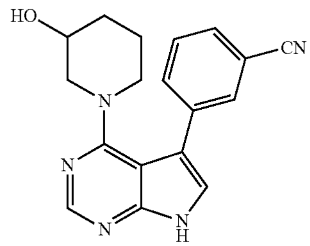 | Method D; C14 | 2.00 minutes[9]; 320 |
| 139 | 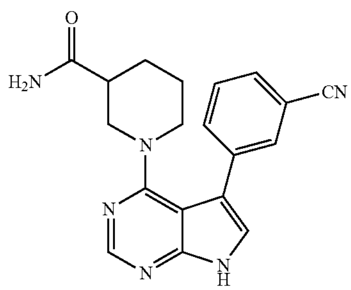 [SMILES: N#Cc1cccc(-c2c[nH]c3ncnc(N4CCCC(C(N)=O)C4)c23)c1] | Method D; C14 | 1.93 minutes[9]; 347 |
| 140 | 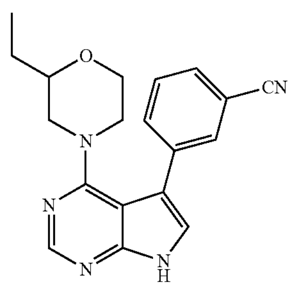 [SMILES: CCC1CN(c2ncnc3[nH]cc(-c4cccc(C#N)c4)c23)CCO1] | Method D; C14 | 2.39 minutes[9]; 334 |
| 141 | 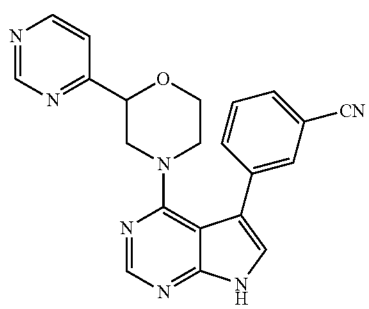 [SMILES: N#Cc1cccc(-c2c[nH]c3ncnc(N4CCOC(c5ccncn5)C4)c23)c1] | Method D; C14[26] | 2.22 minutes[9]; 384 |
| 142 | 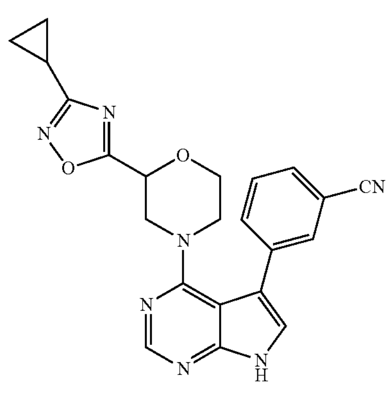 [SMILES: N#Cc1cccc(-c2c[nH]c3ncnc(N4CCOC(c5nc(C6CC6)no5)C4)c23)c1] | Method D; C14 | 2.61 minutes[9]; 414 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 143 | 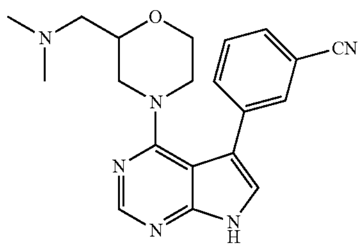 [SMILES: CN(C)CC1CN(c2ncnc3[nH]cc(-c4cccc(C#N)c4)c23)CCO1] | Method D; C14 | 1.87 minutes[9]; 363 |
| 144 | 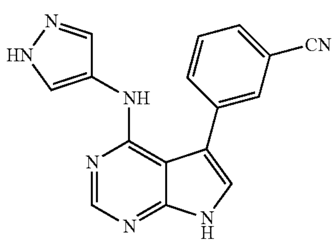 [SMILES: N#Cc1cccc(-c2c[nH]c3ncnc(Nc4cn[nH]c4)c23)c1] | Method D; C14 | 1.86 minutes[9]; 302 |
| 145 | 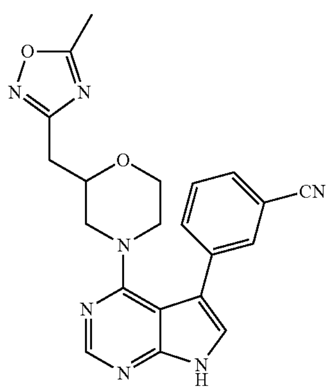 [SMILES: Cc1nc(CC2CN(c3ncnc4[nH]cc(-c5cccc(C#N)c5)c34)CCO2)no1] | Method D; C14[27] | 2.25 minutes[9]; 402 |
| 146 | 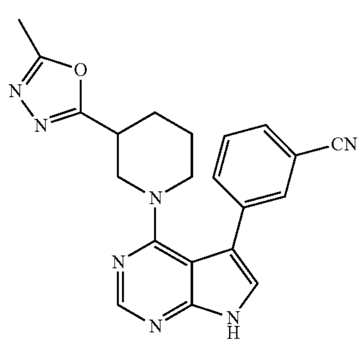 [SMILES: Cc1nnc(C2CCCN(c3ncnc4[nH]cc(-c5cccc(C#N)c5)c34)C2)o1] | Method D; C14 | 2.17 minutes[9]; 386 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
| --- | --- | --- | --- |
| 147 | 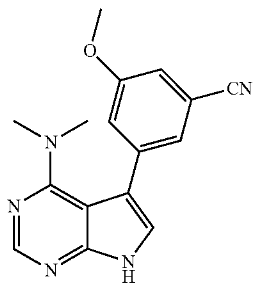 [SMILES: COc1cc(C#N)cc(-c2c[nH]c3ncnc(N(C)C)c23)c1] | Ex 3 | $^1$H NMR (400 MHz, CDCl$_3$) δ 11.32 (br s, 1H), 8.46 (s, 1H), 7.39-7.43 (m, 1H), 7.27-7.30 (m, 1H), 7.24 (s, 1H), 7.08-7.11 (m, 1H), 3.88 (s, 3H), 2.88 (s, 6H); 294.1 |
| 148 | 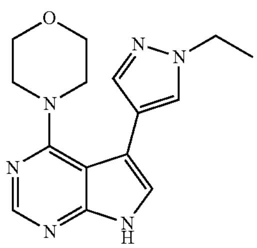 [SMILES: CCn1cc(-c2c[nH]c3ncnc(N4CCOCC4)c23)cn1] | C20[28] | 2.07 minutes[9]; 299 |
| 149 | 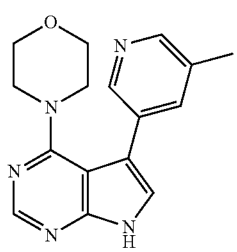 [SMILES: Cc1cncc(-c2c[nH]c3ncnc(N4CCOCC4)c23)c1] | Ex 3 | 8.59 (br d, J = 1.5 Hz, 1H), 8.39 (s, 1H), 8.33-8.36 (m, 1H), 7.73-7.76 (m, 1H), 7.63 (s, 1H), 3.4-3.47 (m, 4H, assumed; partially obscured by water peak), 3.12-3.17 (m, 4H), 2.38 (s 3H); 296.0 |
| 150 | 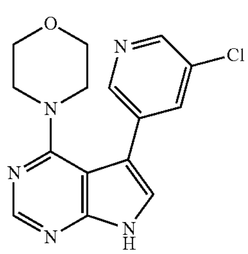 [SMILES: Clc1cncc(-c2c[nH]c3ncnc(N4CCOCC4)c23)c1] | Ex 3 | 8.78 (br s, 1H), 8.54 (br d, J = 2 Hz, 1H), 8.42 (s, 1H), 8.07-8.10 (m, 1H), 7.80 (s, 1H), 3.46-3.54 (m, 4H), 3.11-3.18 (m, 4H); 316.1 |
| 151 | 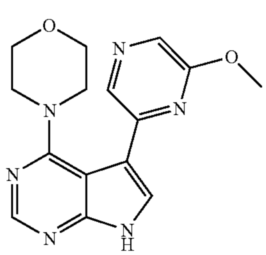 [SMILES: COc1cncc(-c2c[nH]c3ncnc(N4CCOCC4)c23)n1] | Ex 3[29] | 8.48 (s, 1H), 8.36 (s, 1H), 8.13 (s, 1H), 7.87 (s, 1H), 3.99 (s, 3H), 3.49-3.56 (m, 4H), 3.21-3.27 (m, 4H); 313.1 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 152 | 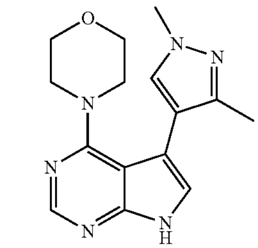 [SMILES: Cc1nn(C)cc1-c1c[nH]c2ncnc(N3CCOCC3)c12] | Ex 3 | 8.30 (s, 1H), 7.61 (s, 1H), 7.22 (s, 1H), 3.80 (s, 3H), 3.4-3.48 (m, 4H, assumed; partially obscured by water peak), 3.15-3.21 (m, 4H), 2.13 (s, 3H); 299.2 |
| 153 | 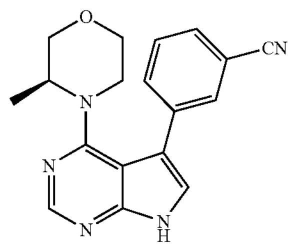 [SMILES: C[C@H]1COCCN1c1ncnc2[nH]cc(-c3cccc(C#N)c3)c12] | Ex 5 | characteristic peaks: 8.40 (s, 1H), 8.00 (br s, 1H), 7.90 (br d, J = 8 Hz, 1H), 7.76 (br d, J = 7 Hz, 1H), 7.65-7.70 (m, 2H), 3.60-3.74 (m, 2H), 0.93 (d, J = 6.5 Hz, 3H); 320.1 |
| 154 | 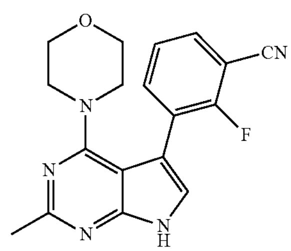 [SMILES: Cc1nc(N2CCOCC2)c2c(-c3cccc(C#N)c3F)c[nH]c2n1] | Ex 1$^7$ | $^1$H NMR (400 MHz, CD$_3$OD) δ 7.80-7.86 (m, 1H), 7.70-7.75 (m, 1H), 7.47 (dd, J = 7.8, 7.8 Hz, 1H), 7.39 (d, J = 1 Hz, 1H), 3.45-3.50 (m, 4H), 3.24-3.28 (m, 4H), 2.58 (s, 3H); 338.2 |
| 155 | 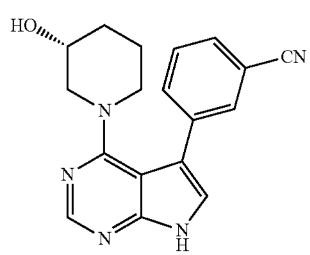 | Ex 6 | characteristic peaks: 12.21 (br s, 1H), 8.33 (s, 1H), 7.94 (br s, 1H), 7.82 (br d, J = 8 Hz, 1H), 7.73 (br d, J = 8 Hz, 1H), 7.60-7.66 (m, 2H), 4.71 (d, J = 4.5 Hz, 1H), 3.70-3.79 (m, 1H), 3.44-3.52 (m, 1H), 2.60-2.70 (m, 1H), 1.73-1.82 (m, 1H), 1.38-1.48 (m, 1H), 1.12-1.26 (m, 2H); 320.1 |
| 156 | 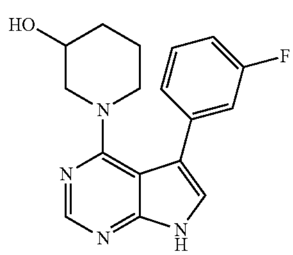 [SMILES: OC1CCCN(c2ncnc3[nH]cc(-c4cccc(F)c4)c23)C1] | Method E | 2.48 minutes$^9$; 313 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 157 | 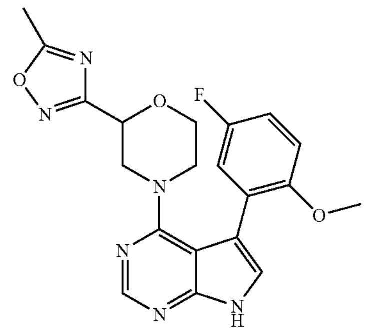 [SMILES: COc1ccc(F)cc1-c1c[nH]c2ncnc(N3CCOC(c4noc(C)n4)C3)c12] | Method E[20] | 2.66 minutes[9]; 411 |
| 158 | 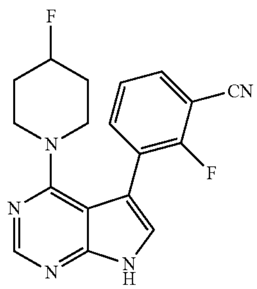 [SMILES: N#Cc1cccc(-c2c[nH]c3ncnc(N4CCC(F)CC4)c23)c1F] | Method E | 2.41 minutes[10]; 340 |
| 159 | 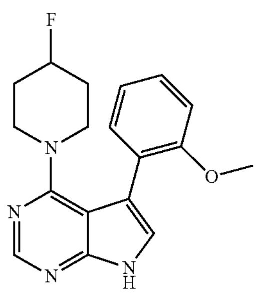 [SMILES: COc1ccccc1-c1c[nH]c2ncnc(N3CCC(F)CC3)c12] | Method E | 2.66 minutes[9]; 327 |
| 160 | 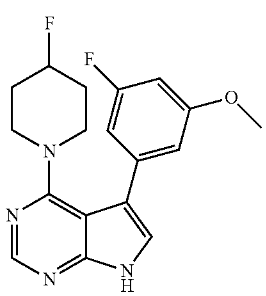 [SMILES: COc1cc(F)cc(-c2c[nH]c3ncnc(N4CCC(F)CC4)c23)c1] | Method E | 2.60 minutes[10]; 345 |
| 161 | 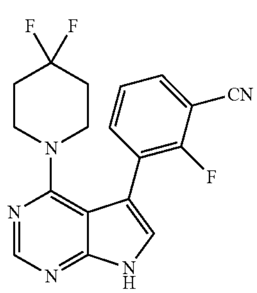 [SMILES: N#Cc1cccc(-c2c[nH]c3ncnc(N4CCC(F)(F)CC4)c23)c1F] | Method E | 2.92 minutes[9]; 358 |

TABLE 1-continued
| Example # | Structure | Method of Preparation; Non-commercial starting materials | $^1$H NMR (400 MHz, DMSO-$d_6$) δ (ppm); Mass spectrum, observed ion m/z (M + H$^+$) or HPLC retention time; Mass spectrum m/z (M + H$^+$) (unless otherwise indicated) |
|---|---|---|---|
| 162 | 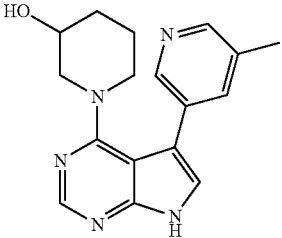 [SMILES: Cc1cncc(-c2c[nH]c3ncnc(N4CCCC(O)C4)c23)c1] | Method E | 1.88 minutes[9]; 310 |
| 163 | 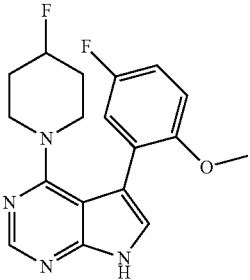 [SMILES: COc1ccc(F)cc1-c1c[nH]c2ncnc(N3CCC(F)CC3)c12] | Method E | 2.47 minutes[10]; 345 |
| 164 | 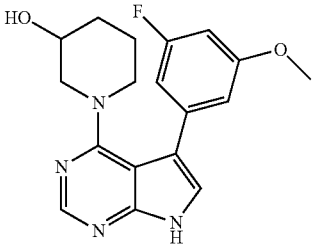 [SMILES: COc1cc(F)cc(-c2c[nH]c3ncnc(N4CCCC(O)C4)c23)c1] | Method E | 2.54 minutes[9]; 343 |
| 165 | 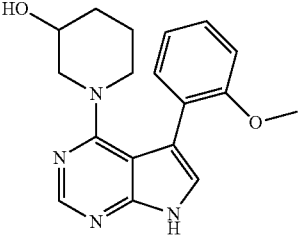 [SMILES: COc1ccccc1-c1c[nH]c2ncnc(N3CCCC(O)C3)c12] | Method E | 2.41 minutes[9]; 325 |
| 166 | 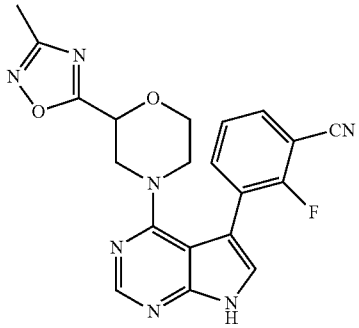 [SMILES: Cc1noc(C2CN(c3ncnc4[nH]cc(-c5cccc(C#N)c5F)c34)CCO2)n1] | Method E | 2.65 minutes[13]; 406 |

TABLE 1-continued

| Example # | Structure | Method of Preparation; Non-commercial starting materials | ¹H NMR (400 MHz, DMSO-d$_6$) δ (ppm); Mass spectrum, observed ion m/z (M + H⁺) or HPLC retention time; Mass spectrum m/z (M + H⁺) (unless otherwise indicated) |
|---|---|---|---|
| 167 | 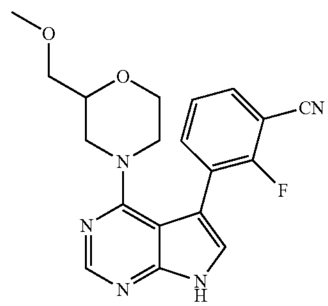 [SMILES: COCC1CN(c2ncnc3[nH]cc(-c4cccc(C#N)c4F)c23)CCO1] | Method E | 2.58 minutes[9]; 368 |
| 168 | 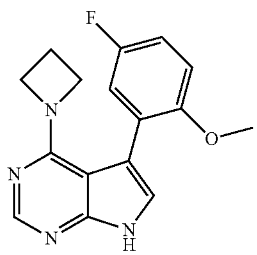 [SMILES: COc1ccc(F)cc1-c1c[nH]c2ncnc(N3CCC3)c12] | Method E | 2.17 minutes[9]; 299 |
| 169 | 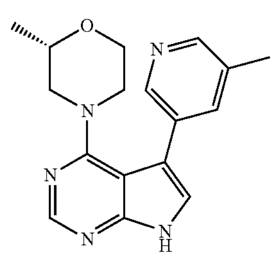 | Method E | 1.74 minutes[9]; 310 |
| 170 | 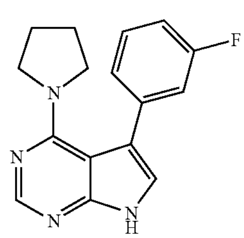 [SMILES: Fc1cccc(-c2c[nH]c3ncnc(N4CCCC4)c23)c1] | Method E | 2.02 minutes[10]; 283 |
| 171 | 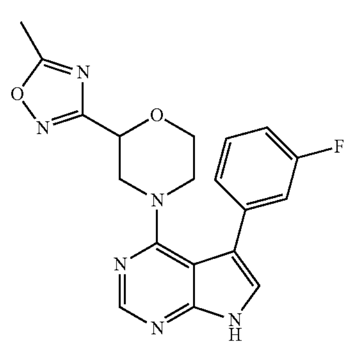 [SMILES: Cc1nc(C2CN(c3ncnc4[nH]cc(-c5cccc(F)c5)c34)CCO2)no1] | Method E | 2.43 minutes[9]; 381 |

TABLE 1-continued

| Example # | Structure | Method of Preparation; Non-commercial starting materials | $^1$H NMR (400 MHz, DMSO-$d_6$) δ (ppm); Mass spectrum, observed ion m/z (M + H$^+$) or HPLC retention time; Mass spectrum m/z (M + H$^+$) (unless otherwise indicated) |
|---|---|---|---|
| 172 | 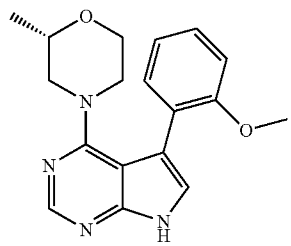 | Method E | 2.27 minutes[9]; 325 |
| 173 | 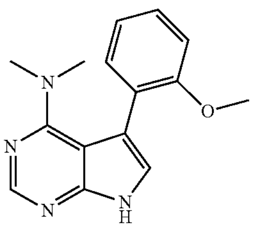 [SMILES: COc1ccccc1-c1c[nH]c2ncnc(N(C)C)c12] | Method E | 2.12 minutes[9]; 269 |
| 174 | 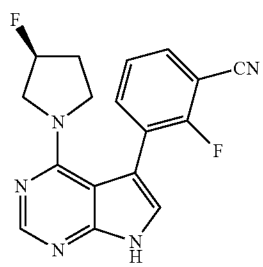 [SMILES: N#Cc1cccc(-c2c[nH]c3ncnc(N4CC[C@H](F)C4)c23)c1F] | Method E | 2.13 minutes[9]; 326 |
| 175 | 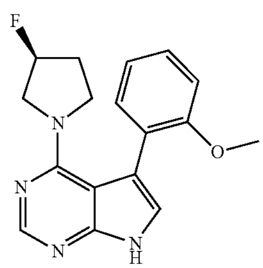 [SMILES: COc1ccccc1-c1c[nH]c2ncnc(N3CC[C@H](F)C3)c12] | Method E | 2.22 minutes[9]; 313 |
| 176 | 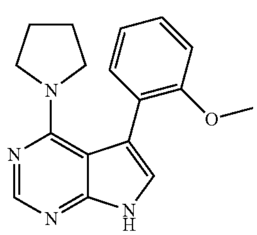 [SMILES: COc1ccccc1-c1c[nH]c2ncnc(N3CCCC3)c12] | Method E | 2.24 minutes[9]; 295 |
| 177 | 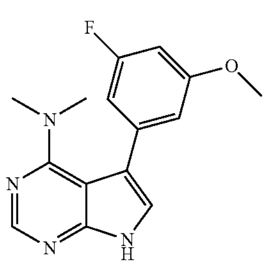 [SMILES: COc1cc(F)cc(-c2c[nH]c3ncnc(N(C)C)c23)c1] | Method E | 2.24 minutes[9]; 287 |

TABLE 1-continued

| Example # | Structure | Method of Preparation; Non-commercial starting materials | $^1$H NMR (400 MHz, DMSO-$d_6$) δ (ppm); Mass spectrum, observed ion m/z (M + H$^+$) or HPLC retention time; Mass spectrum m/z (M + H$^+$) (unless otherwise indicated) |
|---|---|---|---|
| 178 | 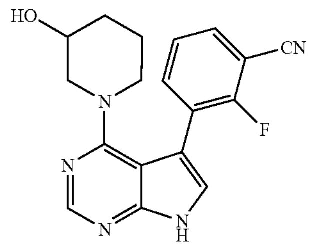 [SMILES: N#Cc1cccc(-c2c[nH]c3ncnc(N4CCCC(O)C4)c23)c1F] | Method E | 2.04 minutes[9]; 338 |
| 179 | 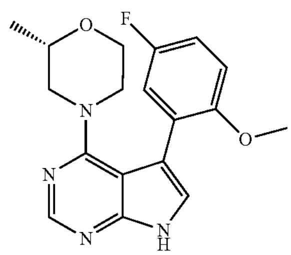 | Method E | 2.31 minutes[9]; 343 |
| 180 | 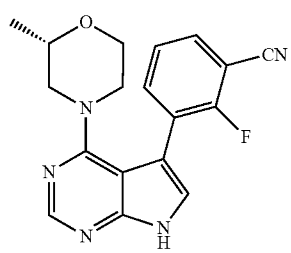 [SMILES: C[C@H]1CN(c2ncnc3[nH]cc(-c4cccc(C#N)c4F)c23)CCO1] | Method E | 2.27 minutes[9]; 338 |
| 181 | 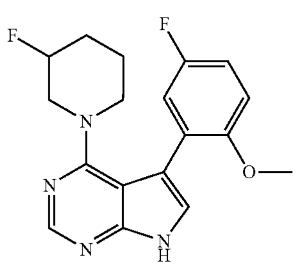 [SMILES: COc1ccc(F)cc1-c1c[nH]c2ncnc(N3CCCC(F)C3)c12] | Method E | 2.13 minutes[10]; 345 |
| 182 | 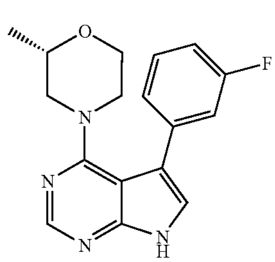 [SMILES: C[C@H]1CN(c2ncnc3[nH]cc(-c4cccc(F)c4)c23)CCO1] | Method E | 2.14 minutes[10]; 313 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 183 | 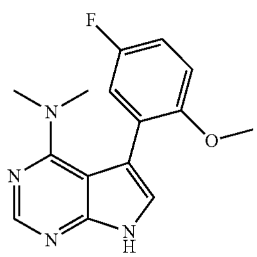 [SMILES: COc1ccc(F)cc1-c1c[nH]c2ncnc(N(C)C)c12] | Method E | 2.15 minutes[9]; 287 |
| 184 | 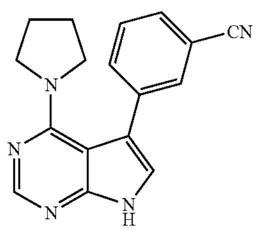 [SMILES: N#Cc1cccc(-c2c[nH]c3ncnc(N4CCCC4)c23)c1] | Method E | 2.12 minutes[9]; 308 |
| 185 | 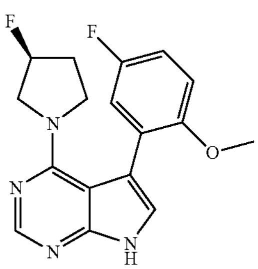 [SMILES: COc1ccc(F)cc1-c1c[nH]c2ncnc(N3CC[C@H](F)C3)c12] | Method E | 2.26 minutes[9]; 331 |
| 186 | 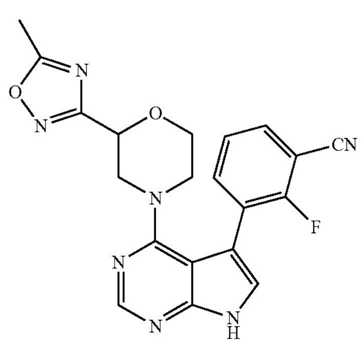 [SMILES: Cc1nc(C2CN(c3ncnc4[nH]cc(-c5cccc(C#N)c5F)c34)CCO2)no1] | Method E[20] | 2.36 minutes[9]; 406 |
| 187 | 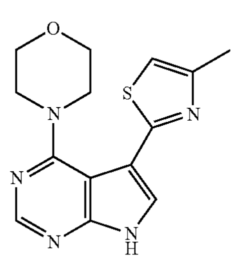 [SMILES: Cc1csc(-c2c[nH]c3ncnc(N4CCOCC4)c23)n1] | Method F; P2 | 2.07 minutes[9]; 302 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 188 | 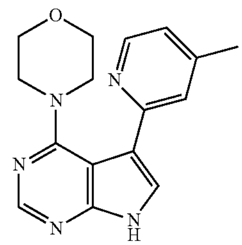 [SMILES: Cc1ccnc(-c2c[nH]c3ncnc(N4CCOCC4)c23)c1] | Method F; P2 | 1.84 minutes[9]; 296 |
| 189 | 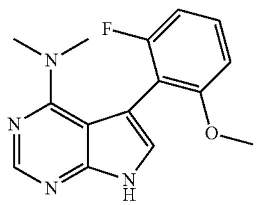 [SMILES: COc1cccc(F)c1-c1c[nH]c2ncnc(N(C)C)c12] | Method F; P7 | 2.29 minutes[9]; 287 |
| 190 | 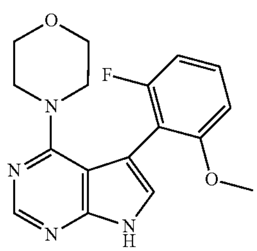 [SMILES: COc1cccc(F)c1-c1c[nH]c2ncnc(N3CCOCC3)c12] | Method F; P2 | 2.33 minutes[9]; 329 |
| 191 | 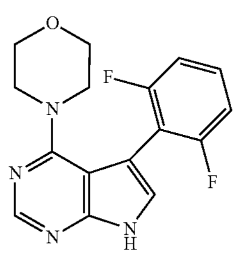 [SMILES: Fc1cccc(F)c1-c1c[nH]c2ncnc(N3CCOCC3)c12] | Method F; P2 | 2.35 minutes[9]; 317 |
| 192 | 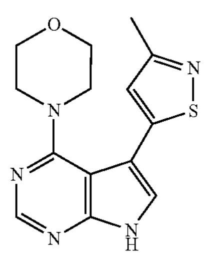 [SMILES: Cc1cc(-c2c[nH]c3ncnc(N4CCOCC4)c23)sn1] | Method F; P2 | 2.18 minutes[9]; 302 |
| 193 | 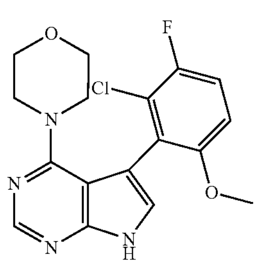 [SMILES: COc1ccc(F)c(Cl)c1-c1c[nH]c2ncnc(N3CCOCC3)c12] | Method F; P2[30] | 2.47 minutes[9]; 363 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 194 | 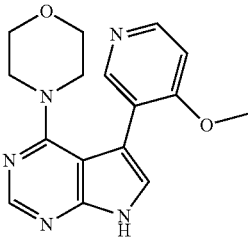 [SMILES: COc1ccncc1-c1c[nH]c2ncnc(N3CCOCC3)c12] | Method F; P2 | 1.94 minutes[13]; 312 |
| 195 | 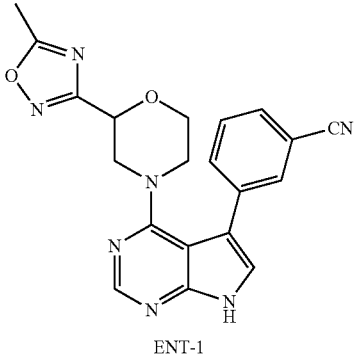 [SMILES: Cc1nc(C2CN(c3ncnc4[nH]cc(-c5cccc(C#N)c5)c34)CCO2)no1] ENT-1 | Ex 5[20, 31, 17] | characteristic peaks: 12.37 (br s, 1H), 8.43 (s, 1H), 7.99-8.02 (m, 1H), 7.85 (ddd, J = 7.8, 1, 1 Hz, 1H), 7.75 (ddd, J = 7.8, 1, 1 Hz, 1H), 7.71 (s, 1H), 7.65 (dd, J = 7.8, 7.8 Hz, 1H), 4.67 (dd, J = 9.5, 2.5 Hz, 1H), 3.85 (br d, J = 13 Hz, 1H), 3.68-3.74 (m, 1H), 3.18 (dd, J = 13, 9 Hz, 1H), 2.86-2.94 (m, 1H), 2.57 (s, 3H); 388.1 |
| 196 | 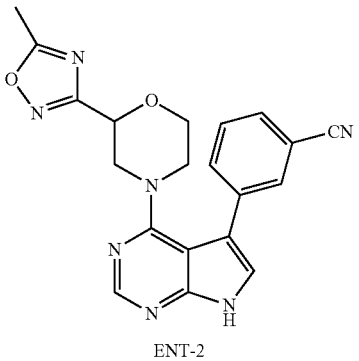 [SMILES: Cc1nc(C2CN(c3ncnc4[nH]cc(-c5cccc(C#N)c5)c34)CCO2)no1] ENT-2 | Ex 5[20, 31, 12] | characteristic peaks: 12.37 (br s, 1H), 8.43 (s, 1H), 8.00 (dd, J = 1.5, 1.5 Hz, 1H), 7.85 (ddd, J = 7.8, 1.5, 1.5 Hz, 1H), 7.75 (ddd, J = 7.8, 1.5, 1.2 Hz, 1H), 7.71 (s, 1H), 7.65 (dd, J = 7.8, 7.8 Hz, 1H), 4.67 (dd, J = 9.7, 2.6 Hz, 1H), 3.85 (br d, J = 13 Hz, 1H), 3.68-3.74 (m, 1H), 3.18 (dd, J = 13.0, 9.5 Hz, 1H), 2.86-2.94 (m, 1H), 2.57 (s, 3H); 388.1 |
| 197 | 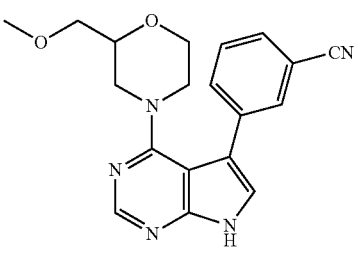 ENT-2 | Ex 6[16, 12] | $^1$H NMR (400 MHz, CDCl$_3$) δ 8.48 (s, 1H), 7.75 (br s, 1H), 7.65-7.70 (m, 2H), 7.59 (dd, J = 7.8, 7.5 Hz, 1H), 7.33 (s, 1H), 4.02 (br d, J = 13.3 Hz, 1H), 3.89 (br d, J = 13.3 Hz, 1H), 3.80 (br dd, J = 12.0, 2.3 Hz, 1H), 3.41-3.54 (m, 2H), 3.29 (s, 3H), 3.25-3.3 (m, 1H), 3.22 (dd, half of ABX pattern, J = 10.2, 4.6 Hz, 1H), 2.98-3.08 (m, 1H), 2.87 (dd, J = 13.2, 10.7 Hz, 1H); 350.2 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 203 | 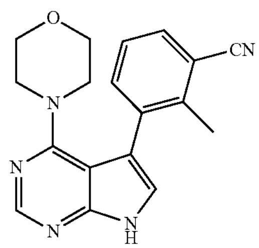 [SMILES: Cc1c(C#N)cccc1-c1c[nH]c2ncnc(N3CCOCC3)c12] | Example 3; P2 | $^1$H NMR (400 MHz, CDCl$_3$) δ 10.10 (br s, 1H), 8.50 (s, 1H), 7.67 (br d, J = 7.5 Hz, 1H), 7.55 (br d, J = 7.5 Hz, 1H), 7.38 (dd, J = 7.9, 7.8 Hz, 1H), 7.11-7.13 (m, 1H), 3.35-3.42 (m, 4H), 3.21-3.26 (m, 4H), 2.49 (s, 3H); 319.9 |
| 204 | 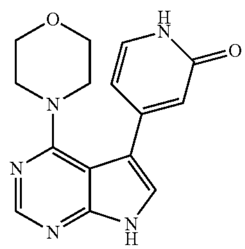 [SMILES: O=c1cc(-c2c[nH]c3ncnc(N4CCOCC4)c23)cc[nH]1] | Example 4; P2 | 8.34 (s, 1H), 7.75 (s, 1H), 7.37 (d, J = 6.5 Hz, 1H), 6.49 (br s, 1H), 6.44 (dd, J = 7.0, 1.5 Hz, 1H), 3.60-3.66 (m, 4H), 3.21-3.27 (m, 4H, assumed; partially obscured by water peak); 297.9 |
| 205 | 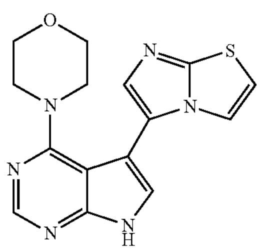 [SMILES: c1nc(N2CCOCC2)c2c(-c3cnc4sccn34)c[nH]c2n1] | Example 3$^{32}$; P2$^{33}$ | $^1$H NMR (400 MHz, CDCl$_3$) δ 10.08 (br s, 1H), 8.51 (s, 1H), 7.36 (d, J = 0.9 Hz, 1H), 7.29-7.31 (m, 1H), 7.25-7.27 (m, 1H, assumed; partially obscured by solvent peak), 6.87 (dd, J = 4.5, 1.0 Hz, 1H), 3.31-3.35 (m, 4H), 3.26-3.31 (m, 4H); 327.1 |
| 206 | (+/−) | Example 4; C14 | $^1$H NMR (400 MHz, CDCl$_3$), characteristic peaks: δ 11.32 (br s, 1H), 8.42 (s, 1H), 7.78 (br s, 1H), 7.72 (br d, J = 7.8 Hz, 1H), 7.62 (br d, J = 7.8 Hz, 1H), 7.52 (dd, J = 7.8, 7.8 Hz, 1H), 7.18 (s, 1H), 4.34 (br dd, J = 5, 5 Hz, 1H), 3.83-3.91 (m, 1H), 3.74 (ddd, J = 8.3, 7.8, 5.3 Hz, 1H), 3.46-3.56 (m, 3H), 3.19 (dd, J = 12.4, 4.9 Hz, 1H), 2.74-2.84 (m, 1H), 1.99-2.10 (m, 1H); 331.9 |
| 207 | (+/−) | Example 4; C14 | $^1$H NMR (400 MHz, CDCl$_3$), δ 10.25 (br s, 1H), 8.43 (s, 1H), 7.81 (br s, 1H), 7.73 (br d, J = 7.8 Hz, 1H), 7.63 (br d, J = 7.8 Hz, 1H), 7.54 (dd, J = 7.8, 7.7 Hz, 1H), 7.18 (s, 1H), 3.71 (br dd, J = 9.0, 6.2 Hz, 2H), 3.56 (br dd, J = 11.3, 7.2 Hz, 2H), 3.47 (dd, J = 9.0, 2.6 Hz, 2H), 3.21 (dd, J = 11.4, 4.1 Hz, 2H), 2.75-2.81 (m, 2H); 331.9 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 208 | (+/−) | Example 4; C14 | 8.49 (s, 1H), 8.14 (br s, 1H), 8.03 (br d, J = 7.8 Hz, 1H), 7.79 (s, 1H), 7.76 (br d, J = 7.5 Hz, 1H), 7.68 (dd, J = 7.8, 7.8 Hz, 1H), 3.4-3.50 (m, 2H, assumed; partially obscured by water peak), 2.92-3.08 (m, 2H), 2.78 (br d, J = 12.3 Hz, 1H), 2.65-2.75 (m, 1H), 2.42-2.5 (m, 1H, assumed; partially obscured by solvent peak), 1.83-1.94 (m, 1H), 1.61-1.83 (m, 2H), 1.47-1.61 (m, 1H), 1.31-1.45 (m, 1H); 345.9 |
| 209 | (+/−) | Example 4; C14 | 8.45 (s, 1H), 8.04 (br s, 1H), 7.91 (br d, J = 8 Hz, 1H), 7.80 (br d, J = 8 Hz, 1H), 7.76 (s, 1H), 7.66 (dd, J = 8, 8 Hz, 1H), 5.06-5.09 (m, 1H), 3.79-3.86 (m, 1H), 3.43-3.52 (m, 2H), 3.3-3.41 (m, 1H, assumed; partially obscured by water peak), 3.10-3.18 (m, 1H), 2.82-2.91 (m, 1H); 353.1 [M + Na$^+$] |
| 210 | 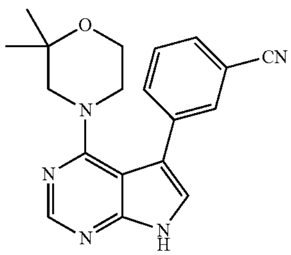 [SMILES: CC1(C)CN(c2ncnc3[nH]cc(-c4cccc(C#N)c4)c23)CCO1] | Example 4; C14 | 8.37 (s, 1H), 7.95 (br s, 1H), 7.87 (br d, J = 7.9 Hz, 1H), 7.78 (br d, J = 7.6 Hz, 1H), 7.64-7.69 (m, 2H), 3.21-3.27 (m, 2H), 3.17 (br s, 2H), 2.87-2.93 (m, 2H), 1.19 (s, 6H); 334.0 |
| 211 | 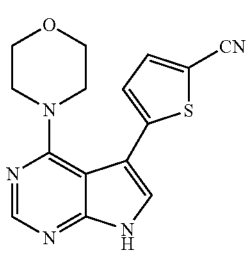 [SMILES: N#Cc1ccc(-c2c[nH]c3ncnc(N4CCOCC4)c23)s1] | Example 3; P2 | 12.54 (br s, 1H), 8.41 (s, 1H), 8.00 (d, J = 3.8 Hz, 1H), 7.78 (d, J = 2.5 Hz, 1H), 7.28 (d, J = 3.8 Hz, 1H), 3.52-3.58 (m, 4H), 3.20-3.26 (m, 4H); 311.9 |
| 212 | 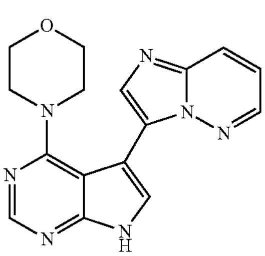 [SMILES: c1cnn2c(-c3c[nH]c4ncnc(N5CCOCC5)c34)cnc2c1] | Example 3; P2 | 8.54 (br d, J = 4.3 Hz, 1H), 8.36 (s, 1H), 8.20 (br d, J = 9.3 Hz, 1H), 7.94 (s, 1H), 7.72 (s, 1H), 7.28 (dd, J = 9.2, 4.4 Hz, 1H), 3.01-3.13 (m, 8H); 321.9 |

TABLE 1-continued

| Example # | Structure | Method of Preparation; Non-commercial starting materials | $^1$H NMR (400 MHz, DMSO-d$_6$) δ (ppm); Mass spectrum, observed ion m/z (M + H$^+$) or HPLC retention time; Mass spectrum m/z (M + H$^+$) (unless otherwise indicated) |
|---|---|---|---|
| 213 | ENT-2 | Example 4$^1$; C1$^{34}$ | $^1$H NMR (400 MHz, DMSO-d$_6$ + D$_2$O) δ 8.41 (s, 1H), 7.80-7.86 (m, 1H), 7.70-7.77 (m, 1H), 7.65 (d, J = 1 Hz, 1H), 7.42 (dd, J = 7.8, 7.8 Hz, 1H), 4.74-4.80 (m, 1H), 3.78-3.85 (m, 1H), 3.60-3.66 (m, 1H), 3.29-3.45 (m, 3H), 2.88-2.97 (m, 1H), 2.34 (s, 3H); LCMS m/z 428.0 [M + Na$^+$] |
| 214 | ENT-1 | Example 4$^1$; C1$^{34}$ | $^1$H NMR (400 MHz, DMSO-d$_6$ + D$_2$O) δ 8.38 (s, 1H), 7.75-7.82 (m, 1H), 7.68-7.74 (m, 1H), 7.60 (s, 1H), 7.40 (dd, J = 7.8, 7.8 Hz, 1H), 4.68-4.74 (m, 1H), 3.71-3.78 (m, 1H), 3.56-3.64 (m, 1H), 3.29-3.44 (m, 3H), 2.89-2.98 (m, 1H), 2.31 (s, 3H); LCMS m/z 428.0 [M + Na$^+$] |
| 215 | ·HCOOH | Example 4; P2 | 12.46 (br s, 1H), 8.40 (s, 1H), 8.23 (br s, 1H), 8.11 (d, J = 2.5 Hz, 1H), 8.06 (dd, J = 8.0, 7.5 Hz, 1H), 7.85-7.90 (m, 2H), 7.77 (br s, 1H), 3.49-3.55 (m, 4H), 3.21-3.27 (m, 4H); 347.1 [M + Na$^+$] |
| 216 | 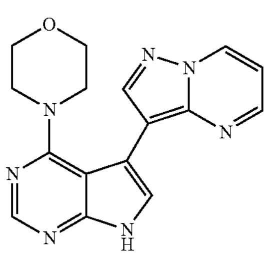 [SMILES: c1cnc2c(-c3c[nH]c4ncnc(N5CCOCC5)c34)cnn2c1] | Example 3$^{35}$; P2 | characteristic peaks: 9.16 (br d, J = 7 Hz, 1H), 8.57-8.60 (m, 1H), 8.41 (s, 1H), 8.35 (s, 1H), 7.58 (s, 1H), 7.06-7.11 (m, 1H), 3.14-3.19 (m, 4H); 322.1 |
| 217 | 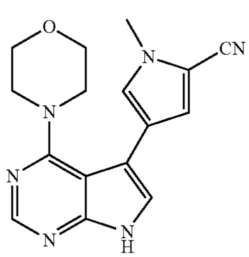 [SMILES: Cn1cc(-c2c[nH]c3ncnc(N4CCOCC4)c23)cc1C#N] | Example 3; P2 | 12.31 (br s, 1H), 8.38 (s, 1H), 7.42 (d, J = 2.3 Hz, 1H), 7.35 (d, J = 1.8 Hz, 1H), 7.08 (d, J = 1.8 Hz, 1H), 3.82 (s, 3H), 3.54-3.60 (m, 4H), 3.27-3.33 (m, 4H); 308.9 |

TABLE 1-continued

| Example # | Structure | Method of Preparation; Non-commercial starting materials | $^1$H NMR (400 MHz, DMSO-$d_6$) δ (ppm); Mass spectrum, observed ion m/z (M + H$^+$) or HPLC retention time; Mass spectrum m/z (M + H$^+$) (unless otherwise indicated) |
|---|---|---|---|
| 218 | (structure) •HCOOH | Example 3; P2 | 12.42 (br s, 1H), 8.40 (s, 1H), 8.13 (s, ~0.6 H), 7.58 (d, J = 2.3 Hz, 1H), 7.53 (d, J = 4.5 Hz, 1H), 7.25 (d, J = 4.3 Hz, 1H), 3.22-3.31 (m, 2H), 3.06-3.14 (m, 2H), 2.97-3.06 (m, 4H), 2.30 (s, 3H); 340.9 |
| 219 | (structure) (+/−) | Example @109; C14 | characteristic peaks: 12.40 (br s, 1H), 8.53 (d, J = 1.5 Hz, 1H), 8.44 (s, 1H), 8.00-8.02 (m, 1H), 7.86 (br d, J = 8 Hz, 1H), 7.75 (br d, J = 8 Hz, 1H), 7.71 (d, J = 2.5 Hz, 1H), 7.66 (dd, J = 8, 8 Hz, 1H), 6.39 (d, J = 1.5 Hz, 1H), 4.66-4.71 (m, 1H), 3.80-3.86 (m, 1H), 3.72-3.78 (m, 1H), 3.04-3.11 (m, 1H), 2.88-2.97 (m, 1H); 394.9 [M + Na$^+$] |
| 220 | (structure) •CF$_3$COOH | Example 4; P2$^{36}$ | 1.43 minutes$^{37}$; 310.3 |
| 221 | (structure) | Method F; P2 | 1.95 minutes$^{38}$; 312.2 |
| 222 | (structure) | Method F; P2 | 1.57 minutes$^{38}$; 321.3 |

TABLE 1-continued

| Example # | Structure | Method of Preparation; Non-commercial starting materials | $^1$H NMR (400 MHz, DMSO-$d_6$) δ (ppm); Mass spectrum, observed ion m/z (M + H$^+$) or HPLC retention time; Mass spectrum m/z (M + H$^+$) (unless otherwise indicated) |
|---|---|---|---|
| 223 | (structure) | Method F; P2 | 1.86 minutes[38]; 323.3 |
| 224 | (structure) ·CF$_3$COOH | Example 4; P2[39] | 1.63 minutes[37]; 310.2 |
| 225 | (structure) (+/−) | Example 4; C14[40] | characteristic peaks: 12.38 (br s, 1H), 8.42 (s, 1H), 8.00 (dd, J = 1.6, 1.4 Hz, 1H), 7.86 (ddd, J = 7.7, 1.7, 1.4 Hz, 1H), 7.77 (ddd, J = 7.6, 1.5, 1.4 Hz, 1H), 7.71-7.73 (m, 1H), 7.69 (dd, J = 8.0, 7.5 Hz, 1H), 3.72-3.79 (m, 1H), 3.60-3.68 (m, 2H), 2.63-2.77 (m, 4H); 344.9 |

1. In this case, tetrakis(triphenylphosphine)palladium(0) was used in the Suzuki reaction.

2. Boronate ester 1-methyl-4-(4,4,5,5-tetramethyl-1,3,2-dioxaborolan-2-yl)-1H-pyrazole was used in the Suzuki reaction.

3. Conditions for analytical HPLC. Column: Waters XBridge C18, 2.1×50 mm, 5 μm; Mobile phase A: 0.1% trifluoroacetic acid in water; Mobile phase B: 0.1% trifluoroacetic acid in acetonitrile; Gradient: 5% B for 1.0 minute, then 5% to 100% B over 5.75 minutes; Flow rate: 0.5 mL/minute.

4. Dichlorobis(triphenylphosphine)palladium(II) was used in the Suzuki reaction.

5. 1 N Sodium hydroxide solution was employed in the Suzuki reaction; this served to remove the (4-methylphenyl)sulfonyl protecting group.

6. In this case, preparative HPLC purification was carried out using a 10 μm Sunfire C-18 column; Eluent: 1:1 acetonitrile/(0.1% formic acid in water).

7. A boronic acid was used rather than a boronic ester.

8. The final deprotection was carried out using tetrabutylammonium fluoride in tetrahydrofuran.

9. Conditions for analytical HPLC. Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.60 minutes; then 5% to 100% B over 3.40 minutes; Flow rate: 0.8 mL/minute.

10. Conditions for analytical HPLC as in footnote 9, except that the gradient employed was 10% to 100% B over 4.00 minutes.

11. The racemic product was separated into its enantiomers using supercritical fluid chromatography. Column: Chiral Technologies Chiralpak® AD, 5 μm; Eluent: 68:32 carbon dioxide/methanol.

12. This Example was the second-eluting enantiomer from the supercritical fluid chromatographic separation.

13. Conditions for analytical HPLC. Column: Waters XBridge C18, 2.1×50 mm, 5 μm; Mobile phase A: 0.05% ammonium hydroxide in water; Mobile phase B: acetonitrile; Gradient: 5% to 100% B over 3.40 minutes; Flow rate: 0.8 mL/minute.

14. [1,1'-Bis(diphenylphosphino)ferrocene]dichloropalladium(II) was used in the Suzuki reaction.

15. The racemic product was separated into its enantiomers using supercritical fluid chromatography. Column: Chiral Technologies Chiralpak® AD, 5 μm; Eluent: 60:40 carbon dioxide/(methanol containing 0.05% diethylamine).

16. The racemic product was separated into its enantiomers using supercritical fluid chromatography. Column: Chiral Technologies Chiralpak® AD, 20 μm; Eluent: 60:40 carbon dioxide/(ethanol containing 0.05% diethylamine).

17. This Example was the first-eluting enantiomer from the supercritical fluid chromatographic separation.

18. The racemic product was separated into its enantiomers using supercritical fluid chromatography. Column: Chiral Technologies Chiralpak® AS, 5 μm; Eluent: 60:40 carbon dioxide/(2-propanol containing 0.05% diethylamine).

19. 3-Iodo-1-methyl-1H-pyrazole was used in the Suzuki reaction.

20. The requisite 2-(5-methyl-1,2,4-oxadiazol-3-yl)morpholine may be prepared from 4-benzylmorpholine-2-carbonitrile using chemistry described by D. Sakai and K. Watanabe, PCT Int. Appl. 2009, WO 2009035159 A1 20090319.

21. In this case, the displacement reaction was carried out at 110° C.

22. The requisite 2-{[(6-methylpyridin-3-yl)oxy]methyl}morpholine may be prepared via a Mitsunobu reaction between tert-butyl 2-(hydroxymethyl)morpholine-4-carboxylate and 6-methylpyridin-3-ol, followed by acidic removal of the protecting group.

23. 2-{[5-(Difluoromethyl)-1,2,4-oxadiazol-3-yl]methyl}morpholine may be prepared in the following manner: reaction of (4-benzylmorpholin-2-yl)acetonitrile with hydroxylamine hydrochloride and base provides 2-(4-benzylmorpholin-2-yl)-N'-hydroxyethanimidamide. Coupling of this compound with difluoroacetic acid may be carried out using any of a number of coupling reagents, such as 1,3-dicyclohexylcarbodiimide. Subsequent cyclization using thermal conditions or tetrabutylammonium fluoride (see A. R. Gangloff et al., Tetrahedron Lett. 2001, 42, 1441-1443), followed by debenzylation, provides the requisite amine.

24. Reaction of 4-benzylmorpholine-2-carbonitrile with hydroxylamine hydrochloride and sodium hydroxide provided 4-benzyl-N'-hydroxymorpholine-2-carboximidamide, which was condensed with cyclopropanecarboxylic acid using 1,3-dicyclohexylcarbodiimide. Cyclization using tetrabutylammonium fluoride (see A. R. Gangloff et al., Tetrahedron Lett. 2001, 42, 1441-1443), followed by debenzylation, afforded 2-(5-cyclopropyl-1,2,4-oxadiazol-3-yl)morpholine.

25. The requisite 3-(morpholin-2-ylmethoxy)benzonitrile may be prepared in a manner analogous to that described in footnote 22.

26. 2-(Pyrimidin-4-yl)morpholine may be prepared from 1-(4-benzylmorpholin-2-yl)ethanone via conversion to the enamine and reaction with 1,3,5-triazine (see D. L. Boger et al., J. Org. Chem. 1982, 47, 2673-2675), followed by debenzylation.

27. 2-[(5-Methyl-1,2,4-oxadiazol-3-yl)methyl]morpholine may be prepared via the chemistry described in footnote 23, by employing acetic acid in place of difluoroacetic acid.

28. Compound C20 was N-alkylated with ethyl iodide and potassium tert-butoxide at 30° C. in tetrahydrofuran. Deprotection was carried out using the procedure described in step 2 of Method C.

29. 2-Chloro-6-methoxypyrazine was used in the Suzuki reaction.

30. 2-Chloro-1-fluoro-3-iodo-4-methoxybenzene may be prepared by iodination of 2-chloro-1-fluoro-4-methoxybenzene according to the method of R. Sanz et al., J. Org. Chem. 2007, 72, 5113-5118.

31. The racemic product was separated into its enantiomers using supercritical fluid chromatography. Column: Chiral Technologies Chiralpak® AS, 5 μm; Eluent: 63:37 carbon dioxide/(methanol containing 0.05% ammonium hydroxide).

32. In this case, potassium phosphate and 1,2-dimethoxyethane were used in place of sodium carbonate and 1,4-dioxane.

33. 5-Bromoimidazo[2,1-b][1,3]thiazole may be prepared via bromination of imidazo[2,1-b][1,3]thiazole using N-bromosuccinimide.

34. The two enantiomers were separated by supercritical fluid chromatography. Example 213 was the second-eluting enantiomer, and Example 214 was the first-eluting isomer, using a Chiral Technologies Chiralcel OJ-3 column, and gradient of 5% to 40% methanol in carbon dioxide containing 0.05% diethylamine.

35. In this case, the Suzuki reaction was carried out using bis[di-tert-butyl(4-dimethylaminophenyl)phosphine]dichloropalladium(II) and cesium fluoride in a mixture of 1,4-dioxane and water at 100° C. for 18 hours.

36. Treatment of 4-bromo-1-methyl-1H-imidazole with lithium diisopropylamide and N,N-dimethylformamide provided 4-bromo-1-methyl-1H-imidazole-2-carbaldehyde, which was converted to the requisite 4-bromo-1-methyl-1H-imidazole-2-carbonitrile via reaction with ammonium hydroxide and iodine, according to the method of J.-J. Shie and J.-M. Fang, J. Org. Chem. 2007, 72, 3141-3144.

37. Conditions for analytical HPLC. Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.

38. Conditions for analytical HPLC. Column: Waters XBridge C18, 4.6×50 mm, 5 μm; Mobile phase A: 0.03% ammonium hydroxide in water (v/v); Mobile phase B: 0.03% ammonium hydroxide in acetonitrile (v/v); Gradient: 5.0% to 95% B, linear over 4.0 minutes; Flow rate: 2 mL/minute).

39. 3-Bromo-1-methyl-1H-pyrazole-5-carbaldehyde was converted to 3-bromo-1-methyl-1H-pyrazole-5-carbonitrile using the method of J.-J. Shie and J.-M. Fang; see footnote 36.

40. Treatment of (4-benzylmorpholin-2-yl)acetonitrile with ammonium cerium(IV) nitrate provided the requisite morpholin-2-ylacetonitrile.

BIOLOGICAL ASSAYS

LRRK2 Assay

LRRK2 kinase activity was measured using Lantha Screen technology from Invitrogen. GST-tagged truncated LRRK2 from Invitrogen (Cat # PV4874) was incubated with a fluorescein-labeled peptide substrate based upon ezrin/radixin/moesin (ERM), also known as LRRKtide (Invitrogen cat # PR8976A), in the presence of a dose response of compound. Upon completion, the assay was stopped and detected with a terbium labeled anti-phospho-ERM antibody (Invitrogen, cat # PR8975A). The assay was carried out under the following protocol: 3 μL of a working solution of substrate (233 nM LRRKtide, 117 μM ATP) prepared in assay buffer (50 mM HEEPES, pH 7.5, 3 mM $MgCl_2$, with 2 mM DTT and 0.01% Brij35 added fresh) was added to a low volume Greiner 384-well plate. The compound dose response was prepared by diluting compound to a top concentration of 3.16 mM in 100% DMSO and serial diluted by half-log in DMSO 11 times. Aliquots (3.5 μL) of the 100% DMSO dose response were mixed with 46.5 μL water then 1 μL of this mixture was added to the 3 μL substrate mix in the 384-well plate. The kinase reaction was started with 3 µL of a working solution of LRRK2 enzyme at a concentration of 4 µg/mL. The final reaction concentrations were 100 nM LRRKtide, 50 µM ATP, 1.7 µg/mL LRRK2 enzyme and a compound dose response with a top dose of 32 µM. The reaction was allowed to progress at room temperature for two hours and then stopped with the addition of 7 µL of detection buffer (20 mM Tris pH 7.6, 0.01% NP-40, 0.02% NaN$_3$, 6 mM EDTA with 2 nM terbium labeled anti-phospho-ERM). After an incubation of 1 hour at room temperature, the plate was read on an Envision with an excitation wavelength of 340 nm and a reading emission at both 520 nm and 495 nm. The ratio of the 520 nm and 495 nm emission was used to analyze the data.

Inhibition of mutant G2019S LRRK2 (Invitrogen cat # PV4881) was measured in the exact same method. All final concentrations of substrate ATP and enzyme were the same. However, since the mutant enzyme is more active the reaction time was reduced to 90 minutes to ensure that inhibition was measured at steady state before any substrate depletion could occur.

Table 2, below, provides the LRRK2 IC$_{50}$ data for the compounds of the invention.

TABLE 2

| Example Number | IUPAC Name | LRRK2 WT IC$_{50}$ (nM)* | LRRK2 G2019S IC$_{50}$ (nM)* |
|---|---|---|---|
| 1 | 5-(1-methyl-1H-pyrazol-4-yl)-4-(morpholin-4-yl)-7H-pyrrolo[2,3-d]pyrimidine | 13[a] | 36[a] |
| 2 | 3-[6-methyl-4-(morpholin-4-yl)-7H-pyrrolo[2,3-d]pyrimidin-5-yl]benzonitrile | 12 | 43 |
| 3 | 6-[4-(morpholin-4-yl)-7H-pyrrolo[2,3-d]pyrimidin-5-yl]pyridine-2-carbonitrile | 9 | 26 |
| 4 | 3-[4-(morpholin-4-yl)-7H-pyrrolo[2,3-d]pyrimidin-5-yl]benzonitrile | 3[a] | 11[a] |
| 5 | 3-[4-(dimethylamino)-7H-pyrrolo[2,3-d]pyrimidin-5-yl]benzonitrile | 5 | 15 |
| 6 | 3-{4-[(2S)-2-methylmorpholin-4-yl]-7H-pyrrolo[2,3-d]pyrimidin-5-yl}benzonitrile | 7 | 37 |
| 7 | (3-{4-[(3S)-3-methylpiperidin-1-yl]-7H-pyrrolo[2,3-d]pyrimidin-5-yl}phenyl)methanol | 18[a] | 18[a] |
| 8 | 4-(morpholin-4-yl)-5-(1H-pyrazol-4-yl)-7H-pyrrolo[2,3-d]pyrimidine, formate salt | 25 | 33 |
| 9 | 3-[2-methyl-4-(morpholin-4-yl)-7H-pyrrolo[2,3-d]pyrimidin-5-yl]benzonitrile | 42 | 513 |
| 10 | {3-[4-(dimethylamino)-7H-pyrrolo[2,3-d]pyrimidin-5-yl]phenyl}methanol | 34 | 23 |
| 11 | 3-[4-(3,3-dimethylpiperidin-1-yl)-7H-pyrrolo[2,3-d]pyrimidin-5-yl]benzonitrile | 90 | 325 |
| 12 | 3-[4-(piperidin-1-yl)-7H-pyrrolo[2,3-d]pyrimidin-5-yl]benzonitrile | 6 | 28 |
| 13 | 1-(5-phenyl-7H-pyrrolo[2,3-d]pyrimidin-4-yl)piperidine-3-carboxamide | 41 | 39 |
| 14 | 3-{4-[(3S)-3-hydroxypiperidin-1-yl]-7H-pyrrolo[2,3-d]pyrimidin-5-yl}benzonitrile | 17[b] | 95[b] |
| 15 | 4-[(3S)-3-methylpiperidin-1-yl]-5-phenyl-7H-pyrrolo[2,3-d]pyrimidine | 91 | 92 |
| 16 | 3-{4-[(3S)-3-methylpiperidin-1-yl]-7H-pyrrolo[2,3-d]pyrimidin-5-yl}benzonitrile | 16[a] | 45[a] |
| 17 | 4-[(3S)-3-methylpiperidin-1-yl]-5-(1-methyl-1H-pyrazol-4-yl)-7H-pyrrolo[2,3-d]pyrimidine | 14 | 12 |
| 18 | 5-phenyl-4-(pyrrolidin-1-yl)-7H-pyrrolo[2,3-d]pyrimidine | 71 | 47 |
| 19 | [1-(5-phenyl-7H-pyrrolo[2,3-d]pyrimidin-4-yl)piperidin-4-yl]methanol | 38 | 29 |
| 20 | 1-{5-[3-(hydroxymethyl)phenyl]-7H-pyrrolo[2,3-d]pyrimidin-4-yl}piperidine-3-carbonitrile | 56 | 31 |
| 21 | 1-[5-(3-cyanophenyl)-7H-pyrrolo[2,3-d]pyrimidin-4-yl]piperidine-3-carbonitrile | 57 | 183 |
| 22 | 4-(3,5-cis-dimethylpiperidin-1-yl)-5-(1-methyl-1H-pyrazol-4-yl)-7H-pyrrolo[2,3-d]pyrimidine | 16 | 16 |
| 23 | 4-methoxy-3-[4-(3-methylpiperidin-1-yl)-7H-pyrrolo[2,3-d]pyrimidin-5-yl]benzonitrile | 25 | 46 |
| 24 | 3-[4-(dimethylamino)-7H-pyrrolo[2,3-d]pyrimidin-5-yl]-4-methoxybenzonitrile | 24 | 30 |
| 25 | 5-(5-chloro-2-methoxyphenyl)-N,N-dimethyl-7H-pyrrolo[2,3-d]pyrimidin-4-amine | 22 | 19 |
| 26 | 3-{4-[4-(1H-imidazol-2-yl)piperidin-1-yl]-7H-pyrrolo[2,3-d]pyrimidin-5-yl}benzonitrile, trifluoroacetate salt | 42 | 230 |
| 27 | 3-{4-[3-(methoxymethyl)piperidin-1-yl]-7H-pyrrolo[2,3-d]pyrimidin-5-yl}benzonitrile | 95 | 219 |
| 28 | 3-[4-(9-methyl-1-oxa-4,9-diazaspiro[5.5]undec-4-yl)-7H-pyrrolo[2,3-d]pyrimidin-5-yl]benzonitrile | 40 | 201 |
| 29 | 3-[4-(3-methoxypiperidin-1-yl)-7H-pyrrolo[2,3-d]pyrimidin-5-yl]benzonitrile | 79 | 154 |
| 30 | 3-{4-[2-(methoxymethyl)morpholin-4-yl]-7H-pyrrolo[2,3-d]pyrimidin-5-yl}benzonitrile | 17 | 121 |

TABLE 2-continued

| Example Number | IUPAC Name | LRRK2 WT IC$_{50}$ (nM)* | LRRK2 G2019S IC$_{50}$ (nM)* |
|---|---|---|---|
| 31 | N$^3$-[5-(3-cyanophenyl)-7H-pyrrolo[2,3-d]pyrimidin-4-yl]-N,N-dimethyl-beta-alaninamide | 54 | 248 |
| 32 | 3-[4-(4,4-difluoropiperidin-1-yl)-7H-pyrrolo[2,3-d]pyrimidin-5-yl]benzonitrile | 67 | 333 |
| 33 | 3-[4-(4-fluoropiperidin-1-yl)-7H-pyrrolo[2,3-d]pyrimidin-5-yl]benzonitrile | 17 | 96 |
| 33A | 3-[4-(4-fluoropiperidin-1-yl)-7H-pyrrolo[2,3-d]pyrimidin-5-yl]benzonitrile | 17 | 56$^b$ |
| 34 | 3-{4-[4-(1H-pyrazol-3-yl)piperidin-1-yl]-7H-pyrrolo[2,3-d]pyrimidin-5-yl}benzonitrile | 69 | 136 |
| 35 | 3-{4-[(3S)-3-fluoropyrrolidin-1-yl]-7H-pyrrolo[2,3-d]pyrimidin-5-yl}benzonitrile | 30 | 155 |
| 36 | 3-{4-[2-(1H-pyrazol-3-yl)morpholin-4-yl]-7H-pyrrolo[2,3-d]pyrimidin-5-yl}benzonitrile | 43 | 238 |
| 37 | 3-{4-[3-(1H-pyrazol-3-yl)piperidin-1-yl]-7H-pyrrolo[2,3-d]pyrimidin-5-yl}benzonitrile | 84 | 200 |
| 38 | 3-{4-[3-(1H-imidazol-2-yl)piperidin-1-yl]-7H-pyrrolo[2,3-d]pyrimidin-5-yl}benzonitrile, formate salt | 53 | 331 |
| 39 | 3-{4-[(1-methylpiperidin-3-yl)amino]-7H-pyrrolo[2,3-d]pyrimidin-5-yl}benzonitrile, formate salt | 78 | 243 |
| 40 | 3-[4-(3-oxo-2,7-diazaspiro[4.5]dec-7-yl)-7H-pyrrolo[2,3-d]pyrimidin-5-yl]benzonitrile | 35 | 119 |
| 41 | 3-[4-(3-methylpiperidin-1-yl)-7H-pyrrolo[2,3-d]pyrimidin-5-yl]benzonitrile, ENT-2 | 70 | 172 |
| 42 | 3-(4-{[2-(morpholin-4-yl)ethyl]amino}-7H-pyrrolo[2,3-d]pyrimidin-5-yl)benzonitrile, formate salt | 89 | 487 |
| 43 | 3-[4-(2-oxa-7-azaspiro[4.5]dec-7-yl)-7H-pyrrolo[2,3-d]pyrimidin-5-yl]benzonitrile | 34 | 244 |
| 44 | N-{1-[5-(3-cyanophenyl)-7H-pyrrolo[2,3-d]pyrimidin-4-yl]piperidin-4-yl}acetamide | 50 | 190 |
| 45 | 5-(1H-indazol-5-yl)-4-[(3S)-3-methylpiperidin-1-yl]-7H-pyrrolo[2,3-d]pyrimidine | 67 | 66$^b$ |
| 46 | 3-{4-[(3S)-3-methylpiperidin-1-yl]-7H-pyrrolo[2,3-d]pyrimidin-5-yl}benzenesulfonamide | 24 | 33$^b$ |
| 47 | 5-(2-fluorophenyl)-4-[(3S)-3-methylpiperidin-1-yl]-7H-pyrrolo[2,3-d]pyrimidine | 97 | 122$^b$ |
| 48 | 5-(1H-indazol-4-yl)-4-[(3S)-3-methylpiperidin-1-yl]-7H-pyrrolo[2,3-d]pyrimidine | 10$^a$ | 14 |
| 49 | 5-(6-fluoro-5-methylpyridin-3-yl)-4-[(3S)-3-methylpiperidin-1-yl]-7H-pyrrolo[2,3-d]pyrimidine, trifluoroacetate salt | 64 | 65$^b$ |
| 50 | 5-{4-[(3S)-3-methylpiperidin-1-yl]-7H-pyrrolo[2,3-d]pyrimidin-5-yl}-2,3-dihydro-1H-isoindol-1-one | 33 | 33$^b$ |
| 51 | 4-[(3S)-3-methylpiperidin-1-yl]-5-(pyridin-3-yl)-7H-pyrrolo[2,3-d]pyrimidine, formate salt | 56 | 95$^b$ |
| 52 | 4-[(3S)-3-methylpiperidin-1-yl]-5-(5-methylpyridin-3-yl)-7H-pyrrolo[2,3-d]pyrimidine, formate salt | 15 | 19$^b$ |
| 53 | 4-[(3S)-3-methylpiperidin-1-yl]-5-(7H-pyrrolo[2,3-b]pyridin-5-yl)-7H-pyrrolo[2,3-d]pyrimidine, formate salt | 74 | 69$^b$ |
| 54 | 6-{4-[(3S)-3-methylpiperidin-1-yl]-7H-pyrrolo[2,3-d]pyrimidin-5-yl}-2,3-dihydro-1H-isoindol-1-one | 68 | 59$^b$ |
| 55 | 4-[(3S)-3-methylpiperidin-1-yl]-5-(1H-pyrrolo[3,2-b]pyridin-6-yl)-7H-pyrrolo[2,3-d]pyrimidine, formate salt | 53 | 50$^b$ |
| 56 | 4-{4-[(3S)-3-methylpiperidin-1-yl]-7H-pyrrolo[2,3-d]pyrimidin-5-yl}phenol | 26 | 28$^b$ |
| 57 | 4-{4-[(3S)-3-methylpiperidin-1-yl]-7H-pyrrolo[2,3-d]pyrimidin-5-yl}benzamide | 13 | 9$^b$ |
| 58 | 3-{4-[(3S)-3-methylpiperidin-1-yl]-7H-pyrrolo[2,3-d]pyrimidin-5-yl}phenol | 9 | 12$^b$ |
| 59 | 5-(2-chloro-5-methylpyridin-3-yl)-4-[(3S)-3-methylpiperidin-1-yl]-7H-pyrrolo[2,3-d]pyrimidine, formate salt | 30 | 30$^b$ |
| 60 | 3-{4-[(3S)-3-methylpiperidin-1-yl]-7H-pyrrolo[2,3-d]pyrimidin-5-yl}benzamide | 86 | 58 |
| 61 | 3-[4-(3-fluoropiperidin-1-yl)-7H-pyrrolo[2,3-d]pyrimidin-5-yl]benzonitrile | 12 | 80 |
| 62 | 3-[4-(4-methylpiperidin-1-yl)-7H-pyrrolo[2,3-d]pyrimidin-5-yl]benzonitrile, hydrochloride salt | 91 | 273 |
| 63 | 3-{4-[(3S)-3-methylpiperidin-1-yl]-7H-pyrrolo[2,3-d]pyrimidin-5-yl}benzoic acid | 55 | 39 |
| 64 | 3-[4-(methylamino)-7H-pyrrolo[2,3-d]pyrimidin-5-yl]benzonitrile | 45 | 97 |
| 65 | 3-[4-(3,5-cis-dimethylpiperidin-1-yl)-7H-pyrrolo[2,3-d]pyrimidin-5-yl]-4-methoxybenzonitrile | 85 | 176 |
| 66 | 4-methoxy-3-{4-[(3S)-3-methylpiperidin-1-yl]-7H-pyrrolo[2,3-d]pyrimidin-5-yl}benzonitrile | 21 | 51 |

TABLE 2-continued

| Example Number | IUPAC Name | LRRK2 WT IC$_{50}$ (nM)* | LRRK2 G2019S IC$_{50}$ (nM)* |
|---|---|---|---|
| 67 | 2-fluoro-3-{4-[(3S)-3-methylpiperidin-1-yl]-7H-pyrrolo[2,3-d]pyrimidin-5-yl}benzonitrile | 11 | 35 |
| 68 | N,N-dimethyl-5-phenyl-7H-pyrrolo[2,3-d]pyrimidin-4-amine | 63 | 39 |
| 69 | 3-[4-(dimethylamino)-7H-pyrrolo[2,3-d]pyrimidin-5-yl]-2-fluorobenzonitrile | 6 | 17 |
| 70 | 3-[4-(pyrrolidin-1-yl)-7H-pyrrolo[2,3-d]pyrimidin-5-yl]benzonitrile | 8 | 64 |
| 71 | 3-[4-(3-methylpyrrolidin-1-yl)-7H-pyrrolo[2,3-d]pyrimidin-5-yl]benzonitrile, ENT-2 | 21 | 102 |
| 72 | 3-[4-(dimethylamino)-7H-pyrrolo[2,3-d]pyrimidin-5-yl]-4-fluorobenzonitrile | 37 | 190 |
| 73 | 3-[4-(diethylamino)-7H-pyrrolo[2,3-d]pyrimidin-5-yl]benzonitrile | 13 | 119 |
| 74 | 3-{4-[2-(methoxymethyl)morpholin-4-yl]-7H-pyrrolo[2,3-d]pyrimidin-5-yl}benzonitrile, ENT-1 | 12 | 100 |
| 75 | 3-[4-(dimethylamino)-7H-pyrrolo[2,3-d]pyrimidin-5-yl]-5-fluorobenzonitrile | 53 | 396 |
| 76 | 3-{4-[2-(1H-pyrazol-3-yl)morpholin-4-yl]-7H-pyrrolo[2,3-d]pyrimidin-5-yl}benzonitrile, ENT-2, formate salt, | 23 | 208 |
| 77 | 3-[4-(3-methylpyrrolidin-1-yl)-7H-pyrrolo[2,3-d]pyrimidin-5-yl]benzonitrile, ENT-1 | 39 | 158 |
| 78 | 2-fluoro-3-[4-(morpholin-4-yl)-7H-pyrrolo[2,3-d]pyrimidin-5-yl]benzonitrile | 2 | 7 |
| 79 | 3-{4-[(2R)-2-methylmorpholin-4-yl]-7H-pyrrolo[2,3-d]pyrimidin-5-yl}benzonitrile | 18 | 69 |
| 80 | 4-fluoro-3-[4-(morpholin-4-yl)-7H-pyrrolo[2,3-d]pyrimidin-5-yl]benzonitrile | 49 | 393 |
| 81 | 4-(4-fluoropiperidin-1-yl)-5-(1-methyl-1H-pyrazol-4-yl)-7H-pyrrolo[2,3-d]pyrimidine | 36 | 50 |
| 82 | 2-[4-(morpholin-4-yl)-7H-pyrrolo[2,3-d]pyrimidin-5-yl]benzonitrile | 95 | 148 |
| 83 | 5-(3-chlorophenyl)-4-(morpholin-4-yl)-7H-pyrrolo[2,3-d]pyrimidine | 8 | 13 |
| 84 | 5-(2-fluorophenyl)-4-(morpholin-4-yl)-7H-pyrrolo[2,3-d]pyrimidine | 22 | 30 |
| 85 | 5-(3-fluoro-5-methoxyphenyl)-4-(morpholin-4-yl)-7H-pyrrolo[2,3-d]pyrimidine | 9 | 20 |
| 86 | 5-(2,5-difluorophenyl)-4-(morpholin-4-yl)-7H-pyrrolo[2,3-d]pyrimidine | 76 | 145 |
| 87 | 5-(2,3-difluorophenyl)-4-(morpholin-4-yl)-7H-pyrrolo[2,3-d]pyrimidine | 12 | 24 |
| 88 | 5-(5-chloro-2-fluorophenyl)-4-(morpholin-4-yl)-7H-pyrrolo[2,3-d]pyrimidine | 9 | 12 |
| 89 | {2-fluoro-3-[4-(morpholin-4-yl)-7H-pyrrolo[2,3-d]pyrimidin-5-yl]phenyl}methanol | 32 | 75 |
| 90 | 5-(2,4-difluorophenyl)-4-(morpholin-4-yl)-7H-pyrrolo[2,3-d]pyrimidine | 41 | 62 |
| 91 | 5-(3-fluorophenyl)-4-(morpholin-4-yl)-7H-pyrrolo[2,3-d]pyrimidine | 9 | 21 |
| 92 | 5-(3,5-difluorophenyl)-4-(morpholin-4-yl)-7H-pyrrolo[2,3-d]pyrimidine | 92 | 238 |
| 93 | 4-(morpholin-4-yl)-5-phenyl-7H-pyrrolo[2,3-d]pyrimidine | 9 | 14 |
| 94 | 5-(5-fluoro-2-methoxyphenyl)-4-(morpholin-4-yl)-7H-pyrrolo[2,3-d]pyrimidine | 7 | 10 |
| 95 | 5-(2-chlorophenyl)-4-(morpholin-4-yl)-7H-pyrrolo[2,3-d]pyrimidine | 21 | 33 |
| 96 | 5-(5-fluoro-2-methylphenyl)-4-(morpholin-4-yl)-7H-pyrrolo[2,3-d]pyrimidine | 91 | 223 |
| 97 | 5-(3-methoxyphenyl)-4-(morpholin-4-yl)-7H-pyrrolo[2,3-d]pyrimidine | 28 | 46 |
| 98 | {2-fluoro-5-[4-(morpholin-4-yl)-7H-pyrrolo[2,3-d]pyrimidin-5-yl]phenyl}methanol | 70 | 135 |
| 99 | 5-(4-fluorophenyl)-4-(morpholin-4-yl)-7H-pyrrolo[2,3-d]pyrimidine | 95 | 154 |
| 100 | {3-[4-(morpholin-4-yl)-7H-pyrrolo[2,3-d]pyrimidin-5-yl]phenyl}methanol | 12 | 19 |
| 101 | 5-(2-methoxyphenyl)-4-(morpholin-4-yl)-7H-pyrrolo[2,3-d]pyrimidine | 14 | 23 |
| 102 | 5-[3-(methylsulfanyl)phenyl]-4-(morpholin-4-yl)-7H-pyrrolo[2,3-d]pyrimidine | 52 | 78 |
| 103 | 4-(morpholin-4-yl)-5-(pyridin-3-yl)-7H-pyrrolo[2,3-d]pyrimidine, formate salt | 35 | 159 |

TABLE 2-continued

| Example Number | IUPAC Name | LRRK2 WT IC$_{50}$ (nM)* | LRRK2 G2019S IC$_{50}$ (nM)* |
|---|---|---|---|
| 104 | 4-[4-(morpholin-4-yl)-7H-pyrrolo[2,3-d]pyrimidin-5-yl]isoquinoline, formate salt | 27 | 51 |
| 105 | 5-(5-bromopyridin-3-yl)-4-(morpholin-4-yl)-7H-pyrrolo[2,3-d]pyrimidine, formate salt | 6 | 14 |
| 106 | 5-(2-chloro-5-methylphenyl)-4-(morpholin-4-yl)-7H-pyrrolo[2,3-d]pyrimidine | 22 | 44 |
| 107 | 5-(3-methylphenyl)-4-(morpholin-4-yl)-7H-pyrrolo[2,3-d]pyrimidine | 13 | 20 |
| 108 | 5-(1-methyl-1H-pyrazol-3-yl)-4-(morpholin-4-yl)-7H-pyrrolo[2,3-d]pyrimidine | 53 | 90 |
| 109 | 3-[4-(4-hydroxypiperidin-1-yl)-7H-pyrrolo[2,3-d]pyrimidin-5-yl]benzonitrile | 52 | 109 |
| 110 | 3-{4-[2-(3-methyl-1,2,4-oxadiazol-5-yl)morpholin-4-yl]-7H-pyrrolo[2,3-d]pyrimidin-5-yl}benzonitrile | 20 | 176 |
| 111 | 3-methyl-5-[4-(morpholin-4-yl)-7H-pyrrolo[2,3-d]pyrimidin-5-yl]benzonitrile | 14[b] | 64[b] |
| 112 | 3-{4-[2-(5-methyl-1,2,4-oxadiazol-3-yl)morpholin-4-yl]-7H-pyrrolo[2,3-d]pyrimidin-5-yl}benzonitrile | 10 | 41 |
| 113 | 3-[4-(6-oxa-3-azabicyclo[3.1.1]hept-3-yl)-7H-pyrrolo[2,3-d]pyrimidin-5-yl]benzonitrile | 58[b] | 523[b] |
| 114 | 3-chloro-5-[4-(morpholin-4-yl)-7H-pyrrolo[2,3-d]pyrimidin-5-yl]benzonitrile | 77[b] | 406[b] |
| 115 | 4-methoxy-3-[4-(morpholin-4-yl)-7H-pyrrolo[2,3-d]pyrimidin-5-yl]benzonitrile | 48 | 121 |
| 116 | 5-(5-chloro-2-methoxyphenyl)-4-(morpholin-4-yl)-7H-pyrrolo[2,3-d]pyrimidine | 85 | 67 |
| 117 | 6-methyl-5-(1-methyl-1H-pyrazol-4-yl)-4-(morpholin-4-yl)-7H-pyrrolo[2,3-d]pyrimidine | 47 | 89 |
| 118 | 3-methoxy-5-[4-(morpholin-4-yl)-7H-pyrrolo[2,3-d]pyrimidin-5-yl]benzonitrile | 77 | 177 |
| 119 | 5-(1-methyl-1H-pyrazol-4-yl)-4-(thiomorpholin-4-yl)-7H-pyrrolo[2,3-d]pyrimidine | 71 | 51 |
| 120 | 1-[5-(1-methyl-1H-pyrazol-4-yl)-7H-pyrrolo[2,3-d]pyrimidin-4-yl]piperidin-3-ol | 44 | 34 |
| 121 | 4-[(2S)-2-methylmorpholin-4-yl]-5-(1-methyl-1H-pyrazol-4-yl)-7H-pyrrolo[2,3-d]pyrimidine | 57 | 59 |
| 122 | 4-[(2R)-2-methylmorpholin-4-yl]-5-(1-methyl-1H-pyrazol-4-yl)-7H-pyrrolo[2,3-d]pyrimidine | 67 | 31 |
| 123 | 4-(3-fluoropiperidin-1-yl)-5-(1-methyl-1H-pyrazol-4-yl)-7H-pyrrolo[2,3-d]pyrimidine | 31 | 27 |
| 124 | {4-[5-(1-methyl-1H-pyrazol-4-yl)-7H-pyrrolo[2,3-d]pyrimidin-4-yl]morpholin-2-yl}methanol | 77 | 80 |
| 125 | 5-(1-methyl-1H-pyrazol-4-yl)-4-(2-{[(6-methylpyridin-3-yl)oxy]methyl}morpholin-4-yl)-7H-pyrrolo[2,3-d]pyrimidine | 54 | 87 |
| 126 | N,N-dimethyl-5-(1-methyl-1H-pyrazol-4-yl)-7H-pyrrolo[2,3-d]pyrimidin-4-amine | 55 | 35 |
| 127 | N-cyclopropyl-N-methyl-5-(1-methyl-1H-pyrazol-4-yl)-7H-pyrrolo[2,3-d]pyrimidin-4-amine | 37 | 37 |
| 128 | 3-[4-(3,3-difluoropiperidin-1-yl)-7H-pyrrolo[2,3-d]pyrimidin-5-yl]benzonitrile | 79 | 169 |
| 129 | 3-[4-(3-aminopiperidin-1-yl)-7H-pyrrolo[2,3-d]pyrimidin-5-yl]benzonitrile | 14 | 21 |
| 130 | 3-[4-(2-{[5-(difluoromethyl)-1,2,4-oxadiazol-3-yl]methyl}morpholin-4-yl)-7H-pyrrolo[2,3-d]pyrimidin-5-yl]benzonitrile | 44 | 134 |
| 131 | 3-{4-[2-(1,3-thiazol-2-yl)morpholin-4-yl]-7H-pyrrolo[2,3-d]pyrimidin-5-yl}benzonitrile | 45 | 181 |
| 132 | 3-[4-(4-oxopiperidin-1-yl)-7H-pyrrolo[2,3-d]pyrimidin-5-yl]benzonitrile | 66 | 223 |
| 133 | 3-{4-[4-fluoro-4-(hydroxymethyl)piperidin-1-yl]-7H-pyrrolo[2,3-d]pyrimidin-5-yl}benzonitrile | 42 | 106 |
| 134 | 3-{4-[2-(3-hydroxyphenyl)morpholin-4-yl]-7H-pyrrolo[2,3-d]pyrimidin-5-yl}benzonitrile | 91 | 281 |
| 135 | 3-{4-[2-(5-cyclopropyl-1,2,4-oxadiazol-3-yl)morpholin-4-yl]-7H-pyrrolo[2,3-d]pyrimidin-5-yl}benzonitrile | 19 | 47 |
| 136 | 3-[4-(3,3-difluoropyrrolidin-1-yl)-7H-pyrrolo[2,3-d]pyrimidin-5-yl]benzonitrile | 74 | 194 |
| 137 | 3-(4-{2-[(3-cyanophenoxy)methyl]morpholin-4-yl}-7H-pyrrolo[2,3-d]pyrimidin-5-yl)benzonitrile | 30 | 51 |
| 138 | 3-[4-(3-hydroxypiperidin-1-yl)-7H-pyrrolo[2,3-d]pyrimidin-5-yl]benzonitrile | 10 | 27 |
| 139 | 1-[5-(3-cyanophenyl)-7H-pyrrolo[2,3-d]pyrimidin-4-yl]piperidine-3-carboxamide | 49 | 136 |
| 140 | 3-[4-(2-ethylmorpholin-4-yl)-7H-pyrrolo[2,3-d]pyrimidin-5-yl]benzonitrile | 61 | 95 |

TABLE 2-continued

| Example Number | IUPAC Name | LRRK2 WT IC$_{50}$ (nM)* | LRRK2 G2019S IC$_{50}$ (nM)* |
|---|---|---|---|
| 141 | 3-{4-[2-(pyrimidin-4-yl)morpholin-4-yl]-7H-pyrrolo[2,3-d]pyrimidin-5-yl}benzonitrile | 79 | 193 |
| 142 | 3-{4-[2-(3-cyclopropyl-1,2,4-oxadiazol-5-yl)morpholin-4-yl]-7H-pyrrolo[2,3-d]pyrimidin-5-yl}benzonitrile | 30 | 84 |
| 143 | 3-(4-{2-[(dimethylamino)methyl]morpholin-4-yl}-7H-pyrrolo[2,3-d]pyrimidin-5-yl)benzonitrile | 45 | 110 |
| 144 | 3-[4-(1H-pyrazol-4-ylamino)-7H-pyrrolo[2,3-d]pyrimidin-5-yl]benzonitrile | 69 | 36 |
| 145 | 3-(4-{2-[(5-methyl-1,2,4-oxadiazol-3-yl)methyl]morpholin-4-yl}-7H-pyrrolo[2,3-d]pyrimidin-5-yl)benzonitrile | 55 | 155 |
| 146 | 3-{4-[3-(5-methyl-1,3,4-oxadiazol-2-yl)piperidin-1-yl]-7H-pyrrolo[2,3-d]pyrimidin-5-yl}benzonitrile | 96 | 217 |
| 147 | 3-[4-(dimethylamino)-7H-pyrrolo[2,3-d]pyrimidin-5-yl]-5-methoxybenzonitrile | 37 | 93 |
| 148 | 5-(1-ethyl-1H-pyrazol-4-yl)-4-(morpholin-4-yl)-7H-pyrrolo[2,3-d]pyrimidine | 77[b] | 92[b] |
| 149 | 5-(5-methylpyridin-3-yl)-4-(morpholin-4-yl)-7H-pyrrolo[2,3-d]pyrimidine | 18 | 30 |
| 150 | 5-(5-chloropyridin-3-yl)-4-(morpholin-4-yl)-7H-pyrrolo[2,3-d]pyrimidine | 28 | 36 |
| 151 | 5-(6-methoxypyrazin-2-yl)-4-(morpholin-4-yl)-7H-pyrrolo[2,3-d]pyrimidine | 32 | 37 |
| 152 | 5-(1,3-dimethyl-1H-pyrazol-4-yl)-4-(morpholin-4-yl)-7H-pyrrolo[2,3-d]pyrimidine, formate salt | 60 | 91 |
| 153 | 3-{4-[(3S)-3-methylmorpholin-4-yl]-7H-pyrrolo[2,3-d]pyrimidin-5-yl}benzonitrile | 44 | 165 |
| 154 | 2-fluoro-3-[2-methyl-4-(morpholin-4-yl)-7H-pyrrolo[2,3-d]pyrimidin-5-yl]benzonitrile | 30 | 365 |
| 155 | 3-{4-[(3R)-3-hydroxypiperidin-1-yl]-7H-pyrrolo[2,3-d]pyrimidin-5-yl}benzonitrile | 8[b] | 37[b] |
| 156 | 1-[5-(3-fluorophenyl)-7H-pyrrolo[2,3-d]pyrimidin-4-yl]piperidin-3-ol | 57 | 86 |
| 157 | 5-(5-fluoro-2-methoxyphenyl)-4-[2-(5-methyl-1,2,4-oxadiazol-3-yl)morpholin-4-yl]-7H-pyrrolo[2,3-d]pyrimidine | 44 | 46 |
| 158 | 2-fluoro-3-[4-(4-fluoropiperidin-1-yl)-7H-pyrrolo[2,3-d]pyrimidin-5-yl]benzonitrile | 18 | 86 |
| 159 | 4-(4-fluoropiperidin-1-yl)-5-(2-methoxyphenyl)-7H-pyrrolo[2,3-d]pyrimidine | 67 | 74 |
| 160 | 5-(3-fluoro-5-methoxyphenyl)-4-(4-fluoropiperidin-1-yl)-7H-pyrrolo[2,3-d]pyrimidine | 84 | 96 |
| 161 | 3-[4-(4,4-difluoropiperidin-1-yl)-7H-pyrrolo[2,3-d]pyrimidin-5-yl]-2-fluorobenzonitrile | N.D.[c] | N.D. |
| 162 | 1-[5-(5-methylpyridin-3-yl)-7H-pyrrolo[2,3-d]pyrimidin-4-yl]piperidin-3-ol, formate salt | 36 | 67 |
| 163 | 5-(5-fluoro-2-methoxyphenyl)-4-(4-fluoropiperidin-1-yl)-7H-pyrrolo[2,3-d]pyrimidine | 25 | 29 |
| 164 | 1-[5-(3-fluoro-5-methoxyphenyl)-7H-pyrrolo[2,3-d]pyrimidin-4-yl]piperidin-3-ol | 29 | 38 |
| 165 | 1-[5-(2-methoxyphenyl)-7H-pyrrolo[2,3-d]pyrimidin-4-yl]piperidin-3-ol | 58 | 62 |
| 166 | 2-fluoro-3-{4-[2-(3-methyl-1,2,4-oxadiazol-5-yl)morpholin-4-yl]-7H-pyrrolo[2,3-d]pyrimidin-5-yl}benzonitrile | 38 | 272 |
| 167 | 2-fluoro-3-{4-[2-(methoxymethyl)morpholin-4-yl]-7H-pyrrolo[2,3-d]pyrimidin-5-yl}benzonitrile | 61 | 372 |
| 168 | 4-(azetidin-1-yl)-5-(5-fluoro-2-methoxyphenyl)-7H-pyrrolo[2,3-d]pyrimidine | 85 | 75 |
| 169 | 4-[(2S)-2-methylmorpholin-4-yl]-5-(5-methylpyridin-3-yl)-7H-pyrrolo[2,3-d]pyrimidine, formate salt | 99 | 280 |
| 170 | 5-(3-fluorophenyl)-4-(pyrrolidin-1-yl)-7H-pyrrolo[2,3-d]pyrimidine | N.D. | N.D. |
| 171 | 5-(3-fluorophenyl)-4-[2-(5-methyl-1,2,4-oxadiazol-3-yl)morpholin-4-yl]-7H-pyrrolo[2,3-d]pyrimidine | N.D. | N.D. |
| 172 | 5-(2-methoxyphenyl)-4-[(2S)-2-methylmorpholin-4-yl]-7H-pyrrolo[2,3-d]pyrimidine | N.D. | N.D. |
| 173 | 5-(2-methoxyphenyl)-N,N-dimethyl-7H-pyrrolo[2,3-d]pyrimidin-4-amine | 43 | 29 |
| 174 | 2-fluoro-3-{4-[(3S)-3-fluoropyrrolidin-1-yl]-7H-pyrrolo[2,3-d]pyrimidin-5-yl}benzonitrile | N.D. | N.D. |
| 175 | 4-[(3S)-3-fluoropyrrolidin-1-yl]-5-(2-methoxyphenyl)-7H-pyrrolo[2,3-d]pyrimidine | 41 | 54 |
| 176 | 5-(2-methoxyphenyl)-4-(pyrrolidin-1-yl)-7H-pyrrolo[2,3-d]pyrimidine | 54 | 68 |

TABLE 2-continued

| Example Number | IUPAC Name | LRRK2 WT IC$_{50}$ (nM)* | LRRK2 G2019S IC$_{50}$ (nM)* |
|---|---|---|---|
| 177 | 5-(3-fluoro-5-methoxyphenyl)-N,N-dimethyl-7H-pyrrolo[2,3-d]pyrimidin-4-amine | 41 | 49 |
| 178 | 2-fluoro-3-[4-(3-hydroxypiperidin-1-yl)-7H-pyrrolo[2,3-d]pyrimidin-5-yl]benzonitrile | 9 | 42 |
| 179 | 5-(5-fluoro-2-methoxyphenyl)-4-[(2S)-2-methylmorpholin-4-yl]-7H-pyrrolo[2,3-d]pyrimidine | 19 | 30 |
| 180 | 2-fluoro-3-{4-[(2S)-2-methylmorpholin-4-yl]-7H-pyrrolo[2,3-d]pyrimidin-5-yl}benzonitrile | 10 | 62 |
| 181 | 5-(5-fluoro-2-methoxyphenyl)-4-(3-fluoropiperidin-1-yl)-7H-pyrrolo[2,3-d]pyrimidine | 22 | 24 |
| 182 | 5-(3-fluorophenyl)-4-[(2S)-2-methylmorpholin-4-yl]-7H-pyrrolo[2,3-d]pyrimidine | 38 | 82 |
| 183 | 5-(5-fluoro-2-methoxyphenyl)-N,N-dimethyl-7H-pyrrolo[2,3-d]pyrimidin-4-amine | 13 | 11 |
| 184 | 2-fluoro-3-[4-(pyrrolidin-1-yl)-7H-pyrrolo[2,3-d]pyrimidin-5-yl]benzonitrile | 15 | 82 |
| 185 | 5-(5-fluoro-2-methoxyphenyl)-4-[(3S)-3-fluoropyrrolidin-1-yl]-7H-pyrrolo[2,3-d]pyrimidine | 15 | 23 |
| 186 | 2-fluoro-3-{4-[2-(5-methyl-1,2,4-oxadiazol-3-yl)morpholin-4-yl]-7H-pyrrolo[2,3-d]pyrimidin-5-yl}benzonitrile | 17 | 90 |
| 187 | 5-(4-methyl-1,3-thiazol-2-yl)-4-(morpholin-4-yl)-7H-pyrrolo[2,3-d]pyrimidine | N.D. | N.D. |
| 188 | 5-(4-methylpyridin-2-yl)-4-(morpholin-4-yl)-7H-pyrrolo[2,3-d]pyrimidine, formate salt | 43 | 90 |
| 189 | 5-(2-fluoro-6-methoxyphenyl)-N,N-dimethyl-7H-pyrrolo[2,3-d]pyrimidin-4-amine | 40 | 27 |
| 190 | 5-(2-fluoro-6-methoxyphenyl)-4-(morpholin-4-yl)-7H-pyrrolo[2,3-d]pyrimidine | 25 | 34 |
| 191 | 5-(2,6-difluorophenyl)-4-(morpholin-4-yl)-7H-pyrrolo[2,3-d]pyrimidine | N.D. | N.D. |
| 192 | 5-(3-methyl-1,2-thiazol-5-yl)-4-(morpholin-4-yl)-7H-pyrrolo[2,3-d]pyrimidine | 23 | 73 |
| 193 | 5-(2-chloro-3-fluoro-6-methoxyphenyl)-4-(morpholin-4-yl)-7H-pyrrolo[2,3-d]pyrimidine | 47 | 51 |
| 194 | 5-(4-methoxypyridin-3-yl)-4-(morpholin-4-yl)-7H-pyrrolo[2,3-d]pyrimidine, formate salt | N.D. | N.D. |
| 195 | 3-{4-[2-(5-methyl-1,2,4-oxadiazol-3-yl)morpholin-4-yl]-7H-pyrrolo[2,3-d]pyrimidin-5-yl}benzonitrile, ENT-1 | 8 | 73 |
| 196 | 3-{4-[2-(5-methyl-1,2,4-oxadiazol-3-yl)morpholin-4-yl]-7H-pyrrolo[2,3-d]pyrimidin-5-yl}benzonitrile, ENT-2 | N.D. | N.D. |
| 197 | 3-{4-[2-(methoxymethyl)morpholin-4-yl]-7H-pyrrolo[2,3-d]pyrimidin-5-yl}benzonitrile, ENT-2 | 214 | 245 |
| 198 | 3-[6-(difluoromethyl)-4-(morpholin-4-yl)-7H-pyrrolo[2,3-d]pyrimidin-5-yl]benzonitrile | 127 | 1080 |
| 199 | 5-(5,6-dihydro-2H-pyran-3-yl)-4-(morpholin-4-yl)-7H-pyrrolo[2,3-d]pyrimidine | 97.8[b] | 351[b] |
| 200 | 5-(3,4-dihydro-2H-pyran-5-yl)-4-(morpholin-4-yl)-7H-pyrrolo[2,3-d]pyrimidine | 76.7[b] | 167[b] |
| 201 | 4-(morpholin-4-yl)-5-[3-(1,2,4-oxadiazol-3-yl)phenyl]-7H-pyrrolo[2,3-d]pyrimidine | 129[b] | 475[b] |
| 202 | 3-{4-[2-(3-methyl-1,2-oxazol-5-yl)morpholin-4-yl]-7H-pyrrolo[2,3-d]pyrimidin-5-yl}benzonitrile | 64.7 | 350 |
| 203 | 2-methyl-3-[4-(morpholin-4-yl)-7H-pyrrolo[2,3-d]pyrimidin-5-yl]benzonitrile | 13.2 | 90.1 |
| 204 | 4-[4-(morpholin-4-yl)-7H-pyrrolo[2,3-d]pyrimidin-5-yl]pyridin-2(1H)-one | 11.7 | 32.7 |
| 205 | 5-(imidazo[2,1-d][1,3]thiazol-5-yl)-4-(morpholin-4-yl)-7H-pyrrolo[2,3-d]pyrimidine | 15.8 | 60.5 |
| 206 | rel-3-{4-[(3aS,6aS)-hexahydro-5H-furo[2,3-c]pyrrol-5-yl]-7H-pyrrolo[2,3-d]pyrimidin-5-yl}benzonitrile | 139 | 591 |
| 207 | rel-3-{4-[(3aR,6aS)-tetrahydro-1H-furo[3,4-c]pyrrol-5(3H)-yl]-7H-pyrrolo[2,3-d]pyrimidin-5-yl}benzonitrile | 223[b] | 687[b] |
| 208 | rel-3-{4-[(4aR,7aS)-hexahydrocyclopenta[b][1,4]oxazin-4(4aH)-yl]-7H-pyrrolo[2,3-d]pyrimidin-5-yl}benzonitrile | 27.2 | 186 |
| 209 | 4-[5-(3-cyanophenyl)-7H-pyrrolo[2,3-d]pyrimidin-4-yl]morpholine-2-carbonitrile | 42.2 | 336 |
| 210 | 3-[4-(2,2-dimethylmorpholin-4-yl)-7H-pyrrolo[2,3-d]pyrimidin-5-yl]benzonitrile | 35.2 | 304 |
| 211 | 5-[4-(morpholin-4-yl)-7H-pyrrolo[2,3-d]pyrimidin-5-yl]thiophene-2-carbonitrile | 21.9 | 118 |
| 212 | 5-(imidazo[1,2-b]pyridazin-3-yl)-4-(morpholin-4-yl)-7H-pyrrolo[2,3-d]pyrimidine | 6.26 | 12.3 |
| 213 | 2-fluoro-3-{4-[2-(3-methyl-1,2,4-oxadiazol-5-yl)morpholin-4-yl]-7H-pyrrolo[2,3-d]pyrimidin-5-yl}benzonitrile, ENT-2 | 7.71 | 95.7 |

TABLE 2-continued

| Example Number | IUPAC Name | LRRK2 WT IC$_{50}$ (nM)* | LRRK2 G2019S IC$_{50}$ (nM)* |
|---|---|---|---|
| 214 | 2-fluoro-3-{4-[2-(3-methyl-1,2,4-oxadiazol-5-yl)morpholin-4-yl]-7H-pyrrolo[2,3-d]pyrimidin-5-yl}benzonitrile, ENT-1 | N.D. | N.D. |
| 215 | 6-[4-(morpholin-4-yl)-7H-pyrrolo[2,3-d]pyrimidin-5-yl]pyridine-2-carboxamide, formate salt | 30.6 | 79.3 |
| 216 | 4-(morpholin-4-yl)-5-(pyrazolo[1,5-a]pyrimidin-3-yl)-7H-pyrrolo[2,3-d]pyrimidine | 35.6 | 119 |
| 217 | 1-methyl-4-[4-(morpholin-4-yl)-7H-pyrrolo[2,3-d]pyrimidin-5-yl]-1H-pyrrole-2-carbonitrile | 6.37 | 13 |
| 218 | 5-(6-methylimidazo[2,1-b)][1,3]thiazol-5-yl)-4-(morpholin-4-yl)-7H-pyrrolo[2,3-d]pyrimidine, formate salt | 37.4[b] | 135[b] |
| 219 | 3-{4-[2-(1,2-oxazol-5-yl)morpholin-4-yl]-7H-pyrrolo[2,3-d]pyrimidin-5-yl}benzonitrile | 37 | 234 |
| 220 | 1-methyl-4-[4-(morpholin-4-yl)-7H-pyrrolo[2,3-d]pyrimidin-5-yl]-1H-imidazole-2-carbonitrile, trifluoroacetate salt | 7.47 | 14.7 |
| 221 | 4-[4-(morpholin-4-yl)-7H-pyrrolo[2,3-d]pyrimidin-5-yl]thiophene-2-carbonitrile | N.D. | N.D. |
| 222 | 4-(morpholin-4-yl)-5-(pyrazolo[1,5-a]pyridin-3-yl)-7H-pyrrolo[2,3-d]pyrimidine | N.D. | N.D. |
| 223 | 1,5-dimethyl-4-[4-(morpholin-4-yl)-7H-pyrrolo[2,3-d]pyrimidin-5-yl]-1H-pyrrole-2-carbonitrile | N.D. | N.D. |
| 224 | 1-methyl-3-[4-(morpholin-4-yl)-7H-pyrrolo[2,3-d]pyrimidin-5-yl]-1H-pyrazole-5-carbonitrile, trifluoroacetate salt | N.D. | N.D. |
| 225 | 3-{4-[2-(cyanomethyl)morpholin-4-yl]-7H-pyrrolo[2,3-d]pyrimidin-5-yl}benzonitrile | N.D. | N.D. |

*Geometric mean of 2-5 determinations unless otherwise indicated
[a]IC$_{50}$ value represents the geometric mean of ≥6 determinations.
[b]IC$_{50}$ value derived from a single determination.
[c]N.D.—not determined Certain of the compounds of the present invention were assessed for kinase selectivity using a commercially available ActiveX targeted kinase probe in which the tissue employed was human peripheral blood mononuclear cells (PBMC). The test compounds were provided to ActivX Biosciences, Inc., 11025 North Torrey Pines Road, Suite 120; LaJolla, Calif., USA 92037. The compounds were run in the ActivX proprietary kinase assay and results were obtained at compound test concentrations of 1 μM (columns 2, 4 and 6) and 0.1 μM (columns 3, 5 and 7). The results as percent inhibition obtained for the compounds of Examples 1, 4 and 217 are provided below in Table 3.

TABLE 3

| Kinase | Example 1 | | Example 4 | | Example 217 | |
|---|---|---|---|---|---|---|
|  | 1 μM | 0.1 μM | 1 μM | 0.1 μM | 1 μM | 0.1 μM |
| ABL, ARG | 22.5 | 25.8 | −0.9 | −29.4 | −1.6 | 4.6 |
| ACK | −8 | 5.2 | 7.7 | 0.8 | −19.5 | −9.8 |
| AKT1 | 18.8 | 11.3 | −6.3 | −8.8 | −3.6 | 5.5 |
| AKT2, AKT3 | 10.7 | 1.6 | 6.8 | −2.6 | −3.8 | −9.7 |
| AMPKa1 | 27 | 1.5 | 16.4 | −2.1 | 48.8 | 27.2 |
| AMPKa1, AMPKa2 | 49.7 | 10.8 | 32.5 | −4.5 | 16.5 | 5.7 |
| BRAF | −51.5 | −6.5 | −1.2 | 1.2 | −10.4 | −8.4 |
| BTK | 3.7 | 8.7 | 9.5 | −2.2 | 8.5 | 24.3 |
| CaMK1a | 6.3 | 2 | 1.9 | −9.2 | −7.1 | −5.4 |
| CaMK1d | 3.2 | 8.4 | 0.9 | −12.1 | 3.1 | 11.7 |
| CaMK2d | −38.1 | −45.3 | 10.8 | −0.4 | 16.1 | 9.8 |
| CaMK2g | −15.5 | −16.9 | 2.9 | −13.6 | 18.7 | 4.3 |
| CDC2 | 14.7 | −4 | 12.9 | −6.7 | 24.4 | 28.7 |
| CDK11, CDK8 | 2.4 | 4.4 | 36 | 5 | −5.2 | −5.6 |
| CDK2 | 9.5 | −12.1 | 9.2 | 11 | 16.5 | 3.6 |
| CDK5 | −35.1 | −6.5 | 0.1 | −12.2 | 7.9 | 0.5 |
| CHK2 | 17.7 | 0.9 | 2.2 | −6.8 | 6.4 | 8.6 |
| DGKA | −16.6 | −21 | −8.7 | −15.9 | 4.7 | −2.8 |
| DNAPK | −30 | −4.4 | 14.7 | −19.3 | 31.5 | 31.0 |

TABLE 3-continued

| Kinase | Example 1 | | Example 4 | | Example 217 | |
|---|---|---|---|---|---|---|
|  | 1 μM | 0.1 μM | 1 μM | 0.1 μM | 1 μM | 0.1 μM |
| eEF2K | −6.5 | −9.6 | 2.8 | −27.1 | 2.2 | −12.1 |
| EphA1 | 19.6 | −9.5 | −2.5 | −17 | −16.1 | 11.1 |
| Erk5 | −41.9 | −32.8 | −6.3 | −5 | −5.4 | −2.6 |
| FAK | 20 | 18 | 11.1 | −8.9 | 17.4 | 8.1 |
| FER | −17.9 | −7.3 | 1.6 | −26.4 | 16.3 | 5.2 |
| FES | −0.9 | 4.3 | 6.9 | −9.2 | 6.2 | 8.4 |
| FGR | 4.6 | 12.9 | 1.7 | −10.8 | −0.5 | −1.2 |
| FRAP | −1.2 | −3.2 | 9.8 | −20.7 | 0.9 | 0.7 |
| FYN | −10.1 | 6.7 | −9.1 | −1.9 | −6.8 | −2.1 |
| FYN, SRC, YES | −56.3 | −24.1 | −8.8 | −22.8 | −1.4 | 18.4 |
| GCK | −6.7 | 4.4 | 31.2 | 3.6 | 27.2 | −5.2 |
| GCN2 | −25.1 | 0.1 | 0.6 | −13.6 | −3.1 | −7.7 |
| GPRK6 | 23.7 | 8.9 | 10.9 | −3.9 | 3.6 | −0.8 |
| GSK3A | −11.4 | −0.2 | 7.2 | −0.9 | 8.9 | 0.6 |
| GSK3B | −5.2 | 2.4 | 6.7 | −3.7 | 12.4 | −4.3 |
| HPK1 | −14.9 | −9.7 | 5.7 | −1.5 | 1.7 | −13.7 |
| IKKa | −40.5 | −20 | −6.6 | −12.1 | −3.7 | −2.5 |
| IKKb | 10.8 | 16.1 | −15.8 | −15.5 | 6.5 | 7.1 |
| IKKe | 17.7 | 2.6 | 7.4 | −7 | 20.4 | −3.0 |
| IKKe, TBK1 | 23.7 | 1.5 | 18.8 | −6.7 | 13.3 | 2.3 |
| ILK | −56.6 | −34 | −31.6 | −8.9 | −3.8 | −6.3 |
| IRAK1 | −9.1 | −13.8 | 2.1 | −2.9 | 7.5 | −1.7 |
| IRAK3 | 68.7 | 30.1 | 33.7 | 29.8 | 72.4 | 16.0 |
| IRAK4 | 34.7 | 17.7 | 10.7 | −12.8 | 34.5 | 14.7 |
| IRE1 | −8 | −1.3 | 1.8 | −16 | −19.5 | 3.2 |
| JAK1 | 54.2 | 15 | 5 | −9.3 | 11.4 | −3.0 |
| JAK1 domain2 | −13.7 | −8.1 | 18.9 | −6.2 | 10.1 | 7.4 |
| JAK2 domain2 | 16.7 | 13.8 | 16.4 | 0.7 | −6.4 | 4.8 |
| JAK3 domain2 | −5.2 | 2.7 | 6.8 | 6.9 | 4.9 | −7.8 |
| JNK1, JNK2, JNK3 | 7.7 | 7.1 | 5.4 | −5.3 | −6.4 | −18.2 |
| KHS1 | 24.6 | 17.8 | 12.9 | −25.9 | 7.6 | 10.7 |
| KSR1, KSR2 | −14 | 1.5 | 11.7 | −8.7 | −6.8 | −6.2 |
| LATS1 | −16.2 | 4.2 | 5.4 | −4.8 | 1.9 | −3.9 |

TABLE 3-continued

| Kinase | Example 1 | | Example 4 | | Example 217 | |
|---|---|---|---|---|---|---|
| | 1 μM | 0.1 μM | 1 μM | 0.1 μM | 1 μM | 0.1 μM |
| LATS2 | 11 | 21.2 | 16.2 | −7.2 | −23.7 | 5.8 |
| LKB1 | −14 | −1.1 | 16.5 | 3.5 | 2.4 | −5.3 |
| LOK | 22.6 | 5.7 | 53.6 | 11.9 | 56.1 | −6.4 |
| LRRK2 | 88.1 | 69 | 94.1 | 79.9 | | 88.4 |
| LYN | 7.8 | 3.8 | 0.8 | −5.4 | −19.2 | 8.3 |
| MAP2K1 | 17 | 3.5 | 14 | −17.2 | −1.5 | 17.2 |
| MAP2K1, MAP2K2 | −2.2 | 1 | 6.4 | −7.1 | −2.6 | 10.9 |
| MAP2K3 | −9 | 14.4 | 6.2 | −12.5 | 3.3 | 2.5 |
| MAP2K4 | 9.6 | 10.1 | 19.2 | −20.5 | 1.6 | 2.3 |
| MAP2K6 | 19 | 17.5 | 13.5 | −15.1 | −0.1 | 11.3 |
| MAP3K1 | 11.9 | −9.4 | 44.5 | 6.4 | 14.8 | −17.3 |
| MAP3K3 | 7.2 | −9.2 | 7.4 | −0.5 | −6.7 | −3.4 |
| MAP3K4 | 6.9 | −14 | 29.8 | 9.7 | −27.4 | −35.5 |
| MAP3K5 | 2.1 | 6.2 | 21.3 | 3.3 | 44.5 | 7.0 |
| MARK2 | 41.6 | 10.1 | 27.3 | −4.7 | 13.1 | −5.0 |
| MARK3 | 29.1 | 1 | 23.7 | −2.6 | 18.4 | 16.2 |
| MAST3 | −6.7 | 9 | 0.8 | 2.6 | 0.4 | −11.7 |
| MLK3 | 4.5 | 1.4 | 19.9 | −14.1 | −9.6 | −13.5 |
| MLKL | 8.4 | 1.6 | 14.5 | −10.1 | −3.3 | 2.5 |
| MSK1 domain1 | −30.4 | −7 | −3.8 | 1 | −2.2 | −12.1 |
| MST1 | 50.8 | 13.2 | 82.2 | 41.9 | 73.5 | 25.6 |
| MST1, MST2 | 24.8 | −14.5 | 70.8 | 34.4 | 72.6 | 21.9 |
| MST2 | 49.4 | 10.1 | 82.6 | 47.3 | 83.2 | 34.9 |
| MST3 | 28.4 | 10.9 | 46.2 | 0.1 | 10.9 | 6.7 |
| MST4, YSK1 | 15.1 | −11.4 | 60.7 | 11.9 | 9.9 | 5.3 |
| NDR1 | −7.8 | −19.6 | 1.7 | −4.4 | −17.7 | 16.3 |
| NDR2 | 31.2 | 22.8 | 22.1 | −18.7 | −6.0 | 28.9 |
| NEK1 | −10.1 | 7 | −1.9 | −8.9 | −5.1 | 4.8 |
| NEK6, NEK7 | −17 | −1.7 | −4.9 | −5.3 | 6.4 | −2.9 |
| NEK7 | −18.8 | −0.6 | 7.3 | 2.2 | −2.3 | −9.0 |
| NEK9 | 12.6 | −0.9 | 1 | −7.1 | 1.5 | −11.0 |
| NuaK2 | 8.9 | 3.6 | 18.1 | −11.9 | 24.9 | 1.3 |
| OSR1 | −4 | −7.8 | −55.4 | −23.1 | −12.3 | 5.2 |
| p38a | −19.8 | −23.5 | −1.7 | −14.6 | −4.6 | −1.1 |
| p38d, p38g | −24 | −37.3 | −5.7 | −17.5 | 1.5 | −0.4 |
| p70S6K | 18.9 | 23 | 11.1 | −9 | −9.6 | 3.5 |
| p70S6K, p70S6Kb | −3.5 | 9.4 | −9.6 | −10.5 | 5.4 | 5.5 |
| p70S6Kb | 10.1 | 15 | 18.5 | 11.4 | −16.7 | −2.2 |
| PAN3 | 0.8 | 0.6 | 15.1 | −0.2 | −7.5 | 5.6 |
| PCTAIRE2, PCTAIRE3 | −2.5 | 7.5 | 24.7 | −5.4 | 15.1 | −2.6 |
| PI4KB | 16.1 | 34 | 4.9 | −7.4 | −0.5 | 9.9 |
| PIK3C3 | 4.8 | 23.3 | 13.6 | −2.4 | 10.2 | 19.9 |
| PIK3CB | −29.8 | −2.6 | −2.5 | 0.5 | −29.7 | −5.3 |
| PIK3CD | −65.4 | −101.6 | −12.4 | −14 | 10.0 | −0.4 |
| PIK3CG | −62.9 | −18.6 | −5.6 | −20.4 | −22.0 | −3.4 |
| PIP4K2A | 6.8 | 12.1 | 1.9 | −12.1 | 8.2 | 7.8 |
| PIP4K2C | −1.4 | 1.4 | 58.4 | 3.1 | −11.9 | 6.2 |
| PIP4K2C | 0.9 | −48 | 54.3 | 9.3 | 4.0 | −4.7 |
| PIP5K3 | 15 | 1.9 | 21.6 | −11.2 | 2.5 | 16.0 |
| PITSLRE | −3.2 | −13 | 10.7 | −12.4 | 6.6 | −6.7 |
| PKD2 | 20.1 | 2.7 | 9.4 | 0.7 | 4.5 | 5.8 |
| PKR | −17.3 | −4.3 | 7.2 | −3.3 | 1.8 | −7.7 |
| PRPK | −13.8 | −3.4 | −3.7 | 3 | 12.5 | 2.6 |
| PYK2 | 19.5 | 5.9 | 2.5 | −3.9 | 8.4 | −1.0 |
| RIPK3 | −4.2 | 5.6 | 8 | −3.2 | −9.1 | −7.3 |
| RSK1 domain1 | 59.8 | 16.3 | 32.9 | −26.8 | 45.6 | 27.6 |
| RSK1 domain2 | 18.1 | −12.7 | 55.8 | 2.7 | 5.0 | −3.4 |
| RSK1, RSK2, RSK3 domain1 | 18.7 | 3 | 13.4 | −0.4 | 48.5 | 5.0 |
| RSK2 domain1 | 5.6 | −6.8 | −11.2 | −6 | 61.6 | 13.2 |
| RSK2 domain2 | 9.1 | 0.6 | 21.4 | −10 | 2.8 | −4.1 |
| RSKL1 domain1 | −0.2 | 5.5 | −1.8 | 1.1 | −30.6 | −15.9 |
| SGK3 | 9.9 | 2.5 | −0.8 | −5.5 | 16.9 | 8.5 |
| SLK | 50.6 | 22.9 | 60.7 | 10.5 | 39.1 | 22.5 |
| SMG1 | −19.2 | −1.3 | 13 | −2.5 | −6.1 | 1.5 |
| smMLCK | −1.9 | −11.5 | 16.2 | −21.6 | 3.5 | 1.7 |
| SRC | 9.7 | 1.5 | −2.2 | −18.3 | 1.1 | −1.0 |
| STLK5 | −46.5 | −1.5 | 1.2 | −15.4 | −11.5 | −6.9 |
| SYK | −6.1 | −8.9 | 7.2 | −8.3 | −5.1 | −2.0 |
| TAO1, TAO3 | −14.9 | −24 | 5.9 | −6.5 | −16.5 | −9.7 |
| TAO2 | −24.2 | −6.3 | −2.5 | −12.7 | −18.4 | −20.2 |
| TBK1 | 13.4 | 0.1 | 16.4 | 7.3 | 0.1 | 1.9 |
| TLK1 | 2.7 | 7.8 | −3.7 | −4.6 | 16.7 | 7.6 |
| TLK2 | −21.1 | −5.8 | −9.4 | −8.4 | 16.0 | 11.1 |
| ULK3 | 8 | −1.9 | 5.2 | 3.1 | 17.4 | −8.6 |
| Wnk1, Wnk2, Wnk3 | −24 | −18.8 | −6 | 1.7 | −21.1 | −6.3 |
| Wnk1, Wnk2, Wnk4 | −13.5 | −15 | −1.3 | −1.9 | −5.4 | 2.2 |
| ZAK | 23.1 | 15 | −42.2 | −20.5 | −1.2 | −2.9 |
| ZAP70 | 3.1 | −23.2 | 6.8 | −4.9 | −6.0 | −25.0 |
| ZC1/HGK, ZC2/TNIK, ZC3/MINK | 4.9 | −18 | 14.8 | −3.2 | 7.7 | −1.2 |
| ZC2/TNIK | 31.2 | −10.6 | 29.2 | −7.9 | 3.9 | −10.7 |

We claim:

1. A pharmaceutical composition comprising a therapeutically effective amount of a compound selected from the group consisting of
   5-(1-methyl-1H-pyrazol-4-yl)-4-(morpholin-4-yl)-7H-pyrrolo[2,3-d]pyrimidine;
   6-[4-(morpholin-4-yl)-7H-pyrrolo[2,3-d]pyrimidin-5-yl]pyridine-2-carbonitrile;
   3-[4-(morpholin-4-yl)-7H-pyrrolo[2,3-d]pyrimidin-5-yl]benzonitrile; and
   3-{4-[(2S)-2-methylmorpholin-4-yl]-7H-pyrrolo[2,3-d]pyrimidin-5-yl}benzonitrile;
or a pharmaceutically acceptable salt thereof together with a pharmaceutically acceptable carrier.

2. The pharmaceutical composition of claim 1, wherein the compound is
   5-(1-methyl-1H-pyrazol-4-yl)-4-(morpholin-4-yl)-7H-pyrrolo[2,3-d]pyrimidine;
or a pharmaceutically acceptable salt thereof.

3. The pharmaceutical composition of claim 1, wherein the compound is
   6-[4-(morpholin-4-yl)-7H-pyrrolo[2,3-d]pyrimidin-5-yl]pyridine-2-carbonitrile;
or a pharmaceutically acceptable salt thereof.

4. The pharmaceutical composition of claim 1, wherein the compound is
   3-[4-(morpholin-4-yl)-7H-pyrrolo[2,3-d]pyrimidin-5-yl]benzonitrile;
or a pharmaceutically acceptable salt thereof.

5. The pharmaceutical composition of claim 1, wherein the compound is
   3-{4-[(2S)-2-methylmorpholin-4-yl]-7H-pyrrolo[2,3-d]pyrimidin-5-yl}benzonitrile;
or a pharmaceutically acceptable salt thereof.

6. A method of treating Parkinson's disease in a patient, the method comprising administering to a patient in need thereof a therapeutically effective amount of a compound selected from the group consisting of
   5-(1-methyl-1H-pyrazol-4-yl)-4-(morpholin-4-yl)-7H-pyrrolo[2,3-d]pyrimidine;
   6-[4-(morpholin-4-yl)-7H-pyrrolo[2,3-d]pyrimidin-5-yl]pyridine-2-carbonitrile;
   3-[4-(morpholin-4-yl)-7H-pyrrolo[2,3-d]pyrimidin-5-yl]benzonitrile; and
   3-{4-[(2S)-2-methylmorpholin-4-yl]-7H-pyrrolo[2,3-d]pyrimidin-5-yl}benzonitrile;
or a pharmaceutically acceptable salt thereof.

7. The method of claim 6, wherein the compound is
5-(1-methyl-1H-pyrazol-4-yl)-4-(morpholin-4-yl)-7H-pyrrolo[2,3-d]pyrimidine;
or a pharmaceutically acceptable salt thereof.

8. The method of claim 6, wherein the compound is
6-[4-(morpholin-4-yl)-7H-pyrrolo[2,3-d]pyrimidin-5-yl]pyridine-2-carbonitrile;
or a pharmaceutically acceptable salt thereof.

9. The method of claim 6, wherein the compound is
3-[4-(morpholin-4-yl)-7H-pyrrolo[2,3-d]pyrimidin-5-yl]benzonitrile;
or a pharmaceutically acceptable salt thereof.

10. The method of claim 6, wherein the compound is
3-{4-[(2S)-2-methylmorpholin-4-yl]-7H-pyrrolo[2,3-d]pyrimidin-5-yl}benzonitrile;
or a pharmaceutically acceptable salt thereof.

* * * * *